US008058288B2

(12) United States Patent
Yao et al.

(10) Patent No.: US 8,058,288 B2
(45) Date of Patent: *Nov. 15, 2011

(54) AMIDO COMPOUNDS AND THEIR USE AS PHARMACEUTICALS

(75) Inventors: Wenqing Yao, Kenneth Square, PA (US); Jincong Zhuo, Garnet Valley, PA (US); Meizhong Xu, Hockessin, DE (US); Colin Zhang, Ambler, PA (US); Brian W. Metcalf, Moraga, CA (US); Chunhong He, Boothwyn, PA (US); Ding-Quan Qian, Newark, DE (US)

(73) Assignee: Incyte Corporation, Wilmington, DE (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/817,887

(22) Filed: Jun. 17, 2010

(65) Prior Publication Data
US 2010/0256114 A1    Oct. 7, 2010

Related U.S. Application Data

(60) Continuation of application No. 12/136,529, filed on Jun. 10, 2008, now Pat. No. 7,776,874, which is a continuation of application No. 11/784,450, filed on Apr. 6, 2007, now abandoned, which is a division of application No. 11/122,309, filed on May 4, 2005, now Pat. No. 7,304,081.

(60) Provisional application No. 60/638,803, filed on Dec. 22, 2004, provisional application No. 60/602,791, filed on Aug. 19, 2004, provisional application No. 60/602,051, filed on Aug. 17, 2004, provisional application No. 60/569,273, filed on May 7, 2004.

(51) Int. Cl.
A61K 31/44    (2006.01)
A61K 31/40    (2006.01)
A61K 31/34    (2006.01)
C07D 491/20   (2006.01)

(52) U.S. Cl. ........ 514/292; 514/293; 514/409; 514/411; 514/424; 514/462; 514/468; 514/473; 546/82; 546/83; 548/410; 549/265

(58) Field of Classification Search .................. 514/292, 514/293, 409, 411, 424, 462, 468, 473; 546/82, 546/83; 548/410; 549/265
See application file for complete search history.

(56) References Cited

U.S. PATENT DOCUMENTS

| 3,097,209 | A |  7/1963 | Jannsen et al. |
| 3,328,156 | A |  6/1967 | Hopkins |
| 3,770,748 | A | 11/1973 | Borck et al. |
| 3,933,829 | A |  1/1976 | Archibald et al. |
| 4,001,422 | A |  1/1977 | Danilewicz et al. |
| 4,013,445 | A |  3/1977 | Bellus et al. |
| 4,076,819 | A |  2/1978 | Maffrand |
| 4,145,435 | A |  3/1979 | Szmuszkovicz |
| 4,439,606 | A |  3/1984 | Du et al. |
| 5,442,064 | A |  8/1995 | Pieper et al. |
| 5,614,534 | A |  3/1997 | Binet et al. |
| 5,633,247 | A |  5/1997 | Baldwin et al. |
| 5,668,138 | A |  9/1997 | Baziard-Mouysset et al. |
| 5,852,029 | A | 12/1998 | Fisher et al. |
| 5,981,754 | A | 11/1999 | Badone et al. |
| 6,547,958 | B1 |  4/2003 | Elomari |
| 7,074,788 | B2 |  7/2006 | Kurz et al. |
| 7,122,532 | B2 | 10/2006 | Walker et al. |
| 7,304,081 | B2 * | 12/2007 | Yao et al. ....................... 514/370 |
| 7,776,874 | B2 * |  8/2010 | Yao et al. ....................... 514/278 |
| 2003/0203922 | A1 | 10/2003 | Patel et al. |
| 2003/0229119 | A1 | 12/2003 | Kym et al. |
| 2004/0188324 | A1 |  9/2004 | Elomari |
| 2005/0020645 | A1 |  1/2005 | Ohta et al. |
| 2005/0080078 | A1 |  4/2005 | Aquila et al. |
| 2005/0282858 | A1 | 12/2005 | Yao et al. |
| 2005/0288317 | A1 | 12/2005 | Yao et al. |
| 2005/0288329 | A1 | 12/2005 | Yao et al. |
| 2005/0288338 | A1 | 12/2005 | Yao et al. |
| 2006/0004049 | A1 |  1/2006 | Yao et al. |
| 2006/0009471 | A1 |  1/2006 | Yao et al. |
| 2006/0009491 | A1 |  1/2006 | Yao et al. |
| 2006/0116382 | A1 |  6/2006 | Yao et al. |
| 2006/0122197 | A1 |  6/2006 | Yao et al. |
| 2006/0122210 | A1 |  6/2006 | Yao et al. |
| 2006/0149070 | A1 |  7/2006 | Rohde et al. |
| 2006/0199816 | A1 |  9/2006 | Gillespie et al. |
| 2007/0066584 | A1 |  3/2007 | Yao et al. |

(Continued)

FOREIGN PATENT DOCUMENTS

AU    2004232939    11/2004

(Continued)

OTHER PUBLICATIONS

Alberts et al., "Selective Inhibition of 11β-Hydroxysteroid Dehydrogenease Type 1 Improves Hepatic Insulin Sensitivity in Hyperglycemic Mice Strains", *Endocrinology*, (2003) 144: 4755-4762.
Albiston et al., "Cloning and tissue distribution of the human 11β-hydroxysteroid dehydrogenase type 2 enzyme", *Mol. Cell. Endocrin.*, (1994) 105: R11-R17.
Banker, G.S. ed. Modern Pharmaceutics, 3$^{rd}$ ed. Marcel Dekker, Inc., New York, 1996, pp. 451 and 596.
Barf et al., "Arylsulfonamidothiazoles as a New Class of Potential Antidiabetic Drugs. Discovery of Potent and Selective Inhibitors of the 11β-Hydroxysteroid Dehydrogenase Type 1", *J. Med. Chem.*, (2002) 45: 3813-3815.
Bellows et al., "Osteoprogenitor Cells in Cell Populations Derived From Mouse and Rat Calvaria Differ in Their Response to Corticosterone, Cortisol and Cortisone", *Bone*, (1998) 23: 119-125.
Ben et al., "Synthesis of Optically Active α-Amino Esters via Dynamic Kinetic Resolution: A Mechanistic Study," *J. Org. Chem.*, 64: 7700-7706 (1999).
Berge et al., "Pharmaceutical Salts", *Journal of Pharmaceutical Science*, 66, 2 (1977).

(Continued)

Primary Examiner — Joseph Kosack
(74) Attorney, Agent, or Firm — Fish & Richardson P.C.

(57) ABSTRACT

The present invention relates to inhibitors of 11-β hydroxyl steroid dehydrogenase type 1, antagonists of the mineralocorticoid receptor (MR), and pharmaceutical compositions thereof. The compounds of the invention can be useful in the treatment of various diseases associated with expression or activity of 11-β hydroxyl steroid dehydrogenase type 1 and/or diseases associated with aldosterone excess.

35 Claims, No Drawings

U.S. PATENT DOCUMENTS

| | | | |
|---|---|---|---|
| 2007/0129345 A1 | 6/2007 | Zhuo et al. |
| 2007/0179142 A1 | 8/2007 | Yao et al. |
| 2007/0197506 A1 | 8/2007 | Yao et al. |
| 2007/0197530 A1 | 8/2007 | Li et al. |
| 2007/0208001 A1 | 9/2007 | Zhuo et al. |
| 2007/0213311 A1 | 9/2007 | Li et al. |
| 2007/0270424 A1 | 11/2007 | Li et al. |
| 2007/0293529 A1 | 12/2007 | Li et al. |
| 2008/0318991 A1 | 12/2008 | Yao et al. |
| 2009/0291946 A1 | 11/2009 | Yao et al. |
| 2009/0298808 A1 | 12/2009 | Yao et al. |

FOREIGN PATENT DOCUMENTS

| | | |
|---|---|---|
| DE | 2623567 | 12/1976 |
| EP | 0273659 | 7/1988 |
| FR | 2289498 | 5/1976 |
| JP | 57-156450 | 9/1982 |
| JP | 04-334357 | 11/1992 |
| WO | WO 00/01702 | 1/2000 |
| WO | WO0001704 A3 | 4/2000 |
| WO | WO 00/59874 | 10/2000 |
| WO | WO 01/05790 | 1/2001 |
| WO | WO0100823 A1 | 2/2001 |
| WO | WO 01/30780 | 5/2001 |
| WO | WO 02/06868 | 1/2002 |
| WO | WO 02/22572 | 3/2002 |
| WO | WO 02/069973 | 9/2002 |
| WO | WO03006364 A1 | 1/2003 |
| WO | WO 03/010138 | 2/2003 |
| WO | WO 03/037271 | 5/2003 |
| WO | WO 03/037847 | 5/2003 |
| WO | WO 03/041641 | 5/2003 |
| WO | WO 03/045912 | 6/2003 |
| WO | WO 03/049736 | 6/2003 |
| WO | WO03049736 A1 | 6/2003 |
| WO | WO 03/053915 | 7/2003 |
| WO | WO 03/099821 | 12/2003 |
| WO | WO 03/104207 | 12/2003 |
| WO | WO 2004/005295 | 1/2004 |
| WO | WO 2004/017961 | 3/2004 |
| WO | WO 2004/018479 | 3/2004 |
| WO | WO 2004/022554 | 3/2004 |
| WO | WO2004033427 A1 | 4/2004 |
| WO | WO 2004/056745 | 7/2004 |
| WO | WO 2004/058727 | 7/2004 |
| WO | WO 2004/065351 | 8/2004 |
| WO | WO 2004/082687 | 9/2004 |
| WO | WO 2004/089470 | 10/2004 |
| WO | WO 2004/089896 | 10/2004 |
| WO | WO2004/094371 | 11/2004 |
| WO | WO 2004/096139 | 11/2004 |
| WO | WO2004094347 A3 | 2/2005 |
| WO | WO 2005/037814 | 4/2005 |
| WO | WO 2005/047286 | 5/2005 |
| WO | WO 2005/060963 | 7/2005 |
| WO | WO 2005/061499 | 7/2005 |
| WO | WO 2005/108359 | 11/2005 |
| WO | WO 2005/110992 | 11/2005 |
| WO | WO 2006/002349 | 1/2006 |
| WO | WO 2006/002350 | 1/2006 |
| WO | WO 2006/002361 | 1/2006 |
| WO | WO 2006/012173 | 2/2006 |
| WO | WO 2006/012226 | 2/2006 |
| WO | WO 2006/012227 | 2/2006 |
| WO | WO 2006/020598 | 2/2006 |
| WO | WO 2006/047176 | 5/2006 |
| WO | WO 2006/053024 | 5/2006 |
| WO | WO 2006/055752 | 5/2006 |
| WO | WO 2007/038138 | 4/2007 |
| WO | WO 2007/067504 | 6/2007 |
| WO | WO 2007/084314 | 7/2007 |
| WO | WO 2007/089683 | 8/2007 |
| WO | WO 2007/101270 | 9/2007 |
| WO | WO 2007/103719 | 9/2007 |

OTHER PUBLICATIONS

Bhargava et al., "The Serum- and Glucocorticoid-Induced Kinase Is a Physiological Mediator of Aldosterone Action", *Endocrinology*, (2001) 142: 1587-1594.

Billaudel and Sutter, "Direct Effect of Corticosterone upon Insulin Secretion Studied by Three Different Techniques", *Horm. Metab. Res.*, (1979) 11: 555-560.

Blum et al., "Enzymology and Molecular Biology of Glucocorticoid Metabolism in Humans", *Prog. Nucl. Acid Res. Mol. Biol.*, (2003) 75:173-216.

Bolm C. et al., *J. Org. Chem.* 2005, 70, 2346.

Borthwick et al., "Design and Synthesis of Pyrrolidine-5.5'-*trans*-Lactams (5-Oxo-hexahydropyrrolo[3,2-*b*]pyrroles) as Novel Mechanism-Based Inhibitors of Human Cytomegalovirus Protease. 4. Antiviral Activity and Plasma Stability", *J. Med. Chem.*, (2003) 46, 4428.

Bujalska et al. "Does central obesity reflect 'Cushing's disease of the omentum'?", *Lancet.*, (1997) 349: 1210-1213.

Burke et al., "α,α-Disubstituted Boron Enolates in the Asymmetric Synthesis of Quaternary Carbon Centers", *Organic Letters*, 6/(3), pp. 405-407, 2004.

Buzas et al., "Synthèse et propriétés pharmacologiques de nouveaux dérivés de l'acide pyrrolidone-2-carboxylique-4", *Chimica Therapeutica, The European Journal of Medicinal Chemistry*,7 (5), pp. 361-426, 1972 (translation provided).

Bursavich, M. G. And Rich, D. H., "Solid-Phase Synthesis of Aspartic Peptidase Inhibitors: 3-Alkoyx-4-Aryl Piperidines", *Org. Lett.*, (2001) 3, 2625.

Bydal et al., "Inhibition of type 2 17β-hydroxysteroid dehydrogenase by estradiol derivatives bearing a lactone on the D-ring: structure-activity relationshps", *Steroids*, (2004) 69, 325-342.

Canalis, E., "Clinical Review 83—Mechanisms of Glucocorticoid Action in Bone: Implications to Glucocorticoid-Induced Osteoporosis", *J. Clin. Endocrinol. Metab.*, (1996) 81: 3441-3447.

Cheng et al., *Eur. I Med. Chem.*, (1991) vol. 26(2), pp. 125-128.

Combs et al., "N-Arylation of Primary and Secondary Aliphatic Amines on Solid Supports", *J. Comb. Chem.*, 2002, 4, 179.

Conn, J., "Part II. Primary Aldosteronism, A New Clinical Syndrome", *J. Lab. Clin. Med.*, (1955) 45: 6-17.

Cooper et al. "Expression and Functional Consequences of 11β-Hydroxysteroid Dehydrogenase Activity in Human Bone", *Bone*, (2000) 27: 375-381.

Coutts, I.G.C. et al., *J. Chem. Soc. Perk. Trans.*, 1 (3), pp. 767-771, 1990.

Dankwardt et al., "Solid Phase Synthesis of Aryl and Benzylpiperazines and their Application in Combinatorial Chemistry", *Tetrahedron Lett.*, (1995) 36, 4923.

Database CAPLUS on STN (Columbus, OH, USA) No, 108:131815, Preparation and testing of f7-amino-1,3-dihydro-2H-imidazo[4,5-b]quinolin-2-ones as phosphodiesterase and blood platelet aggregation inhibitors', abstract, Meanwell, et al. (1988) see RN 113288-90-7.

Database CAPLUS on STN (Columbus, OH, USA) No. 118:255342, "Preparation of N-heterocyclylcarbonyl)amino acids and analogs as prolyl endopeptidases" abstract, Hosoda et al. (1993) see RN 147635-61-8.

Database CAPLUS on STN (Columbus, OH, USA) No. 126:317635, "Alpha-amino acids derived from ornithine as building blocks for peptide synthesis" abstract, Gescrinier et al. j. Pep. Res. 49(2):183-189 (1997).

Database CAPLUS on STN (Columbus, OH, USA) No. 143:78479, "Preparation of amino acid derivatives as novel M3 muscarinic acetylcholine receptor antagonists" abstract, Busch et al. (2005), see RN 902149-23-9 and 854750-92-8.

Database CAPLUS on STN (Columbus, OH, USA) No. 143:7612, Preparation of Heterocyclic Spiro Compounds for Treatment of Stress Related Diseases, RN 64097-78-5, (2005).

Database CAPLUS on STN (Columbus, OH, USA) No. 135:257227, "Preparation of pyrrolidinone derivatives having .sigma.-receptor affinity", RN-362518-14-7, RN 362518-16-9, RN 362518-15-8, RN 363518-17-0; (2001).

Database CAPLUS on STN (Columbus, OH, USA) No. 55:87498, "Synthetic drugs. VI. A new type of spirosusccinimade", RN-64097-71-8; RN-102654-82-0; RN- 113251-47-1, RN-113687-61-9, RN-114509-25-0; (1961).
Database CAPLUS ACS on STN, 2006, Caplus English Abstract US 2005288317, Dec. 29, 2005, see: RN 872412-08-3 structure, abstract, and patent family details (2 pages).
Database CAPLUS ACS on STN, 2006, DN 144:6815,See RN869970-58-1, 2005 structure, abstract, and patent family (1 page).
Database CAPLUS on STN (Columbus, OH, USA) No. 1983: 107002, "1-(4-chlorophenyl)-1-cyclopentanecarboxylic acid derivatives", abstract of JP57-156450, XP002514476.
Database CAPLUS on STN (Columbus, OH, USA) No. 2004:802077, "Zeolite SSZ-65 synthesis, properties, and use as petroleum and hydrocarbon refining catalysts", abstract, XP002514477.
Davani et al. "Type 1 11β-Hydroxysteroid Dehydrogenase Mediates Glucocorticoid Activation and Insulin Release in Pancreatic Islets",*J Biol. Chem.*, (2000) 275: 34841-34844.
De Costa et al., *J Med. Chem.*, (1990) vol. 33(11), pp. 3100-3110.
Dorwald, F.A. Side Reactions in Organic Synthesis, Wiley-VCH, Weinheim, p. IX of Preface, pp. 1-16, and pp. 40-41, 2005.
Draper et al.,"Mutations in the genes encoding 11β-hydroxysteroid dehydrogenase type 1 and hexose-6-phosphate dehydrogenase interact to cause cortisone reductase deficiency", *Nat. Genet.*, (2003) 34: 434-439.
Edwards et al., "Localisation of 11β-Hydroxysteroid Dehydrogenase-Tissue Specific Protector of the Mineralocorticoid Receptor", *Lancet.*, (1988) 2: 986-989.
Engeli et al., "Regulation of 11β-HSD Genes in Human Adipose Tissue: Influence of Central Obesity and Weight Loss", *Obes. Res.*, (2004) 12: 9-17.
Funder et al., "Mineralocorticoid Action: Target Tissue Specificity is Enzyme, not Receptor, Mediated", *Science*, (1988) 242: 583-585.
Gless et al. *J. Org. Chem.*, 1979, 44 (8), pp. 1324-1336.
Greene et al., Protective Groups in Organic Synthesis, 2d. Ed., Wiley & Sons, 1991.
Grundy et al., "Diagnosis and Management of the Metabolic Syndrome", *Circulation, Journal of the American Heart Association*, 2005, 112; pp. 2735-2752.
Gu et al., "Discovery of 4-heteroarylbicyclo[2.2.2]octyltriazoles as potent and selective inhibitors of 11β-HSD1: Novel therapeutic agents for the treatment of metabolic syndrome,"*Bioorg. Med. Chem. Lett.*, 15:5266-5269 (2005).
Huber, R. "11βHSD1 Inhibitors for Type 2 Diabetes: A Systematic Development Strategy to Assess Pharmacodynamic Activity and Obtain Proof-of-Concept in Man," IBC's 5th Annual Targeting Metabolic Disorders Conference, Feb. 26-27, 2007.
Huber, R. "11βHSD1 Inhibition as an Entrée to Cardio-Metabolic Benefit in Type 2 Diabetes," presentation at Discovery on Target: Targeting Diabetes with Novel Therapeutics. Boston, MA, Oct. 22, 2008.
Huber, R. "Proof-of-Concept for 1 lbeta-HSD1 Inhibition in Man: Evidence for Metabolic Improvements in Type 2 Diabetic Subjects after Short-Term INCB013739 Therapy." Presentation at Targeting Metabolic Disorders, Chapel Hill, NC Mar. 18, 2008.
Huber, R. "INCB013739, a Selective Inhibitor of 11b-Hydroxysteroid Dehydrogenase Type 1 (11βHSD1), Improves Insulin Sensitivity and Lowers Plasma Cholesterol Over 28 Days in Patients with Type 2 Diabetes Mellitus." American Diabetes Association 68th Scientific Sessions, San Francisco, CA Jun. 9, 2008.
Huber, R. "Incyte 11βHSD1 Inhibitor Program In Type 2, Diabetes Mellitus." 2008 Therapeutic Area Partnerships Conference. Philadelphia, PA Nov. 4, 2008.
Huber et al., Efficacy and Safety of the 11-beta-HSD1 Inhibitor, INCB13739, Added to Metformin Therapy in Patients with Type 2 Diabetes. 44th Annual Meeting of the European Association for the Study of Diabetes, Vienna, Austria, Sep. 27-Oct. 2, 2009 (17 pgs.).
Hughes et al, "The Total Synthesis of (-)-Amathaspiramide F**," *Angew. Chem. Int. Ed.*, 2002, 41(23) 4556-4559.
Incyte Corporation, "Review of Phase IIb Results for INCB13739; 69th Scientific Sessions of the American Diabetes Association, Jun. 7, 2009." (21 pgs.) Slide Presentation presented at a Webcast and Conference Call Held on Jun. 7, 2009.
Incyte Corporation, "Results Presented at the ADA 69th Scientific Sessions Demonstrate that INCB13739, Incyte's Oral 11beta-HSD1 Inhibitor, Significantly Improves Glycemic Control, Insulin Sensitivity and Total Cholesterol in Patients with Type 2 Diabetes." (3 pgs.) Press Release Issued on Jun. 6, 2009.
Irikura, Tsutomu and Kasuga, Kazunori, "New Antiulcer Agents. Syntheases and biological Activities of 1-Acyl-2, -3-, and -4-Substituted Benzamidopiperidine", *Journal of Medicinal Chemistry*, 14 (4), pp. 357-361, 1971.
Jausons-Loffreda et al., "Chimeric Receptors as a Tool for Luminescent Measurement of Biological Activities of Steroid Hormones", *J. Biolumin and Chemilumin*, 1994, 9: 217-221.
Knochel et al., "Highly Functionalized Organomagnesium Reagents Prepared through Halogen-Metal Exchange", *Angew. Chem. Int. Ed.*, (2003) 42, 4302-4320.
"Known 2-iodomethylbenzoates" (from Office Action mailed Jul. 31, 2007) for U.S. Appl. No. 11/281,648.
Kotelevstev et al., "11β-Hydroxysteroid dehydrogenase type 1 knockout mice show attenuated glucocorticoid-inducible responses and resist hyperglycemia on obesity or stress", *Proc. Natl. Acad. Sci.*, (1997) 94: 14924-14929.
Kurukulasuriya et al., "Potential Drug Targets and Progress Towards Pharmacologic Inhibition of Hepatic Glucose Production", *Curr. Med. Chem.*, (2003) 10: 123-53.
Leonardi, A. et al., "Synthesis, Pharmacological Evaluation, and Structure—Activity Relationship and Qunatitative Structure—Activity Relationship Studies on Novel Derivatives of 2,4-Diamino-6,7-dimethoxyquinazoline alpha1-Adrenoceptor Antagonists" J. Med. Chem. 42(3):427-437 (1999).
Lewis et al. J.Chem. Soc. Perkin Trans. 2:Phy. Org. Chem. (1972-1999) (1991), vol, 10. pp. 1625-1630.
Li et al. Syntheses and SAR of piperidin-3-yl ureas as potent and selective 11β-HSD-1 inhibitors, MEDI 54 Abstract of Presentation at the 233RD ACS National Meeting, Chicago, IL, Mar. 25-29, 2007.
Li et al. Syntheses and SAR of Piperidin-3-yl Ureas as Potent and Selective 11β-HSD-1 inhibitors, Presentation at the 233rd ACS National Meeting, Chicago, IL, Mar. 25-29, 2007.
Li et al. Syntheses and SAR of piperidin-3-yl ureas as potent and selective 11β-HSD-1 inhibitors, MEDI 54 Abstract of Presentation at the 234th ACS National Meeting, Boston, MA Aug. 19-23, 2007.
Li et al. Syntheses and SAR of Piperidin-3-yl Ureas as Potent and Selective 11β-HSD-1 inhibitors, Presentation at the 234th ACS National Meeting, Boston, MA Aug. 19-23, 2007.
Lindsay et al., "Subcutaneous Adipose 11β-Hydroxysteroid Dehydrogenase Type 1 Activity and Messenger Ribonucleic Acid Levels are Associated with Adiposity and Insulinemia in Pima Indians and Caucasians", *J. Clin. Endocrinol. Metal.*, (2003) 88: 2738-2744.
Livingstone et al., "Understanding the Role of Glucocorticoids in Obesity: Tissue-Specific Alterations of Corticosterone Metabolism in Obese Zucker Rats", *Endocrinology*, (2000) 131: 560-563.
Louie, J. and Hartwig, J. F., "Palladium-Catalyzed Synthesis of Arylamines from Aryl Halides. Mechanistic Studies Lead to Coupling in the Absence of Tin Reagents", *Tetrahedron Lett.*, (1995) 36, 3609.
Low et al., "'Liver-type' 11β-hydroxysteroid dehydrogenase cDNA encodes reductase but not dehydrogenase activity in intact mammalian COS-7 cells", *J. Mol. Endocrin.*, (1994) 13: 167-174.
Lupien et al., "Cortisol levels during human aging predict hippocampal atrophy and memory deficits", *Nat. Neurosci.*, (1998) 1: 69-73.
Mallams, A.K. et al., "Inhibitors of Farnesyl Protein Transferase, 4-Amido, 4-Carbamoyl, and 4-Carboxamido Derivatives of 1-(8-Chloro-6,11-dihydro-5H-benzo[5,6]-cyclohepta[1,2-b]pyridin-11-yl)piperazine and 1-(3-Bromo-8-chloro-6,11-dihydro-5H-benzo[5,6]cyclohepta[1,2-b]pyridin-11-yl)piperazine" J. Med. Chem. 41(6):877-893 (1998).
Manthorpe et al., *Agnew. Chem. Int.*, vol. 41, No. 13, pp. 2338-2341, 2002.
Markees et al., J. Am. Chem. Soc. (1949), vol. 71, pp. 2031-2035.

Martin et al., "Do Structurally Similar Molecules Have Similar Biological Activity?", *J. Med. Chem.*, (2002) 45, 4350-4358.

Masuzaki et al., "A Transgenic Model of Visceral Obesity and the Metabolic Syndrome", *Science*, (2001) 294: 2166-2170.

Masuzaki et al., "Transgenic amplification of glucocorticoid action in adipose tissue causes high blood pressure in mice", *J. Clinical Invest.*, (2003) 112: 83-90.

Masuzaki et al., "Tissue-Specific Glucocorticoid Reactivating Enzyme, 11β-Hydroxysteroid Dehydrogenase Type 1 (11β-HSDI)—A Promising Drug Target for the Treatment of Metabolic Syndrome", *Curr. Drug Targets Immune Endocr. Metabol. Disord.*, (2003)3: 255-62.

Matsumoto et al., "Direkte Aminolyse von nicht aktivierten Estern bei hohm Druck," *Angew. Chem.* 98: 569-570 (1986) (translation provided).

Matsuzawa et al., "Molecular Mechanism of Metabolic Syndrome X: Contribution of Adipocytokines-Adipocyte-derived Bioactive Substances", (1999) *Ann. N.Y. Acad. Sci.* 892: 146-154.

McEwen and Sapolsky, "Stress and cognitive function", *Curr. Opin. Neurobiol.*, (1995) 5: 205-216.

Mehrotra et al., "Discovery of Novel 2,8-Diazaspiro[4,5]decanes as orally Active Glycoprotein IIb-IIIa Antagonist", J. Med. Chem.., 47,, pp. 2037-2061, 2004.

Messinger et al. "New inhibitors of 17b-hydroxysteroid dehydrogenase type 1," Mol. Cell. Endocrin. (2006), 248, 192-198.

Miller and Chrousos (2001) Endocrinology and Metabolism, eds. Felig and Frohman (McGraw-Hill, New York), 4th Ed.: 387-524.

Mirzoeva et al., *J. Med. Chem.*, 2002, 45 (3), pp. 563-566.

Mishani et al., "Formation of Phenylpiperazines by a Novel Alumina Supported Bis-Alkylation.", *Tetrahedron Lett.* (1996) 37, 319.

Moeller et al., "Anodic Amide Oxidations in the Presence of Electron-Rich Phenyl Rings: Evidence for an Intramolecular Electron-Transfer Mechanism" J. Org. Chem., 1991, vol. 56(3):1058-1067 (1991).

Morris et al., "Amathaspiramides A-F, Novel Brominated Alkaloids from the Marine Bryozoan," *J. Nat. Prod*, 1999, 62, 688-693.

Moya et al., "Synthesis and Biological Evaluation of New Analogies of the Active Fungal Metabolites N-(2-Methyl-3-oxodecanoyl)-2-pyrroline and N-(2-Methyl-3-oxodec-8-enoyl)-2-pyrroline,"*J. Agric. Food Chem.*, 47: 3866-3871 (1999).

Morton et al., "Improved Lipid and Lipoprotein Profile, Hepatic Insulin Sensitivity, and Glucose Tolerance in 11β-Hydroxysteroid Dehydrogenase Type 1 Null Mice", *J. Biol. Chem.*, (2001) 276: 41293-41300.

Morton et al., "Novel Adipose Tissue—Mediated Resistance to Diet-Induced Visceral Obesity in 11β-Hydroxysteroid Dehydrogenase Type 1—Deficient Mice", *Diabetes*, (2004) 53: 931-938.

Nojima et al., "Spiro Compounds Formation by the Reaction of Cycloalkene with Friedel-Crafts Catalyst. I. Reaction of Cyclohexene with Aluminum Chloride. The Rearrangement of Cyclohexylcyclohexene", *Journal of Organic Chemistry*, 31 (12), pp. 3966-3969, 1966.

Ogawa et al., "Roses of Insulin Resistance and β-Cell Dysfunction in Dexamethasone-induced Diabetes", *J. Clin. Invest.*, (1992) 90: 497-504.

Ogura et al., "[1,4] Addition of (Methylthio *p*-Tolyl Sulfone to α,β-Unaturated Carbonyl Compounds", *Journal of Organic Chemistry*, 51, pp. 508-512, 1986.

Pitt et al., "The Effect of Spironolactone on Morbidity and Mortality in Patients with Severe Heart Failure", *New England J. Med.*, (1999) 341: 709-719.

Pitt et al., "Eplerenone, a Selective Aldosterone Blocker, in Patients with Left Ventricular Dysfunction after Myocardial Infarction", *New England J. Med.*, (2003) 348: 1309-1321.

Poirier et al., "Inhibitors of type II 17βP-hydroxysteroid dehydrogenase", *Mol. Cell. Endocrin.*, (2001) 171, 119-128.

Rajan et al. "11β-Hydroxysteroid Dehydrogenase in Cultured Hippocampal Cells Reactivates Inert 11-Dehydrocorticosterone, Potentiating Neurotoxicity", *J. Neurosci.*, (1996) 16: 65-70.

Rask et al. "Tissue-specific dysregulation of cortisol metabolism in human obesity", *J. Clin. Endocrinol. Metab.*, (2001) 86: 1418-1421.

Rauz et al., "Expression and Putative Role of 11β-Hydroxysteroid Dehydrogenase Isozymes within the Human Eye", *Invest. Ophthahnol. Vis. Sci.*, (2001) 42: 2037-2042.

Reaven, G., "Role of Insulin Resistance in Human Disease (Syndrome X): An Expanded Definition", *Ann. Rev. Med.*, (1993) 44: 121-131.

Remington's Pharmaceutical Sciences, 17th ed., Mack Publishing Company, Easton, Pa., 1985, p. 1418.

RN 147635-61-8 structure, abstract, and patent family details (3 pages), 1993.

RN 113288-90-7 structure, abstract, and patent family details (3 pages), 1988.

Rosenstock et al., "Efficacy and Safety of the 11-beta-HSD1 Inhibitor, INCB13739, Added to Metformin Therapy in Patients with Type 2 Diabetes", 69th *Scientific Sessions of the American Diabetes Association*, New Orleans, LA, Jun. 5-9, 2009.

Rosenstock et al., "The 11-Beta-Hydroxysteroid Dehydrogenase Type 1 Inhibitor INCB13739 Improves Hyperglycemia in Patients with Type 2 Diabetes Inadequately Controlled by Metformin Monotherapy", American Diabetes Association, *Diabetes Care*, published online Apr. 22, 2010 (14 pgs.).

Schelsinger et al., "N-Substituted-Amides," *J. Am. Chem. Soc.*, 78: 6123-6127 (1956).

Süess, R., "Regiospecific reduction of 1,3,3-trisubstituted succinimides by diborane", *Helvetica Chimica Acta*, vol. 60(5), 1977-Nr.165 (translation provided), 1650-1656.

Stokes et al., "Distribution of Glucocorticoid and Mineralocorticoid Receptors and 11β-Hydroxysteroid Dehydrogenases in Human and Rat Ocular Tissues", *Invest. Ophthalmol. Vis. Sci.*, (2000) 41: 1629-1683.

T. Higuchi and V. Stella, "Pro-drugs as Novel Delivery Systems," vol. 14 of the A.C.S. Symposium Series, and in Bioreversible Carriers in Drug Design, ed. Edward B. Roche, American Pharmaceutical Association and Pergamon Press, 1987.

Wang et al., "Amino-substituted heterocycles as isosteres of *trans*-cinnamides: design and synthesis of heterocyclic biaryl sulfides as potent antagonists of LFA-1/ICAM-1 binding", *Biorg. & Med. Chem. Lett.*, (2005) 15, 195.

Wajchenberg, B., "Subcutaneous and Visceral Adipose Tissue: Their Relation to the Metabolic Syndrome", *Endocr. Rev.*, (2000) 21: 697-738.

Wake et al., "Local and systemic Impact of Transcriptional Up-Regulation of 11β-Hydroxysteroid Dehydrogenase Type 1 in Adipose Tissue in Human Obesity", *J. Clin. Endocrinol. Metab.*, (2003) 88: 3983-3988.

Walker et al., "Relation Between Blood Pressure and Renin, Renin Substrate, Angiotensin II, Aldosterone and Urinary Sodium and Potassium in 574 Ambulatory Subjects", *Hypertension*, (1979) 1: 287-291.

Wilson et al., "A genetic defect resulting in mild low-renin hypertension", *Proc. Natl. Acad Sci.*, (1998) 95: 10200-10205.

Wheatley et al., "Basic Ethers Derived from β-Hydroxyphenethylamines," *J. Org. Chem.*, 23: 1360-1363 (1958).

Wolff, M.E. Burger's Medicinal Chemistry, 5th ed., Part I, John Wiley & Sons, 1995, pp. 975-977.

Xu, et al., "Synthesis of Aza/Oxaspiro-γ-lactams by Radical Translocation Cyclization Reastions," Synlett 2005, 12, 1865-1868.

Yao, W. et al. Discovery of potent and selective 11β-HSD-1 Inhibitors, MEDI 228 Abstract of Presentation at the 233rd ACS National Meeting, Chicago, IL, Mar. 25-29, 2007.

Yao, W. Discovery of Potent and Orally Active Inhibitors of 11β-Hydroxysteroid Dehydrogenase I, presentation at the 233rd ACS National Meeting, Chicago, IL, Mar. 27, 2007.

Yau et al., "Lack of tissue glucocorticoid reactivation in 11β-hydroxysteroid dehydrogenase type 1 knockout mice ameliorates age-related learning impairments", *Proc. Natl. Acad. Sci.*, (2001) 98: 4716-4721.

Yeh et al., "Discovery of orally active butyrolactam 11β-HSD1 inhibitors," *Bioorg. Med. Chem. Lett.*, 16:5555-5560 (2006).

Yeh et al., "Synthesis and biological evaluation of heterocycle containing adamantine 11β-HSD1 inhibitors," *Bioorg. Med. Chem. Lett.*, 16:5414-5419 (2006).

Yokoyama et al., "The First Effective Syntheses of Cyanoflurormethylated Amides, Thioamides, and Phosphorus Compunds Using 2-Cyano-2-fluoro-2-phenylacetonitrile and $ET_3GeNa$," *Synthesis*, 8: 1319-1324 (1999).

Zhuo, J. et al. Discovery and synthesis of nipecotic amide as novel, potent and selective 11β-HSD-1-inhibitors MEDI 48 Abstract, 233rd ACS National Meeting, Chicago, IL, Mar. 25-29, 2007.

Zhuo J. et al. Discovery of Nipecotic Amides as Novel, Potent and Selective 11βHSD1 Inhibitors, poster at the 233rd ACS National Meeting, Chicago, IL, Mar. 25-29, 2007.

Amendment and Response in Reply to Office Action of Mar. 29, 2007 submitted Jun. 28, 2007 for U.S. Appl. No. 11/281,648.

Amendment in Reply to Action of Jul. 31, 2007 submitted Oct. 30, 2007 in connection with U.S. Appl. No. 11/281,648.

Examination Report (New Zealand Patent Office) dated Mar. 3, 2009 for New Zealand Patent Application. No. 550775 (2 pgs.).

International Preliminary Report on Patentability (Chapter I) for International Appln. No. PCT/US05/15559.

International Preliminary Report on Patentability (Chapter I) for International Appln. No. PCT/US05/041763.

International Search Report for International Appln. No. PCT/US2007/063050, dated Jun. 20, 2007.

International Search Report for International Appln. No. PCT/US2007/063055 dated Oct. 8, 2007.

International Search Report for International Appln. No. PCT/US05/22308 dated Dec. 2, 2005.

International Search Report for International Appln. No. PCT/US06/036652 dated Mar. 8, 2007.

International Search Report for International Appln. No. PCT/US05/22411 dated Sep. 23, 2005.

International Search Report for International Appln. No. PCT/US05/22307 dated Apr. 25, 2006.

International Search Report for International Appln. No. PCT/US05/22170 dated Sep. 28, 2005.

International Search Report for International Appln. No. PCT/US05/22434 dated Dec. 16, 2005.

International Search Report for International Appln. No. PCT/US05/28201 dated Oct. 10, 2006.

International Search Report for International Appln. No. PCT/US05/40550 dated Mar. 26, 2007.

International Search Report and International Preliminary Report on Patentability for International Appln. No. PCT/US05/41763 dated Dec. 22, 2006.

International Search Report for International Appln. No. PCT/US2006/036652 dated Mar. 8, 2007.

International Search Report for International Appln. No. PCT/US2006/046306 dated Aug. 28, 2007.

International Search Report for International Appln. No. PCT/US2007/002360 dated Jun. 6, 2007.

International Search Report for International Appln. No. PCDUS2007/000695 dated Jan. 22, 2008.

International Search Report for International Appln. No. PCT/US2007/069033 dated Apr. 28, 2008.

International Search Report for International Appln. No. PCT/US2007/067753 dated Feb. 10, 2007.

International Search Report for International Appln. No. PCT/US2007/063055 dated Oct. 22, 2007.

International Search Report for International Appln. No. PCT/US2007/063050 dated Jul. 9, 2007.

International Search Report for International Appln. No. PCT/US2006/046309 dated Sep. 7, 2007.

International Search Report for International Appln. No. PCT/US05/15559 dated Jul. 22, 2005.

Letter (from Yitzak Hess and Partners) dated Apr. 26, 2010 regarding Israeli Patent Application No. 179,042 (4 pgs.).

Office Action (non-final) mailed Mar. 29, 2007 for U.S. Appl. No. 11/281,648.

Office Action (final) mailed Dec. 13, 2007 for U.S. Appl. No. 11/281,648.

Office Action (non-final) mailed Apr. 14, 2008 for U.S. Appl. No. 11/159,865.

Office Action (non-final) mailed May 6, 2008 for U.S. Appl. No. 11/159,862.

Office Action (non-final) mailed Mar. 24, 2008 for U.S. Appl. No. 11/159,724.

Office Action (non-final) mailed Mar. 4, 2008 for U.S. Appl. No. 11/199,763.

Office Action (U.S. Patent and Trademark Office) dated May 6, 2008 for U.S. Appl. No. 11/159,862 (US20050288338A1) (9 pgs.).

Office Action (non-final) mailed Jul. 31, 2007 for U.S. Appl. No. 11/281,648.

Office Action (U.S. Patent and Trademark Office) dated Sep. 4, 2009 for U.S. Appl. No. 11/159,724 (US20060009471A1) (11 pgs.).

Office Action (U.S. Patent and Trademark Office), dated Aug. 19, 2009 for U.S. Appl. No. 11/159,488 (US20060009491A1) (12 pgs.).

Opposition filed by Lineth Magally Fallas Cordero on behalf of Asociación de la Industria Farmacéutica Nacional (ASIFAN) for Costa Rican Patent Application. No. 8702 dated Apr. 13, 2009, with English translation (17 pgs.).

Supplementary Partial European Search Report dated Feb. 11, 2009 for EP Appln. No. 05745656.8.

Written Opinion and Search Report (issued by the Australian Patent Office) for Singaporean Patent Appln. No. SG 2006 07426-4 dated Dec. 14, 2007 (9 pgs.).

Written Opinion of the International Searching Authority mailed Apr. 24, 2007 for International Appln. No. PCT/US05/15559.

Examiner's First Report dated Aug. 9, 2010 for Australian Appln. No. 2005243222, 4 pgs.

First Office Action dated Jun. 30, 2010 for Indian Appln. No. Indian Appln. No. 3130/KOLNP/2006, 2 pgs.

Office Action and Search Report dated Oct. 2, 2010 for Taiwanese Appln. No. 094113962 8 pgs.

Leyendecker, Use of (2S, 4R)-hydroxyproline derivatives as ligands in chiral copper(I) complexes, Tetrahedron Letters, 1983, vol. 24, No. 33, pp. 3517-3520.

Japanese Patent Office, Official Action for Japanese Patent Application No. 2007-511571, dated Aug. 23, 2011, 5 pages.

* cited by examiner

AMIDO COMPOUNDS AND THEIR USE AS PHARMACEUTICALS

CROSS REFERENCE TO RELATED APPLICATIONS

This application is a continuation of Ser. No. 12/136,529, filed Jun. 10, 2008, now U.S. Pat. No. 7,776,874 which is a continuation of U.S. Ser. No. 11/784,450, filed Apr. 6, 2007, now abandoned which is a divisional of U.S. Ser. No. 11/122,309, filed May 4, 2005, now U.S. Pat. No. 7,304,081 which claims the benefit of U.S. Ser. Nos. 60/569,273, filed May 7, 2004; 60/602,051, filed Aug. 17, 2004; 60/602,791, filed Aug. 19, 2004; and 60/638,803, filed Dec. 22, 2004, the disclosures of each of which are incorporated herein by reference in their entireties.

FIELD OF THE INVENTION

The present invention relates to modulators of 11-β hydroxyl steroid dehydrogenase type 1 (11βHSD1) and/or mineralocorticoid receptor (MR), compositions thereof and methods of using the same.

BACKGROUND OF THE INVENTION

Glucocorticoids are steroid hormones that regulate fat metabolism, function and distribution. In vertebrates, glucocorticoids also have profound and diverse physiological effects on development, neurobiology, inflammation, blood pressure, metabolism and programmed cell death. In humans, the primary endogenously-produced glucocorticoid is cortisol. Cortisol is synthesized in the zona fasciculate of the adrenal cortex under the control of a short-term neuroendocrine feedback circuit called the hypothalamic-pituitary-adrenal (HPA) axis. Adrenal production of cortisol proceeds under the control of adrenocorticotrophic hormone (ACTH), a factor produced and secreted by the anterior pituitary. Production of ACTH in the anterior pituitary is itself highly regulated, driven by corticotropin releasing hormone (CRH) produced by the paraventricular nucleus of the hypothalamus. The HPA axis maintains circulating cortisol concentrations within restricted limits, with forward drive at the diurnal maximum or during periods of stress, and is rapidly attenuated by a negative feedback loop resulting from the ability of cortisol to suppress ACTH production in the anterior pituitary and CRH production in the hypothalamus.

Aldosterone is another hormone produced by the adrenal cortex; aldosterone regulates sodium and potassium homeostasis. Fifty years ago, a role for aldosterone excess in human disease was reported in a description of the syndrome of primary aldosteronism (Conn, (1955), J. Lab. Clin. Med. 45: 6-17). It is now clear that elevated levels of aldosterone are associated with deleterious effects on the heart and kidneys, and are a major contributing factor to morbidity and mortality in both heart failure and hypertension.

Two members of the nuclear hormone receptor superfamily, glucocorticoid receptor (GR) and mineralocorticoid receptor (MR), mediate cortisol function in vivo, while the primary intracellular receptor for aldosterone is the MR. These receptors are also referred to as 'ligand-dependent transcription factors,' because their functionality is dependent on the receptor being bound to its ligand (for example, cortisol); upon ligand-binding these receptors directly modulate transcription via DNA-binding zinc finger domains and transcriptional activation domains.

Historically, the major determinants of glucocorticoid action were attributed to three primary factors: 1) circulating levels of glucocorticoid (driven primarily by the HPA axis), 2) protein binding of glucocorticoids in circulation, and 3) intracellular receptor density inside target tissues. Recently, a fourth determinant of glucocorticoid function was identified: tissue-specific pre-receptor metabolism by glucocorticoid-activating and -inactivating enzymes. These 11-beta-hydroxysteroid dehydrogenase (11-β-HSD) enzymes act as pre-receptor control enzymes that modulate activation of the GR and MR by regulation of glucocorticoid hormones. To date, two distinct isozymes of 11-beta-HSD have been cloned and characterized: 11βHSD1 (also known as 11-beta-HSD type 1, 11betaHSD1, HSD11B1, HDL, and HSD11L) and 11βHSD2. 11βHSD1 and 11βHSD2 catalyze the interconversion of hormonally active cortisol (corticosterone in rodents) and inactive cortisone (11-dehydrocorticosterone in rodents). 11βHSD1 is widely distributed in rat and human tissues; expression of the enzyme and corresponding mRNA have been detected in lung, testis, and most abundantly in liver and adipose tissue. 11βHSD1 catalyzes both 11-beta-dehydrogenation and the reverse 11-oxoreduction reaction, although 11βHSD1 acts predominantly as a NADPH-dependent oxoreductase in intact cells and tissues, catalyzing the activation of cortisol from inert cortisone (Low et al. (1994) J. Mol. Endocrin. 13: 167-174) and has been reported to regulate glucocorticoid access to the GR. Conversely, 11βHSD2 expression is found mainly in mineralocorticoid target tissues such as kidney, placenta, colon and salivary gland, acts as an NAD-dependent dehydrogenase catalyzing the inactivation of cortisol to cortisone (Albiston et al. (1994) Mol. Cell. Endocrin. 105: R11-R17), and has been found to protect the MR from glucocorticoid excess, such as high levels of receptor-active cortisol (Blum, et al., (2003) Prog. Nucl. Acid Res. Mol. Biol. 75:173-216).

In vitro, the MR binds cortisol and aldosterone with equal affinity. The tissue specificity of aldosterone activity, however, is conferred by the expression of 11βHSD2 (Funder et al. (1988), Science 242: 583-585). The inactivation of cortisol to cortisone by 11βHSD2 at the site of the MR enables aldosterone to bind to this receptor in vivo. The binding of aldosterone to the MR results in dissociation of the ligand-activated MR from a multiprotein complex containing chaperone proteins, translocation of the MR into the nucleus, and its binding to hormone response elements in regulatory regions of target gene promoters. Within the distal nephron of the kidney, induction of serum and glucocorticoid inducible kinase-1 (sgk-1) expression leads to the absorption of $Na^+$ ions and water through the epithelial sodium channel, as well as potassium excretion with subsequent volume expansion and hypertension (Bhargava et al., (2001), Endo 142: 1587-1594).

In humans, elevated aldosterone concentrations are associated with endothelial dysfunction, myocardial infarction, left ventricular atrophy, and death. In attempts to modulate these ill effects, multiple intervention strategies have been adopted to control aldosterone overactivity and attenuate the resultant hypertension and its associated cardiovascular consequences. Inhibition of angiotensin-converting enzyme (ACE) and blockade of the angiotensin type 1 receptor (AT1R) are two strategies that directly impact the rennin-angiotensin-aldosterone system (RAAS). However, although ACE inhibition and AT1R antagonism initially reduce aldosterone concentrations, circulating concentrations of this hormone return to baseline levels with chronic therapy (known as 'aldosterone escape'). Importantly, co-administration of the MR antagonist Spironolactone or Eplerenone directly blocks the deleterious effects of this escape mechanism and dramatically reduces patient mortality (Pitt et al., New England J. Med. (1999), 341: 709-719; Pitt et al., New England J. Med. (2003), 348: 1309-1321). Therefore, MR antagonism may be an important treatment strategy for many patients with hypertension and cardiovascular disease, particularly those hypertensive patients at risk for target-organ damage.

Mutations in either of the genes encoding the 11-beta-HSD enzymes are associated with human pathology. For example, 11βHSD2 is expressed in aldosterone-sensitive tissues such as the distal nephron, salivary gland, and colonic mucosa where its cortisol dehydrogenase activity serves to protect the intrinsically non-selective MR from illicit occupation by cortisol (Edwards et al. (1988) Lancet 2: 986-989). Individuals with mutations in 11βHSD2 are deficient in this cortisol-inactivation activity and, as a result, present with a syndrome of apparent mineralocorticoid excess (also referred to as 'SAME') characterized by hypertension, hypokalemia, and sodium retention (Wilson et al. (1998) Proc. Natl. Acad. Sci. 95: 10200-10205). Likewise, mutations in 11βHSD1, a primary regulator of tissue-specific glucocorticoid bioavailability, and in the gene encoding a co-localized NADPH-generating enzyme, hexose 6-phosphate dehydrogenase (H6PD), can result in cortisone reductase deficiency (CRD), in which activation of cortisone to cortisol does not occur, resulting in adrenocorticotropin-mediated androgen excess. CRD patients excrete virtually all glucocorticoids as cortisone metabolites (tetrahydrocortisone) with low or absent cortisol metabolites (tetrahydrocortisols). When challenged with oral cortisone, CRD patients exhibit abnormally low plasma cortisol concentrations. These individuals present with ACTH-mediated androgen excess (hirsutism, menstrual irregularity, hyperandrogenism), a phenotype resembling polycystic ovary syndrome (PCOS) (Draper et al. (2003) Nat. Genet. 34: 434-439).

The importance of the HPA axis in controlling glucocorticoid excursions is evident from the fact that disruption of homeostasis in the HPA axis by either excess or deficient secretion or action results in Cushing's syndrome or Addison's disease, respectively (Miller and Chrousos (2001) Endocrinology and Metabolism, eds. Felig and Frohman (McGraw-Hill, New York), 4$^{th}$ Ed.: 387-524). Patients with Cushing's syndrome (a rare disease characterized by systemic glucocorticoid excess originating from the adrenal or pituitary tumors) or receiving glucocorticoid therapy develop reversible visceral fat obesity. Interestingly, the phenotype of Cushing's syndrome patients closely resembles that of Reaven's metabolic syndrome (also known as Syndrome X or insulin resistance syndrome) the symptoms of which include visceral obesity, glucose intolerance, insulin resistance, hypertension, type 2 diabetes and hyperlipidemia (Reaven (1993) Ann. Rev. Med. 44: 121-131). However, the role of glucocorticoids in prevalent forms of human obesity has remained obscure because circulating glucocorticoid concentrations are not elevated in the majority of metabolic syndrome patients. In fact, glucocorticoid action on target tissue depends not only on circulating levels but also on intracellular concentration, locally enhanced action of glucocorticoids in adipose tissue and skeletal muscle has been demonstrated in metabolic syndrome. Evidence has accumulated that enzyme activity of 11βHSD1, which regenerates active glucocorticoids from inactive forms and plays a central role in regulating intracellular glucocorticoid concentration, is commonly elevated in fat depots from obese individuals. This suggests a role for local glucocorticoid reactivation in obesity and metabolic syndrome.

Given the ability of 11βHSD1 to regenerate cortisol from inert circulating cortisone, considerable attention has been given to its role in the amplification of glucocorticoid function. 11βHSD1 is expressed in many key GR-rich tissues, including tissues of considerable metabolic importance such as liver, adipose, and skeletal muscle, and, as such, has been postulated to aid in the tissue-specific potentiation of glucocorticoid-mediated antagonism of insulin function. Considering a) the phenotypic similarity between glucocorticoid excess (Cushing's syndrome) and the metabolic syndrome with normal circulating glucocorticoids in the latter, as well as b) the ability of 11βHSD1 to generate active cortisol from inactive cortisone in a tissue-specific manner, it has been suggested that central obesity and the associated metabolic complications in syndrome X result from increased activity of 11βHSD1 within adipose tissue, resulting in 'Cushing's disease of the omentum' (Bujalska et al. (1997) Lancet 349: 1210-1213). Indeed, 11βHSD1 has been shown to be upregulated in adipose tissue of obese rodents and humans (Livingstone et al. (2000) Endocrinology 131: 560-563; Rask et al. (2001) J. Clin. Endocrinol. Metab. 86: 1418-1421; Lindsay et al. (2003) J. Clin. Endocrinol. Metab. 88: 2738-2744; Wake et al. (2003) J. Clin. Endocrinol. Metab. 88: 3983-3988).

Additional support for this notion has come from studies in mouse transgenic models. Adipose-specific overexpression of 11βHSD1 under the control of the aP2 promoter in mouse produces a phenotype remarkably reminiscent of human metabolic syndrome (Masuzaki et al. (2001) Science 294: 2166-2170; Masuzaki et al. (2003) J. Clinical Invest. 112: 83-90). Importantly, this phenotype occurs without an increase in total circulating corticosterone, but rather is driven by a local production of corticosterone within the adipose depots. The increased activity of 11βHSD1 in these mice (2-3 fold) is very similar to that observed in human obesity (Rask et al. (2001) J. Clin. Endocrinol. Metab. 86: 1418-1421). This suggests that local 11βHSD1-mediated conversion of inert glucocorticoid to active glucocorticoid can have profound influences whole body insulin sensitivity.

Based on this data, it would be predicted that the loss of 11βHSD1 would lead to an increase in insulin sensitivity and glucose tolerance due to a tissue-specific deficiency in active glucocorticoid levels. This is, in fact, the case as shown in studies with 11βHSD1-deficient mice produced by homologous recombination (Kotelevstev et al. (1997) Proc. Natl. Acad. Sci. 94: 14924-14929; Morton et al. (2001) J. Biol. Chem. 276: 41293-41300; Morton et al. (2004) Diabetes 53: 931-938). These mice are completely devoid of 11-keto reductase activity, confirming that 11βHSD1 encodes the only activity capable of generating active corticosterone from inert 11-dehydrocorticosterone. 11βHSD1-deficient mice are resistant to diet- and stress-induced hyperglycemia, exhibit attenuated induction of hepatic gluconeogenic enzymes (PEPCK, G6P), show increased insulin sensitivity within adipose, and have an improved lipid profile (decreased triglycerides and increased cardio-protective HDL). Additionally, these animals show resistance to high fat diet-induced obesity. Taken together, these transgenic mouse studies confirm a role for local reactivation of glucocorticoids in controlling hepatic and peripheral insulin sensitivity, and suggest that inhibition of 11βHSD1 activity may prove beneficial in treating a number of glucocorticoid-related disorders, including obesity, insulin resistance, hyperglycemia, and hyperlipidemia.

Data in support of this hypothesis has been published. Recently, it was reported that 11βHSD1 plays a role in the pathogenesis of central obesity and the appearance of the metabolic syndrome in humans. Increased expression of the 11βHSD1 gene is associated with metabolic abnormalities in obese women and that increased expression of this gene is suspected to contribute to the increased local conversion of cortisone to cortisol in adipose tissue of obese individuals (Engeli, et al., (2004) Obes. Res. 12: 9-17).

A new class of 11βHSD1 inhibitors, the arylsulfonamidothiazoles, was shown to improve hepatic insulin sensitivity and reduce blood glucose levels in hyperglycemic strains of mice (Barf et al. (2002) J. Med. Chem. 45: 3813-3815; Alberts et al. Endocrinology (2003) 144: 4755-4762). Furthermore, it was recently reported that selective inhibitors of 11βHSD1 can ameliorate severe hyperglycemia in genetically diabetic obese mice. Thus, 11βHSD1 is a promising pharmaceutical target for the treatment of the Metabolic Syndrome (Masuzaki, et al., (2003) Curr. Drug Targets Immune Endocr. Metabol. Disord. 3: 255-62).

A. Obesity and Metabolic Syndrome

As described above, multiple lines of evidence suggest that inhibition of 11βHSD1 activity can be effective in combating obesity and/or aspects of the metabolic syndrome cluster, including glucose intolerance, insulin resistance, hyperglycemia, hypertension, and/or hyperlipidemia. Glucocorticoids are known antagonists of insulin action, and reductions in local glucocorticoid levels by inhibition of intracellular cortisone to cortisol conversion should increase hepatic and/or peripheral insulin sensitivity and potentially reduce visceral adiposity. As described above, 11βHSD1 knockout mice are resistant to hyperglycemia, exhibit attenuated induction of key hepatic gluconeogenic enzymes, show markedly increased insulin sensitivity within adipose, and have an improved lipid profile. Additionally, these animals show resistance to high fat diet-induced obesity (Kotelevstev et al. (1997) Proc. Natl. Acad. Sci. 94: 14924-14929; Morton et al. (2001) J. Biol. Chem. 276: 41293-41300; Morton et al. (2004) Diabetes 53: 931-938). Thus, inhibition of 11βHSD1 is predicted to have multiple beneficial effects in the liver, adipose, and/or skeletal muscle, particularly related to alleviation of component(s) of the metabolic syndrome and/or obesity.

B. Pancreatic Function

Glucocorticoids are known to inhibit the glucose-stimulated secretion of insulin from pancreatic beta-cells (Billaudel and Sutter (1979) Horm. Metab. Res. 11: 555-560). In both Cushing's syndrome and diabetic Zucker fa/fa rats, glucose-stimulated insulin secretion is markedly reduced (Ogawa et al. (1992) J. Clin. Invest. 90: 497-504). 11βHSD1 mRNA and activity has been reported in the pancreatic islet cells of ob/ob mice and inhibition of this activity with carbenoxolone, an 11βHSD1 inhibitor, improves glucose-stimulated insulin release (Davani et al. (2000) J. Biol. Chem. 275: 34841-34844). Thus, inhibition of 11βHSD1 is predicted to have beneficial effects on the pancreas, including the enhancement of glucose-stimulated insulin release.

C. Cognition and Dementia

Mild cognitive impairment is a common feature of aging that may be ultimately related to the progression of dementia. In both aged animals and humans, inter-individual differences in general cognitive function have been linked to variability in the long-term exposure to glucocorticoids (Lupien et al. (1998) Nat. Neurosci. 1: 69-73). Further, dysregulation of the HPA axis resulting in chronic exposure to glucocorticoid excess in certain brain subregions has been proposed to contribute to the decline of cognitive function (McEwen and Sapolsky (1995) Curr. Opin. Neurobiol. 5: 205-216). 11βHSD1 is abundant in the brain, and is expressed in multiple subregions including the hippocampus, frontal cortex, and cerebellum (Sandeep et al. (2004) Proc. Natl. Acad. Sci. Early Edition: 1-6). Treatment of primary hippocampal cells with the 11βHSD1 inhibitor carbenoxolone protects the cells from glucocorticoid-mediated exacerbation of excitatory amino acid neurotoxicity (Rajan et al. (1996) J. Neurosci. 16: 65-70). Additionally, 11βHSD1-deficient mice are protected from glucocorticoid-associated hippocampal dysfunction that is associated with aging (Yau et al. (2001) Proc. Natl. Acad. Sci. 98: 4716-4721). In two randomized, double-blind, placebo-controlled crossover studies, administration of carbenoxolone improved verbal fluency and verbal memory (Sandeep et al. (2004) Proc. Natl. Acad. Sci. Early Edition: 1-6). Thus, inhibition of 11βHSD1 is predicted to reduce exposure to glucocorticoids in the brain and protect against deleterious glucocorticoid effects on neuronal function, including cognitive impairment, dementia, and/or depression.

D. Intra-Ocular Pressure

Glucocorticoids can be used topically and systemically for a wide range of conditions in clinical ophthalmology. One particular complication with these treatment regimens is corticosteroid-induced glaucoma. This pathology is characterized by a significant increase in intra-ocular pressure (IOP). In its most advanced and untreated form, IOP can lead to partial visual field loss and eventually blindness. IOP is produced by the relationship between aqueous humour production and drainage. Aqueous humour production occurs in the non-pigmented epithelial cells (NPE) and its drainage is through the cells of the trabecular meshwork. 11βHSD1 has been localized to NPE cells (Stokes at al. (2000) Invest. Ophthalmol. Vis. Sci. 41: 1629-1683; Rauz et al. (2001) Invest. Ophthalmol. Vis. Sci. 42: 2037-2042) and its function is likely relevant to the amplification of glucocorticoid activity within these cells. This notion has been confirmed by the observation that free cortisol concentration greatly exceeds that of cortisone in the aqueous humour (14:1 ratio). The functional significance of 11βHSD1 in the eye has been evaluated using the inhibitor carbenoxolone in healthy volunteers (Rauz et al. (2001) Invest. Ophthalmol. Vis. Sci. 42: 2037-2042). After seven days of carbenoxolone treatment, IOP was reduced by 18%. Thus, inhibition of 11βHSD1 in the eye is predicted to reduce local glucocorticoid concentrations and IOP, producing beneficial effects in the management of glaucoma and other visual disorders.

E. Hypertension

Adipocyte-derived hypertensive substances such as leptin and angiotensinogen have been proposed to be involved in the pathogenesis of obesity-related hypertension (Matsuzawa et al. (1999) Ann. N.Y. Acad. Sci. 892: 146-154; Wajchenberg (2000) Endocr. Rev. 21: 697-738). Leptin, which is secreted in excess in aP2-11βHSD1 transgenic mice (Masuzaki et al. (2003) J. Clinical Invest. 112: 83-90), can activate various sympathetic nervous system pathways, including those that regulate blood pressure (Matsuzawa et al. (1999) Ann. N.Y. Acad. Sci. 892: 146-154). Additionally, the renin-angiotensin system (RAS) has been shown to be a major determinant of blood pressure (Walker et al. (1979) Hypertension 1: 287-291). Angiotensinogen, which is produced in liver and adipose tissue, is the key substrate for renin and drives RAS activation. Plasma angiotensinogen levels are markedly elevated in aP2-11βHSD1 transgenic mice, as are angiotensin II and aldosterone (Masuzaki et al. (2003) J. Clinical Invest. 112: 83-90). These forces likely drive the elevated blood pressure observed in aP2-11βHSD1 transgenic mice. Treatment of these mice with low doses of an angiotensin II receptor antagonist abolishes this hypertension (Masuzaki et al. (2003) J. Clinical Invest. 112: 83-90). This data illustrates the importance of local glucocorticoid reactivation in adipose tissue and liver, and suggests that hypertension may be caused or exacerbated by 11βHSD1 activity. Thus, inhibition of 11βHSD1 and reduction in adipose and/or hepatic glucocorticoid levels is predicted to have beneficial effects on hypertension and hypertension-related cardiovascular disorders.

F. Bone Disease

Glucocorticoids can have adverse effects on skeletal tissues. Continued exposure to even moderate glucocorticoid doses can result in osteoporosis (Cannalis (1996) J. Clin. Endocrinol. Metab. 81: 3441-3447) and increased risk for fractures. Experiments in vitro confirm the deleterious effects of glucocorticoids on both bone-resorbing cells (also known as osteoclasts) and bone forming cells (osteoblasts). 11βHSD1 has been shown to be present in cultures of human primary osteoblasts as well as cells from adult bone, likely a mixture of osteoclasts and osteoblasts (Cooper et al. (2000) Bone 27: 375-381), and the 11βHSD1 inhibitor carbenoxolone has been shown to attenuate the negative effects of glucocorticoids on bone nodule formation (Bellows et al. (1998) Bone 23: 119-125). Thus, inhibition of 11βHSD1 is predicted to decrease the local glucocorticoid concentration within osteoblasts and osteoclasts, producing beneficial effects in various forms of bone disease, including osteoporosis.

Small molecule inhibitors of 11βHSD1 are currently being developed to treat or prevent 11βHSD1-related diseases such as those described above. For example, certain amide-based inhibitors are reported in WO 2004/089470, WO 2004/089896, WO 2004/056745, and WO 2004/065351.

Antagonists of 11βHSD1 have been evaluated in human clinical trials (Kurukulasuriya, et al., (2003) Curr. Med. Chem. 10: 123-53).

In light of the experimental data indicating a role for 11βHSD1 in glucocorticoid-related disorders, metabolic syndrome, hypertension, obesity, insulin resistance, hyperglycemia, hyperlipidemia, type 2 diabetes, androgen excess (hirsutism, menstrual irregularity, hyperandrogenism) and polycystic ovary syndrome (PCOS), therapeutic agents aimed at augmentation or suppression of these metabolic pathways, by modulating glucocorticoid signal transduction at the level of 11βHSD1 are desirable.

Furthermore, because the MR binds to aldosterone (its natural ligand) and cortisol with equal affinities, compounds that are designed to interact with the active site of 11βHSD1 (which binds to cortisone/cortisol) may also interact with the MR and act as antagonists. Because the MR is implicated in heart failure, hypertension, and related pathologies including atherosclerosis, arteriosclerosis, coronary artery disease, thrombosis, angina, peripheral vascular disease, vascular wall damage, and stroke, MR antagonists are desirable and may also be useful in treating complex cardiovascular, renal, and inflammatory pathologies including disorders of lipid metabolism including dyslipidemia or hyperlipoproteinaemia, diabetic dyslipidemia, mixed dyslipidemia, hypercholesterolemia, hypertriglyceridemia, as well as those associated with type 1 diabetes, type 2 diabetes, obesity, metabolic syndrome, and insulin resistance, and general aldosterone-related target-organ damage.

As evidenced herein, there is a continuing need for new and improved drugs that target 11βHSD1 and/or MR. The compounds, compositions and methods described herein help meet this and other needs.

SUMMARY OF THE INVENTION

The present invention provides, inter alia, compounds of Formulas I, II, III, IV, Va, Vb, VI, VII, and VIII:

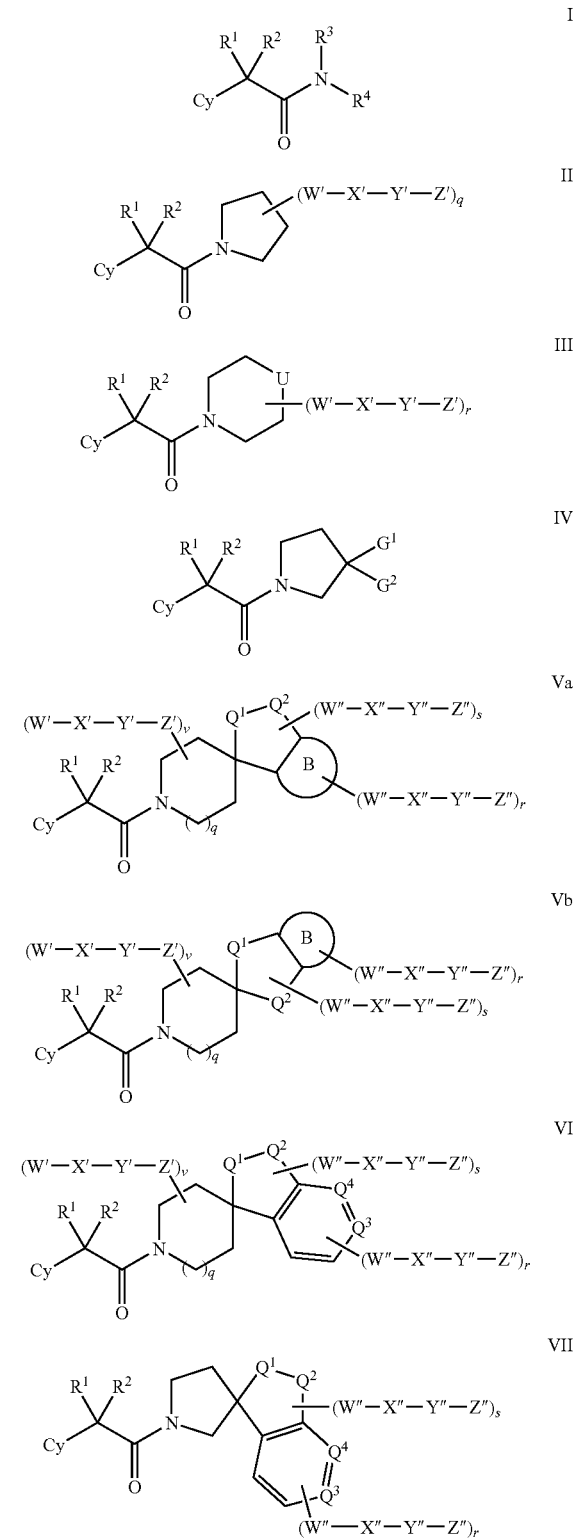

-continued

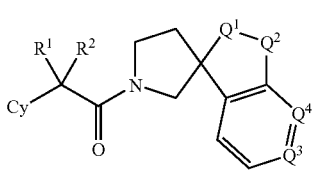

VIII or pharmaceutically acceptable salts or prodrugs thereof, wherein constituent members are defined herein.

The present invention further provides compositions comprising compounds of the invention and a pharmaceutically acceptable carrier.

The present invention further provides methods of modulating 11βHSD1 or MR by contacting the 11βHSD1 or MR with a compound of the invention.

The present invention further provides methods of treating diseases associated with activity or expression of 11βHSD1 or MR.

DETAILED DESCRIPTION

The present invention provides, inter alia, compounds of Formula I:

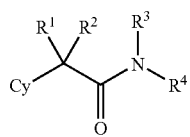

or pharmaceutically acceptable salts or prodrugs thereof, wherein:

Cy is aryl, heteroaryl, cycloalkyl or heterocycloalkyl, each optionally substituted by 1,2,3, 4 or 5-W—X—Y—Z;

$R^1$ and $R^2$ together with the C atom to which they are attached form a 3-, 4-, 5-, 6- or 7-membered cycloalkyl group or a 3-, 4-, 5-, 6- or 7-membered heterocycloalkyl group, each optionally substituted by 1, 2 or 3 $R^5$;

$R^3$ and $R^4$ together with the N atom to which they are attached form a 4-15 membered heterocycloalkyl group optionally substituted by 1, 2, 3, or 4-W'—X'—Y'—Z';

$R^5$ is halo, $C_{1-6}$ alkyl, $C_{2-6}$ alkenyl, $C_{2-6}$ alkynyl, $C_{1-4}$ haloalkyl, aryl, cycloalkyl, heteroaryl, heterocycloalkyl, CN, $NO_2$, $OR^a$, $SR^a$, $C(O)R^b$, $C(O)NR^cR^d$, $C(O)OR^a$, $OC(O)R^b$, $OC(O)NR^cR^d$, $NR^cR^d$, $NR^cC(O)R^d$, $NR^cC(O)OR^a$, $S(O)R^b$, $S(O)NR^cR^d$, $S(O)_2R^b$, or $S(O)_2NR^cR^d$;

W, W' and W" are each, independently, absent, $C_{1-6}$alkylenyl, $C_{1-6}$alkenylenyl, $C_{2-6}$alkynylenyl, O, S, $NR^e$, CO, CS, COO, $CONR^e$, $OCONR^e$, SO, $SO_2$, $SONR^e$, or $NR^eCONR^f$, wherein said $C_{1-6}$ alkylenyl, $C_{2-6}$ alkenylenyl, $C_{2-6}$ alkynylenyl are each optionally substituted by 1, 2 or 3 halo, OH, $C_{1-4}$ alkoxy, $C_{1-4}$haloalkoxy, amino, $C_{1-4}$ alkylamino or $C_{2-8}$ dialkylamino;

X, X' and X" are each, independently, absent, $C_{1-8}$ alkylenyl, $C_{2-8}$ alkenylenyl, $C_{2-8}$ alkynylenyl, aryl, cycloalkyl, heteroaryl, heterocycloalkyl, arylalkyl, cycloalkylalkyl, heteroarylalkyl, heterocycloalkylalkyl, arylalkenyl, cycloalkylalkenyl, heteroarylalkenyl, heterocycloalkylalkenyl, arylalkynyl, cycloalkylalkynyl, heteroarylalkynyl, heterocycloalkylalkynyl, each of which is optionally substituted by one or more halo, CN, $NO_2$, OH, $C_{1-4}$ alkoxy, $C_{1-4}$ haloalkoxy, amino, $C_{1-4}$ alkylamino or $C_{2-8}$ dialkylamino;

Y, Y' and Y" are each, independently, absent, $C_{1-6}$ alkylenyl, $C_{2-6}$ alkenylenyl, $C_{2-6}$ alkynylenyl, O, S, $NR^e$, CO, CS, COO, $CONR^e$, $OCONR^e$, SO, $SO_2$, $SONR^e$, or $NR^eCONR^f$, wherein said $C_{1-6}$ alkylenyl, $C_{2-6}$ alkenylenyl, $C_{2-6}$ alkynylenyl are each optionally substituted by 1, 2 or 3 halo, OH, $C_{1-4}$ alkoxy, $C_{1-4}$ haloalkoxy, amino, $C_{1-4}$ alkylamino or $C_{2-8}$ dialkylamino;

Z, Z' and Z" are each, independently, H, halo, CN, $NO_2$, OH, $C_{1-4}$ alkoxy, $C_{1-4}$ haloalkoxy, amino, $C_{1-4}$ alkylamino or $C_{2-8}$ dialkylamino, $C_{1-6}$ alkyl, $C_{2-6}$ alkenyl, $C_{2-6}$ alkynyl, aryl, cycloalkyl, heteroaryl or heterocycloalkyl, wherein said $C_{1-6}$ alkyl, $C_{2-6}$ alkenyl, $C_{2-6}$ alkynyl, aryl, cycloalkyl, heteroaryl or heterocycloalkyl is optionally substituted by 1, 2 or 3 halo, $C_{1-6}$ alkyl, $C_{2-6}$ alkenyl, $C_{2-4}$ alkynyl, $C_{1-4}$ haloalkyl, aryl, cycloalkyl, heteroaryl, heterocycloalkyl, CN, $NO_2$, $OR^a$, $SR^a$, $C(O)R^b$, $C(O)NR^cR^d$, $C(O)OR^a$, $OC(O)R^b$, $OC(O)NR^cR^d$, $NR^cR^d$, $NR^cC(O)R^d$, $NR^cC(O)OR^a$, $S(O)R^b$, $S(O)NR^cR^d$, $S(O)_2R^b$, or $S(O)_2NR^cR^d$;

wherein two —W—X—Y—Z attached to the same atom optionally form a 3-20 membered cycloalkyl or heterocycloalkyl group optionally substituted by 1, 2 or 3-W"—X"—Y"—Z";

wherein two —W'—X'—Y'—Z' attached to the same atom optionally form a 3-20 membered cycloalkyl or heterocycloalkyl group optionally substituted by 1, 2 or 3-W"—X"—Y"—Z";

wherein —W—X—Y—Z is other than H;
wherein —W'—X'—Y'—Z' is other than H;
wherein —W"—X"—Y"—Z" is other than H;

$R^a$ is H, $C_{1-6}$ alkyl, $C_{1-6}$ haloalkyl, $C_{2-6}$ alkenyl, ($C_{1-6}$ alkoxy)-$C_{1-6}$ alkyl, $C_{2-6}$ alkynyl, aryl, cycloalkyl, heteroaryl or heterocycloalkyl;

$R^b$ is H, $C_{1-6}$ alkyl, $C_{1-6}$ haloalkyl, $C_{2-6}$ alkenyl, $C_{2-6}$ alkynyl, aryl, cycloalkyl, heteroaryl or heterocycloalkyl;

$R^c$ and $R^d$ are each, independently, H, $C_{1-6}$ alkyl, $C_{1-6}$ haloalkyl, $C_{2-6}$ alkenyl, $C_{2-6}$ alkynyl, aryl, cycloalkyl, arylalkyl, or cycloalkylalkyl;

or $R^c$ and $R^d$ together with the N atom to which they are attached form a 4-, 5-, 6- or 7-membered heterocycloalkyl group; and $R^e$ and $R^f$ are each, independently, H, $C_{1-6}$ alkyl, $C_{1-6}$ haloalkyl, $C_{2-6}$ alkenyl, $C_{2-6}$ alkynyl, aryl, cycloalkyl, arylalkyl, or cycloalkylalkyl;

or $R^e$ and $R^f$ together with the N atom to which they are attached form a 4-, 5-, 6- or 7-membered heterocycloalkyl group.

In some embodiments, when $R^3$ and $R^4$ together with the N-atom to which they are attached form piperidinyl, the piperidinyl is unsubstituted or substituted by other than:

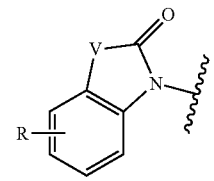

wherein:
V is $CH_2CH_2$, CH=CH, or $CH_2O$; and
R is H, halo or $C_{1-5}$ alkyl.

In some embodiments, when $R^3$ and $R^4$ together with the N-atom to which they are attached form piperazinyl, the Cy is substituted by at least one —W—X—Y—Z.

In some embodiments, Cy is aryl or heteroaryl, each optionally substituted by 1, 2, 3, 4 or 5-W—X—Y—Z.

In some embodiments, Cy is aryl optionally substituted by 1, 2, 3, 4 or 5-W—X—Y—Z.

In some embodiments, Cy is aryl optionally substituted by 1, 2 or 3 halo, $C_{1-4}$ alkyl, $C_{1-4}$ alkoxy, $C_{1-4}$ haloalkyl, or $C_{1-4}$ haloalkoxy.

In some embodiments, Cy is phenyl optionally substituted by 1, 2 or 3 halo, $C_{1-4}$ alkyl, $C_{1-4}$ alkoxy, $C_{1-4}$ haloalkyl, or $C_{1-4}$ haloalkoxy.

In some embodiments, $R^1$ and $R^2$ together with the C atom to which they are attached form a 3-, 4-, 5-, 6- or 7-membered cycloalkyl group.

In some embodiments, $R^1$ and $R^2$ together with the C atom to which they are attached form a cyclopropyl group.

In some embodiments, $R^3$ and $R^4$ together with the N atom to which they are attached form a 4-7 membered heterocycloalkyl group optionally substituted by 1, 2, 3, or 4-W'—X'—Y'—Z'.

In some embodiments, $R^3$ and $R^4$ together with the N atom to which they are attached form a piperidinyl or pyrrolidinyl group, each optionally substituted by 1, 2, 3, or 4-W'—X'—Y'—Z'.

In some embodiments, $R^3$ and $R^4$ together with the N atom to which they are attached form a piperidinyl or pyrrolidinyl group, each substituted by 2, 3, or 4-W'—X'—Y'—Z'; wherein two —W'—X'—Y'—Z' are attached to the same atom and optionally form a 3-20 membered cycloalkyl or heterocycloalkyl group optionally substituted by 1, 2 or 3-W''—X''—Y''—Z''.

In some embodiments, —W—X—Y—Z is halo, cyano, $C_{1-4}$ cyanoalkyl, nitro, $C_{1-8}$ alkyl, $C_{2-8}$ alkenyl, $C_{1-8}$ haloalkyl, $C_{1-4}$ alkylthio, $C_{1-4}$ haloalkylthio, $C_{1-8}$ alkoxy, $C_{2-8}$ alkenyloxy, $C_{1-4}$ haloalkoxy, OH, ($C_{1-4}$ alkoxy)-$C_{1-4}$ alkyl, amino, $C_{1-4}$ alkylamino, $C_{2-8}$ dialkylamino, $OC(O)NR^cR^d$, $NR^cC(O)R^d$, $NR^cC(O)OR^a$, $NR^cS(O)_2R^d$, $C(O)OR^a$, $C(O)R^a$, $C(O)NR^aNR^cR^d$, $S(O)_2R^d$, $SR^d$, $C(O)NR^cR^d$, $C(S)NR^cR^d$, aryloxy, heteroaryloxy, cycloalkyloxy, cycloalkenyloxy, heterocycloalkyloxy, arylalkyloxy, heteroarylalkyloxy, cycloalkylalkyloxy, heterocycloalkylalkyloxy, heteroaryloxyalkyl, aryloxyalkyl, aryl, heteroaryl, cycloalkyl, heterocycloalkyl, arylalkyl, arylalkenyl, arylalkynyl, heteroarylalkyl, heteroarylalkenyl, heteroarylalkynyl, cycloalkylalkyl, or heterocycloalkylalkyl;

wherein each of said $C_{1-8}$ alkyl, $C_{2-8}$ alkenyl, $C_{1-8}$ haloalkyl, $C_{1-4}$ alkylthio, $C_{1-4}$ haloalkylthio, $C_{1-8}$ alkoxy, aryloxy, heteroaryloxy, arylalkyloxy, heteroarylalkyloxy, heteroaryloxyalkyl, aryloxy, heteroaryloxy, cycloalkyloxy, cycloalkenyloxy, heterocycloalkyloxy, arylalkyloxy, heteroarylalkyloxy, cycloalkylalkyloxy, heterocycloalkylalkyloxy, heteroaryloxyalkyl, aryloxyalkyl, aryl, heteroaryl, cycloalkyl, heterocycloalkyl, arylalkyl, arylalkenyl, arylalkynyl, heteroarylalkyl, heteroarylalkenyl, heteroarylalkynyl, cycloalkylalkyl, or heterocycloalkylalkyl is optionally substituted by 1, 2, or 3 halo, cyano, nitro, hydroxyl-($C_{1-6}$alkyl), aminoalkyl, dialkylaminoalkyl, $C_{1-4}$ alkyl, $C_{1-4}$ haloalkyl, $C_{1-4}$ cyanoalkyl, $C_{1-4}$ alkoxy, $C_{1-4}$ haloalkoxy, OH, $OR^a$, ($C_{1-4}$ alkoxy)-$C_{1-4}$ alkyl, amino, $C_{1-4}$ alkylamino, $C_{2-8}$ dialkylamino, $C(O)NR^cR^d$, $C(O)OR^a$, $C(O)R^a$, (cyclocalkylalkyl)-C(O)—, $NR^cC(O)R^d$, $NR^cC(O)OR^a$, $NR^cS(O)_2R^d$, $C(S)NR^c R^d$, $S(O)_2R^d$, $SR^d$, ($C_{1-4}$ alkyl)sulfonyl, arylsulfonyl, aryl optionally substituted by halo, heteroaryl, cycloalkylalkyl, cycloalkyl, or heterocycloalkyl.

In some embodiments, —W—X—Y—Z is halo, cyano, $C_{1-4}$ cyanoalkyl, nitro, $C_{1-8}$ alkyl, $C_{1-8}$ alkenyl, $C_{1-8}$ haloalkyl, $C_{1-10}$ alkoxy, $C_{1-8}$ haloalkoxy, OH, $C_{1-8}$ alkoxyalkyl, amino, $C_{1-8}$ alkylamino, $C_{2-8}$ dialkylamino, $OC(O)NR^cR^d$, $NR^cC(O)R^d$, $NR^cC(O)OR^a$, aryloxy, heteroaryloxy, arylalkyloxy, heteroarylalkyloxy, heteroaryloxyalkyl, aryloxyalkyl, aryl, heteroaryl, cycloalkyl, heterocycloalkyl, arylalkyl, arylalkenyl, arylalkynyl, heteroarylalkyl, heteroarylalkenyl, heteroarylalkynyl, cycloalkylalkyl, or heterocycloalkylalkyl;

wherein each of said $C_{1-8}$ alkyl, $C_{1-8}$ alkenyl, $C_{1-8}$ haloalkyl, $C_{1-8}$ alkoxy, aryloxy, heteroaryloxy, arylalkyloxy, heteroarylalkyloxy, heteroaryloxyalkyl, aryloxyalkyl, aryl, heteroaryl, cycloalkyl, heterocycloalkyl, arylalkyl, arylalkenyl, arylalkynyl, heteroarylalkyl, heteroarylalkenyl, heteroarylalkynyl, cycloalkylalkyl, or heterocycloalkylalkyl is optionally substituted by 1, 2, or 3 halo, cyano, nitro, hydroxyl-($C_{1-6}$ alkyl), aminoalkyl, dialkylaminoalkyl, $C_{1-4}$ alkyl, $C_{1-4}$ haloalkyl, $C_{1-4}$ alkoxy, $C_{1-4}$ haloalkoxy, OH, $C_{1-8}$ alkoxyalkyl, amino, $C_{1-4}$ alkylamino, $C_{2-8}$ dialkylamino, $C(O)NR^cR^d$, $C(O)OR^a$, $NR^cC(O)R^d$, $NR^cS(O)_2R^d$, ($C_{1-4}$ alkyl)sulfonyl, arylsulfonyl, aryl, heteroaryl, cycloalkyl, or heterocycloalkyl.

In some embodiments —W—X—Y—Z is halo, cyano, $C_{1-4}$ cyanoalkyl, nitro, $C_{1-4}$ nitroalkyl, $C_{1-4}$ alkyl, $C_{1-4}$ haloalkyl, $C_{1-4}$ alkoxy, $C_{1-4}$haloalkoxy, OH, ($C_{1-4}$ alkoxy)-$C_{1-4}$ alkyl, amino, $C_{1-4}$ alkylamino, $C_{2-8}$ dialkylamino, aryl, heteroaryl, cycloalkyl, heterocycloalkyl, arylalkyl, heteroarylalkyl, cycloalkylalkyl, or heterocycloalkylalkyl.

In some embodiments, —W—X—Y—Z is halo, $C_{1-4}$ alkyl, or $C_{1-4}$ alkoxy.

In some embodiments, —W'—X'—Y'—Z' is halo, OH, cyano, CHO, COOH, $C(O)O$—($C_{1-4}$ alkyl), $C(O)$—($C_{1-4}$ alkyl), $SO_2$—($C_{1-4}$ alkyl), $C_{1-4}$ alkyl, $C_{1-4}$ alkoxy or -L-$R^7$, wherein said $C_{1-4}$ alkyl or $C_{1-4}$ alkoxy is optionally substituted by one or more halo, OH, COOH or $C(O)O$—($C_{1-4}$ alkyl);

In some embodiments, —W'—X'—Y'—Z' is halo; $C_{1-4}$ alkyl; $C_{1-4}$ haloalkyl; OH; $C_{1-4}$ alkoxy; $C_{1-4}$ haloalkoxy; hydroxyalkyl; alkoxyalkyl; aryl; heteroaryl; aryl substituted by halo, $C_{1-4}$ alkyl, $C_{1-4}$ alkoxy, aryl, heteroaryl, or aryloxy; or heteroaryl substituted by halo, $C_{1-4}$ alkyl, $C_{1-4}$ alkoxy, aryl, or heteroaryl.

In some embodiments, —W'—X'—Y'—Z' are attached to the same atom and optionally form a 3-20 membered cycloalkyl or heterocycloalkyl group optionally substituted by 1, 2 or 3-W''—X''—Y''—Z''.

In some embodiments, —W''—X''—Y''—Z'' is halo, cyano, $C_{1-4}$ cyanoalkyl, nitro, $C_{1-4}$ nitroalkyl, $C_{1-4}$ alkyl, $C_{1-4}$ haloalkyl, $C_{1-4}$ alkoxy, $C_{1-4}$ haloalkoxy, OH, ($C_{1-4}$ alkoxy)-$C_{1-4}$ alkyl, amino, $C_{1-4}$ alkylamino, $C_{2-8}$ dialkylamino, aryl, heteroaryl, cycloalkyl, heterocycloalkyl, arylalkyl, heteroarylalkyl, cycloalkylalkyl, or heterocycloalkylalkyl.

In some embodiments:

—W'—X'—Y'—Z' is halo, OH, cyano, CHO, COOH, $C(O)O$—($C_{1-4}$ alkyl), $C(O)$—($C_{1-4}$ alkyl), $SO_2$—($C_{1-4}$ alkyl), $C_{1-4}$ alkyl, $C_{1-4}$ alkoxy or -L-$R^7$, wherein said $C_{1-4}$ alkyl or $C_{1-4}$ alkoxy is optionally substituted by one or more halo, OH, COOH or $C(O)O$—($C_{1-4}$ alkyl);

L is absent, O, $CH_2$, $NHSO_2$, $N[C(O)$—($C_{1-4}$ alkyl)]; and $R^7$ is aryl or heteroaryl, each is optionally substituted by 1, 2, or 3 halo, OH, cyano, CHO, COOH, $C(O)O$—($C_{1-4}$ alkyl), $C(O)$—($C_{1-4}$ alkyl), $SO_2$—($C_{1-4}$ alkyl), $SO_2$—$NH(C_{1-4}$ alkyl), $C_{1-4}$ alkyl, $C_{1-4}$ alkoxy, $C_{1-4}$ haloalkyl, $C_{1-4}$ hydroxyalkyl, aryl, heteroaryl or aryloxy.

In some embodiments, the compounds of the invention have Formula II:

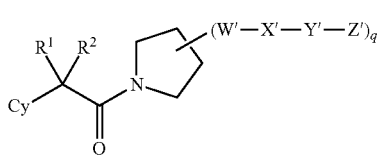

including pharmaceutically acceptable salts or prodrugs thereof, wherein constituent variables are defined herein above, and q is 0, 1, 2, 3 or 4.

In some embodiments, Cy is aryl or heteroaryl, each optionally substituted by 1, 2, 3, 4 or 5-W—X—Y—Z.

In some embodiments, q is 1, 2, 3 or 4.

In some embodiments, q is 2, 3 or 4.

In some embodiments, two —W'—X'—Y'—Z' attached to the same atom form a 3-20 membered cycloalkyl or heterocycloalkyl group optionally substituted by 1, 2 or 3-W"—X"—Y"—Z".

The present invention further provides compounds of Formula III:

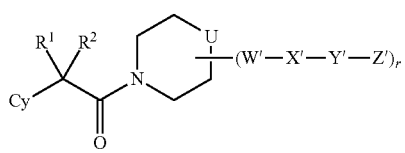

or pharmaceutically acceptable salts or prodrugs thereof, wherein constituent variables are defined hereinabove; and r is 0, 1, 2, 3 or 4.

In some embodiments, when U is $CH_2$, then —W'—X'—Y'—Z' forms a group other than:

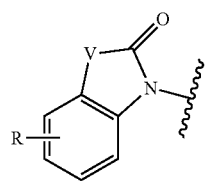

wherein:

V is $CH_2CH_2$, CH=CH, or $CH_2O$; and

R is H, halo or $C_{1-5}$ alkyl.

In some embodiments, when U is NH, Cy is substituted by at least one —W—X—Y—Z.

In some embodiments, r is 1, 2, 3 or 4.

In some embodiments, r is 2, 3 or 4.

In some embodiments, U is $CH_2$.

In some embodiments, two —W'—X'—Y'—Z' attached to the same atom form a 3-20 membered cycloalkyl or heterocycloalkyl group optionally substituted by 1, 2 or 3-W"—X"—Y"—Z".

The present invention further provides compounds of Formula IV:

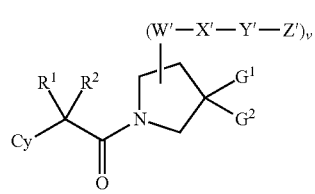

or pharmaceutically acceptable salts or prodrugs thereof, wherein constituent variables are defined hereinabove:

$G^1$ and $G^2$ together with the carbon atom to which they are attached form a 3-20 membered cycloalkyl or heterocycloalkyl group optional substituted by 1, 2 or 3-W"—X"—Y"—Z"; and v is 0, 1 or 2.

In some embodiments, v is 0.

In some embodiments, v is 1.

In some embodiments, $G^1$ and $G^2$ together with the carbon atom to which they are attached form a 9-14 membered cycloalkyl or heterocycloalkyl group optional substituted by 1, 2 or 3-W"—X"—Y"—Z".

In some embodiments, —W"—X"—Y"—Z" is halo, cyano, $C_{1-4}$ cyanoalkyl, nitro, $C_{1-4}$ nitroalkyl, $C_{1-4}$ alkyl, $C_{1-4}$ haloalkyl, $C_{1-4}$ alkoxy, $C_{1-4}$ haloalkoxy, OH, ($C_{1-4}$alkoxy)-$C_{1-4}$alkyl, amino, $C_{1-4}$ alkylamino, $C_{2-8}$ dialkylamino, aryl, heteroaryl, cycloalkyl, heterocycloalkyl, arylalkyl, heteroarylalkyl, cycloalkylalkyl, or heterocycloalkylalkyl.

The present invention further provides compounds of Formula Va or Vb:

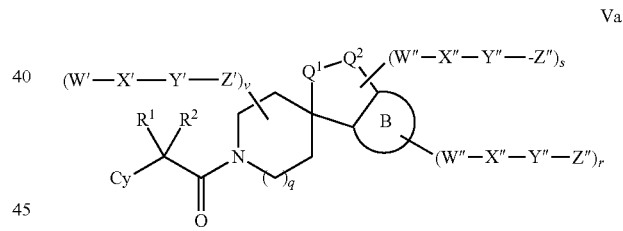

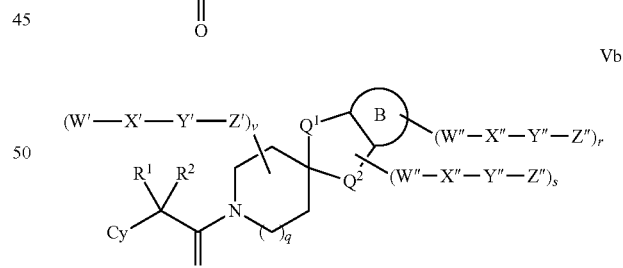

or pharmaceutically acceptable salts or prodrugs thereof, wherein constituent variables are defined herein above:

ring B is a fused 5 or 6-membered aryl or heteroaryl group;

$Q^1$ is O, S, NH, $CH_2$, CO, CS, SO, $SO_2$, $OCH_2$, $SCH_2$, $NHCH_2$, $CH_2CH_2$, CH=CH, $COCH_2$, CONH, COO, $SOCH_2$, SONH, $SO_2CH_2$, or $SO_2NH$;

$Q^2$ is O, S, NH, $CH_2$, CO, CS, SO, $SO_2$, $OCH_2$, $SCH_2$, $NHCH_2$, $CH_2CH_2$, CH=CH, $COCH_2$, CONN, COO, $SOCH_2$, SONH, $SO_2CH_2$, or $SO_2NH$;

q is 0 or 1;

v is 0, 1 or 2;

r is 0, 1 or 2;

s is 0, 1 or 2; and the sum of r and s is 0, 1 or 2.

In some embodiments, $Q^1$ and $Q^2$ are selected to form a 1-, 2-, or 3-atom spacer. In further embodiments, $Q^1$ and $Q^2$ when bonded together form a spacer group having other than an O—O or O—S ring-forming bond.

In some embodiments, $Q^1$ is O, S, NH, $CH_2$ or CO, wherein each of said NH and $CH_2$ is optionally substituted by —W"—X"—Y"—Z".

In some embodiments, $Q^1$ is O, NH, $CH_2$ or CO, wherein each of said NH and $CH_2$ is optionally substituted by —W"—X"—Y"—Z".

In some embodiments, $Q^2$ is O, S, NH, $CH_2$, CO, or $SO_2$, wherein each of said NH and $CH_2$ is optionally substituted by —W"—X"—Y"—Z".

In some embodiments, one of $Q^1$ and $Q^2$ is O and the other is CO or CONH, wherein said CONH is optionally substituted by —W"—X"—Y"—Z".

In some embodiments, one of $Q^1$ and $Q^2$ is CO and the other is O, NH, or $CH_2$, and wherein each of said NH and $CH_2$ is optionally substituted by —W"—X"—Y"—Z".

In some embodiments, one of $Q^1$ and $Q^2$ is $CH_2$ and the other is O, S, NH, or $CH_2$, and wherein each of said NH and $CH_2$ is optionally substituted by —W"—X"—Y"—Z".

In some embodiments, one of $Q^1$ and $Q^2$ is CO.

In some embodiments, the compound has Formula Va wherein one of $Q^1$ and $Q^2$ is CO and the other is O, NH, or $CH_2$, and wherein each of said NH and $CH_2$ is optionally substituted by —W"—X"—Y"—Z".

In some embodiments, the compound has Formula Va wherein one of $Q^1$ and $Q^2$ is $CH_2$ and the other is O, S, NH, or $CH_2$, and wherein each of said NH and $CH_2$ is optionally substituted by —W"—X"—Y"—Z".

In some embodiments, the compound has Formula Vb wherein one of $Q^1$ and $Q^2$ is CO.

In some embodiments, the compound has Formula Va.

In some embodiments, the compound has Formula Vb.

In some embodiments, ring B is phenyl or pyridyl.

In some embodiments, ring B is phenyl.

In some embodiments, r is 0.

In some embodiments, r is 0 or 1.

In some embodiments, s is 0 or 1.

The present invention further provides compounds of Formula VI:

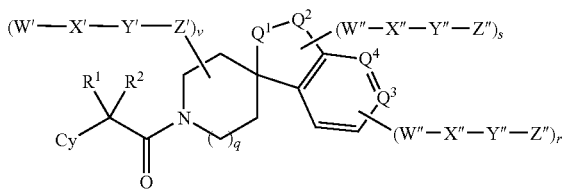

VI pharmaceutically acceptable salt forms and prodrugs thereof, wherein constituent variables are defined hereinabove, and $Q^3$ and $Q^4$ are each, independently, CH or N.

In some embodiments, $Q^3$ is CH optionally substituted by —W"—X"—Y"—Z".

In some embodiments, $Q^3$ is N.

In some embodiments, $Q^4$ is CH optionally substituted by —W"—X"—Y"—Z".

In some embodiments, $Q^4$ is N.

In some embodiments, $Q^3$ is CH and $Q^4$ is CH, each optionally substituted by —W"—X"—Y"—Z".

In some embodiments, $Q^3$ is CH and $Q^4$ is N, wherein said $Q^3$ is optionally substituted by —W"—X"—Y"—Z".

In some embodiments, $Q^3$ is N and $Q^4$ is CH optionally substituted by —W"—X"—Y"—Z".

In some embodiments, $Q^1$ is O, NH, $CH_2$ or CO, wherein each of said NH and $CH_2$ is optionally substituted by —W"—X"—Y"—Z".

In some embodiments, $Q^2$ is O, S, NH, $CH_2$, CO, or $SO_2$, wherein each of said NH and $CH_2$ is optionally substituted by —W"—X"—Y"—Z".

In some embodiments, one of $Q^1$ and $Q^2$ is CO and the other is O, NH, or $CH_2$, wherein each of said NH and $CH_2$ is optionally substituted by —W"—X"—Y"—Z".

In some embodiments, one of $Q^1$ and $Q^2$ is $CH_2$ and the other is O, S, NH, or $CH_2$, wherein each of said NH and $CH_2$ is optionally substituted by —W"—X"—Y"—Z".

In some embodiments, one of $Q^1$ and $Q^2$ is O and the other is CO or CONH, wherein said CONH is optionally substituted by —W"—X"—Y"—Z".

In some embodiments, r is 0 or 1.

In some embodiments, s is 0 or 1.

The present invention further provides compounds of Formula VII:

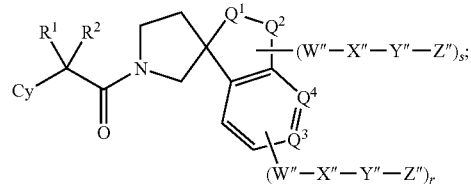

VII pharmaceutically acceptable salts and prodrugs thereof, wherein constituent variables are defined hereinabove.

The present invention further provides compounds of having Formula VIII:

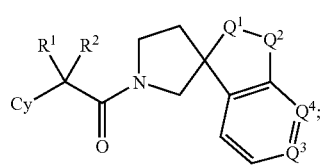

VIII pharmaceutically acceptable salts and prodrugs thereof, wherein constituent variables are defined hereinabove.

In some embodiments, $Q^1$ is O, NH, $CH_2$ or CO, wherein each of said NH and $CH_2$ is optionally substituted by —W"—X"—Y"—Z".

In some embodiments, $Q^2$ is O, S, NH, $CH_2$, CO, or $SO_2$, wherein each of said NH and $CH_2$ is optionally substituted by —W"—X"—Y"—Z".

In some embodiments, one of $Q^1$ and $Q^2$ is CO and the other is O, NH, or $CH_2$, wherein each of said NH and CH, is optionally substituted by —W"—X"—Y"—Z".

In some embodiments, one of $Q^1$ and $Q^2$ is $CH_2$ and the other is O, S, NH, or $CH_2$, wherein each of said NH and $CH_2$ is optionally substituted by —W"—X"—Y"—Z".

In some embodiments, one of $Q^1$ and $Q^2$ is O and the other is CO or CONH, wherein said CONH is optionally substituted by —W"—X"—Y"—Z".

In some embodiments, $Q^3$ is CH optionally substituted by —W"—X"—Y"—Z".

In some embodiments, $Q^3$ is N.

In some embodiments, $Q^4$ is CH optionally substituted by —W"—X"—Y"—Z".

In some embodiments, $Q^4$ is N.

In some embodiments, r is 0 or 1.

In some embodiments, s is 0 or 1.

At various places in the present specification, substituents of compounds of the invention are disclosed in groups or in ranges. It is specifically intended that the invention include each and every individual subcombination of the members of such groups and ranges. For example, the term "$C_{1-6}$ alkyl" is specifically intended to individually disclose methyl, ethyl, $C_3$ alkyl, $C_4$ alkyl, $C_5$ alkyl, and $C_6$ alkyl.

For compounds of the invention in which a variable appears more than once, each variable can be a different moiety selected from the Markush group defining the variable. For example, where a structure is described having two R groups that are simultaneously present on the same compound; the two R groups can represent different moieties selected from the Markush group defined for R. In another example, when an optionally multiple substituent is designated in the form:

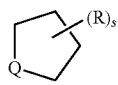

then it is understood that substituent R can occur s number of times on the ring, and R can be a different moiety at each occurrence. Further, in the above example, should the variable Q be defined to include hydrogens, such as when Q is said to be $CH_2$, NH, etc., any floating substituent such as R in the above example, can replace a hydrogen of the Q variable as well as a hydrogen in any other non-variable component of the ring.

It is further intended that the compounds of the invention are stable. As used herein "stable" refers to a compound that is sufficiently robust to survive isolation to a useful degree of purity from a reaction mixture, and preferably capable of formulation into an efficacious therapeutic agent.

It is further appreciated that certain features of the invention, which are, for clarity, described in the context of separate embodiments, can also be provided in combination in a single embodiment. Conversely, various features of the invention which are, for brevity, described in the context of a single embodiment, can also be provided separately or in any suitable subcombination.

As used herein, the term "alkyl" is meant to refer to a saturated hydrocarbon group which is straight-chained or branched. Example alkyl groups include methyl (Me), ethyl (Et), propyl (e.g., n-propyl and isopropyl), butyl (e.g., n-butyl, isobutyl, t-butyl), pentyl (e.g., n-pentyl, isopentyl, neopentyl), and the like. An alkyl group can contain from 1 to about 20, from 2 to about 20, from 1 to about 10, from 1 to about 8, from 1 to about 6, from 1 to about 4, or from 1 to about 3 carbon atoms. The term "alkylenyl" refers to a divalent alkyl linking group.

As used herein, "alkenyl" refers to an alkyl group having one or more double carbon-carbon bonds. Example alkenyl groups include ethenyl, propenyl, cyclohexenyl, and the like.

The term "alkenylenyl" refers to a divalent linking alkenyl group. An example $C_1$ alkenylenyl is —CH=.

As used herein, "alkynyl" refers to an alkyl group having one or more triple carbon-carbon bonds. Example alkynyl groups include ethynyl, propynyl, and the like. The term "alkynylenyl" refers to a divalent linking alkynyl group.

As used herein, "haloalkyl" refers to an alkyl group having one or more halogen substituents. Example haloalkyl groups include $CF_3$, $C_2F_5$, $CHF_2$, $CCl_3$, $CHCl_2$, $C_2Cl_5$, and the like.

As used herein, "aryl" refers to monocyclic or polycyclic (e.g., having 2, 3 or 4 fused rings) aromatic hydrocarbons such as, for example, phenyl, naphthyl, anthracenyl, phenanthrenyl, indanyl, indenyl, and the like. In some embodiments, aryl groups have from 6 to about 20 carbon atoms.

As used herein, "cycloalkyl" refers to non-aromatic cyclic hydrocarbons including cyclized alkyl, alkenyl, and alkynyl groups. Cycloalkyl groups can include mono- or polycyclic (e.g., having 2, 3 or 4 fused rings) ring systems as well as 2-ring, 3-ring, 4-ring spiro system (e.g., having 8 to 20 ring-forming atoms). Example cycloalkyl groups include cyclopropyl, cyclobutyl, cyclopentyl, cyclohexyl, cycloheptyl, cyclopentenyl, cyclohexenyl, cyclohexadienyl, cycloheptatrienyl, norbornyl, norpinyl, norcarnyl, adamantyl, and the like. Also included in the definition of cycloalkyl are moieties that have one or more aromatic rings fused (i.e., having a bond in common with) to the cycloalkyl ring, for example, benzo, pryido or thieno derivatives of pentane, pentene, hexane, and the like. Carbon atoms of the cycloalkyl group can be optionally oxidized, e.g. bear an oxo or sulfildo group to form CO or CS.

As used herein, "heteroaryl" groups refer to an aromatic heterocycle having at least one heteroatom ring member such as sulfur, oxygen, or nitrogen. Heteroaryl groups include monocyclic and polycyclic (e.g., having 2, 3 or 4 fused rings) systems. Examples of heteroaryl groups include without limitation, pyridyl, N-oxopyridyl, pyrimidinyl, pyrazinyl, pyridazinyl, triazinyl, furyl, quinolyl, isoquinolyl, thienyl, imidazolyl, thiazolyl, indolyl, pyrryl, oxazolyl, benzofuryl, benzothienyl, benzthiazolyl, isoxazolyl, pyrazolyl, triazolyl, tetrazolyl, indazolyl, 1,2,4-thiadiazolyl, isothiazolyl, benzothienyl, purinyl, carbazolyl, benzimidazolyl, indolinyl, and the like. In some embodiments, the heteroaryl group has from 1 to about 20 carbon atoms, and in further embodiments from about 3 to about 20 carbon atoms. In some embodiments, the heteroaryl group contains 3 to about 14, 3 to about 7, or 5 to 6 ring-forming atoms. In some embodiments, the heteroaryl group has 1 to about 4, 1 to about 3, or 1 to 2 heteroatoms.

As used herein, "heterocycloalkyl" refers to non-aromatic heterocycles including cyclized alkyl, alkenyl, and alkynyl groups where one or more of the ring-forming carbon atoms is replaced by a heteroatom such as an O, N, or S atom. Also included in the definition of heterocycloalkyl are moieties that have one or more aromatic rings fused (i.e., having a bond in common with) to the nonaromatic heterocyclic ring, for example phthalimidyl, naphthalimidyl, and benzo derivatives of heterocycles such as indolene and isoindolene groups. Heterocycloalkyl groups can be mono- or polycyclic (e.g., having 2, 3, 4 or more fused rings or having a 2-ring, 3-ring, 4-ring spiro system (e.g., having 8 to 20 ring-forming atoms)). Heteroatoms or carbon atoms of the heterocycloalkyl group can be optionally oxidized, e.g., bearing one or two oxo or sulfildo groups to form SO, $SO_2$, CO, NO, etc. In some embodiments, the heterocycloalkyl group has from 1 to about 20 carbon atoms, and in further embodiments from about 3 to about 20 carbon atoms. In some embodiments, the heterocycloalkyl group contains 3 to about 14, 3 to about 7, or 5 to 6 ring-forming atoms. In some embodiments, the heterocycloalkyl group has 1 to about 4, 1 to about 3, or 1 to 2 heteroatoms. In some embodiments, the heterocycloalkyl group contains 0 to 3 double bonds. In some embodiments, the heterocycloalkyl group contains 0 to 2 triple bonds. Example "heterocycloalkyl" groups include morpholino, thiomorpholino, piperazinyl, tetrahydrofuranyl, tetrahydrothienyl, 2,3-dihydrobenzofuryl, 1,3-benzodioxole, benzo-1,4-dioxane, piperidinyl, pyrrolidinyl, isoxazolidinyl, isothiazolidinyl, pyrazolidinyl, oxazolidinyl, thiazolidinyl, imidazolidinyl, as well as radicals of 3H-isobenzofuran-1-one, 1,3-dihydro-isobenzofuran, 2,3-dihydro-benzo[d] isothiazole 1,1-dioxide, and the like.

As used herein, "halo" or "halogen" includes fluoro, chloro, bromo, and iodo.

As used herein, "alkoxy" refers to an —O-alkyl group. Example alkoxy groups include methoxy, ethoxy, propoxy (e.g., n-propoxy and isopropoxy), t-butoxy, and the like.

As used here, "haloalkoxy" refers to an —O-haloalkyl group. An example haloalkoxy group is $OCF_3$.

As used herein, "arylalkyl" refers to alkyl substituted by aryl and "cycloalkylalkyl" refers to alkyl substituted by cycloalkyl. An example arylalkyl group is benzyl.

As used herein, "amino" refers to $NH_2$.

As used herein, "alkylamino" refers to an amino group substituted by an alkyl group.

As used herein, "dialkylamino" refers to an amino group substituted by two alkyl groups.

The compounds described herein can be asymmetric (e.g., having one or more stereocenters). All stereoisomers, such as enantiomers and diastereomers, are intended unless otherwise indicated. Compounds of the present invention that contain asymmetrically substituted carbon atoms can be isolated in optically active or racemic forms. Methods on how to prepare optically active forms from optically active starting materials are known in the art, such as by resolution of racemic mixtures or by stereoselective synthesis. Many geometric isomers of olefins, C=N double bonds, and the like can also be present in the compounds described herein, and all such stable isomers are contemplated in the present invention. Cis and trans geometric isomers of the compounds of the present invention are described and may be isolated as a mixture of isomers or as separated isomeric forms.

Resolution of racemic mixtures of compounds can be carried out by any of numerous methods known in the art. An example method includes fractional recrystallizaion using a "chiral resolving acid" which is an optically active, salt-forming organic acid. Suitable resolving agents for fractional recrystallization methods are, for example, optically active acids, such as the D and L forms of tartaric acid, diacetyltartaric acid, dibenzoyltartaric acid, mandelic acid, malic acid, lactic acid or the various optically active camphorsulfonic acids such as β-camphorsulfonic acid. Other resolving agents suitable for fractional crystallization methods include stereoisomerically pure forms of α-methylbenzylamine (e.g., S and R forms, or diastereomerically pure forms), 2-phenylglycinol, norephedrine, ephedrine, N-methylephedrine, cyclohexylethylamine, 1,2-diaminocyclohexane, and the like.

Resolution of racemic mixtures can also be carried out by elution on a column packed with an optically active resolving agent (e.g., dinitrobenzoylphenylglycine). Suitable elution solvent composition can be determined by one skilled in the art.

Compounds of the invention also include tautomeric forms, such as keto-enol tautomers.

Compounds of the invention can also include all isotopes of atoms occurring in the intermediates or final compounds. Isotopes include those atoms having the same atomic number but different mass numbers. For example, isotopes of hydrogen include tritium and deuterium.

The phrase "pharmaceutically acceptable" is employed herein to refer to those compounds, materials, compositions, and/or dosage forms which are, within the scope of sound medical judgement, suitable for use in contact with the tissues of human beings and animals without excessive toxicity, irritation, allergic response, or other problem or complication, commensurate with a reasonable benefit/risk ratio.

The present invention also includes pharmaceutically acceptable salts of the compounds described herein. As used herein, "pharmaceutically acceptable salts" refers to derivatives of the disclosed compounds wherein the parent compound is modified by converting an existing acid or base moiety to its salt form. Examples of pharmaceutically acceptable salts include, but are not limited to, mineral or organic acid salts of basic residues such as amines; alkali or organic salts of acidic residues such as carboxylic acids; and the like. The pharmaceutically acceptable salts of the present invention include the conventional non-toxic salts or the quaternary ammonium salts of the parent compound formed, for example, from non-toxic inorganic or organic acids. The pharmaceutically acceptable salts of the present invention can be synthesized from the parent compound which contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; generally, non-aqueous media like ether, ethyl acetate, ethanol, isopropanol, or acetonitrile are preferred. Lists of suitable salts are found in *Remington's Pharmaceutical Sciences,* 17th ed., Mack Publishing Company, Easton, Pa., 1985, p. 1418 and *Journal of Pharmaceutical Science,* 66, 2 (1977), each of which is incorporated herein by reference in its entirety.

The present invention also includes prodrugs of the compounds described herein. As used herein, "prodrugs" refer to any covalently bonded carriers which release the active parent drug when administered to a mammalian subject. Prodrugs can be prepared by modifying functional groups present in the compounds in such a way that the modifications are cleaved, either in routine manipulation or in vivo, to the parent compounds. Prodrugs include compounds wherein hydroxyl, amino, sulfhydryl, or carboxyl groups are bonded to any group that, when administered to a mammalian subject, cleaves to form a free hydroxyl, amino, sulfhydryl, or carboxyl group respectively. Examples of prodrugs include, but are not limited to, acetate, formate and benzoate derivatives of alcohol and amine functional groups in the compounds of the invention. Preparation and use of prodrugs is discussed in T. Higuchi and V. Stella, "Pro-drugs as Novel Delivery Systems," Vol. 14 of the A.C.S. Symposium Series, and in *Bioreversible Carriers in Drug Design*, ed. Edward B. Roche, American Pharmaceutical Association and Pergamon Press, 1987, both of which are hereby incorporated by reference in their entirety.

Synthesis

The novel compounds of the present invention can be prepared in a variety of ways known to one skilled in the art of organic synthesis. The compounds of the present invention can be synthesized using the methods as hereinafter described below, together with synthetic methods known in the art of synthetic organic chemistry or variations thereon as appreciated by those skilled in the art.

The compounds of this invention can be prepared from readily available starting materials using the following general methods and procedures. It will be appreciated that where typical or preferred process conditions (i.e., reaction temperatures, times, mole ratios of reactants, solvents, pressures, etc.) are given; other process conditions can also be used unless otherwise stated. Optimum reaction conditions may vary with the particular reactants or solvent used, but such conditions can be determined by one skilled in the art by routine optimization procedures.

The processes described herein can be monitored according to any suitable method known in the art. For example, product formation can be monitored by spectroscopic means, such as nuclear magnetic resonance spectroscopy (e.g., $^1$H or $^{13}$C) infrared spectroscopy, spectrophotometry (e.g., UV-visible), or mass spectrometry, or by chromatography such as high performance liquid chromatography (HPLC) or thin layer chromatography.

Preparation of compounds can involve the protection and deprotection of various chemical groups. The need for protection and deprotection, and the selection of appropriate protecting groups can be readily determined by one skilled in the art. The chemistry of protecting groups can be found, for example, in Greene, et al., *Protective Groups in Organic Synthesis*, 2d. Ed., Wiley & Sons, 1991, which is incorporated herein by reference in its entirety.

The reactions of the processes described herein can be carried out in suitable solvents which can be readily selected by one of skill in the art of organic synthesis. Suitable solvents can be substantially nonreactive with the starting materials (reactants), the intermediates, or products at the temperatures at which the reactions are carried out, i.e., temperatures which can range from the solvent's freezing temperature to the solvent's boiling temperature. A given reaction can be carried out in one solvent or a mixture of more than one solvent. Depending on the particular reaction step, suitable solvents for a particular reaction step can be selected.

The compounds described herein can be asymmetric (e.g., having one or more stereocenters). All stereoisomers, such as enantiomers and diastereomers, are intended unless otherwise indicated. Compounds of the present invention that contain asymmetrically substituted carbon atoms can be isolated in optically active or racemic forms. Methods on how to prepare optically active forms from optically active starting materials are known in the art, such as by resolution of racemic mixtures or by stereoselective synthesis.

Resolution of racemic mixtures of compounds can be carried out by any of numerous methods known in the art. An example method includes fractional recrystallization using a "chiral resolving acid" which is an optically active, salt-forming organic acid. Suitable resolving agents for fractional recrystallization methods are, for example, optically active acids, such as the D and L forms of tartaric acid, diacetyltartaric acid, dibenzoyltartaric acid, mandelic acid, malic acid, lactic acid or the various optically active camphorsulfonic acids. Resolution of racemic mixtures can also be carried out by elution on a column packed with an optically active resolving agent (e.g., dinitrobenzoylphenylglycine). Suitable elution solvent composition can be determined by one skilled in the art.

The compounds of the invention can be prepared, for example, using the reaction pathways and techniques as described below.

A series of cycloalkylcarboxmides of formula 2 can be prepared by the method outlined in Scheme 1. The carboxylic acids 1 can be coupled to an amine using coupling reagents such as BOP to provide the desired product 2.

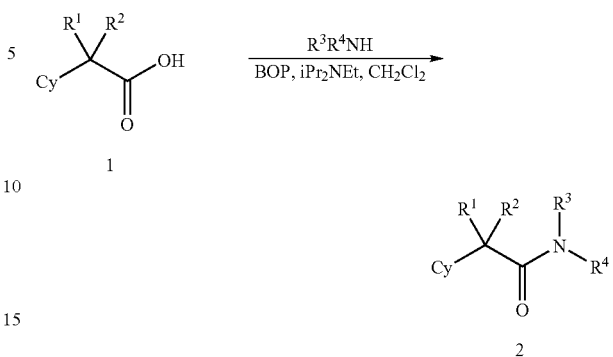

A series of cycloalkylcarboxylic acids formula 3 can be prepared by the method outlined in Scheme 2. Mono-alkylation of alpha-substituted methyl 4 with an alkylenedihalide such as ethylene bromide, 1,3-dibromopropane, and 1,4-dibromobutane provides mono-alkylated product 5, followed by treatment with either 1) sodium hydride in DMSO or DMF or 2) LDA in THF provides the cycloalkylcarboxylic acid esters 6. Hydrolysis of 6 gives the corresponding acid 3.

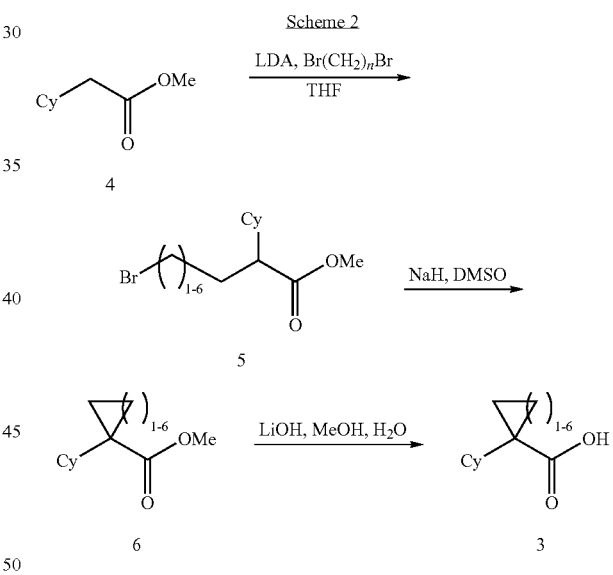

Alternatively, a series of cycloalkylcarboxylic acids of formula 7 can be prepared from the corresponding nitrile as exemplified in Scheme 3. Alpha-substituted acetonitrile 8 can be treated with potassium hydroxide and alkylenedihalides such as 1,3-dibromopropane to provide substituted cycloalkylcarbonitriles 10, which is then followed by hydrolysis to afford the desired cycloalkylcarboxylic acid 7.

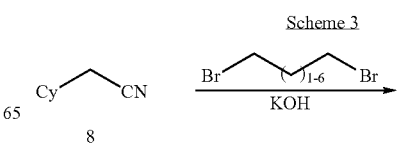

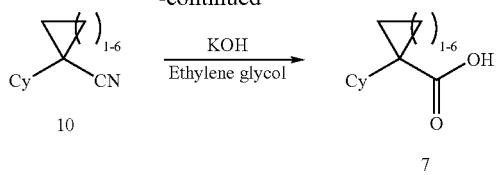

A series of 3-substituted pyrrolidines 10 and 11 can be prepared by the method outlined in Scheme 4 ($R^x$ can be, for example, alkyl or cycloalkyl). Compound 12 can be treated with organolithium or Grignard reagent to provide alcohol 13. The Boc protecting group of 13 can be removed by treating with TFA to give 3-substituted pyrrolidine 10. Alternatively, 13 can be treated with HCl to provide the alkene 14, followed by the dehydrogenation to give 3-substituted pyrrolidine 11.

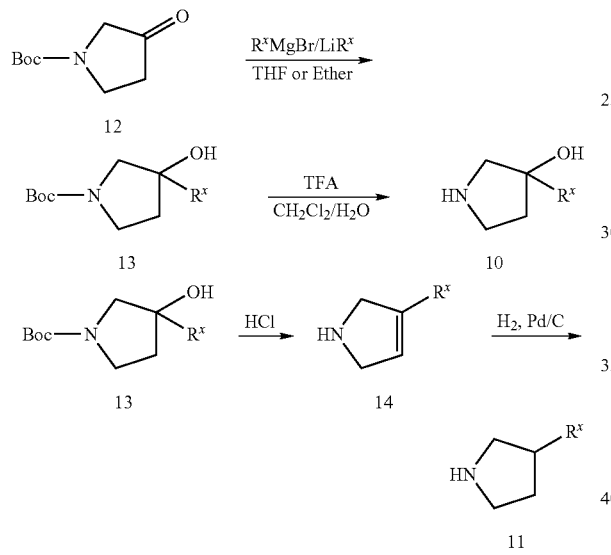

A series of 3-substituted pyrrolidines 11a can be prepared by the method outlined in Scheme 5 (Ar can be, for example, aryl or heteroaryl). Palladium catalyzed Heck coupling reaction of alkene 15 with arylbromides or heteroarylbromides, followed by hydrogenation directly provides the desired 3-substituted pyrrolidine 11a (Ho, C. et al *Tetrahedron Lett.* 2004, 45, 4113).

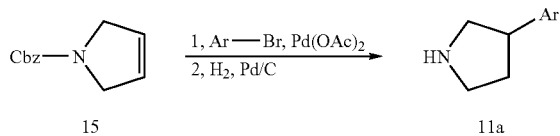

A series of 3-hydroxyl, 4-substituted pyrrolidines 16 can be prepared by the method outlined in Scheme 6 (Ar can be, for example, aryl or heteroaryl; X can be halo). Alkene 15 can be reacted with MCPBA to provide the epoxide 17, followed by treatment with organolithium and Lewis acid, such as Al(Me)$_3$, to give the desired 3-hydroxyl, 4-substituted pyrrolidine 16.

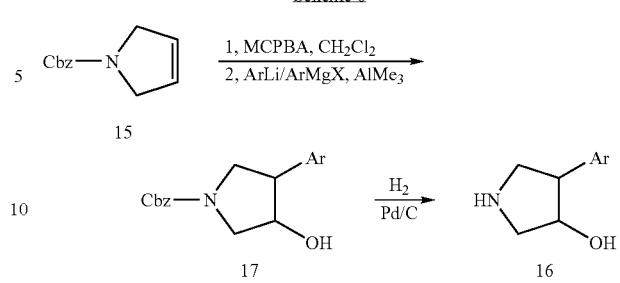

A series of di-substituted pyrrolidines or piperidines 18 are prepared by the method outlined in Scheme 7 (Ar is, for example, aryl or heteroaryl; n is 1 or 2 and m is 1 or 2). Ketone 19 can be treated with a Wittig reagent to provide vinyl compound 20, followed by reacting with Ar$_2$CuLi to provide the addition product 21. The Cbz protecting group of 21 can be removed by hydrogenation to provide the desired disubstituted pyrrolidine or disubstituted piperidine 18.

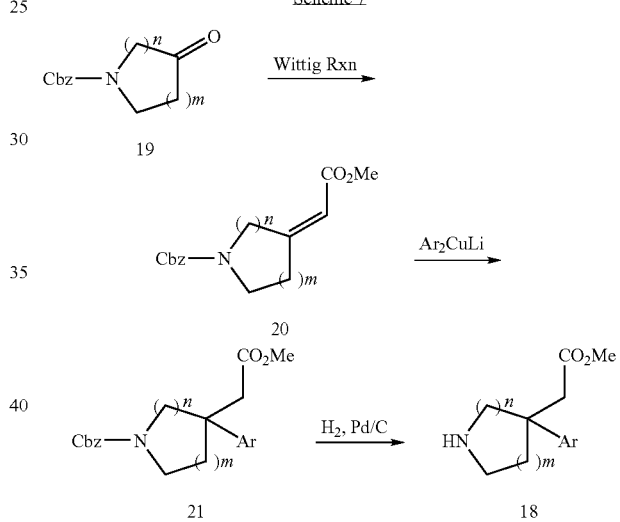

A series of compounds 22 can be prepared by the method outlined in Scheme 8 (Ar is, for example, aryl or heteroaryl; and NR$^i$R$^{ii}$ is, for example, amine, alkylamine, dialkylamine and derivatives thereof). The carboxylic acid 1 can be coupled with an amino alcohol using BOP or other amide bond formation reagents to provide the coupled product 23. The hydroxyl group of the coupled product 23 can be alkylated with 2-bromoacetate to give compound 24 and the tert-butyl group of 24 can be removed by treatment with TFA, followed by a standard coupling reaction with a variety amines to give compounds 22.

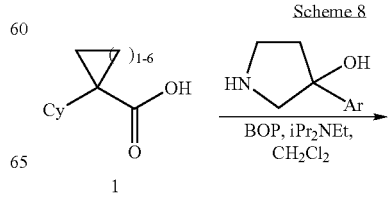

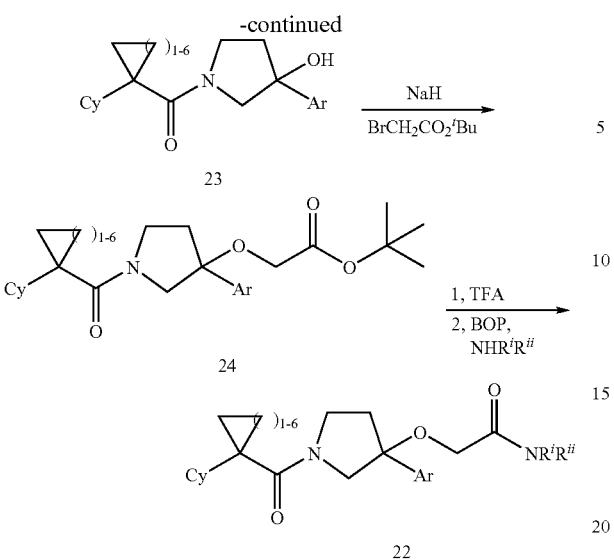

According to Scheme 9 (Ar is, for example, aryl or heteroaryl), the hydroxyl group of 23 can be alkylated with protected 2-amino ethyl bromide to give compound 25. The protecting group of 25 can be removed by TFA. The resulting free amino group of compound 26 can be converted into a variety analogs 27 by methods known to those skilled in the art.

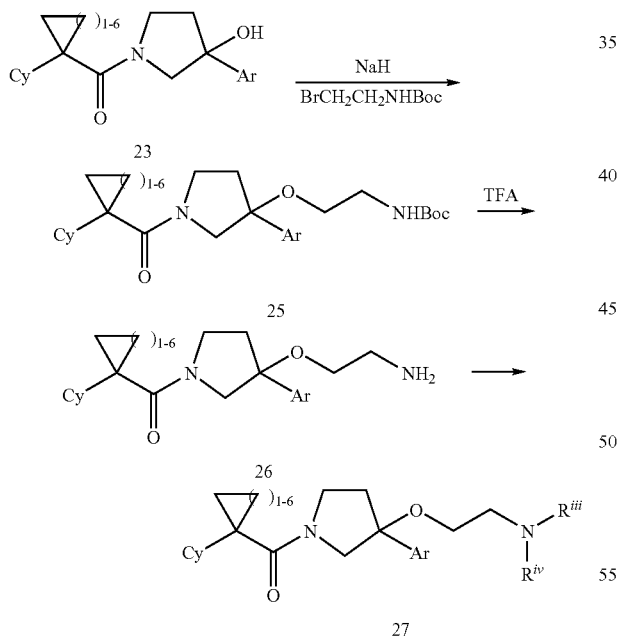

A series of compounds 28 can be prepared by the method outlined in Scheme 10. Compound 29 can be treated with alkyldihalides such as 1,2-dibromoethane or a similar reagent to give the desired cycloalkyl product 30. Both benzyl (Bn) groups of 30 can be removed by hydrogenation to give the deprotected compound 31. Treatment with cyclic amines $NHR^3R^4$ can provide amides of formula 32. The free hydroxyl group of 32 can be converted to a variety ether analogs 28 by methods known to those skilled in the art such as by substitution reactions employing base (e.g., NaH) and electrophile (RX where R is alkyl, cycloalkyl, etc. and X is halo or other leaving group).

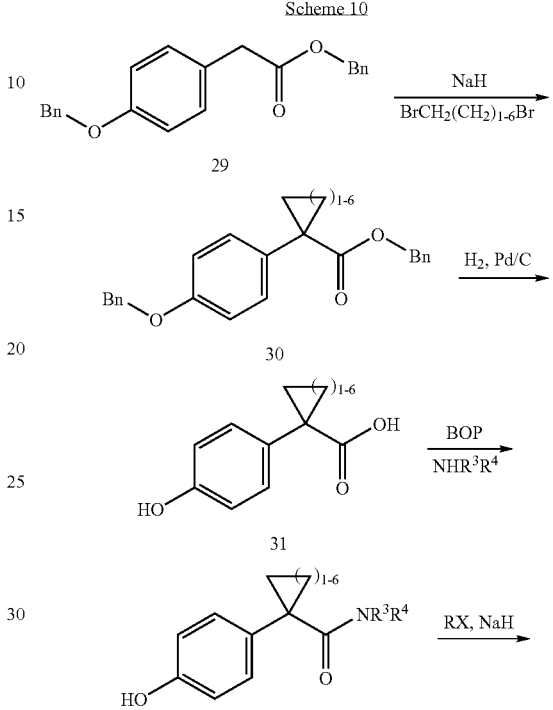

A series of compounds 33 can be prepared by the method outlined in Scheme 11 (Ar is, for example, aryl or heteroaryl or derivatives thereof). The free hydroxyl group of 32 can be protected to yield 34, which then can undergo Pd catalyzed coupling to provide compounds 33.

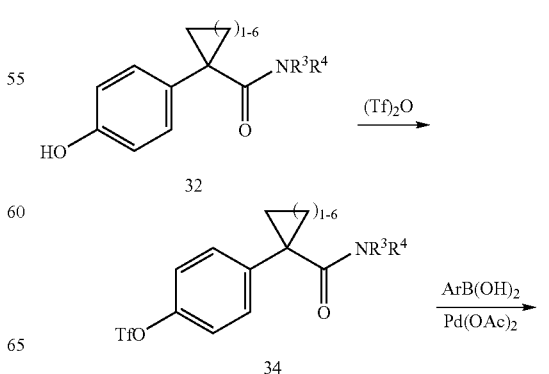

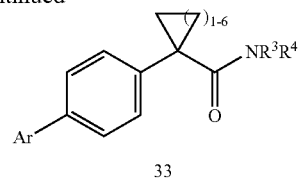

33

A series of compounds 35 can be prepared by the method outlined in Scheme 12 (Ar can be, for example, aryl or heteroaryl or derivatives thereof). The free phenol group of 32 can be coupled with ArB(OH)$_2$ directly to provide the aryl or heteroaryl ether coupling product 35 (Bolm, C. et al. *J. Org. Chem.* 2005, 70, 2346).

Scheme 12

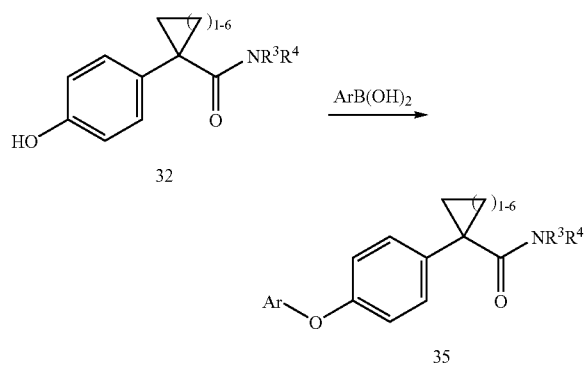

A series of 4-heterocyclo-substituted ether compounds 36 and 37 can be prepared by the method outlined in Scheme 13 (G is, e.g., O, NBoc, NMe, etc.). The free phenol of 32 can be treated with a variety of heterocycloalkylalkyl triflates or heterocycloalkylalkyl halides to provide 4-heterocycloalkyl-substituted ether compounds 36 and 37, respectively.

Scheme 13

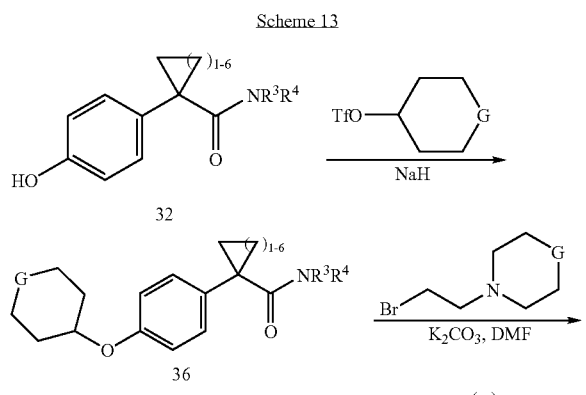

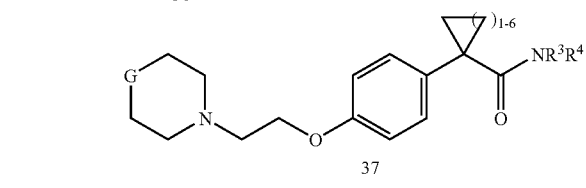

Spiro-pyrrolidines 56 can be prepared according to Scheme 14. Halogen metal exchange between aryl iodide 54 and isopropylmagnesium bromide followed by reaction with N-Boc-3-oxo-pyrrolidine provides spiro-lactone 55 which upon acidic cleavage of the Boc group yields the desired pyrrolidine 56.

Scheme 14

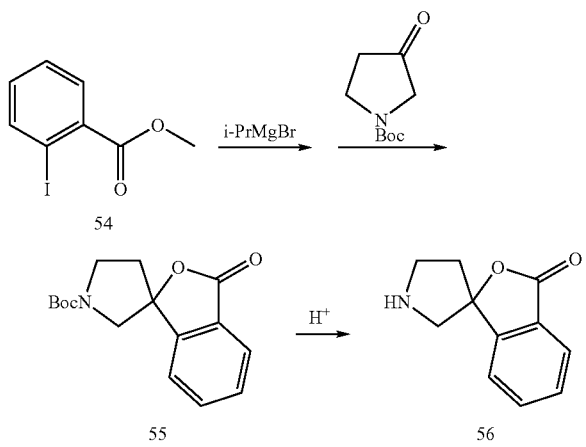

Spiro-pyrrolidines 59 can be prepared according to Scheme 15. Ortho-lithiation of carboxylic acid 57, followed by reaction of the resulting organolithium with N-Boc-3-oxo-pyrrolidine yields spiro-lactone 58, which upon acidic cleavage of the Boc group provides the desired pyrrolidine 59.

Scheme 15

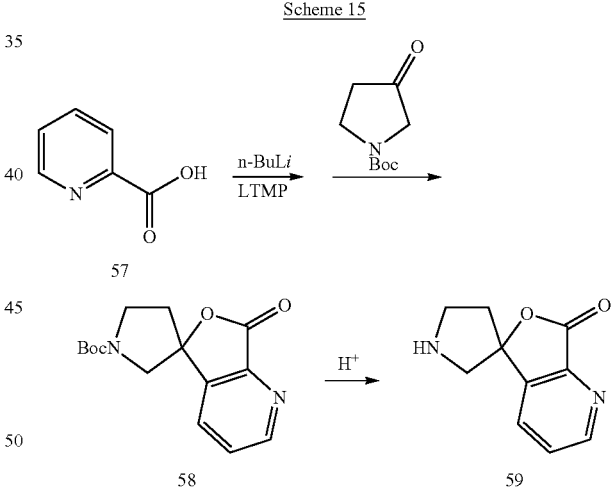

Spiro-pyrrolidine 64 can be prepared according to the method outlined in Scheme 16.

Scheme 16

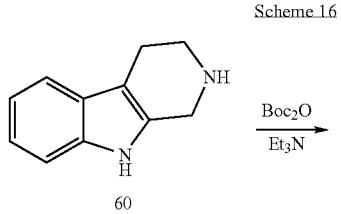

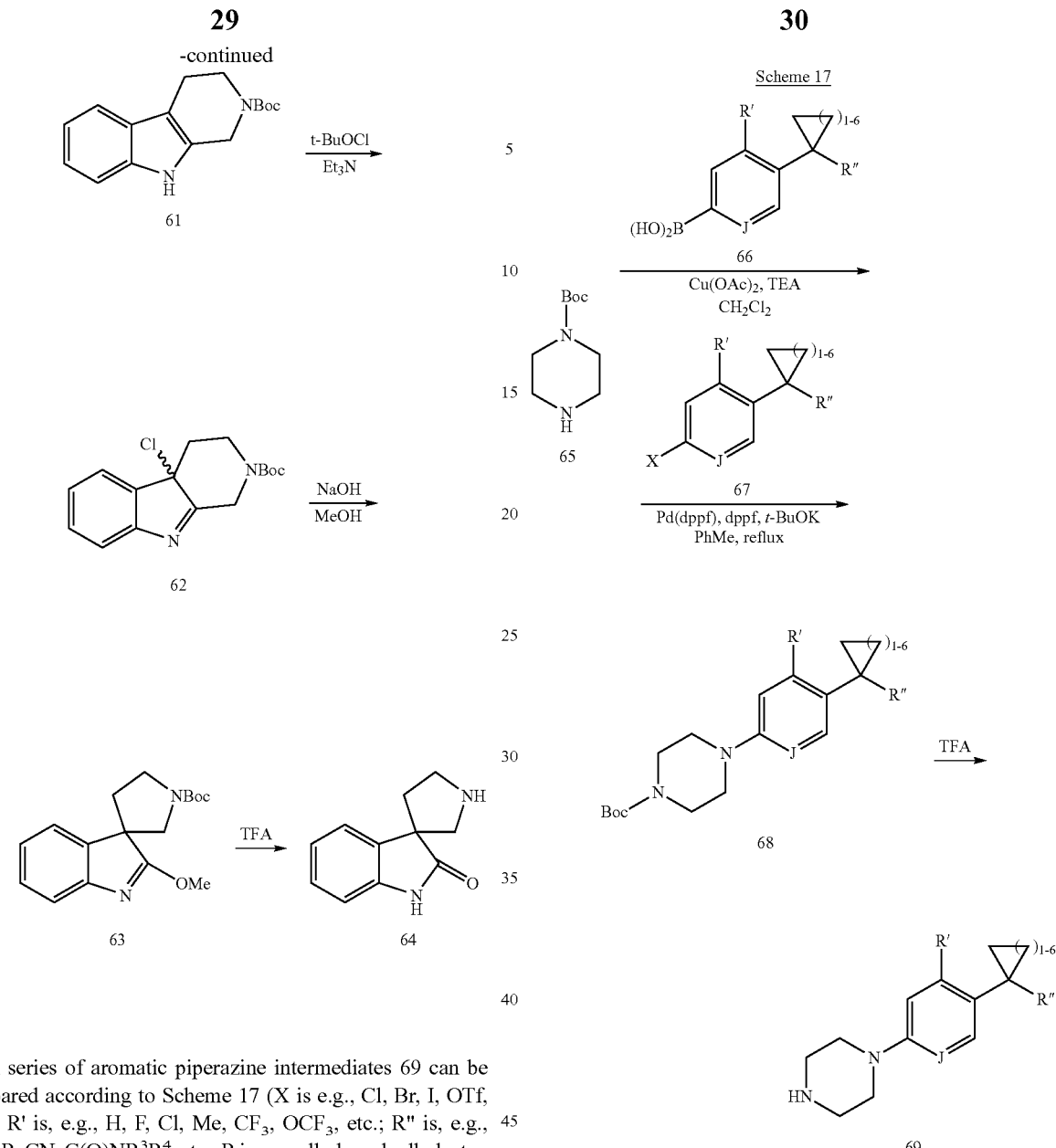

A series of aromatic piperazine intermediates 69 can be prepared according to Scheme 17 (X is e.g., Cl, Br, I, OTf, etc.; R' is, e.g., H, F, Cl, Me, CF$_3$, OCF$_3$, etc.; R" is, e.g., CO$_2$R, CN, C(O)NR$^3$R$^4$, etc.; R is e.g., alkyl, cycloalkyl, etc.; and J is, e.g., CH or N) by reacting Boc-piperazine 65 with a variety of boronic acids 66 under the catalysis of copper (II) acetate (Combs, A. P.; Tadesse, S.; Rafalski, M.; Hague, T. S.; Lam, P. Y. S. *J. Comb. Chem.* 2002, 4, 179) or with a variety of aryl or heteroaryl halides 67 using Buchwald/Hartwig conditions (Louie, J; Hartwig, J. F. *Tetrahedron Lett.* 1995, 36, 3609 & Bolm, C. et al. *J. Org. Chem.* 2005, 70, 2346.). Aromatic piperazine intermediates 69 can also be prepared through classical ring closure of appropriately substituted anilines and bis-(2-chloroethyl)amine hydrochloride in the presence of base (E. Mishani, et. al. *Tetrahedron Lett.* 1996, 37, 319), or through direct nucleophilic aromatic substitution of the piperazine (S. M. Dankwardt, at al., *Tetrahedron Lett.* 1995, 36, 4923). After removal of the Boc group with TFA, the secondary amine 69 can be coupled with sulfonyl chlorides, acyl chlorides, carboxylic acids, alkyl halides, or undergo reductive amination by using procedures known to those skilled in the art.

Amines can be coupled to the pyridyl halide 67 in the absence of a palladium catalyst by heating the two reagents in DMSO as outlined in Scheme 18 (X is, e.g., Cl, Br, etc.; R' is, e.g., H, F, Cl, Me, CF$_3$, OCF$_3$, etc.; R" is, e.g., CO$_2$R, CN, C(O)NR$^3$R$^4$, etc.; R is, e.g., alkyl, cycloalkyl, etc.; R* and R** are independently, e.g., H, alkyl, cycloalkyl, etc.; von Geldern, Thomas W. et al. *Biorg. & Med. Chem. Lett.* 2005, 15, 195).

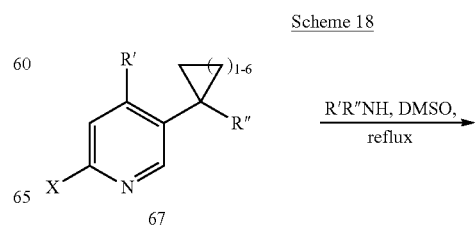

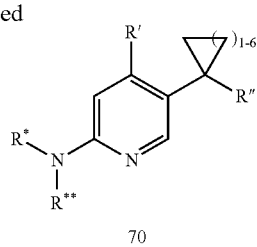

A series of aryl tetrahydropyridines 73 can be prepared by first converting the tert-butoxycarbonyl-piperid-4-one 71 to the corresponding enol triflate 74 using LDA and N-phenyl-trifluoromethanesulfonamide according to Scheme 19 (M is Li, Na, MgBr; X is, e.g., Cl, Br, I, OTf, etc.; R' is, e.g., H, F, Cl, Me, $CF_3$, $OCF_3$, etc.; R" is, e.g., $CO_2R$, CN, $C(O)NR^3R^4$, etc.; R is, e.g., alkyl, cycloalkyl, etc.; J is CH or N). The enol triflate can then be used directly in a Suzuki-type coupling reaction with a variety of aromatic boronic acids 66 to produce the aryl- or heteroaryl-tetrahydropyridines 76 (M. G. Bursavich, D. H. Rich, *Org. Lett.* 2001, 3, 2625). Alternatively, the enol triflate can be converted to the corresponding enol boronic ester 75 or acid via palladium mediated coupling and then subsequently coupled with an aryl halide through a Suzuki-type reaction.

After removal of the Boc group of compound 76 with TFA, the secondary amine 73 can be coupled with sulfonyl chlorides, acyl chlorides, carboxylic acids, alkyl halides, or undego reductive amination by using procedures known to those skilled in the art.

Aromatic tetrahydropyridines 73 can also be prepared through alternative methods known by those skilled in the art of organic synthesis, such as direct nucleophilic addition of an aryl or heteroaryl anion 72 to a piperidone 71 followed by dehydration and deprotection of the resultant alcohol compound.

Scheme 19

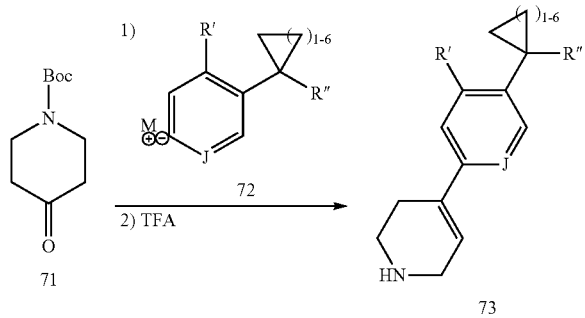

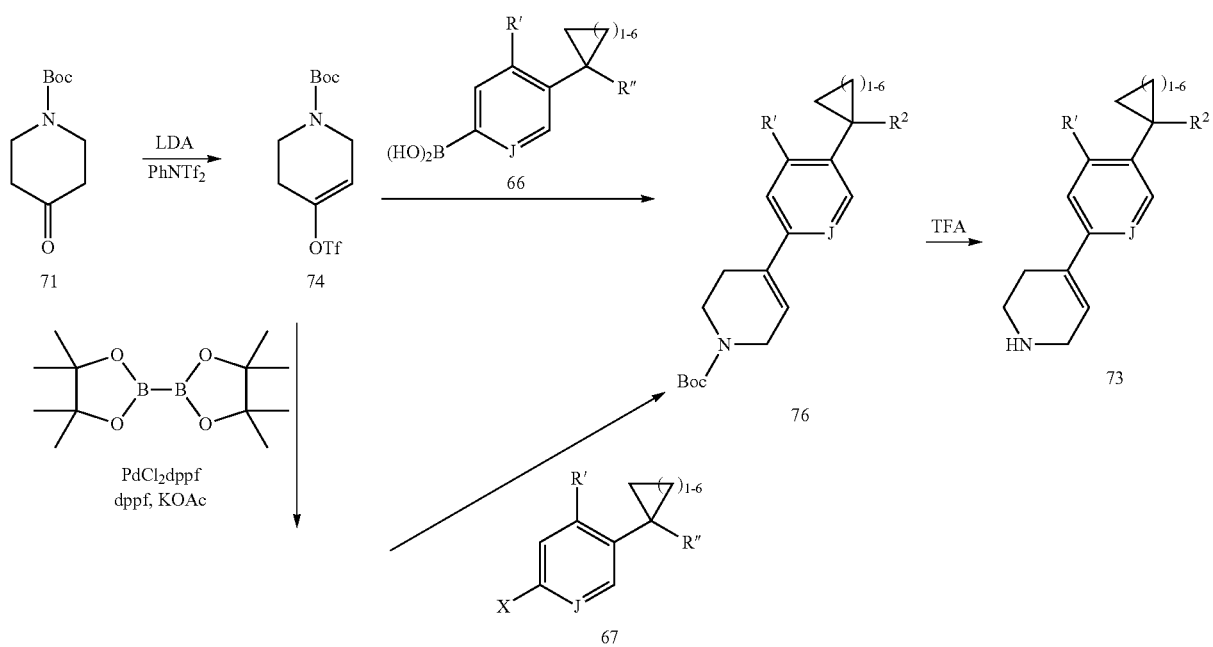

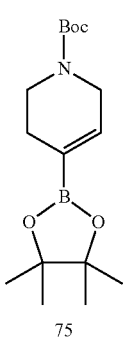

75

A series of aromatic piperidine derivatives 78 can be prepared according to Scheme 20 (X is, e.g., Cl, Br, I, OTf, etc.; R' is, e.g., H, F, Cl, Me, CF$_3$, OCF$_3$, etc.; R" is, e.g., CO$_2$R, CN, C(O)NR$^3$R$^4$, etc.; R is, e.g., alkyl, cycloalkyl, etc.; J is CH or N) by catalytic hydrogenation of the above formed aryl- or heteroaryl-tetrahydropyridines 73 or by coupling 4-bromopyridine with an aromatic boronic acid 66 in the presence of a palladium catalyst followed by hydrogenation. The resulting secondary amine 78 can then be coupled with sulfonyl chlorides, acyl chlorides, carboxylic acids, alkyl halides, or undego reductive amination by using procedures known to those skilled in the art.

In addition to using the Buckwald/Hartwig conditions described above to form the C—N bond, copper (1) mediated coupling reactions can be used when the amine is α to an sp$^2$ carbon such as in the case of a pyrrazole, oxazolidin-2-one, 2-oxo-pyrrolidine, imidazole, indazole, 1H-benzimidazole, pyrid-2-one, t-butyl carbamate, etc. according to Scheme 21 (X is, e.g., Cl, Br, I, OTf, etc.; Q is O, S or CH$_2$; R' is, e.g., H, F, Cl, Me, CF$_3$, OCF$_3$, etc.; R" is, e.g., CO$_2$R, CN, C(O)NR$^3$R$^4$, etc.; R is, e.g., alkyl, cycloalkyl, etc.; J is CH or N; R* and R** are independently H, alkyl, cycloalkyl, etc.); Woolven, James M. et al. *J. Med. Chem.* 2003, 46, 4428).

Scheme 20

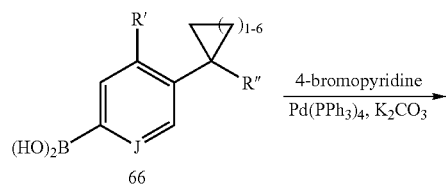

Scheme 21

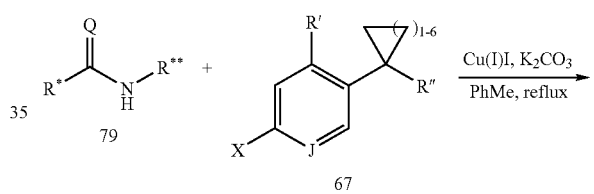

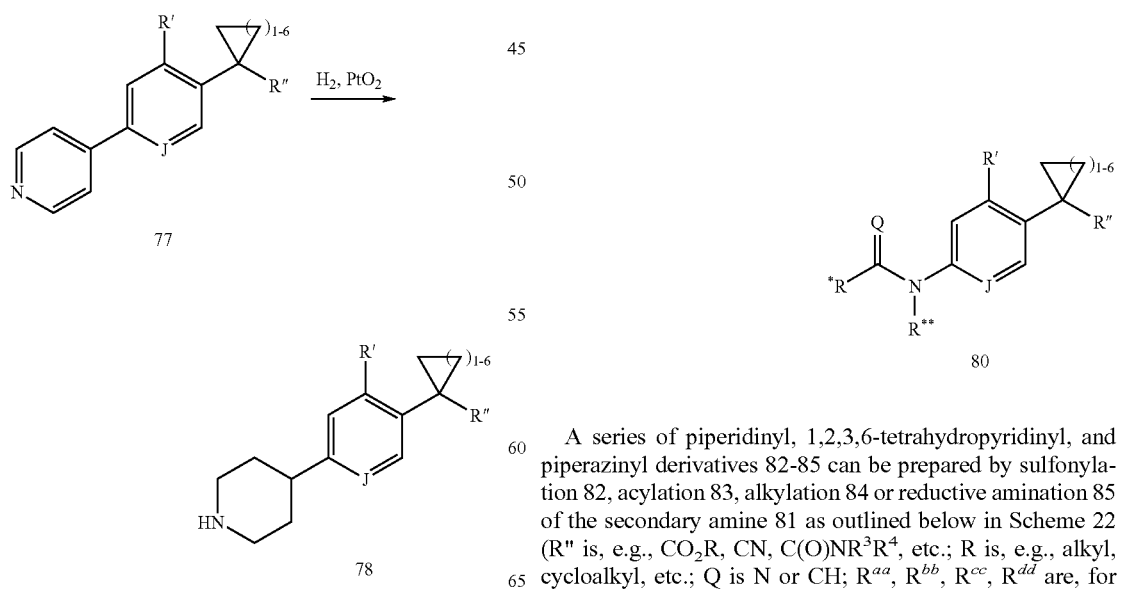

A series of piperidinyl, 1,2,3,6-tetrahydropyridinyl, and piperazinyl derivatives 82-85 can be prepared by sulfonylation 82, acylation 83, alkylation 84 or reductive amination 85 of the secondary amine 81 as outlined below in Scheme 22 (R" is, e.g., CO$_2$R, CN, C(O)NR$^3$R$^4$, etc.; R is, e.g., alkyl, cycloalkyl, etc.; Q is N or CH; R$^{aa}$, R$^{bb}$, R$^{cc}$, R$^{dd}$ are, for example, alkyl, cycloalkyl, aryl, heterocycloalkyl, heteroaryl, heterocycloalkyl and derivatives thereof).

Scheme 22

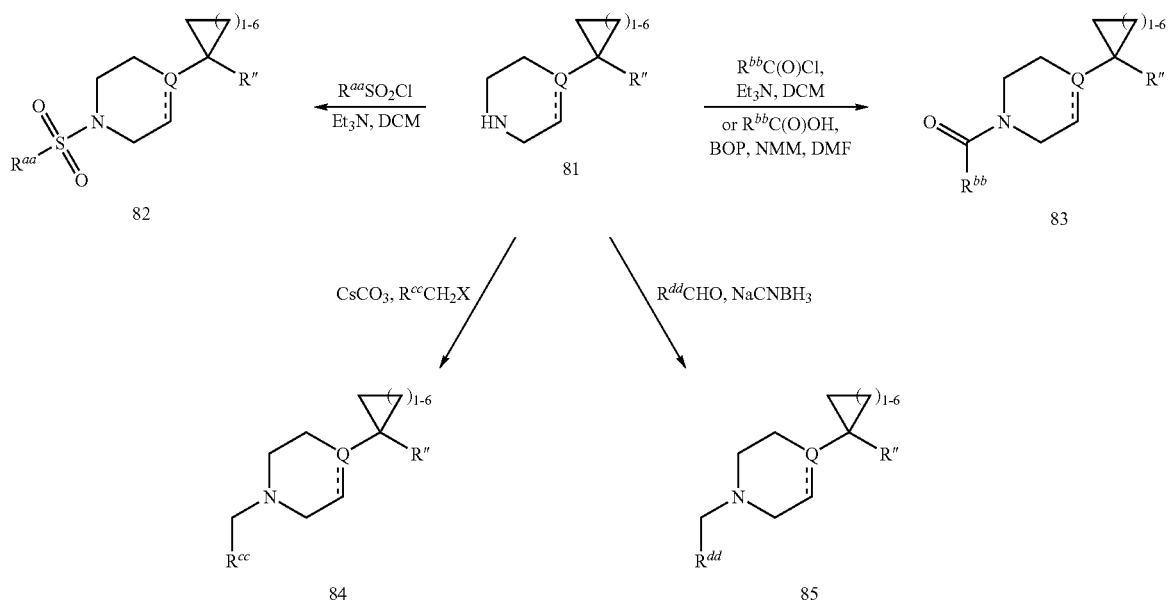

Methods

Compounds of the invention can modulate activity of 11βHSD1 and/or MR. The term "modulate" is meant to refer to an ability to increase or decrease activity of an enzyme or receptor. Accordingly, compounds of the invention can be used in methods of modulating 11βHSD1 and/or MR by contacting the enzyme or receptor with any one or more of the compounds or compositions described herein. In some embodiments, compounds of the present invention can act as inhibitors of 11βHSD1 and/or MR. In further embodiments, the compounds of the invention can be used to modulate activity of 11βHSD1 and/or MR in an individual in need of modulation of the enzyme or receptor by administering a modulating amount of a compound of the invention.

The present invention further provides methods of inhibiting the conversion of cortisone to cortisol in a cell, or inhibiting the production of cortisol in a cell, where conversion to or production of cortisol is mediated, at least in part, by 11βHSD1 activity. Methods of measuring conversion rates of cortisone to cortisol and vice versa, as well as methods for measuring levels of cortisone and cortisol in cells, are routine in the art.

The present invention further provides methods of increasing insulin sensitivity of a cell by contacting the cell with a compound of the invention. Methods of measuring insulin sensitivity are routine in the art.

The present invention further provides methods of treating disease associated with activity or expression, including abnormal activity and overexpression, of 11βHSD1 and/or MR in an individual (e.g., patient) by administering to the individual in need of such treatment a therapeutically effective amount or dose of a compound of the present invention or a pharmaceutical composition thereof. Example diseases can include any disease, disorder or condition that is directly or indirectly linked to expression or activity of the enzyme or receptor. An 11βHSD1-associated disease can also include any disease, disorder or condition that can be prevented, ameliorated, or cured by modulating enzyme activity.

Examples of 11βHSD1-associated diseases include obesity, diabetes, glucose intolerance, insulin resistance, hyperglycemia, hypertension, hyperlipidemia, cognitive impairment, dementia, glaucoma, cardiovascular disorders, osteoporosis, and inflammation. Further examples of 11βHSD1-associated diseases include metabolic syndrome, type 2 diabetes, androgen excess (hirsutism, menstrual irregularity, hyperandrogenism) and polycystic ovary syndrome (PCOS).

The present invention further provides methods of modulating MR activity by contacting the MR with a compound of the invention, pharmaceutically acceptable salt, prodrug, or composition thereof. In some embodiments, the modulation can be inhibition. In further embodiments, methods of inhibiting aldosterone binding to the MR (optionally in a cell) are provided. Methods of measuring MR activity and inhibition of aldosterone binding are routine in the art.

The present invention further provides methods of treating a disease associated with activity or expression of the MR. Examples of diseases associated with activity or expression of the MR include, but are not limited to hypertension, as well as cardiovascular, renal, and inflammatory pathologies such as heart failure, atherosclerosis, arteriosclerosis, coronary artery disease, thrombosis, angina, peripheral vascular disease, vascular wall damage, stroke, dyslipidemia, hyperlipoproteinaemia, diabetic dyslipidemia, mixed dyslipidemia, hypercholesterolemia, hypertriglyceridemia, and those associated with type 1 diabetes, type 2 diabetes, obesity metabolic syndrome, insulin resistance and general aldosterone-related target organ damage.

As used herein, the term "cell" is meant to refer to a cell that is in vitro, ex vivo or in vivo. In some embodiments, an ex vivo cell can be part of a tissue sample excised from an organism such as a mammal. In some embodiments, an in vitro cell can be a cell in a cell culture. In some embodiments, an in vivo cell is a cell living in an organism such as a mammal. In some embodiments, the cell is an adipocyte, a pancreatic cell, a hepatocyte, neuron, or cell comprising the eye.

As used herein, the term "contacting" refers to the bringing together of indicated moieties in an in vitro system or an in vivo system. For example, "contacting" the 11βHSD1 enzyme with a compound of the invention includes the administration of a compound of the present invention to an individual or patient, such as a human, having 11βHSD1, as well as, for example, introducing a compound of the invention into a sample containing a cellular or purified preparation containing the 11βHSD1 enzyme.

As used herein, the term "individual" or "patient," used interchangeably, refers to any animal, including mammals, preferably mice, rats, other rodents, rabbits, dogs, cats, swine, cattle, sheep, horses, or primates, and most preferably humans.

As used herein, the phrase "therapeutically effective amount" refers to the amount of active compound or pharmaceutical agent that elicits the biological or medicinal response that is being sought in a tissue, system, animal, individual or human by a researcher, veterinarian, medical doctor or other clinician, which includes one or more of the following:

(1) preventing the disease; for example, preventing a disease, condition or disorder in an individual who may be predisposed to the disease, condition or disorder but does not yet experience or display the pathology or symptomatology of the disease (non-limiting examples are preventing metabolic syndrome, hypertension, obesity, insulin resistance, hyperglycemia, hyperlipidemia, type 2 diabetes, androgen excess (hirsutism, menstrual irregularity, hyperandrogenism) and polycystic ovary syndrome (PCOS);

(2) inhibiting the disease; for example, inhibiting a disease, condition or disorder in an individual who is experiencing or displaying the pathology or symptomatology of the disease, condition or disorder (i.e., arresting further development of the pathology and/or symptomatology) such as inhibiting the development of metabolic syndrome, hypertension, obesity, insulin resistance, hyperglycemia, hyperlipidemia, type 2 diabetes, androgen excess (hirsutism, menstrual irregularity, hyperandrogenism) or polycystic ovary syndrome (PCOS), stabilizing viral load in the case of a viral infection; and (3) ameliorating the disease; for example, ameliorating a disease, condition or disorder in an individual who is experiencing or displaying the pathology or symptomatology of the disease, condition or disorder (i.e., reversing the pathology and/or symptomatology) such as decreasing the severity of metabolic syndrome, hypertension, obesity, insulin resistance, hyperglycemia, hyperlipidemia, type 2 diabetes, androgen excess (hirsutism, menstrual irregularity, hyperandrogenism) and polycystic ovary syndrome (PCOS), or lowering viral load in the case of a viral infection.

Pharmaceutical Formulations and Dosage Forms

When employed as pharmaceuticals, the compounds of Formula I can be administered in the form of pharmaceutical compositions. These compositions can be prepared in a manner well known in the pharmaceutical art, and can be administered by a variety of routes, depending upon whether local or systemic treatment is desired and upon the area to be treated. Administration may be topical (including ophthalmic and to mucous membranes including intranasal, vaginal and rectal delivery), pulmonary (e.g., by inhalation or insufflation of powders or aerosols, including by nebulizer; intratracheal, intranasal, epidermal and transdermal), ocular, oral or parenteral. Methods for ocular delivery can include topical administration (eye drops), subconjunctival, periocular or intravitreal injection or introduction by balloon catheter or ophthalmic inserts surgically placed in the conjunctival sac. Parenteral administration includes intravenous, intraarterial, subcutaneous, intraperitoneal or intramuscular injection or infusion; or intracranial, e.g., intrathecal or intraventricular, administration. Parenteral administration can be in the form of a single bolus dose, or may be, for example, by a continuous perfusion pump. Pharmaceutical compositions and formulations for topical administration may include transdermal patches, ointments, lotions, creams, gels, drops, suppositories, sprays, liquids and powders. Conventional pharmaceutical carriers, aqueous, powder or oily bases, thickeners and the like may be necessary or desirable.

This invention also includes pharmaceutical compositions which contain, as the active ingredient, one or more of the compounds of the invention above in combination with one or more pharmaceutically acceptable carriers. In making the compositions of the invention, the active ingredient is typically mixed with an excipient, diluted by an excipient or enclosed within such a carrier in the form of, for example, a capsule, sachet, paper, or other container. When the excipient serves as a diluent, it can be a solid, semi-solid, or liquid material, which acts as a vehicle, carrier or medium for the active ingredient. Thus, the compositions can be in the form of tablets, pills, powders, lozenges, sachets, cachets, elixirs, suspensions, emulsions, solutions, syrups, aerosols (as a solid or in a liquid medium), ointments containing, for example, up to 10% by weight of the active compound, soft and hard gelatin capsules, suppositories, sterile injectable solutions, and sterile packaged powders.

In preparing a formulation, the active compound can be milled to provide the appropriate particle size prior to combining with the other ingredients. If the active compound is substantially insoluble, it can be milled to a particle size of less than 200 mesh. If the active compound is substantially water soluble, the particle size can be adjusted by milling to provide a substantially uniform distribution in the formulation, e.g. about 40 mesh.

Some examples of suitable excipients include lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, water, syrup, and methyl cellulose. The formulations can additionally include: lubricating agents such as talc, magnesium stearate, and mineral oil; wetting agents; emulsifying and suspending agents; preserving agents such as methyl- and propylhydroxy-benzoates; sweetening agents; and flavoring agents. The compositions of the invention can be formulated so as to provide quick, sustained or delayed release of the active ingredient after administration to the patient by employing procedures known in the art.

The compositions can be formulated in a unit dosage form, each dosage containing from about 5 to about 100 mg, more usually about 10 to about 30 mg, of the active ingredient. The term "unit dosage forms" refers to physically discrete units suitable as unitary dosages for human subjects and other mammals, each unit containing a predetermined quantity of active material calculated to produce the desired therapeutic effect, in association with a suitable pharmaceutical excipient.

The active compound can be effective over a wide dosage range and is generally administered in a pharmaceutically effective amount. It will be understood, however, that the amount of the compound actually administered will usually be determined by a physician, according to the relevant circumstances, including the condition to be treated, the chosen route of administration, the actual compound administered, the age, weight, and response of the individual patient, the severity of the patients symptoms, and the like.

For preparing solid compositions such as tablets, the principal active ingredient is mixed with a pharmaceutical excipient to form a solid preformulation composition containing a homogeneous mixture of a compound of the present invention. When referring to these preformulation compositions as homogeneous, the active ingredient is typically dispersed evenly throughout the composition so that the composition can be readily subdivided into equally effective unit dosage forms such as tablets, pills and capsules. This solid preformulation is then subdivided into unit dosage forms of the type described above containing from, for example, 0.1 to about 500 mg of the active ingredient of the present invention.

The tablets or pills of the present invention can be coated or otherwise compounded to provide a dosage form affording the advantage of prolonged action. For example, the tablet or pill can comprise an inner dosage and an outer dosage component, the latter being in the form of an envelope over the former. The two components can be separated by an enteric layer which serves to resist disintegration in the stomach and permit the inner component to pass intact into the duodenum or to be delayed in release. A variety of materials can be used for such enteric layers or coatings, such materials including a number of polymeric acids and mixtures of polymeric acids with such materials as shellac, cetyl alcohol, and cellulose acetate.

The liquid forms in which the compounds and compositions of the present invention can be incorporated for administration orally or by injection include aqueous solutions, suitably flavored syrups, aqueous or oil suspensions, and flavored emulsions with edible oils such as cottonseed oil, sesame oil, coconut oil, or peanut oil, as well as elixirs and similar pharmaceutical vehicles.

Compositions for inhalation or insufflation include solutions and suspensions in pharmaceutically acceptable, aqueous or organic solvents, or mixtures thereof, and powders. The liquid or solid compositions may contain suitable pharmaceutically acceptable excipients as described supra. In some embodiments, the compositions are administered by the oral or nasal respiratory route for local or systemic effect. Compositions in can be nebulized by use of inert gases. Nebulized solutions may be breathed directly from the nebulizing device or the nebulizing device can be attached to a face masks tent, or intermittent positive pressure breathing machine. Solution, suspension, or powder compositions can be administered orally or nasally from devices which deliver the formulation in an appropriate manner.

The amount of compound or composition administered to a patient will vary depending upon what is being administered, the purpose of the administration, such as prophylaxis or therapy, the state of the patient, the manner of administration, and the like. In therapeutic applications, compositions can be administered to a patient already suffering from a disease in an amount sufficient to cure or at least partially arrest the symptoms of the disease and its complications. Effective doses will depend on the disease condition being treated as well as by the judgment of the attending clinician depending upon factors such as the severity of the disease, the age, weight and general condition of the patient, and the like.

The compositions administered to a patient can be in the form of pharmaceutical compositions described above. These compositions can be sterilized by conventional sterilization techniques, or may be sterile filtered. Aqueous solutions can be packaged for use as is, or lyophilized, the lyophilized preparation being combined with a sterile aqueous carrier prior to administration. The pH of the compound preparations typically will be between 3 and 11, more preferably from 5 to 9 and most preferably from 7 to 8. It will be understood that use of certain of the foregoing excipients, carriers, or stabilizers will result in the formation of pharmaceutical salts.

The therapeutic dosage of the compounds of the present invention can vary according to, for example, the particular use for which the treatment is made, the manner of administration of the compound, the health and condition of the patient, and the judgment of the prescribing physician. The proportion or concentration of a compound of the invention in a pharmaceutical composition can vary depending upon a number of factors including dosage, chemical characteristics (e.g., hydrophobicity), and the route of administration. For example, the compounds of the invention can be provided in an aqueous physiological buffer solution containing about 0.1 to about 10% w/v of the compound for parenteral administration. Some typical dose ranges are from about 1 μg/kg to about 1 g/kg of body weight per day. In some embodiments, the dose range is from about 0.01 mg/kg to about 100 mg/kg of body weight per day. The dosage is likely to depend on such variables as the type and extent of progression of the disease or disorder, the overall health status of the particular patient, the relative biological efficacy of the compound selected, formulation of the excipient, and its route of administration. Effective doses can be extrapolated from dose-response curves derived from in vitro or animal model test systems.

The compounds of the invention can also be formulated in combination with one or more additional active ingredients which can include any pharmaceutical agent such as antiviral agents, antibodies, immune suppressants, anti-inflammatory agents and the like.

Labeled Compounds and Assay Methods

Another aspect of the present invention relates to radio-labeled compounds of the invention that would be useful not only in radio-imaging but also in assays, both in vitro and in vivo, for localizing and quantitating the enzyme in tissue samples, including human, and for identifying ligands by inhibition binding of a radio-labeled compound. Accordingly, the present invention includes enzyme assays that contain such radio-labeled compounds.

The present invention further includes isotopically-labeled compounds of the invention. An "isotopically" or "radio-labeled" compound is a compound of the invention where one or more atoms are replaced or substituted by an atom having an atomic mass or mass number different from the atomic mass or mass number typically found in nature (i.e., naturally occurring). Suitable radionuclides that may be incorporated in compounds of the present invention include but are not limited to $^2H$ (also written as D for deuterium), $^3H$ (also written as T for tritium), $^{11}C$, $^{13}C$, $^{14}C$, $^{13}N$, $^{15}N$, $^{15}O$, $^{17}O$, $^{18}O$, $^{18}F$, $^{35}S$, $^{36}Cl$, $^{82}Br$, $^{75}Br$, $^{76}Br$, $^{77}Br$, $^{123}I$, $^{124}I$, $^{125}I$ and $^{131}I$. The radionuclide that is incorporated in the instant radio-labeled compounds will depend on the specific application of that radio-labeled compound. For example, for in vitro receptor labeling and competition assays, compounds that incorporate $^3H$, $^{14}C$, $^{82}Br$, $^{125}I$, $^{131}I$, $^{35}S$ or will generally be most useful. For radio-imaging applications $^{11}C$, $^{18}F$, $^{125}I$, $^{123}I$, $^{124}I$, $^{131}I$, $^{75}Br$, $^{76}Br$ or $^{77}Br$ will generally be most useful.

It is understood that a "radio-labeled" or "labeled compound" is a compound that has incorporated at least one radionuclide. In some embodiments the radionuclide is selected from the group consisting of $^3H$, $^{14}C$, $^{125}I$, $^{35}S$ and $^{82}Br$.

Synthetic methods for incorporating radio-isotopes into organic compounds are applicable to compounds of the invention and are well known in the art.

A radio-labeled compound of the invention can be used in a screening assay to identify/evaluate compounds. In general terms, a newly synthesized or identified compound (i.e., test compound) can be evaluated for its ability to reduce binding of the radio-labeled compound of the invention to the enzyme. Accordingly, the ability of a test compound to compete with the radio-labeled compound for binding to the enzyme directly correlates to its binding affinity.

Kits

The present invention also includes pharmaceutical kits useful, for example, in the treatment or prevention of 11βHSD1-associated diseases or disorders, obesity, diabetes and other diseases referred to herein which include one or more containers containing a pharmaceutical composition comprising a therapeutically effective amount of a compound of the invention. Such kits can further include, if desired, one or more of various conventional pharmaceutical kit components, such as, for example, containers with one or more pharmaceutically acceptable carriers, additional containers, etc., as will be readily apparent to those skilled in the art. Instructions, either as inserts or as labels, indicating quantities of the components to be administered, guidelines for administration, and/or guidelines for mixing the components, can also be included in the kit.

The invention will be described in greater detail by way of specific examples. The following examples are offered for illustrative purposes, and are not intended to limit the invention in any manner. Those of skill in the art will readily recognize a variety of noncritical parameters which can be changed or modified to yield essentially the same results.

EXAMPLES

Example 1

(3S)-1-((1-(4-Chlorophenyl)cyclopropyl)carbonyl)pyrrolidin-3-ol

To a solution of 1-(4-chlorophenyl)cyclopropanecarboxylic acid (50 mg, 0.25 mmol), (3S)-pyrrolidin-3-ol (24.4 mg, 0.28 mmol) and BOP (116.0 mg, 0.26 mmol) in 0.4 mL DMF was added hunig base (0.066 ml, 0.38 mmol). The mixture was stirred at room temperature overnight and directly purified by prep. HPLC to provide (3S)-1-((1-(4-chlorophenyl)cyclopropyl)carbonyl)pyrrolidin-3-ol (20 mg). LCMS: m/z 266.0 (M+H)$^+$; 553.1 (2M+Na)$^+$.

Example 2

(3S)-1-[(1-Phenylcyclopropyl)carbonyl]pyrrolidin-3-ol

This compound was prepared using procedures analogous to those described for Example 1. LCMS: m/z 232.1 (M+H)$^+$.

Example 3

(3R)-1-[(1-Phenylcyclopropyl)carbonyl]pyrrolidin-3-ol

This compound was prepared using procedures analogous to those described for Example 1. LCMS: m/z 232.1 (M+H)$^+$.

Example 4

1-([1-(4-Chlorophenyl)cyclopropyl]carbonyl)-2-phenylpyrrolidine

To a solution of 30 mg of 1-(4-chlorophenyl)cyclopropanecarboxylic acid and 81 mg BOP reagent in 0.5 mL methylene chloride wad added 27 mg of 2-phenylpyrrolidine, followed by the addition of 53 ul of Hunig base. The reaction mixture was stirred at r.t. for 2 hours and directly purified by flash column using ethyl/hexane as the eluting solvent to provide the desired 1-{[1-(4-chlorophenyl)cyclopropyl]carbonyl}-2-phenylpyrrolidine. LCMS (ESI): 326.1 (M+H$^+$).

Example 5

1'-{[1-(4-Chlorophenyl)cyclopropyl]carbonyl}-2,3-dihydrospiro[indene-1,4'-piperidine]

This compound was prepared using procedures analogous to those described for Example 4.

Example 6

1-{[1-(4-Chlorophenyl)cyclopropyl]carbonyl}-3-phenylpiperidine

This compound was prepared using procedures analogous to those described for Example 4. (ESI): 340.1 (M+H$^+$). Cal. MS: 339.1 Ms(ESI): (M+H)$^+$=340.1.

Example 7

1-{[1-(4-Chlorophenyl)cyclopropyl]carbonyl}-4-phenylpiperidine-4-carbonitrile

This compound was prepared using procedures analogous to those described for Example 4. (ESI): 365.0 (M+H$^+$).

Example 8

1-{[1-(4-Chlorophenyl)cyclopropyl]carbonyl}-4-phenoxypiperidine

This compound was prepared using procedures analogous to those described for Example 4. (ESI): 356.0 (M+H$^+$).

Example 9

1'-{[1-(4-chlorophenyl)cyclopropyl]carbonyl}-1-methylspiro[indole-3,4'-piperidin]-2(1H)-one This compound was prepared using procedures analogous to those described for Example 4. (ESI): 395.1 (M+H$^+$).

Example 10

1-{[1-(4-Chlorophenyl)cyclopropyl]carbonyl}-4-phenylpiperidin-4-ol

This compound was prepared using procedures analogous to those described for Example 4. (ESI): 356.1 (M+H$^+$).

Example 11

Methyl 3-(1-{[1-(4-chlorophenyl)cyclopropyl]carbonyl}piperidin-4-yl)benzoate

This compound was prepared using procedures analogous to those described for Example 4. (ESI): 398.1 (M+H$^+$).

Example 12

4-Benzyl-1-{[1-(4-chlorophenyl)cyclopropyl]carbonyl}piperidin-4-ol

This compound was prepared using procedures analogous to those described for Example 4. (ESI): 370.1 (M+H$^+$).

Example 13

4-(4-tert-Butyl-1,3-thiazol-2-yl)-1-{[1-(4-chlorophenyl)cyclopropyl]carbonyl}piperidine This compound was prepared using procedures analogous to those described for Example 4. (ESI): 403.1 (M+H$^+$).

Example 14

Methyl 4-(1-{[1-(4-chlorophenyl)cyclopropyl]carbonyl}piperidin-4-yl)benzoate

This compound was prepared using procedures analogous to those described for Example 4. (ESI): 398.1 (M+H$^+$).

Example 15 tert-Butyl 1'-{[1-(4-chlorophenyl)cyclopropyl]carbonyl}spiro[indole-3,4'-piperidine]-1(2H)-carboxylate This compound was prepared using procedures analogous to those described for Example 4. (ESI): 467.1 (M+H$^+$).

Example 16

1'-{[1-(4-Chlorophenyl)cyclopropyl]carbonyl}-2,3-dihydro-1H-spiro[isoquinoline-4,4'-piperidine]

This compound was prepared using procedures analogous to those described for Example 1. (ESI): 381.1 (M+H$^+$).

Example 17

8-{[1-(4-Chlorophenyl)cyclopropyl]carbonyl}-3-phenyl-1-oxa-2,8-diazaspiro[4.5]dec-2-ene This compound was prepared using procedures analogous to those described for Example 1. (ESI): 395.1 (M+H$^+$).

Example 18

1-{[1-(4-Chlorophenyl)cyclopropyl]carbonyl}-4-[3-(trifluoromethyl)phenyl]piperidine This compound was prepared using procedures analogous to those described for Example 4. (ESI): 408.1 (M+H$^+$).

Example 19

1-{[1-(4-Chlorophenyl)cyclopropyl]carbonyl}-4-(4-phenyl-1,3-thiazol-2-yl)piperidine This compound was prepared using procedures analogous to those described for Example 1. (ESI): 423.1 (M+H$^+$).

Example 20 tert-Butyl 7-{[1-(4-chlorophenyl)cyclopropyl]carbonyl}-2,7-diazaspiro[4.5]decane-2-carboxylate This compound was prepared using procedures analogous to those described for Example 1. Ms(ESI): (M+Na)$^+$=441.2, 363.0 (M-$^t$Bu).

Example 21 tert-Butyl 1'-{[1-(4-chlorophenyl)cyclopropyl]carbonyl}-1H-spiro[isoquinoline-4,4'-piperidine]-2(3H)-carboxylate This compound was prepared using procedures analogous to those described for Example 1. (ESI): 481.2 (M+H$^+$).

Example 22 tert-Butyl 7-{[1-(4-chlorophenyl)cyclopropyl]carbonyl}-2,7-diazaspiro[3.5]nonane-2-carboxylate This compound was prepared using procedures analogous to those described for Example 1. (ESI): 405.1 (M+H$^+$), 349.1 (M-$^t$Bu).

Example 23

4-(1-{[1-(4-Chlorophenyl)cyclopropyl]carbonyl}pyrrolidin-3-yl)pyridine

This compound was prepared using procedures analogous to those described for example 1. LCMS (ESI): 327.1 (M+H$^+$).

Example 24

4-((3S)-1-{[1-(4-Chlorophenyl)cyclopropyl]carbonyl}pyrrolidin-3-yl)pyridine

This compound was obtained by chiral HPLC purification of 4-(1-{[1-(4-chlorophenyl)cyclopropyl]carbonyl}pyrrolidin-3-yl)pyridine of Example 23. LCMS (ESI): 327.0 (M+H$^+$).

Example 25

4-((3R)-1-{[1-(4-Chlorophenyl)cyclopropyl]carbonyl}pyrrolidin-3-yl)pyridine

This compound was obtained by chiral HPLC purification of 4-(1-{[1-(4-chlorophenyl)cyclopropyl]carbonyl}pyrrolidin-3-yl)pyridine. LCMS (ESI): 327.0 (M+H$^+$).

Example 26

1-{[1-(4-Chlorophenyl)cyclopropy]carbonyl}-3-phenylpyrrolidine

This compound was prepared using procedures analogous to those described for Example 4. LCMS (ESI): 326.1 (M+H$^+$).

Example 27

2-(1-{[1-(4-Chlorophenyl)cyclopropyl]
carbonyl}pyrrolidin-3-yl)pyrazine

This compound was prepared using procedures analogous to those described for Example 4. LCMS (ESI): 328.0 (M+H$^+$).

Example 28

3-(1-{[1-(4-Chlorophenyl)cyclopropyl]
carbonyl}pyrrolidin-3-yl)pyridine

This compound was prepared using procedures analogous to those described for Example 4. LCMS (ESI): 327.0 (M+H$^+$).

Example 29

(3R)-1-{[1-(4-Chlorophenyl)cyclopropyl]carbonyl}-
3-phenylpyrrolidine

This compound was prepared using procedures analogous to those described for example 4. LCMS (ESI): 326.0 (M+H$^+$).

Example 30

3-(3-Chlorophenyl)-1-{[1-(4-chlorophenyl)cyclopropyl]carbonyl}pyrrolidine

This compound was prepared using procedures analogous to those described for example 4. LCMS (ESI): 360.0 (M+H$^+$).

Example 31

1-{[1-(4-chlorophenyl)cyclopropyl]carbonyl}-3-[3-
(trifluoromethyl)phenyl]pyrrolidine This compound was prepared using procedures analogous to those described for example 4. LCMS (ESI): 394.0 (M+H$^+$).

Example 32

2-(1-{[1-(4-Chlorophenyl)cyclopropyl]
carbonyl}pyrrolidin-3-yl)pyridine

This compound was prepared using procedures analogous to those described for example 4. LCMS (ESI): 327.1 (M+H$^+$).

Example 33

1-{[1-(4-Chlorophenyl)cyclopropyl]carbonyl}-3-
phenylpyrrolidin-3-ol

This compound was prepared using procedures analogous to those described for example 1. LCMS (ESI): 342.1 (M+H$^+$).

Example 34

1-{[1-(4-Chlorophenyl)cyclopropyl]carbonyl}-3-(2-
naphthyl)pyrrolidine

This compound was prepared using procedures analogous to those described for example 4. LCMS (ESI): 376.1 (M+H$^+$).

Example 35

3-Benzyl-1-{[1-(4-chlorophenyl)cyclopropyl]
carbonyl}pyrrolidine

This compound was prepared using procedures analogous to those described for example 4. LCMS (ESI): 340.1 (M+H$^+$).

Example 36

1-{[1-(4-Chlorophenyl)cyclopropyl]carbonyl}-3-
(phenylsulfonyl)pyrrolidine

This compound was prepared using procedures analogous to those described for example 4. LCMS (ESI): 390.1 (M+H$^+$).

Example 37

2-{[1-(4-Chlorophenyl)cyclopropyl]carbonyl}-5-(4-
fluorophenyl)-2,5-diazabicyclo[2.2.1]heptane This compound was prepared using procedures analogous to those described for example 1. LCMS (ESI): 371.1 (M+H$^+$).

Example 38

1-{[1-(4-Chlorophenyl)cyclopropyl]carbonyl}-3-(4-
phenoxyphenyl)pyrrolidine

This compound was prepared using procedures analogous to those described for example 4. LCMS (ESI): 418.0 (M+H$^+$).

Example 39

Methyl (3S,4R)-1-{[1-(4-chlorophenyl)cyclopropyl]
carbonyl}-4-phenylpyrrolidine-3-carboxylate This compound was prepared using procedures analogous to those described for example 4. LCMS (ESI): 384.1 (M+H$^+$).

Example 40

1-{[1-(4-Chlorophenyl)cyclopropyl]carbonyl}-3-(4-
methoxyphenyl)pyrrolidine

This compound was prepared using procedures analogous to those described for example 4. LCMS: m/z 356.1 (M+H$^+$).

Example 41

1-((1-(4-chlorophenyl)cyclopropyl)carbonyl)-3-(4-trifluorophenyl)pyrrolidine

This compound was prepared using procedures analogous to those described for example 4. LCMS: m/z 394.0 (M+H)$^+$.

Example 42

3-(4-chlorophenyl)-1-{[1-(4-chlorophenyl)cyclopropyl]carbonyl}pyrrolidine

This compound was prepared using procedures analogous to those described for example 4. LCMS: m/z 360.0 (M+H)$^+$; 382.0 (M+Na)$^+$.

Example 43

4-(1-{[1-(2,4-dichlorophenyl)cyclopropyl]carbonyl}pyrrolidin-3-yl)pyridine

This compound was prepared using procedures analogous to those described for example 4. LCMS: m/z 361.0 (M+); 384.0 (M+Na)+.

Example 44

4-(1-{[1-(4-methoxyphenyl)cyclopropyl]carbonyl}pyrrolidin-3-yl)pyridine

This compound was prepared using procedures analogous to those described for example 4. LCMS: m/z 323.1 (M+H)$^+$; 345.0 (M+Na)$^+$.

Example 45

4-(1-{[144-Methylphenyl)cyclopropyl]carbonyl}pyrrolidin-3-yl)pyridine

This compound was prepared using procedures analogous to those described for example 4. LCMS: m/z 307.1 (M+H)$^+$; 329.1 (M+Na)$^+$.

Example 46

1-{[1-(4-Chlorophenyl)cyclopropyl]carbonyl}-4-phenylpiperidine

This compound was prepared using procedures analogous to those described for example 4. LCMS: m/z 340.1 (M+H)$^+$; 362.1 (M+Na)$^+$; 701.2 (2M+Na)$^+$.

Example 47

3-{[1-(4-Chlorophenyl)cyclopropyl]carbonyl}-1,2,3,4,4a,5,6,10b-octahydrobenzo[f]isoquinoline This compound was prepared using procedures analogous to those described for example 4. LCMS: (M+H)$^+$=366.0/368.1.

Example 48

2-{[1-(4-Chlorophenyl)cyclopropyl]carbonyl}-2,3,3a,4,5,9b-hexahydro-1H-benzo[e]isoindole This compound was prepared using procedures analogous to those described for example 4. LCMS: (M+H)$^+$=352.1/354.0.

Example 49

2-{[1-(4-Chlorophenyl)cyclopropyl]carbonyl}-1,2,3,3a,8,8a-hexahydroindeno[1,2-c]pyrrole This compound was prepared using procedures analogous to those described for example 4. LCMS: (M+H)$^+$=338.0/340.0.

Example 50

1'-{[1-(4-Chlorophenyl)cyclopropyl]carbonyl}-1,3-dihydrospiro[indene-2,4'-piperidine]

This compound was prepared using procedures analogous to those described for example 4. LCMS: (M+H)$^+$=366.1/368.1.

Example 52

3-{[1-(4-Chlorophenyl)cyclopropyl]carbonyl}-2,3,4,4a,5,6-hexahydro-1H-pyrazino[1,2-a]quinoline This compound was prepared using procedures analogous to those described for example 4. LCMS: (M+H)$^+$=367.1/369.1.

Example 53

2-{[1-(4-Chlorophenyl)cyclopropyl]carbonyl}-1,2,3,4,10,10a-hexahydropyrazino[1,2-a]indole This compound was prepared using procedures analogous to those described for example 4, LCMS: (M+H)$^+$=353.1/355.1

Example 54

1'-{[1-(4-Chlorophenyl)cyclopropyl]carbonyl}spiro[chromene-2,4'-piperidine]

This compound was prepared using procedures analogous to those described for example 4, LCMS: (M+H)$^+$=380.1/382.1.

Example 55

1'-{[1-(4-Chlorophenyl)cyclopropyl]carbonyl}-3H-spiro[2-benzofuran-1,4'-piperidine]

This compound was prepared using procedures analogous to those described for example 4, LCMS: (M+H)$^+$=368.1/369.2.

Example 56

1'-{[1-(4-Chlorophenyl)cyclopropyl]carbonyl}spiro[indole-3,4'-piperidin]-2(1H)-one This compound was prepared using procedures analogous to those described for example 4, LCMS: $(M+H)^+=381.0/383.0$.

Example 57

8-{[1-(4-Chlorophenyl)cyclopropyl]carbonyl}-2,8-diazaspiro[4.5]decan-3-one

This compound was prepared using procedures analogous to those described for example 4, LCMS: $(M+H)^+=333.0/335.1$.

Example 58

2-{[1-(4-Chlorophenyl)cyclopropyl]carbonyl}-1,2,3,4-tetrahydroisoquinoline

This compound was prepared using procedures analogous to those described for example 4.

Example 59

6-{[1-(4-Chlorophenyl)cyclopropyl]carbonyl}-4,5,6,7-tetrahydrothieno[2,3-c]pyridine This compound was prepared using procedures analogous to those described for example 4, LCMS: $(M+H)^+=318.0/320.0$.

Example 60

1-{[1-(4-Chlorophenyl)cyclopropyl]carbonyl}indoline

This compound was prepared using procedures analogous to those described for example 4, LCMS: $(M+H)^+=298.0/300.0$.

Example 61

2-{[1-(4-Chlorophenyl)cyclopropyl]carbonyl}isoindoline

This compound was prepared using procedures analogous to those described for example 4, LCMS: $(M+H)^+=298.0/300.0$.

Example 62

8-{[1-(4-Chlorophenyl)cyclopropyl]carbonyl}-1-phenyl-1,3,8-triazaspiro[4.5]decan-4-one This compound was prepared using procedures analogous to those described for example 4, LCMS: $(M+H)^+=410.1/412.1$.

Example 63

4-Benzylidene-1-{[1-(4-chlorophenyl)cyclopropyl]carbonyl}piperidine

This compound was prepared using procedures analogous to those described for example 4, LCMS: $(M+H)^+=352.1/354.1$.

Example 64

1'-{[1-(4-Chlorophenyl)cyclopropyl]carbonyl}-1,4'-bipiperidine

This compound was prepared using procedures analogous to those described for example 4, LCMS: $(M+H)^+=347.2/349.2$.

Example 65

4-(1-{[1-(4-Chlorophenyl)cyclopropyl]carbonyl}piperidin-4-yl)pyridine

This compound was prepared using procedures analogous to those described for example 4, LCMS: $(M+H)^+=341.1/343.1$.

Example 66

1-{[1-(4-Chlorophenyl)cyclopropyl]carbonyl}-3-(4-fluorophenyl)pyrrolidine

This compound was prepared using procedures analogous to those described for example 4, LCMS: $(M+H)^+=344.1/346.1$.

Example 67

1-{[1-(4-Chlorophenyl)cyclopropyl]carbonyl}-3-(3-fluorophenyl)pyrrolidine

This compound was prepared using procedures analogous to those described for example 4, LCMS: $(M-H)^+=344.1/346.1$.

Example 68

N-(1-{[1-(4-Chlorophenyl)cyclopropyl]carbonyl}piperidin-4-yl)-N-phenylpropanamide This compound was prepared using procedures analogous to those described for example 4, LCMS: $(M+H)^+=411.2/413.2$.

Example 69

2-{[1-(4-Chlorophenyl)cyclopropyl]carbonyl}octahydropyrrolo[1,2-a]pyrazine

This compound was prepared using procedures analogous to those described for example 4, LCMS: $(M+H)^+=305.2/307.1$.

Example 70

4-{[1-(4-Chlorophenyl)cyclopropyl]carbonyl}piperazine-1-carbaldehyde

This compound was prepared using procedures analogous to those described for example 4, LCMS: (M+H)$^+$=293.1/295.1.

Example 71

4-{[1-(4-Chlorophenyl)cyclopropyl]carbonyl}-2-methyl-1-phenylpiperazine

This compound was prepared using procedures analogous to those described for example 4, LCMS: (M+H)$^+$=355.2/357.2.

Example 72

1-{[1-(4-Chlorophenyl)cyclopropyl]carbonyl}-4-(pyridin-4-ylmethyl)piperazine

This compound was prepared using procedures analogous to those described for example 4, LCMS: (M+H)$^+$=356.1/358.1.

Example 73

1-{[1-(4-Chlorophenyl)cyclopropyl]carbonyl}-4-(2-thienylsulfonyl)piperazine

This compound was prepared using procedures analogous to those described for example 4, LCMS: (M+H)$^+$=411.0/412.9.

Example 74

2-(1-{[1-(4-Chlorophenyl)cyclopropyl]carbonyl}piperidin-2-yl)ethanol

This compound was prepared using procedures analogous to those described for example 4, LCMS: (M+H)$^+$=308.1/310.0.

Example 75

2-(1-{[1-(4-Chlorophenyl)cyclopropyl]carbonyl}piperidin-4-yl)ethanol

This compound was prepared using procedures analogous to those described for example 4, LCMS: (M+H)$^+$=308.1/310.0.

Example 76

1-{[1-(4-Chlorophenyl)cyclopropyl]carbonyl}-4-(4-fluorophenyl)piperidine

This compound was prepared using procedures analogous to those described for example 4, LCMS: (M+H)$^+$=358.1/360.1.

Example 77

4-(4-Chlorophenyl)-1-{[1-(4-chlorophenyl)cyclopropyl]carbonyl}-1,2,3,6-tetrahydropyridine This compound was prepared using procedures analogous to those described for example 4, LCMS: (M+H)$^+$=372.1/374.1.

Example 78

(1-{[1-(4-Chlorophenyl)cyclopropyl]carbonyl}piperidin-2-yl)methanol

This compound was prepared using procedures analogous to those described for example 4, LCMS: (M+H)$^+$=294.1/296.1.

Example 79

2-(1-{[1-(4-Chlorophenyl)cyclopropyl]carbonyl}pyrrolidin-2-yl)ethanol

This compound was prepared using procedures analogous to those described for example 4, LCMS: (M+H)$^+$=294.1/296.1.

Example 80

((2S)-1-{[1-(4-Chlorophenyl)cyclopropyl]carbonyl}pyrrolidin-2-yl)methanol

This compound was prepared using procedures analogous to those described for example 4, LCMS: (M+H)$^+$=280.1/282.1.

Example 81

((2R)-1-{[1-(4-Chlorophenyl)cyclopropyl]carbonyl}pyrrolidin-2-yl)methanol

This compound was prepared using procedures analogous to those described for example 4, LCMS: (M+H)$^+$=280.0/282.0.

Example 82

1'-{[1-(4-Chlorophenyl)cyclopropyl]carbonyl}spiro[1,2-benzisothiazole-3,3'-pyrrolidine]1,1-dioxide Step 1. Synthesis of N-(tert-butyl)benzenesulfonamide To a solution of benzenesulfonyl chloride (722 µL, 0.00566 mol), potassium carbonate (0.939 g, 0.00679 mol) in acetonitrile (15 mL, 0.29 mol) was added tert-butylamine (0.652 mL, 0.00623 mol). The resulting mixture was stirred at r.t. for 30 minutes, followed by filtration and concentration. The resulting residue was diluted with ethyl acetate, and the resulting solution was washed with water then with brine, then dried with MgSO$_4$ followed by concentration. The crude material was purified by flash chromatography on silica gel with 40% AcOEt in hexanes to give the desired compound (1.21 g, 85% yield). MS (ESI): 236.0 (M+Na$^+$).

Step 2: Synthesis of 2-(1-benzyl-3-hydroxypyrrolidin-3-yl)-N-(tert-butyl)benzenesulfonamide To a solution of N-(tert-butyl)benzenesulfonamide (536 mg, 0.00251 mol) in ether (10 mL, 0.1 mol) was added 1.7 M of tert-butyllithium in pentane (4.4 mL) under nitrogen at −78° C. The mixture was stirred at −78 Celsius for 15 min, then at 0 Celsius for 1 hour, and then cooled down to −78 Celsius again. A solution of 1-benzylpyrrolidin-3-one (400.0 mg, 0.002283 mol) in ether (3 mL) was added to the above solution. The reaction solution was stirred at −78 Celsius for 2 hours, then quenched with saturated NH$_4$Cl aqueous solution, and then extracted with EtOAc. The organic phase was washed with brine, then dried over MgSO$_4$. The residue was purified by flash chromatography on silica gel column with 30% AcOEt in hexanes to give the desired compound (350 mg, 39% yield). MS (ESI): 389.1 (M+H$^+$).

Step 3: Synthesis of 1'-benzylspiro[1,2-benzisothiazole-3,3'-pyrrolidine]1,1-dioxide To a solution of 2-(1-benzyl-3-hydroxypyrrolidin-3-yl)-N-(tert-butyl)benzene sulfonamide (350 mg, 0.00090 mol) in acetonitrile (15 mL, 0.29 mol) were added sodium iodide (418 mg, 0.00279 mol) and chlorotrimethylsilane (0.354 mL, 0.00279 mol). The reaction mixture was refluxed under nitrogen for 1 hour and then cooled down to room temperature, then quenched with 10% aqueous sodium thiosulfate solution (10 mL), and then extracted with EtOAc. The organic phase was washed with water then brine, and then dried over MgSO$_4$ followed by filtration. The filtrate was concentrated to give the desired compound (170 mg, 60% yield). MS (ESI): 315.0 (M+H$^+$).

Step 4: Synthesis of spiro[1,2-benzisothiazole-3,3'-pyrrolidine]1,1-dioxide

To a solution of 1'-benzylspiro[1,2-benzisothiazole-3,3'-pyrrolidine]1,1-dioxide (170 mg, 0.00054 mol) in methanol were added Pd black (150 mg) and formic acid (0.2 mL, 0.005 mol). The resulting reaction mixture was refluxed overnight, then cooled to room temperature, and then filtered and concentrated to give the desired compound (50 mg, 42% Yield). MS (ESI): 225.1 (M+H$^+$).

Step 5: Synthesis of 1'-{[1-(4-chlorophenyl)cyclopropyl]carbonyl}spiro[1,2-benzisothiazole-3,3'-pyrrolidine]1,1-dioxide To a solution of 1-(4-chlorophenyl)cyclopropanecarboxylic acid (40.0 mg, 0.000203 mol) in N,N-dimethylformamide (0.5 mL, 0.006 mol) at 0 Celsius were added spiro[1,2-benzisothiazole-3,3'-pyrrolidine]1,1-dioxide (45.6 mg, 0.000203 mol) and benzotriazol-1-yloxytris(dimethylamino)phosphonium hexafluorophosphate (99.0 mg, 0.000224 mol). The reaction mixture was stirred for 3 minutes, then N,N-Diisopropylethylamine (88.6 μL, 0.000508 mol) was added. The solution was then stirred at r.t. overnight. The crude material was purified by prep-HPLC to give the desired compound. MS (ESI): 404.0 (M+H$^+$).

Example 83

1'-{[1-(4-Chlorophenyl)cyclopropyl]carbonyl}-3H-spiro[2-benzofuran-1,3'-pyrrolidin]-3-one Step 1: Synthesis of tert-butyl 3-oxo-1'H,3H-spiro[2-benzofuran-1,3'-pyrrolidine]-1'-carboxylate To a solution of methyl-2-iodobenzoate (0.952 mL, 0.00648 mol) in tetrahydrofuran (10 mL, 0.1 mol) at −40 Celsius was added 1.0 M of isopropylmagnesium bromide in tetrahydrofuran (7.6 mL), and the mixture was stirred at −40 Celsius for 1 hour. A solution of tert-butyl 3-oxopyrrolidine-1-carboxylate (1000 mg, 0.005 mol) in THF (2 mL) was added to the above mixture, the resulting mixture was then warmed up to r.t and continued to be stirred at r. t. for 2 hours. The reaction was quenched with small amount of brine, then extracted with ethyl acetate, and then dried over MgSO$_4$ and concentrated. The residue was purified by flash chromatography on silica gel column with 40% AcOEt in hexanes to give the desired compound (0.9 g, 60% yield). MS (ESI): 312.0 (M+Na$^+$).

Step 2: Synthesis of 3H-spiro[2-benzofuran-1,3'-pyrrolidin]-3-one hydrochloride

Tert-butyl 3-oxo-1'H,3H-spiro[2-benzofuran-1,3'-pyrrolidine]-1'-carboxylate (900 mg, 0.003 mol) was added to 4 M of HCl in 1,4-dioxane (5 mL). The reaction mixture was stirred at room temperature for 60 min and then concentrated to give desired product (660 mg, 95% Yield). MS (ESI): 190.1 (M+H$^+$).

Step 3: Synthesis of 1'-{[1-(4-chlorophenyl)cyclopropyl]carbonyl}-3H-spiro[2-benzofuran-1,3'-pyrrolidin]-3-one This compound was prepared using procedures analogous to those described in example 82 (Step 5). MS (ESI): 368.1 (M+H$^+$).

Example 84

1'-({1-[4-(Pyridin-2-yloxy)phenyl]cyclopropyl}carbonyl)-3H-spiro[2-benzofuran-1,3'-pyrrolidin]-3-one This compound was prepared using procedures analogous to those for Example 83. MS (ESI): 427.1 (M+H$^+$) 449.1 (M+Na$^+$).

Example 85

1'-{[1-(4-Chlorophenyl)cyclobutyl]carbonyl}-3H-spiro[2-benzofuran-1,3'-pyrrolidin]-3-one This compound was prepared using procedures analogous to those for Example 83. MS (ESI): 382.1 (M+H$^+$)

Example 86

1'-{[1-(4-Methylphenyl)cyclopropyl]carbonyl}-3H-spiro[2-benzofuran-1,3'-pyrrolidin]-3-one This compound was prepared using procedures analogous to those for Example 83. MS (ESI): 348.1 (M+H$^+$).

Example 87

1'-{[1-(4-Methoxyphenyl)cyclopropyl]carbonyl}-3H-spiro[2-benzofuran-1,3'-pyrrolidin]-3-one This compound was prepared using procedures analogous to those for Example 83. MS (ESI): 364.1 (M+H$^+$).

Example 88

1'-{[1-(2,4-Dichlorophenyl)cyclopropyl]carbonyl}-3H-spiro[2-benzofuran-1,3'-pyrrolidin]-3-one This compound was prepared using procedures analogous to those for Example 83. MS (ESI): 402.0 (M+H$^+$).

Example 89

1'-{[1-(4-Chlorophenyl)cyclopropyl]carbonyl}-3H-spiro[2-benzofuran-1,3'-pyrrolidine]

Step 1: Synthesis of 1-benzyl-3-[2-(hydroxymethyl)phenyl]pyrrolidin-3-ol

To a solution of (2-iodophenyl)methanol (5.88 g, 0.0251 mol) in tetrahydrofuran (40 mL, 0.5 mol) at −78 Celsius was added 1.600 M of n-butyllithium in hexane (31.7 mL). The mixture was stirred at −4 celsius for 1 hour, then cooled to −78 Celsius. A solution of 1-benzylpyrrolidin-3-one (3.67 mL, 0.0228 mol) in THF (2 mL) was added to the above mixture, and the resulting mixture was stirred at −78 Celsius for 2 hours. The reaction was quenched with small amount of brine, then extracted with ethyl acetate. The organic phase was dried over MgSO$_4$ and concentrated. The residue was purified by flash chromatography on silica gel column with 70% AcOEt in hexanes to give the desired compound (3.5 g, 54% yield). MS (ESI): 284.1 (M+H$^+$).

Step 2: Synthesis of 1'-benzyl-3H-spiro[2-benzofuran-1,3'-pyrrolidine]

Diethyl azodicarboxylate (4.44 mL, 0.0282 mol) in 1 ml of THF was added to a mixture of 1-benzyl-3-[2-(hydroxymethyl)phenyl]pyrrolidin-3-ol (3.50 g, 0.0124 mol) and triphenylphosphine (7.40 g, 0.0282 mol) in tetrahydrofuran (50 mL, 0.6 mol) at room temperature. The mixture was stirred at room temperature overnight. The reaction solution was concentrated and the residue was flash chromatographed on silica gel column with 50% AcOEt in hexanes to give the desired compound (1.5 g, 46% yield). MS (ESI): 266.1 (M+H$^+$).

Step 3: Synthesis of 3H-spiro[2-benzofuran-1,3'-pyrrolidine]

To a solution of 1'-benzyl-3H-spiro[2-benzofuran-1,3'-pyrrolidine] (200 mg, 0.0008 mol) in methanol (10 mL) was added Pd/C (150 mg), and the suspension was hydrogenated under H2 (50 psi) overnight. The mixture was filtered and then concentrated to give the desired compound (110 mg, 92% yield). MS (ESI): 176.1 (M+H$^+$).

Step 4: Synthesis of 1'-{[1-(4-chlorophenyl)cyclopropyl]carbonyl}-3H-spiro[2-benzofuran-1,3'-pyrrolidine]

This compound was prepared using procedures analogous to those described in Example 82 (Step 5). MS (ESI): 354.1 (M+H$^+$).

Example 90

1'-{[1-(4-Chlorophenyl)cyclopropyl]carbonyl}-7H-spiro[furo[3,4-b]pyridine-5,3'-pyrrolidin]-7-one Step 1: Synthesis of 7H-spiro[furo[3,4-b]pyridine-5,3'-pyrrolidin]-one A solution of 2,2,6,6-tetramethyl-piperidine (0.820 mL, 0.00486 mol) in tetrahydrofuran (5 mL, 0.06 mol) at −75 Celsius was added to 1.600 M of n-butyllithium in hexane (4.05 mL). After the mixture was stirred for 15 min, a solution of 2-pyridinecarboxylic acid (199 mg, 0.00162 mmol) was added. The resulting mixture was stirred at −75 Celsius for 10 minutes, then at −20 Celsius for 30 minutes. A solution of tert-butyl 3-oxopyrrolidine-1-carboxylate (250 mg, 0.0013 mol) in THF (2 mL) was then added to the above mixture. The reaction mixture continued to be stirred at −20 Celsius for 20 minutes, then was warmed up to r.t. and then stirred for additional 1 hour. The reaction mixture was quenched with water, then concentrated to remove THF, and then acidified to pH ~1 using 6M aqueous HCl solution, and then stirred at r.t. overnight. The resulting mixture was extracted with methylene chloride. The aqueous layer was concentrated and the residue was directly purified by flash chromatography on silica gel column with 10% methanol in methylene chloride to give the desired compound. MS (ESI): 190.9 (M+H$^+$).

Step 2: Synthesis of 1'-{[1-(4-chlorophenyl)cyclopropyl]carbonyl}-7H-spiro[furo[3,4-b]pyridine-5,3'-pyrrolidin]-7-one This compound was prepared using procedures analogous to those described in Example 82 (Step 5). MS (ESI): 369.0 (M+H$^+$).

Example 91

1'-{[1-(4-Chlorophenyl)cyclopropyl]carbonyl}-3H-spiro[furo[3,4-c]pyridine-1,3'-pyrrolidin]-3-one This compound was prepared using procedures analogous to Example 90. MS (ESI): 369.0 (M+H$^+$)

Example 92

1'-{[1-(4-Chlorophenyl)cyclopropyl]carbonyl}-1H-spiro[furo[3,4-c]pyridine-3,3'-pyrrolidin]-1-one This compound was prepared using procedures analogous to example 90. MS (ESI): 369.0 (M+H$^+$)

Example 93

1'-{[1-(4-Chlorophenyl)cyclopropyl]carbonyl}spiro[indole-3,3'-pyrrolidin]-2(1H)-one Step 1: Synthesis of ten-butyl 1,3,4,9-tetrahydro-2H-β-carboline-2-carboxylase To a solution of 2,3,4,9-tetrahydro-1H-β-carboline (500 mg, 0.003 mol) in methylene chloride (10 mL, 0.2 mol) were added di-tert-butyldicarbonate (697 mg, 0.00319 mol) and N,N-diisopropylethylamine (0.607 mL, 0.00348 mol). The solution was stirred at room temperature for 2 hours. The reaction solution was diluted with AcOEt, then washed with saturated aqueous NaHCO$_3$ solution, then dried with MgSO$_4$, and then concentrated to give desired compound (780 mg, 100% yield). MS (ESI): 273.0 (M+H$^+$).

Step 2: Synthesis of tert-butyl 2-methoxy-1'H-spiro[indole-3,3'-pyrrolidine]-1'-carboxylate To a solution of tert-butyl 1,3,4,9-tetrahydro-2H-β-carboline-2-carboxylate (780 mg, 0.0029 mol) in methylene chloride (15 mL, 0.23 mol) was added triethylamine (0.439 mL, 0.00315 mol). The solution was stirred at 5 Celsius under darkness and nitrogen. To the above solution with stirring, a solution of tert-butyl hypochlorite (0.373 mL, 0.00329 mol) in CCl$_4$ (5 ml) was added dropwise at 5 Celsius. The mixture was stirred at 5 Celsius until TLC showed that starting material was consumed.

The above mixture was then added to a solution of sodium hydroxide (1.146 g, 0.02864 mol) in methanol (50 mL, 1 mol) under reflux. The resulting reaction mixture was under reflux overnight and then concentrated. The residue was diluted with AcOEt and water. The organic phase was washed with brine, then dried over MgSO$_4$ and concentrated. The residue was flash chromatographed on silica gel column with 50% AcOEt in hexanes to give the desired compound (660 mg, 76% yield). MS (ESI): 303.0 (M+

Step 3: Synthesis of spiro[indole-3,3'-pyrrolidin]-2(1H)-one

Tert-butyl 2-methoxy-1'H-spiro[indole-3,3'-pyrrolidine]-1'-carboxylate (660 mg, 0.0022 mol) was mixed with trifluoroacetic acid (1 mL) and water (18 mL), and the mixture was stirred under reflux for 3 hours. The mixture was then cooled down to room temperature, then adjusted to basic condition (pH~10) using ammonium hydroxide, and then extracted with CH$_2$Cl$_2$. The organic phase from the extraction was dried with MgSO$_4$, then concentrated to give the desired product (350 mg, 85% Yield). MS (ESI): 189.0 (M+H$^+$)

Step 4: Synthesis of 1'-{[1-(4-chlorophenyl)cyclopropyl]carbonyl}spiro[indole-3,3r-pyrrolidin]-2(1H)-one This compound was prepared using procedures analogous to those described in Example 82 (Step 5). MS (ESI): 367.0 (M+H$^+$).

Example 94

(1R)-1'-({1-[4-(1H-pyrazol-1-yl)phenyl]cyclopropyl}carbonyl)-3H-spiro[furo[3,4-c]pyridine-1,3'-pyrrolidin]-3-one Step A: Butyl 1-[4-(1H-pyrazol-1-yl)phenyl]cyclopropanecarboxylate A mixture of butyl 1-(4-bromophenyl)cyclopropanecarboxylate (297.2 mg, 1.0 mmol), pyrrazole (102.1 mg, 1.5 mmol), copper iodide (9.6 mg, 0.050 mmol), ethanediamine (11.0 μL, 0.103 mmol) and potassium phosphate (430.0 mg, 2.026 mmol) in toluene (2.0 mL) was deaerated and charged with nitrogen. The resulting mixture was heated at 100° C. overnight. Ethyl acetate (10 mL) was added to the mixture. The resulting mixture was filtered through a pad of celite, and then washed with ethyl acetate. The filtrate was concentrated and the residue was purified by flash chromatography to give butyl 1-[4-(1H-pyrazol-1-yl)phenyl]cyclopropanecarboxylate Step B: 1-[4-(1H-pyrazol-1-yl)phenyl]cyclopropanecarboxylic acid Trifluoroacetic acid (1.0 mL) was added to butyl 1-[4-(1H-pyrazol-1-yl)phenyl]cyclopropanecarboxylate (60 mg) in methylene chloride (1.0 mL). The mixture was stirred at room temperature overnight, and then concentrated to give a crude product which was directly used in the reaction of next step without further purification.

Step C: (1R)-1'-({1-[4-(1H-pyrazol-1-yl)phenyl]cyclopropyl}carbonyl)-3H-spiro[furo[3,4-c]pyridine-1,3'-pyrrolidin]-3-one 4-Methylmorpholine (55 μL, 0.50 mmol) was added to a mixture of 1-[4-(1H-pyrazol-1-yl)phenyl]cyclopropanecarboxylic acid (0.10 mmol), 3H-spiro[furo[3,4-c]pyridine-1,3'-pyrrolidin]-3-one dihydrochloride (0.026 g, 0.10 mmol), and BOP (0.057 g, 0.11 mmol) in DMF (1 mL). The mixture was stirred at room temperature for 2 hours, then adjusted to be acidic (pH=2.0) with TFA, and then diluted with DMF (0.8 mL). The resulting solution was purified by a prep-LCMS followed by chiral HPLC to give (1R)-1'-({1-[4-(1H-pyrazol-1-yl)phenyl]cyclopropyl}carbonyl)-3H-spiro[furo[3,4-c]pyridine-1,3'-pyrrolidin]-3-one (30%). MS (ESI): (M+H)$^+$ =401.1

Example 95

(1R)-1'-({1-[4-(Difluoromethoxy)phenyl]cyclopropyl}carbonyl)-3H-spiro[furo[3,4-c]pyridine-1,3'-pyrrolidin]-3-one Step A: 1-[4-(Difluoromethoxy)phenyl]cyclopropanecarboxylic acid Sodium hydroxide [50% aqueous solution (3.20 g)], was added to a mixture of [4-(difluoromethoxy)phenyl]acetonitrile (1.00 g, 5.4 mmol), benzyltriethylammonium chloride (0.10 g, 0.4 mmol) and 1-bromo-2-chloro-ethane (1.58 g, 11.0 mmol) at 50° C. overnight. 1,2-Ethanediol (10.00 mL) was then added to the mixture, and the resulting mixture was heated at 100° C. overnight. The mixture was then poured into ice-water (30 mL) and the resulting mixture was then extracted with ethyl ether (2×10 mL). The aqueous phase was acidified (pH=2) with 1N aqueous HCl solution, and then was extracted with ethyl acetate (4×15 mL). The combined organic phase was washed with brine (10 mL), then dried over Na$_2$SO$_4$, then filtered, and then concentrated under reduced pressure. The residue was the desired product which was directly used in the reaction of next step without further room temperature purification.

Step B: (1R)-1'-({1-[4-(difluoromethoxy)phenyl]cyclopropyl}carbonyl)-3H-spiro[furo[3,4-c]pyridine-1,3'-pyrrolidin]-3-one BOP (0.18 g, 0.42 mmol) was added to a mixture of 1-[4-(difluoromethoxy)phenyl]cyclopropanecarboxylic acid (0.10 g, 0.46 mmol) and 3H-spiro[furo[3,4-c]pyridine-1,3'-pyrrolidin]-3-one dihydrochloride (0.10 g, 0.38 mmol) in DMF (2.5 mL). After 5 min, 4-methylmorpholine (0.2 mL, 2.0 mmol) was added to the mixture. The resulting mixture was stirred at room temperature overnight, then was adjusted to be acidic (pH=2.0) with TFA, and then was purified by prep-LCMS to give 1'-({1-[4-(difluoromethoxy)phenyl]cyclopropyl}carbonyl)-3H-spiro[furo[3,4-c]pyridine-1,3'-pyrrolidin]-3-one TFA salt. The purified salt was neutralized by an addition of NaHCO$_3$ aqueous solution (7.5%). The mixture was extracted with ethyl acetate and the organic phase was concentrated to give 1'-({1-[4-(difluoromethoxy)phenyl]cyclopropyl}carbonyl)-3H-spiro[furo[3,4-c]pyridine-1,3'-pyrrolidin]-3-one. The desired stereo-isomer was isolated by chiral column to afford (1R)-1'-({1-[4-(difluoromethoxy)phenyl]cyclopropyl}carbonyl)-3H-spiro[furo[3,4-c]pyridine-1,3'-pyrrolidin]-3-one (49.5 mg, 31%).

Example 96

(1R)-1'-{[1-(6-Phenylpyridin-3-yl)cyclopropyl]carbonyl}-3H-spiro[2-benzofuran-1,3'-pyrrolidin]-3-one

Step 1. Benzyl 3-oxo-1'H,3H-spiro[2-benzofuran-1,3'-pyrrolidine]-1'carboxylate To a solution of methyl-2-iodobenzoate (8.8 mL, 0.060 mol) in THF (300 mL) at −60° C. was slowly added a solution of isopropylmagnesium bromide in THF (1.0 M, 66.0 mL), and the mixture was stirred below −50° C. for 1 h. A solution of benzyl-3-oxopyrrolidine-1-carboxylate (11.0 g, 0.05 mol) in THF (20.0 mL) was added to the above mixture and the reaction mixture was stirred below −20° C. for 2 h. The reaction was quenched by an addition of saturated NH$_4$Cl aqueous solution, and the resulting mixture was extracted with ethyl acetate several times. The combined extract was washed with water followed by brine, then dried and then concentrated. The product was purified by CombiFlash using Hexane/Ethyl acetate.

Step 2. (1S)-(+)-10-Camphorsulfonic acid-3H-spiro-[2-benzofuran-1,3'-pyrrolidin]-3-one Palladium on carbon (10%, 0.5 g) was added to a solution of benzyl 3-oxo-1'H,3H-spiro[2-benzofuran-1,3'-pyrrolidine]-1' carboxylate (5.0 g, 15.5 mmol) in methanol (100 mL) and the mixture was stirred under hydrogen balloon for 4 h (HPLC completion). The solvent of the mixture was removed under vacuum. The residue was dissolved in acetonitrile (200 mL), and (1S)-(+)-10-camphorsulfonic acid (3.6 g, 15.5 mmol) in acetonitrile (20 mL) was then slowly added at 50° C. The formed solid was filtered and dried to give the desired product. LC-MS: 190.1 (M+H)$^+$.

Step 3: Ethyl 1-(6-phenylpyridin-3-yl)cyclopropanecarboxylate

Sodium carbonate (42.4 mg, 0.400 mmol) in water (0.20 mL) was added to a mixture of ethyl 1-(6-chloropyridin-3-yl)cyclopropanecarboxylate (45.1 mg, 0.200 mmol), Phenylboronic acid (24.4 mg, 0.200 mmol) and tetrakis(triphenylphosphine)palladium(0) (7.15 mg) in toluene (200.0 µL) and ethanol (100.0 µL). The resulting mixture was irradiated by microwave at 120° C. for 15 minutes. Ethyl acetate (5 mL) was then added to the mixture. The resulting mixture was washed with water followed by brine. The organic layer was dried over Na$_2$SO$_4$, then filtered, and then concentrated under reduced pressure. The residue was purified by flash chromatography with ethyl acetate/hexane to give ethyl 1-(6-phenylpyridin-3-yl)cyclopropanecarboxylate.

Step 4. 1-(6-Phenylpyridin-3-yl)cyclopropanecarboxylic acid

Lithium hydroxide, monohydrate (0.016 g, 037 mmol) was added to ethyl 1-(6-phenylpyridin-3-yl)cyclopropanecarboxylate (50.0 mg, 0.19 mmol) in methanol (1.5 mL) and water (0.5 mL). The mixture was stirred at room temperature for overnight, then was adjusted to be acidic (pH=5) with 1N HCl aqueous solution, and then concentrated to give a crude product which was directly used in the reaction of the next step without further purification.

Step 5: (1R)-1'-{[1-(6-Phenylpyridin-3-yl)cyclopropyl]carbonyl}-3H-spiro[2-benzofuran-1,3'-pyrrolidin]-3-one 1-(6-Phenylpyridin-3-yl)cyclopropanecarboxylic acid was then coupled with (1S)-(+)-10-camphorsulfonic acid salt of (1R)-3H-spiro-[2-benzofuran-1,3'-pyrrolidin]-3-one using procedures analogous to those of Example 83 to afford (1R)-1'-{[1-(6-Phenylpyridin-3-yl)cyclopropyl]carbonyl}-3H-spiro[2-benzofuran-1,3'-pyrrolidin]-3-one. MS (ESI): (M+H)$^+$=411.1

Example 97

1'-{[1-(6-Phenylpyridin-3-yl)cyclopropyl]carbonyl}-3H-spiro[furo[3,4-c]pyridine-1,3'-pyrrolidin]-3-one This compound was prepared using procedures analogous to those for example 96. The yield: 40%. MS (ESI): (M+H)$^+$=412.1

Example 98

(1R)-1'-{[1-(4-Pyrrolidin-1-ylphenyl)cyclopropyl]carbonyl}-3H-spiro[furo[3,4-c]pyridine-1,3'-pyrrolidin]-3-one

Step 1: tert-Butyl 1-(4-pyrrolidin-1-ylphenyl)cyclopropanecarboxylate

A mixture of tert-butyl 1-(4-bromophenyl)cyclopropanecarboxylate (297.1 mg, 1.0 mmol), pyrrolidine (100.0 µL, 1.2 mmol), sodium tert-pentoxide (154.2 mg, 1.40 mmol), [1,1'-bis(diphenylphosphino)ferrocene]dichloropalladium (II), complex with dichloromethane (1:1) (24.5 mg, 0.030 mmol) and 1,1'-bis(diphenylphosphino)ferrocene (16.6 mg, 0.030 mmol) was deareated under vacuum and then charged with nitrogen. To the mixture was added toluene (2.0 mL). The resulting mixture was heated at 100° C. for overnight. After cooling, the mixture was poured into ice-water and the resulting mixture was extracted with ethyl acetate (4×10 mL) The combined organic phase was washed with water and brine, then dried over Na$_2$SO$_4$, then filtered, and then concentrated under reduced pressure. The residue was purified by flash chromatography with ethyl acetate/hexane to afford tert-butyl 1-(4-pyrrolidin-1-ylphenyl)cyclopropanecarboxylate.

Step 2: (1R)-1'-{[1-(4-pyrrolidin-1-ylphenyl)cyclopropyl]carbonyl}-3H-spiro[furo[3,4-q]pyridine-1,3'-pyrrolidin]-3-one The above material of tert-butyl 1-(4-pyrrolidin-1-ylphenyl)cyclopropanecarboxylate was treated with TFA in methylene chloride to remove the tert-butyl group, the resulting acid was then coupled with 3H-spiro[furo[3,4-c]pyridine-1,3'-pyrrolidin]-3-one dihydrochloride using procedures analogous to those for Example 94 to afford (1R)-1'-{[1-(4-pyrrolidin-1-ylphenyl)cyclopropyl]carbonyl}-3H-spiro[furo[3,4-c]pyridine-1,3'-pyrrolidin]-3-one. MS (ESI): (M+H)$^+$=404.1

Example 99

(1R)-1'-{[1-(4-Pyrrolidin-1-ylphenyl)cyclopropyl]carbonyl}-3H-spiro[2-benzofuran-1,3'-pyrrolidin]-3-one This compound was prepared using procedures analogous to those for example 96. The yield: 7%. MS (ESI): (M+H)$^+$=403.1

Example 100

(1R)-1'-{[1-(6-Pyrrolidin-1-ylpyridin-3-yl)cyclopropyl]carbonyl}-3H-spiro[furo[3,4-c]pyridine-1,3'-pyrrolidin]-3-one Step 1: Ethyl 1-(6-pyrrolidin-1-ylpyridin-3-yl)cyclopropanecarboxylate A mixture of ethyl 1-(6-chloropyridin-3-yl)cyclopropanecarboxylate (69.8 mg, 0.309 mmol) and pyrrolidine (250.0 μL, 3.0 mmol) in a sealed tube was heated at 100° C. for 4 hours. Then the excess pyrrolidine in the mixture was removed under reduced pressure. The residue was purified by flash chromatography column to afford ethyl 1-(6-pyrrolidin-1-ylpyridin-3-yl)cyclopropanecarboxylate.

Step 2: (1R)-1'-{[1-(6-pyrrolidin-1-ylpyridin-3-yl)cyclopropyl]carbonyl}-3H-spiro[furo[3,4-c]pyridine-1,3'-pyrrolidin]-3-one The above material of ethyl 1-(6-pyrrolidin-1-ylpyridin-3-yl)cyclopropanecarboxylate was treated with LiOH in methanol to afford the corresponding acid, which was then coupled with 3H-spiro[furo[3,4-c]pyridine-1,3'-pyrrolidin]-3-one dihydrochloride using procedures analogous to those for example 96 to afford (1R)-1'-{[1-(6-pyrrolidin-1-ylpyridin-3-yl)cyclopropyl]carbonyl}-3H-spiro[furo[3,4-c]pyridine-1,3'-pyrrolidin]-3-one. MS (ESI): (M+H)$^+$=405.1

Example 101

(1R)-1'-{[1-(6-Pyrrolidin-1-ylpyridin-3-yl)cyclopropyl]carbonyl}-3H-spiro[2-benzofuran-1,3'-pyrrolidin]-3-one This compound was prepared using procedures analogous to those for example 96. The yield: 0.54%. MS (EI): (M+H)$^+$=404.2

Example 102

(1R)-1'-({1-[4-(2-Oxo-1,3-oxazolidin-3-yl)phenyl]cyclopropyl}carbonyl)-3H-spiro[2-benzofuran-1,3'-pyrrolidin]-3-one Step 1: tert-Butyl 1-[4-(2-oxo-1,3-oxazolidin-3-yl)phenyl]cyclopropanecarboxylate.

A mixture of tert-butyl 1-(4-bromophenyl)cyclopropanecarboxylate (297.2 mg, 1.0 mmol), 2-oxo-1,3-oxazolidine (1.2 mmol), copper(I) iodide (20.0 mg, 0.1 mmol), (trans)-cyclohexane-1,2-diamine (22.8 mg, 0.2 mmol) and potassium carbonate (300.0 mg, 2.17 mmol) was deaerated under vacuum and then charged with nitrogen. To the mixture was added toluene (2.0 mL). The resulting mixture was heated at 100° C. for overnight. Then ethyl acetate (10 mL) was added to the mixture. The resulting mixture was filtered through a pad of celite, and the solid was washed with additional ethyl acetate. The filtrate was concentrated. The residue was purified by flash chromatography with ethyl acetate/hexane to afford tert-butyl 1-[4-(2-oxo-1,3-oxazolidin-3-yl)phenyl]cyclopropanecarboxylate.

Step 2: (1R)-1'-({1-[4-(2-oxo-1,3-oxazolidin-3-yl)phenyl]cyclopropyl}carbonyl)-3H-spiro[2-benzofuran-1,3'-pyrrolidin]-3-one t-Butyl 1-[4-(2-oxo-1,3-oxazolidin-3-yl)phenyl]cyclopropanecarboxylate was converted to the final compound using the procedures analogous to those for example 96. MS (ESI): (M+H)$^+$=419.1

Example 103

(1R)-1'-({1-[4-(2-Oxopyrrolidin-1-yl)phenyl]cyclopropyl}carbonyl)-3H-spiro[2-benzofuran-1,3'-pyrrolidin]-3-one Step A: tert-Butyl 1-[4-(2-oxopyrrolidin-1-yl)phenyl]cyclopropanecarboxylate A mixture of tert-butyl 1-(4-bromophenyl)cyclopropanecarboxylate (297.2 mg, 1.0 mmol), t-oxo-pyrrolidine (1.2 mmol), copper(I) iodide (20.0 mg, 0.1 mmol), (trans)-cyclohexane-1,2-diamine (22.8 mg, 0.2 mmol) and potassium carbonate (300.0 mg, 2.17 mmol) was dearated under vacuum and then charged with nitrogen. To the mixture was added toluene (2.0 mL). The resulting mixture was heated at 100° C. for overnight. Then ethyl acetate (10 mL) was added to the mixture. The resulting mixture was filtered through a pad of celite, and the solid was washed with additional ethyl acetate. The filtrate was concentrated. The residue was purified by flash chromatography with ethyl acetate/hexane to afford tert-butyl 1-[4-(2-oxo-pyrrolidin-1-yl)phenyl]cyclopropanecarboxylate.

Step B: (1R)-1'-({1-[4-(2-oxopyrrolidin-1-yl)phenyl]cyclopropyl}carbonyl)-3H-spiro[2-benzofuran-1,3'-pyrrolidin]-3-one tert-Butyl 1-[4-(2-oxopyrrolidin-1-yl)phenyl]cyclopropanecarboxylate was converted to the final compound using the procedures analogous to those for example 96. MS (ESI): (M+H)$^+$=425.1

Example 104

1'-({1-[4-(2-Phenylethoxy)phenyl]cyclopropyl}carbonyl)-3H-spiro[furo[3,4-c]pyridine-1,3'-pyrrolidin]-3-one Step 1

1-(4-Hydroxyphenyl)cyclopropane-carboxylic acid (0.19 g, 1.0 mmol), benzotriazol-1-yloxytris(dimethylamino)phosphonium hexafluorophosphate (0.24 g, 1.0 mmol) and N,N-dimethylformamide (1.5 ml) were mixed with stirring at room temperature for ten minutes. To the mixture, with stirring, was added 3H-spiro[furo[3,4-c]pyridine-1,3'-pyrrolidin]-3-one dihydrochloride (0.47 g, 1.0 mmol), followed by N,N-Diisopropylethylamine (0.55 ml, 3.2 mmol). The resulting mixture was stirred at r.t. overnight. Then the reaction was quenched with water, and the reaction mixture was extracted with ethyl acetate. The extract was washed with saturated $KH_2PO_4$ solution (x2), water (x1), saturated $NaHCO_3$ solution (x2), water (x1) and brine (x1) successively; then dried over $Na_2SO_4$; and then filtered. The filtrate was concentrated. The residue was further dried under high vacuum, and the desired product was obtained (0.43 g).

Step 2

A mixture of 1'-{[1-(4-hydroxyphenyl)cyclopropyl]carbonyl}-3H-spiro[furo[3,4-c]pyridine-1,3'-pyrrolidin]-3-one (15 mg, purity: 80%, 0.034 mmol), (2-iodoethyl)-benzene (12 mg, 0.051 mmol), and tetra-n-butylammonium iodide (1 mg, 0.003 mmol), and Cesium Carbonate (28 mg, 0.086 mmol) in Dimethyl sulfoxide (0.3 ml) was stirred at r.t. overnight. Then the desired product was obtained from the mixture by prep-HPLC (0.24 mg). LCMS: m/z 455.1 (M+H)$^+$; 477.0 (M+Na)$^+$.

Example 105

1'-[(1-{4-[(1-Methylcyclopropyl)methoxy]phenyl}cyclopropyl)-carbonyl]-3H-spiro[furo[3,4-c]pyridine-1,3'-pyrrolidin]-3-one 1'-{[1-(4-Hydroxyphenyl)cyclopropyl]-carbonyl}-3H-spiro[furo[3,4-c]pyridine-1,3'-pyrrolidin]-3-one (8.2 mg, 0.023 mmol), triethylamine (3.6 ul, 0.026 mmol), triphenylphosphine (15 mg, 0.056 mmol), and diisopropyl azodicarboxylate (11 ul, 0.056 mmol) were mixed in tetrahydrofuran (0.2 ml) at room temperature for 10 minutes. To the mixture, with stirring, was added (1-methylcyclopropyl)methanol (4.8 mg, 0.056 mmol). The resulting mixture then was stirred at room temperature overnight. The desired product was obtained from the mixture by prep-HPLC (5.8 mg, 59%). LCMS: m/z 419.1 (M+H)$^+$.

Example 106

1'-[(1-{4-[(2-Fluorobenzyl)oxy]phenyl}cyclopropyl)carbonyl]-3H-spiro[furo[3,4-c]pyridine-1,3'-pyrrolidin]-3-one This compound was prepared using similar procedures to those described in example 104. LCMS: m/z 459.2 (M+H)$^+$; 481.3 (M+Na)$^+$.

Example 107

1'-({1-[4-(Quinolin-2-ylmethoxy)phenyl]cyclopropyl}carbonyl)-3H-spiro[furo[3,4-c]pyridine-1,3'-pyrrolidin]-3-one This compound was prepared using similar procedures to those described in example 104. LCMS: m/z 492.3 (M+H)$^+$; 514.2 (M+Na)$^+$.

Example 108

1'-[(1-{4-[(3-Fluorobenzyl)oxy]phenyl}cyclopropyl)carbonyl]-3H-spiro[furo[3,4-c]pyridine-1,3'-pyrrolidin]-3-one This compound was prepared using similar procedures to those described in example 104. LCMS: m/z 459.2 (M+H)+; 481.1 (M+Na)+.

Example 109

1'-({1-[4-(1,3-Benzothiazol-2-ylmethoxy)phenyl]cyclopropyl}-carbonyl)-3H-spiro[furo[3,4-c]pyridine-1,3'-pyrrolidin]-3-one This compound was prepared using similar procedures to those described in example 105. LCMS: m/z 498.2 (M+H)$^+$; 520.1 (M+Na)$^+$.

Example 110

1'-{[1-(4-{[3,5-Bis(trifluoromethyl)benzyl]oxy}phenyl)-cyclopropyl]carbonyl}-3H-spiro[furo[3,4-c]pyridine-1,3'-pyrrolidin]-3-one This compound was prepared using similar procedures to those described in example 104. LCMS: m/z 577.2 (M+H)$^+$; 599.2 (M+Na)$^+$.

Example 111

1'-[(1-{4-[2-(4-Fluorophenyl)ethoxy]phenyl}cyclopropyl)-carbonyl]-3H-spiro[furo[3,4-c]pyridine-1,3'-pyrrolidin]-3-one This compound was prepared using similar procedures to those described in example 104. LCMS: m/z 473.2 (M+H)$^+$; 495.1 (M+Na)$^+$.

Example 112

4-[(4-{1-[(3-Oxo-1'H,3H-spiro[furo[3,4-c]pyridine-1,3'-pyrrolidin]-1'-yl)carbonyl]cyclopropyl}phenoxy)methyl]benzonitrile This compound was prepared using similar procedures to those described in example 104. LCMS: m/z 466.2 (M+H)+; 488.2 (M+Na)+.

Example 113

1'-{[1-(4-Phenoxyphenyl)cyclopropyl]carbonyl}-3H-spiro[furo[3,4-c]pyridine-1,3'-pyrrolidin]-3-one A mixture of 1-(4-phenoxyphenyl)cyclopropanecarboxylic acid (15 mg, 0.059 mmol), 3H-spiro[furo[3,4-c]pyridine-1,3'-pyrrolidin]-3-one dihydrochloride (16 mg, 0.059 mmol), benzotriazol-1-yloxytris(dimethylamino)phosphonium hexafluorophosphate (27.4 mg, 0.062 mmol), and N,N-diisopropylethylamine (36 ul, 0.21 mmol) in N,N-dimethylformamide (1 ml) was stirred at room temperature for 4 hours. The desired product then was obtained from the mixture by prep-HPLC (6.2 mg, 25%). LCMS: m/z 427.1 (M+H)+; 449.1 (M+Na)+.

Example 114

(1R)-1'-({1-[4-(Pyridin-4-ylmethoxy)phenyl]cyclopropyl}-carbonyl)-3H-spiro[2-benzofuran-1,3'-pyrrolidin]-3-one Step 1

A mixture of 1-(4-hydroxyphenyl)cyclopropanecarboxylic acid (0.20 g, 1.1 mmol), [(1S,4R)-7,7-dimethyl-2-oxobicyclo[2.2.1]hept-1-yl]methanesulfonic acid-(1R)-3H-spiro[2-benzofuran-1,3'-pyrrolidin]-3-one salt (0.47 g, 1.1 mmol), Benzotriazol-1-yloxytris(dimethylamino)phosphonium hexafluorophosphate (0.55 g, 1.2 mmol), and N,N-diisopropylethylamine (0.49 ml, 2.8 mmol) in methylene chloride (3 ml) was stirred at r.t. overnight. Then the reaction was quenched with water, and the reaction mixture was extracted with ethyl acetate. The extract was washed with 1N HCl aqueous solution (x2), water and brine successively; then dried over Na₂SO₄; and then filtered. The filtrate was concentrated to afford the desired product (0.35 g, yield: 89%).

Step 2

A mixture of (1R)-1'-{[1-(4-hydroxyphenyl)cyclopropyl]carbonyl}-3H-spiro[2-benzofuran-1,3'-pyrrolidin]-3-one (15 mg, 0.043 mmol), 4-(bromomethyl)pyridine hydrobromide (13 mg, 0.052 mmol), Cesium Carbonate (56 mg, 0.17 mmol), and Tetra-n-butylammonium iodide (1.6 mg, 0.004 mmol) in Dimethyl sulfoxide (0.3 ml) was stirred at r.t. overnight. Then the desired product was obtained from the mixture by prep-HPLC (10.0 mg, yield: 53%). LCMS: m/z 441.1 (M+H)⁺, 463.1 (M+Na)⁺.

Example 115

(1R)-1'-({1-[4-(Pyridin-2-ylmethoxy)phenyl]cyclopropyl}-carbonyl)-3H-spiro[2-benzofuran-1,3'-pyrrolidin]-3-one This compound was prepared using similar procedures to those described in example 114. LCMS: m/z 441.2 (M+H)⁺; 463.3 (M+Na)⁺.

Example 116

(1R)-1'-{[1-(4-pyridin-4-ylphenyl)cyclopropyl]carbonyl}-3H-spiro[2-benzofuran-1,3'-pyrrolidin]-3-one Step 1

A mixture of 1-(4-bromophenyl)cyclopropanecarboxylic acid (1.0 g, 4.1 mmol), [(1S,4R)-7,7-dimethyl-2-oxobicyclo[2.2.1]hept-1-yl]methane sulfonic acid-(1R)-3H-spiro[2-benzofuran-1,3'-pyrrolidin]-3-one (1:1) salt (1.7 g, 4.1 mmol), benzotriazol-1-yloxytris(dimethylamino)phosphonium hexafluorophosphate (1.8 g, 4.1 mmol), and N,N-diisopropylethylamine (1.8 ml, 10 mmol) in methylene chloride (7 ml) was stirred at room temperature for 4 hours. Then the mixture was diluted with ethyl acetate. The resulting solution was washed with saturated KH₂PO₄ solution (x2), water, saturated NaHCO₃ solution, water and brine successively; then dried over Na₂SO₄; and then filtered. The filtrate was concentrated to afford the product (1.5 g).

Step 2

A mixture of (1R)-1'-{[1-(4-bromophenyl)cyclopropyl]carbonyl}-3H-spiro[2-benzofuran-1,3'-pyrrolidin]-3-one (25 mg, 0.061 mmol), 4-(tributylstannyl)pyridine (24 mg, 0.067 mmol), tris(dibenzylideneacetone)dipalladium(0) (3 mg, 0.003 mmol), tri-tert-butylphosphine (1.5 mg, 0.007 mmol), and potassium fluoride (12 mg, 0.20 mmol) in tetrahydrofuran (0.3 ml) was microwave irradiated at 90° C. for 15 minutes. Then the desired product was obtained from the mixture by prep-HPLC (3.2 mg, yield: 13%). LCMS: m/z 411.1 (M+H)+; 433.0 (M+Na)+.

Example 117

(1R)-1'-{[1-(4-cyclopropylphenyl)cyclopropyl]carbonyl}-3H-spiro[2-benzofuran-1,3'-pyrrolidin]-3-one This compound was prepared using similar procedures to those described in example 116. LCMS: m/z 374.1 (M+H)⁺; 396.1 (M+Na)⁺.

Example 118

(1R)-1'-{[1-(2-Fluoro-4-pyridin-2-ylphenyl)cyclopropyl]-carbonyl}-3H-spiro[2-benzofuran-1,3'-pyrrolidin]-3-one Step 1

A mixture of 1-(4-chloro-2-fluorophenyl)cyclopropanecarboxylic acid (0.15 g, 0.7 mmol), [(1S,4R)-7,7-dimethyl-2-oxobicyclo[2.2.1]hept-1-yl]methanesulfonic acid-(1R)-3H-spiro[2-benzofuran-1,3'-pyrrolidin]-3-one (1:1) salt (0.29 g, 0.7 mmol), benzotriazol-1-yloxytris(dimethylamino)phosphonium hexafluorophosphate (0.34 g, 0.77 mmol), and N,N-diisopropylethylamine (0.43 ml, 2.4 mmol) in N,N-dimethylformamide (2.0 ml) was stirred at room temperature overnight. The mixture then was diluted with ethyl acetate. The resulting solution was washed with saturated NaHCO₃ solution, water, 1N HCl solution, water and brine successively; then dried over Na₂SO₄; and then filtered. The filtrate was concentrated to afford the desired product (275 mg).

Step 2

A mixture of (1R)-1'-{[1-(4-chloro-2-fluorophenyl)cyclopropyl]carbonyl}-3H-spiro[2-benzofuran-1,3'-pyrrolidin]-3-one (20 mg, purity: 80%, 0.04 mmol), 2-(tributylstannyl)pyridine (17 mg, 0.046 mmol), Tris(dibenzylideneacetone)dipalladium(0) (2 mg, 0.002 mmol), tri-tert-butylphosphine (0.8 mg, 0.004 mmol), and cesium carbonate (16 mg, 0.05 mmol) in 1,4-dioxane (0.5 ml) was microwave irradiated at 100° C. for 30 minutes. The product was obtained from the mixture by prep-HPLC. LCMS: m/z 429.2 (M+H)⁺; 451.1 (M+Na)⁺.

Example 119

(1R)-1'-[(1-{4-[(E)-2-(4-Methylphenyl)vinyl]phenyl}-cyclopropyl)carbonyl]-3H-spiro[2-benzofuran-1,3'-pyrrolidin]-3-one A mixture of (1R)-1'-{[1-(4-bromophenyl)cyclopropyl]carbonyl}-3H-spiro[2-benzofuran-1,3'-pyrrolidin]-3-one (25 mg, 0.061 mmol), [(E)-2-(4-methylphenyl)vinyl]boronic acid (11 mg, 0.067 mmol), tri-tert-butylphosphine (1.5 mg, 0.007 mmol), tris(dibenzylideneacetone)dipalladium(0) (3 mg, 0.003 mmol), potassium fluoride (12 mg, 0.2 mmol) in tetrahydrofuran (0.4 ml) was microwave irradiated at 90° C. for 20 minutes. The desired product was obtained from the mixture by prep-HPLC (13.7 mg, yield: 50%). LCMS: m/z 450.2 (M+H)⁺; 472.2 (M+Na)⁺.

Example 120

(1R)-1'-({1-[4-(2-Pyridin-2-ylethoxy)phenyl]cyclopropyl}-carbonyl)-3H-spiro[2-benzofuran-1,3'-pyrrolidin]-3-one (1R)-1'-{[1-(4-Hydroxyphenyl)-cyclopropyl]carbonyl}-3H-spiro[2-benzofuran-1,3'-pyrrolidin]-3-one (15 mg, 0.043 mmol), diisopropyl azodicarboxylate (20 ul, 0.10 mmol), and triphenylphosphine (24 ul, 0.10 mmol) were mixed in tetrahydrofuran (0.2 ml) at room temperature for 5 minutes. To the mixture, with stirring, was added 2-(2-pyridyl)ethanol (13 mg, 0.10 mmol). The resulting mixture then was stirred at room temperature overnight. Then the desired product was obtained from the mixture by prep-HPLC (6.4 mg, yield: 33%). LCMS: m/z 455.2 (M+H)$^+$.

Example 121

1'-({1-[4-(2-Pyridin-2-ylethoxy)phenyl] cyclopropyl}carbonyl)-3H-spiro[furo[3,4-c]pyridine-1,3'-pyrrolidin]-3-one This compound was prepared using similar procedures to those described in example 105. LCMS: m/z Example 122

(1R)-1'-[(1-{4-[(E)-2-Pyridin-4-ylvinyl] phenyl}cyclopropyl)-carbonyl]-3H-spiro[2-benzofuran-1,3'-pyrrolidin]-3-one A mixture of POPd1 catalyst (CombiPhos Catalysts, Inc) (2 mg), (1R)-1'-{[1-(4-bromophenyl)cyclopropyl]-carbonyl}-3H-spiro[2-benzofuran-1,3'-pyrrolidin]-3-one (15 mg, 0.036 mmol), 4-vinylpyridine (19 mg, 0.18 mmol), potassium carbonate (5.5 mg, 0.04 mmol) in N,N-dimethylformamide (0.3 ml) was microwave irradiated at 135° C. for 30 minutes. Then the desired product was obtained from the mixture by prep-HPLC followed by chiral HPLC (13 mg, 82%). LCMS: m/z 437.2 (M+H)$^+$; 459.2 (M+Na)$^+$.

Example 123

(1R)-1'-({1-[4-(3,5-Dimethylisoxazol-4-yl)phenyl] cyclopropyl}carbonyl)-3H-spiro[2-benzofuran-1,3'-pyrrolidin]-3-one Step 1a: Synthesis of 1-(4-bromophenyl)cyclopropanecarboxylic acid 2-(4-Bromophenyl)acetonitrile (10.0 g, 0.0510 mol), 1-bromo-2-chloro-ethane (5.5 mL, 0.066 mol) and benzyltriethylammonium chloride (200 mg, 0.001 mol) were added to a flask with vigorously stirring, then 19.4 M of sodium hydroxide in water (18.4 mL) was added dropwise. The mixture was stirred at 4° C. overnight. The reaction mixture was diluted with water and extract with ethyl acetate. The organic phase was washed with 1N HCl aqueous solution and brine successively; then dried with MgSO$_4$; and then concentrate.

To a mixture of the above residue (6.0 g, 0.027 mol) and 19.4 M of sodium hydroxide in water (5.6 mL) was added 1,2-ethanediol (60 mL, 1 mol). The resulting mixture was refluxed at 120 Celsius for 20 hours. The reaction mixture was cooled down to r.t., then poured into water and the resulting mixture was extracted with ether. The aqueous phase was acidified with HCl aqueous solution and extracted with ethyl acetate. Then the ethyl acetate phase was washed with brine, then dried with MgSO$_4$, and then concentrated to afford the desired compound. MS (ESI): 241.0.0 (M+H)$^+$ Step 1b: Synthesis of (1R)-1'-{[1-(4-bromophenyl) cyclopropyl]carbonyl}-3H-spiro[2-benzofuran-1,3'-pyrrolidin]-3-one To a solution of 1-(4-bromophenyl)cyclopropanecarboxylic acid (1.0 g, 0.0041 mol) in N,N-dimethylformamide (5 mL, 0.06 mol) was added [(1S,4S)-7,7-dimethyl-2-oxobicyclo[2.2.1]hept-1-yl]methanesulfonic acid-(1R)-3H-spiro[2-benzofuran-1,3'-pyrrolidin]-3-one (1:1) (1.75 g, 0.00415 mol). The solution was cooled to 0° C., and benzotriazol-1-yloxytris(dimethylamino)phosphonium hexafluorophosphate (2.02 g, 0.00456 mol) was added. After stirring for about 3 minutes, N,N-diisopropylethylamine (2.17 mL, 0.0124 mol) was added to the mixture. The resulting solution was stirred at 0° C. for 20 minutes, then at r.t. overnight.

Then the solution was poured into a saturated NaHCO$_3$ aqueous solution, and the mixture was extracted with ethyl acetate. The organic phase was washed with saturated NaHCO$_3$ aqueous solution (x3), water and brine successively; then dried with MgSO$_4$; and then concentrate. The residue was flash chromatographed on silica gel column with 50% AcOEt in Hexanes to afford the desired compound. MS (ESI): 414.0.0 (M+H$^+$), 412.00 (M–H$^+$).

Step 1c (1R)-1'-({1-[4-(3,5-dimethylisoxazol-4-yl) phenyl]cyclopropyl}carbonyl)-3H-spiro[2-benzofuran-1,3'-pyrrolidin]-3-one To a solution of (1R)-1'-{[1-(4-bromophenyl)cyclopropyl]carbonyl}-3H-spiro[2-benzofuran-1,3'-pyrrolidin]-3-one (20 mg, 0.00005 mol) in tetrahydrofuran (1.0 mL, 0.012 mol) were added 3,5-dimethyl-4-(4,4,5,5-tetramethyl-1,3,2-dioxaborolan-2-yl)isoxazole (11.9 mg, 0.0000534 mol), tris (dibenzylideneacetone)dipalladium(0) (0.2 mg, 0.0000002 mol), tri-tert-butylphosphine (0.12 mg, 5.8E-7 mol) and potassium fluoride (9.3 mg, 0.00016 mol), and the resulting mixture was heated at 150 Celsius under microwave for 50 minutes. The mixture then was cooled down to r.t. and filtered. The filtrate was diluted with methanol, and the desired compound was obtained by revised phase prep-HPLC. MS (ESI): 429.2 (M+H$^+$).

Example 124

(1R)-1'-({1-[4-(1-Methyl-1H-pyrazol-4-yl)phenyl] cyclopropyl}carbonyl)-3H-spiro[2-benzofuran-1,3'-pyrrolidin]-3-one This compound was prepared using procedures analogous to step 1c in example 123. MS (ESI): 414.1 (M+H$^+$)

Example 125

(1R)-1'-({1-[4'-(Methylsulfonyl)biphenyl-4-yl] cyclopropyl}carbonyl)-3H-spiro[2-benzofuran-1,3'-pyrrolidin]-3-one This compound was prepared using procedures analogous to step 1c in example 123. MS (ESI): 488.1 (M+H$^+$)

Example 126

1'-({1-[4-(3-Methyl-1H-pyrazol-1-yl)phenyl] cyclopropyl}carbonyl)-3H-spiro[furo[3,4-c]pyridine-1,3'-pyrrolidin]-3-one To a solution of 1'-{[1-(4-bromophenyl)cyclopropyl]carbonyl}-3H-spiro[furo[3,4-c]pyridine-1,3'-pyrrolidin]-3-one (30 mg, 0.00007 mol), 3-methyl-1H-pyrazole (7.15 mg, 0.0000871 mol) in toluene (0.5 mL, 0.005 mol) and N,N-dimethylformamide (0.5 mL, 0.006 mol) were added (1S, 2S)—N,N'-dimethylcyclohexane-1,2-diamine (2.1 mg, 0.000014 mol), copper(I) iodide (1 mg, 0.000007 mol), and potassium carbonate (21.1 mg, 0.000152 mol). The mixture was heated at 150 Celsius under microwave for 60 minutes. Then the mixture was cooled down to r.t. and filtered. The filtrate was diluted with methanol, and the desired compound was obtained by reversed phase prep-HPLC. MS (ESI): 415.1 (M+H$^+$).

Example 127

1'-[(1-{4-[3-(Trifluoromethyl)-1H-pyrazol-1-yl]phenyl}cyclopropyl)carbonyl]-3H-spiro[furo[3,4-c]pyridine-1,3'-pyrrolidin]-3-one This compound was prepared using procedures analogous to those in example 126. MS (ESI): 469.1 (M+H$^+$)

Example 128

1'-({1-[4-(4-Methyl-1H-pyrazol-1-yl)phenyl]cyclopropyl}carbonyl)-3H-spiro[furo[3,4-c]pyridine-1,3'-pyrrolidin]-3-one This compound was prepared using procedures analogous to those in example 126. MS (ESI): 415.1 (M+H$^+$)

Example 129

(1R)-1'-({1-[4-(2H-Indazol-2-yl)phenyl]cyclopropyl}carbonyl)-3H-spiro[furo[3,4-c]pyridine-1,3'-pyrrolidin]-3-one To a solution of 1'-{[1-(4-bromophenyl)cyclopropyl]carbonyl}-3H-spiro[furo[3,4-c]pyridine-1,3'-pyrrolidin]-3-one (30 mg, 0.00007 mol), 1H-Indazole (10.3 mg, 0.0000871 mol) in toluene (1 mL, 0.01 mol) were added (1S,2S)—N,N'-dimethylcyclohexane-1,2-diamine (2.1 mg, 0.000014 mol), copper(I) iodide (1 mg, 0.000007 mol), and potassium phosphate (32.4 mg, 0.000152 mol) in a sealed vial. The mixture was microwaved at 150 Celsius for 60 minutes. Then the mixture was cooled down to r.t. and filtered. The filtrate was diluted with methanol, and the desired compound was obtained by revised phase prep-HPLC. MS (ESI): 451.1 (M+H$^+$). The enantiomers were separated by chiral HPLC.

Example 130

(1R)-1'-({1-[4-(1H-benzimidazol-1-yl)phenyl]cyclopropyl}carbonyl)-3H-spiro[furo[3,4-c]pyridine-1,3'-pyrrolidin]-3-one To a solution of 1'-{[1-(4-bromophenyl)cyclopropyl]carbonyl}-3H-spiro[furo[3,4-c]pyridine-1,3'-pyrrolidin]-3-one (30 mg, 0.00007 mol), 1H-Imidazole, 2-methyl-(7.15 mg, 0.0000871 mol) in N,N-dimethylformamide (1 mL, 0.01 mol) were added (1S,2S)—N,N'-dimethylcyclohexane-1,2-diamine (2.1 mg, 0.000014 mol), copper(I) iodide (1 mg, 0.000007 mol), and cesium carbonate (49.7 mg, 0.000152 mol). The mixture was microwaved at 200 Celsius for 60 minutes. Then the mixture was cooled down to r.t. and filtered. The filtrate was adjusted to be acidic using TFA and stirred for 30 minutes, then diluted with methanol and purified by revised phase prep-HPLC followed by chiral HPLC to afford the desired compound. MS (ESI): 451.1 (M+H$^+$).

Example 131

(1R)-1'-({1-[4-(2-Methyl-1H-imidazol-1-yl)phenyl]cyclopropyl}carbonyl)-3H-spiro[furo[3,4-c]pyridine-1,3'-pyrrolidin]-3-one This compound was prepared using procedures analogous to those in example 130. MS (ESI): 415.1 (M+H$^+$)

Example 132

(1R)-1'-({1-[4-(1H-1,2,4-triazol-1-yl)phenyl]cyclopropyl}carbonyl)-3H-spiro[2-benzofuran-1,3'-pyrrolidin]-3-one This compound was prepared using procedures analogous to those in example 129. MS (ESI): 401.1 (M+H$^+$)

Example 133

(1R)-1'-({1-[4-(1-Hydroxycyclopentyl)phenyl]cyclopropyl}carbonyl)-3H-spiro[2-benzofuran-1,3'-pyrrolidin]-3-one Step 1a: 1-[4-(1-hydroxycyclopentyl)phenyl]cyclopropanecarboxylic acid A solution of 1-(4-bromophenyl)cyclopropanecarboxylic acid (600.0 mg, 0.002489 mol) in tetrahydrofuran (20 mL, 0.2 mol) was cooled below −20 Celsius under N$_2$ atmosphere, and 1.0 M of dibutylmagnesium in heptane (1.3 mL) was slowly added to the solution while maintaining the temperature below −20 Celsius. Then n-butyllithium (2.5 M in hexane, 1.1 mL) was slowly added to the slurry while maintaining the temperature below −20 Celsius with effective stirring. After the mixture was stirred at −20 Celsius for 1 hour, a solution of cyclopentanone (0.264 mL, 0.00299 mol) in THF (20.0 mL) was added to the mixture. Then after stirring at −20 Celsius for 1 hour, the reaction was quenched with ammonium chloride and the reaction mixture was extracted with ethyl acetate. The organic phase was washed with brine, then dried over Na$_2$SO$_4$, and then filtered. The filtrate was concentrated. The residue was flash chromatographed on silica gel column with 30% ethyl acetate in hexanes to afford the desired compound. MS (ESI): 229.1 (M-OH$^-$), 269.1 (M+Na$^+$).

Step 1b: (1R)-1'-({1-[4-(1-hydroxycyclopentyl)phenyl]cyclopropyl}carbonyl)-3H-spiro[2-benzofuran-1,3'-pyrrolidin]-3-one This compound was prepared using procedures analogous to step 1b in example 123. MS (ESI): 400.1 (M−OH$^-$)

Example 134

(1R)-1'-{[1-(4-Cyclopentylphenyl)cyclopropyl]carbonyl}-3H-spiro[furo[3,4-c]pyridine-1,3'-pyrrolidin]-3-one Step 1a. 1-(4-cyclopentylphenyl)cyclopropanecarboxylic acid The mixture of 1-[4-(1-hydroxycyclopentyl)phenyl]cyclopropanecarboxylic acid (120 mg, 0.00049 mol), triethylsilane (389 μL, 0.00244 mol) and TFA 0.3 mL was stirred at r.t. overnight. The mixture was concentrated to afford desired product. MS (ESI): 231.1 (M+H$^+$).

Step 1b: (1R)-1'-{[1-(4-cyclopentylphenyl)cyclopropyl]carbonyl}-3H-spiro[furo[3,4-c]pyridine-1,3'-pyrrolidin]-3-one This compound was prepared using procedures analogous to step 1b in example 123. MS (ESI): 403.1 (M+H$^+$)

Example 135

(1R)-1'-({1-[4-(1-Hydroxycyclopentyl)phenyl]cyclopropyl}carbonyl)-3H-spiro[furo[3,4-c]pyridine-1,3'-pyrrolidin]-3-one This compound was prepared using procedures analogous to those in example 133. MS (ESI): 401.1 (M-OH⁻)

Example 136

(1R)-1'-({1-[4-(1-Hydroxycyclobutyl)phenyl]cyclopropyl}carbonyl)-3H-spiro[2-benzofuran-1,3'-pyrrolidin]-3-one This compound was prepared using procedures analogous to those in example 133. MS (ESI): 404.3 (M+H⁺)

Example 137

(1R)-1'-({1-[4-(1-Hydroxycyclobutyl)phenyl]cyclopropyl}carbonyl)-3H-spiro[furo[3,4-c]pyridine-1,3'-pyrrolidin]-3-one This compound was prepared using procedures analogous to those in example 133. MS (ESI): 387.2 (M-OH⁻), 405.2 (M+H⁺)

Example 138

(1R)-1'-({1-[4-(Tetrahydro-2H-pyran-4-yl)phenyl]cyclopropyl}carbonyl)-3H-spiro[furo[3,4-c]pyridine-1,3'-pyrrolidin]-3-one This compound was prepared using procedures analogous to those in example 134. MS (ESI): 419.1 (M+H⁺)

Example 139

(1R)-1'-{[1-(4-Cyclobutylphenyl)cyclopropyl]carbonyl}-3H-spiro[furo[3,4-c]pyridine-1,3'-pyrrolidin]-3-one This compound was prepared using procedures analogous to those in example 134. MS (ESI): 389.0 (M+H⁺).

Example 140

(1R)-1'-({1-[4-(4-hydroxytetrahydro-2H-pyran-4-yl)phenyl]cyclopropyl}carbonyl)-3R-spiro[2-benzofuran-1,3'-pyrrolidin]-3-one This compound was prepared using procedures analogous to those in example 133. MS (ESI): 434.0 (M+H⁺)

Example 141

(1R)-1'-({1-[4-(4-Hydroxytetrahydro-2H-pyran-4-yl)phenyl]cyclopropyl}carbonyl)-3H-spiro[furo[3,4-c]pyridine-1,3'-pyrrolidin]-3-one This compound was prepared using procedures analogous to those in example 133. MS (ESI): 417 (M-OH⁻), 435.0 (M+H⁺)

Example 142

(1R)-1'-({1-[4-(2-Amino-1,3-thiazol-4-yl)phenyl]cyclopropyl}carbonyl)-3H-spiro[2-benzofuran-1,3'-pyrrolidin]-3-one Step 1. Methyl 1-phenylcyclopropanecarboxylate Methyl iodide (2.8 mL, 45.0 mmol) was added to a mixture of 1-phenylcyclopropanecarboxylic acid (4.9 g, 30.0 mmol) and potassium carbonate (8.3 g, 60.0 mmol) in DMF (50 mL) at room temperature and the reaction mixture was stirred for 1 h. Then the reaction mixture was diluted with diethyl ether. The resulting mixture was washed with water (×2) and brine successively, then dried and concentrated to afford the desired product.

Step 2. Methyl 1-[4-(chloroacetyl)phenyl]cyclopropanecarboxylate

Aluminium trichloride (7.9 g, 60.0 mmol) was added in portions to a mixture of methyl 1-phenylcyclopropanecarboxylate (3.5 g, 20.0 mmol) and chloroacetyl chloride (2.0 mL, 26.0 mmol) in carbon disulfide (40.0 mL) at 15-25° C. The reaction mixture was stirred for 2 hours at room temperature. Then the mixture was poured into concentrated HCl (10.0 mL) in ice (100 g). The resulting mixture was extracted with diethyl ether several times. The combined organic phase was washed with brine, then dried and concentrated. The crude product was purified by CombiFlash using hexane/ethyl acetate.

Step 3. Methyl 1-[4-(2-amino-1,3-thiazol-4-yl)phenyl]cyclopropanecarboxylate

A mixture of methyl 1-[4-(chloroacetyl)phenyl]cyclopropanecarboxylate (0.30 g, 1.2 mmol) and thiourea (0.18 g, 2.4 mmol) in ethanol (5.0 ml) was refluxed overnight. The reaction mixture was diluted with ethyl acetate and washed with saturated NaHCO₃ and brine successively; then dried; and then concentrated. The residue was triturated with ether followed by filtration to afford the product. LC-MS: 275.1 (M+H)⁺.

Step 4. 1-[4-(2-Amino-1,3-thiazol-4-yl)phenyl]cyclopropanecarboxylic acid

Lithium hydroxide monohydrate (0.24 g, 5.8 mmol) was added to a mixture of methyl 1-[4-(2-amino-1,3-thiazol-4-yl)phenyl]cyclopropanecarboxylate (0.2 g, 0.73 mmol) in THF (3.0 ml) and water (1.0 mL), and the resulting mixture was refluxed for 30 minutes. Then the reaction mixture was concentrated and the residue was adjusted to be acidic (pH=~3) by 1N HCl aqueous solution. The precipitate framed was filtered and washed with water to afford the desired product. LC-MS: 261.0 (M+H)⁺, Step 5

N,N-Diisopropylethylamine (50 µL, 0.3 mmol) was added to a mixture of 1-[4-(2-amino-1,3-thiazol-4-yl)phenyl]cyclopropanecarboxylic acid (26.0 mg, 0.1 mmol), (1S)-(+)-10-camphorsulfonic acid-3H-spiro-[2-benzofuran-1,3'-pyrrolidin]-3-one (1:1) (42.1 mg, 0.01 mmol) and BOP (57.0 mg, 0.13 mmol) in DMF (0.5 mL) at room temperature, and the reaction mixture was stirred for about 5 hours (the completion

Example 143

(1R)-1'-({1-[4-(2-Methyl-1,3-thiazol-4-yl)phenyl]cyclopropyl}carbonyl)-3H-spiro[2-benzofuran-1,3'-pyrrolidin]-3-one This compound was prepared using procedures analogous to those in example 142. LC-MS: 431.1 (M+H)+.

Example 144

(1R)-1'-({1-[4-(2-Ethyl-1,3-thiazol-4-yl)phenyl]cyclopropyl}carbonyl)-3H-spiro[2-benzofuran-1,3'-pyrrolidin]-3-one This compound was prepared using procedures analogous to those in example 142. LC-MS: 445.2 (M+H)+.

Example 145

(1R)-1'-({1-[4-(2-Amino-1,3-thiazol-4-yl)phenyl]cyclopropyl}carbonyl)-3H-spiro[furo[3,4-c]pyridine-1,3'-pyrrolidin]-3-one This compound was prepared using procedures analogous to those in examples 142. LC-MS: 433.2 (M+H)+.

Example 146

(1R)-1'-({1-[4-(2-Methyl-1,3-thiazol-4-yl)phenyl]cyclopropyl}carbonyl)-3H-spiro[furo[3,4-c]pyridine-1,3'-pyrrolidin]-3-one This compound was prepared using procedures analogous to those in examples 142. LC-MS: 432.1 (M+H)+.

Example 147

(1R)-1'-({1-[4-(1,3-Thiazol-4-yl)phenyl]cyclopropyl}carbonyl)-3H-spiro[2-benzofuran-1,3'-pyrrolidin]-3-one Isoamyl nitrite (10.0 μL) was added to a solution of (1R)-1'-({1-[4-(2-amino-1,3-thiazol-4-yl)phenyl]cyclopropyl}carbonyl)-3H-spiro[2-benzofuran-1,3'-pyrrolidin]-3-one (25.0 mg, 0.06 mmol) in 1,4-dioxane (1.0 mL), and the reaction mixture was stirred at 80° C. for 2 hours. Then the solvent from the mixture was removed and the crude product was purified by prep-HPLC. LC-MS: 417.1 (M+H)+.

Example 148

4-(1-{[1-(4-Chlorophenyl)-3-(methoxymethoxy)cyclobutyl]carbonyl}pyrrolidin-3-yl)pyridine Step 1. 1-(4-chlorophenyl)-3-(methoxymethoxy)cyclobutanecarboxylic acid A solution of 1-(4-chlorophenyl)-3-(methoxymethoxy)cyclobutanecarbonitrile, KOH, and ethylene glycol was heated to 198° C. for 6 h and then cooled to rt. The reaction mixture was washed with ether (2×10 mL) and then the aqueous solution was acidified (pH 3-4) with 4 M HCl (~5 mL). The resulting aqueous mixture then was extracted with ether (2×20 mL) and the combined organic layers were dried over MgSO$_4$, filtered and concentrated to afford 0.6158 g of a brown oil (the reaction was monitored by the consumption of the starting material by TLC). The identification of the product was confirmed by $^1$H NMR and LCMS. LC-MS: 271.1 (M+H+).

Step 2

To a solution of 1-(4-chlorophenyl)-3-(methoxymethoxy)cyclobutanecarboxylic acid in methylene chloride was add DIEA, and the mixture was stirred for 10 minutes. Then BOP was added and the mixture was stirred for 20 minutes. Then 4-pyrrolin-3-ylpyridine hydrochloride was added and the resulting mixture was stirred at room temperature overnight. The completion of the reaction was determined by LCMS. The reaction mixture then was poured in to a saturated NaHCO$_3$ aqueous solution and the resulting mxitre was extract with CH$_2$Cl$_2$ (2×). The combined organic layers were dried over MgSO$_4$, then filtered and then concentrated in-vacuo. The crude product was purified by flash column chromatography with MeOH/CH$_2$Cl$_2$ (1%, 3%, 5%, 7%) to afford the desired product (24.1 mg). The identification of the product was confirmed by LCMS and $^1$H NMR. LC/MS: 401.2 (M+H+).

Example 149

3-(3-Chlorophenyl)-1-{[1-(4-chlorophenyl)-3-(methoxymethoxy)cyclobutyl]carbonyl}pyrrolidine This compound was prepared using procedures analogous to those in example 148. LC-MS: 435.1 (M+H)+.

Example 150

1'-{[trans-1-(4-Chlorophenyl)-3-hydroxycyclobutyl]carbonyl}-3H-spiro[2-benzofuran-1,3'-pyrrolidin]-3-one Step 1. trans-1-(4-Chlorophenyl)-3-hydroxycyclobutanecarboxylic acid The corresponding aldehyde was dissolved in t-BuOH/THF/2-methylbut-2-ene and the mixture was stirred at room temperature. A solution of sodium chlorite and sodium dihydrogen phosphate in water was added to the mixture with stirring. The resulting mixture was stirred for 2 hours, then the volatiles were removed from the mixture. The residue was acidified (to pH 2) with 1N HCl aqueous solution. The resulting mixture was then extracted with EtOAc (3×). The combined organic phase was dried over MgSO$_4$, then filtered and concentrated to afford the desired carboxylic acid.

Step 2

This compound was prepared by using a procedure analogous to that described in example 4. LC/MS: 398.9 (M+H+).

Example 151

1'-{[cis-1-(4-Chlorophenyl)-3-fluorocyclobutyl]carbonyl}-3H-spiro[2-benzofuran-1,3'-pyrrolidin]-3-one This compound was prepared by using a procedure analogous to that described in example 150 starting with the corresponding aldehyde. LC/MS: 400.1 (M+H+).

Example 152

1'-{[cis-1-(4-Chlorophenyl)-3-fluorocyclobutyl]carbonyl}-3H-spiro[2-benzofuran-1,3'-pyrrolidine]

This compound was prepared by using a procedure analogous to that described in example 150 starting with the corresponding aldehyde and 3H-spiro[2-benzofuran-1,3'-pyrrolidine]hydrochloride. LC/MS: 386.1 (M−H⁺).

Example 153

1'-{[cis-1-(4-Chlorophenyl)-3-fluorocyclobutyl]carbonyl}-3H-spiro[furo[3,4-c]pyridine-1,3'-pyrrolidin]-3-one This compound was prepared by using a procedure analogous to that described in example 150 starting with the corresponding aldehyde and 7H-spiro[furo[3,4-b]pyridine-5,3'-pyrrolidin]-7-one hydrochloride. The compound was purified by prep-HPLC. LC/MS: 401.1 (M+H⁺).

Example 154

1'-{[cis-1-(4-Chlorophenyl)-3-fluorocyclobutyl]carbonyl}-7H-spiro[furo[3,4-b]pyridine-5,3'-pyrrolidin]-7-one This compound was prepared by using a procedure analogous to that described in example 153. LC/MS: 401.1 (M+H⁺).

Example 155

3-(1-{[1-(4-Chlorophenyl)cyclobutyl]carbonyl}pyrrolidin-3-yl)pyridine

This compound was prepared by using a procedure analogous to that described in example 1. LC/MS: 341.1 (M+H⁺).

Example 156

(1R)-1'-{[1-(4-Chlorophenyl)cyclobutyl]carbonyl}-7H-spiro[furo[3,4-b]pyridine-5,3'-pyrrolidin]-7-one To a solution of piperidine, 2,2,6,6-tetramethyl-(1.20 mL, 0.00713 mol) in tetrahydrofuran (30 mL, 0.4 mol) at −75 degrees celsius was added 2.5 M of n-butyllithium in hexane (3.8 mL), and the mixture was stirred for 15 minutes. Then a suspension of 2-pyridinecarboxylic acid (0.292 g, 0.00238 mol) in THF was added and the resulting mixture was then stirred at −75 degrees celsius for 10 minutes and then at 0° C. for 1 hour. A solution of 1-{[1-(4-chlorophenyl)cyclobutyl]carbonyl}pyrrolidin-3-one (550 mg, 0.0020 mol) in THF (2 mL) was added to the above mixture, and the resulting mixture was stirred at 0 degrees celsius for 20 minutes and then at 0° C. 1 hour. The reaction mixture was acidified (to pH ~0.1) using 6 M HCl aqueous solution and stirred at room temperature overnight. The reaction mixture then was neutralized (to pH ~7), extracted with AcOEt. The organic phase was washed with brine, then dried over MgSO₄, and concentrated. The crude product was purified by Combiflash and then the enantiomers were separated using a chiral column. LC/MS: 383.1 (M+H⁺).

Example 157

(1R)-1'-({1-[4-(1H-Indazol-1-yl)phenyl]cyclobutyl}carbonyl)-3H-spiro[furo[3,4-c]pyridine-1,3'-pyrrolidin]-3-one Step 1. 1'-{[1-(4-Bromophenyl)cyclobutyl]carbonyl}-3H-spiro[furo[3,4-c]pyridine-1,3'-pyrrolidin]-3-one This compound was prepared by using a procedure analogous to that described in example 90. LC/MS: 429.1 and 427.1 (M+H⁺).

Step 2

To a solution of 1'-{[1-(4-bromophenyl)cyclobutyl]carbonyl}-3H-spiro[furo[3,4-c]pyridine-1,3'-pyrrolidin]-3-one (30 mg, 0.00007 mol), and 1H-benzimidazole (0.010 g, 0.000087 mol) in toluene (0.5 mL, 0.005 mol) and N,N-dimethylformamide (0.5 mL, 0.006 mol), were added (1S, 2S)—N,N'-dimethylcyclohexane-1,2-diamine (2.1 mg, 0.000014 mol), copper(I) iodide (1 mg, 0.000007 mol), and potassium carbonate (21.1 mg, 0.000152 mol), and the mixture was stirred at 120° C. overnight. The reaction mixture was then filtered and the filtrate was diluted with methanol. The product was purified using prep-HPLC followed by chiral HPLC. LC-MS: 465.2 (M+H)+.

Example 158

(1R)-1'-[(1-{4-[3-(Trifluoromethyl)-1H-pyrazol-1-yl]phenyl}cyclobutyl)-carbonyl]-3H-spiro[furo[3,4-c]pyridine-1,3'-pyrrolidin]-3-one This compound was prepared by using a procedure analogous to that described in example 157, with the exception that the reaction was heated to 200° C. for 1 h in the microwave. LC/MS: 483.2 (M+H⁺).

Example 159

(1R)-1'-({1-[4-(1H-Benzimidazol-1-yl)phenyl]cyclobutyl}carbonyl)-3H-spiro[furo[3,4-c]pyridine-1,3'-pyrrolidin]-3-one This compound was prepared by using a procedure analogous to that described in example 157. LC/MS: 465.2 (M+H⁺).

Example 160

(1R)-1'-({1-[4-(2-Oxo-1,3-oxazolidin-3-yl)phenyl]cyclobutyl}carbonyl)-3H-spiro[2-benzofuran-1,3'-pyrrolidin]-3-one Step 1. (1R)-1'-{[7-(4-bromophenyl)cyclobutyl]carbonyl}-3H-spiro[2-benzofuran-1,3'-pyrrolidin]-3-one This compound was prepared by using a procedure analogous to that described in example 116. LC/MS: 426.1 and 428.1 (M+H⁺).

Step 2

To a solution of (1R)-1'-{[1-(4-bromophenyl)cyclobutyl]carbonyl}-3H-spiro[2-benzofuran-1,3'-pyrrolidin]-3-one (20.7 mg, 0.0000485 mol) and oxazolidin-2-one (12.7 mg, 0.000146 mol) in freshly distilled toluene (0.34 mL, 0.0032 mol), were added tris(dibenzylidene acetone)dipalladium(0) (4.4 mg, 0.0000048 mol), tri-tert-butylphosphine (2.0 mg, 0.0000097 mol) and cesium carbonate (15.8 mg, 0.0000485 mol), and the mixture was heated to 50° C. overnight. The reaction mixture then was cooled to rt, filtered over celite and concentrated under reduced pressure. The crude product was purified by prep-HPLC. LC/MS (M+H) 433.2.

Example 161

(1R)-1'-[(1-Pyridin-4-ylcyclobutyl)carbonyl]-3H-spiro[2-benzofuran-1,3'-pyrrolidin]-3-one Lithium hydroxide, monohydrate (0.013 g, 0.00031 mol) was added to a solution of ethyl 1-pyridin-4-ylcyclobutanecarboxylate (32 mg, 0.00016 mol) in tetrahydrofuran (1.6 mL, 0.020 mol) and water (0.3 mL, 0.02 mol). The mixture was stirred at room temperature until the reaction was complete. The mixture was acidified (to pH=5) with 4 M HCl (75 µL) and concentrated to afford the carboxylic acid. Then [(1R,4S)-7,7-dimethyl-2-oxobicyclo[2.2.1]hept-1-yl]methanesulfonic acid-(1R)-3H-spiro[2-benzofuran-1,3'-pyrrolidin]-3-one (1:1) (0.033 g, 0.000078 mol) and (benzotriazol-1-yloxy)tripyrrolidinophosphonium hexafluorophosphate (0.041 g, 0.000078 mol) were added to the above crude product of the carboxylic acid, followed by 4-methylmorpholine (6.0 µL, 0.00055 mol). The reaction mixture was stirred at room temperature for 2 hours. The crude product was purified by prep-LCMS. LC/MS:349.1 (M+H$^+$).

Example 162

(1R)-1'-{[1-(4-Pyridin-4-ylphenyl)cyclobutyl]carbonyl}-3H-spiro[2-benzofuran-1,3'-pyrrolidin]-3-one This compound was prepared by a coupling procedure similar to that described in example 122 using 4-pyridinyl boronic acid and the corresponding aryl bromide. LCMS: m/z 425.2 (M+H)$^+$; 447.2 (M+Na)$^+$.

Example 163

N,N-Dimethyl-4-[5-(1-{[(1R)-3-oxo-1'H,3H-spiro[2-benzofuran-1,3'-pyrrolidin]-1'-yl]carbonyl}cyclopropyl)pyridin-2-yl]piperazine-1-carboxamide Step 1. Ethyl 1-(6-chloropyridin-3-yl)cyclopropanecarboxylate Sodium hydride (60% in mineral oil, 0.60 g, 15 mmol) was added to a solution of ethyl (6-chloropyridin-3-yl)acetate (1.0 g, 0.0050 mol) in N,N-dimethylformamide (10 mL, 0.1 mol) at rt under an atmosphere of nitrogen. After 30 minutes, 1-bromo-2-chloro-ethane (0.84 mL, 0.010 mol) was added to the mixture at 0° C. The reaction mixture was stirred at 35° C. for 4 hours and then at room temperature overnight. The mixture was poured into a mixture of ice-water (50 ml) and EtOAc (50 ml) and the resulting mixture was acidified (to pH 2) by slow addition of 6 N HCl. The layers were separated and the organic layer was washed successively with water and brine, dried over MgSO$_4$ and concentrated. The residue was chromatographed by combiflash (ethyl acetate in hexanes: 80%, on silica gel) to afford the desired product. LC/MS: 226.0 and 228.0 (M+H$^+$).

Step 2. tert-Butyl 4-{5-[1-(ethoxycarbonyl)cyclopropyl]pyridin-2-yl}piperazine-1-carboxylate A mixture of ethyl 1-(6-chloropyridin-3-yl)cyclopropanecarboxylate (225.7 mg, 0.001000 mol) and tert-butyl piperazine-1-carboxylate (3.0 eq.) was heated at 130° C. for 6 h. After cooling, the mixture was flash chromatographed on a silica gel column to afford the desired product. LC/MS: 376.5 (M+H$^+$).

Step 3. tert-Butyl 4-[5-(1-{[(1R)-3-oxo-1'H,3H-spiro[2-benzofuran-1,3'-pyrrolidin]-1'-yl]carbonyl}cyclopropyl)pyridin-2-yl]piperazine-1-carboxylate To a solution of tent-Butyl 4-{5-[1-(ethoxycarbonyl)cyclopropyl]pyridin-2-yl}-piperazine-1-carboxylate (113 mg, 0.000300 mol) in THF (1.00 mL) and water (1.00 mL) and methanol (1.00 mL) was added lithium hydroxide in water (2.00 M, 0.500 mL). The mixture was irradiated under microwave at 100° C. for 30 minutes, and then was neutralized with 2 M HCl (0.50 mL). The mixture was concentrated and the residue was dissolved in DMF (3.0 mL). To the solution were added [(1S)-7,7-dimethyl-2-oxobicyclo[2.2.1]hept-1-yl]methanesulfonic acid-(1R)-3H-spiro[2-benzofuran-1,3'-pyrrolidin]-3-one (1:1) (164 mg, 0.000390 mol), benzotriazol-1-yloxytris(dimethylamino)phosphonium hexafluorophosphate (146 mg, 0.000330 mol) and 4-methylmorpholine (160 µL, 0.0014 mol). The resulting mixture was stirred at room temperature for 3 hours. The reaction mixture then was adjusted to be acidic (to pH=2.0) with TFA and diluted with DMF (2.0 mL). The solution was purified by prep-HPLC to give the desired product. LC/MS: 519.6 (M+H$^+$).

Step 4. N,N-Dimethyl-4-[5-(1-{[(1R)-3-oxo-1'H,3H-spiro[2-benzofuran-1,3'-pyrrolidin]-1'-yl]carbonyl}cyclopropyl)pyridin-2-yl]piperazine-1-carboxamide To a solution of tert-Butyl 4-[5-(1-{[(1R)-3-oxo-1'H,3H-spiro[2-benzofuran-1,3'-pyrrolidin]-1'-yl]carbonyl}cyclopropyl)pyridin-2-yl]piperazine-1-carboxylate (10.4 mg, 0.0000200 mol) was added hydrogen chloride in 1,4-dioxane (4.0 M, 20.0 µL), and the mixture was stirred at room temperature for 1 hour. The solvent of the mixture then was evaporated, and to the resulting residue were added acetonitrile (1.00 mL, 0.0191 mol), N,N-diisopropylethylamine (20.0 mL, 0.000115 mol), and N,N-dimethylcarbamoyl chloride (4.8 µL, 0.000052 mol). The mixture was stirred at room temperature for 30 minutes, then acidified (pH=2.0) with TFA, and then diluted with methanol (0.8 mL). The resulting solution was purified by prep-HPLC to give the desired product. LC/MS: 490.6 (M+H$^+$).

Example 164

(1R)-1'-[(1-{6-[4-(Methylsulfonyl)piperazin-1-yl]pyridin-3-yl}cyclopropyl)carbonyl]-3H-spiro[2-benzofuran-1,3'-pyrrolidin]-3-one This compound was prepared by procedures analogous to those described in example 163, with the exception that N,N- dimethylcarbamoyl chloride was substituted for methanesulfonyl chloride in step 4. LC/MS: 497.6 (M+H$^+$).

Example 165

(1R)-1'-[(1-{6-[4-(2-Fluorophenyl)piperazin-1-yl]pyridin-3-yl}cyclopropyl)carbonyl]-3H-spiro[2-benzofuran-1,3'-pyrrolidin]-3-one This compound was prepared by procedures analogous to those described in example 163 (steps 1-3). LC/MS: 513.6 (M+H$^+$).

Example 166

(1R)-1'-({1-[6-(3,3-Difluoropyrrolidin-1-yl)pyridin-3-yl]cyclopropyl}carbonyl)-3H-spiro[2-benzofuran-1,3'-pyrrolidin]-3-one This compound was prepared by procedures analogous to those described in example 163 (steps 1-3). LC/MS: 440.5 (M+H$^+$).

Example 167

(1R)-1'-[(1-{6-[(3S)-3-Hydroxypyrrolidin-1-yl]pyridin-3-yl}cyclopropyl)carbonyl]-3H-spiro[2-benzofuran-1,3'-pyrrolidin]-3-one This compound was prepared by procedures analogous to those described in example 163 (steps 1-3). LC/MS: 420.5 (M+H$^+$).

Example 168

N-{(3R)-1-[5-(1-{[(1R)-3-Oxo-1'H,3H-spiro[2-benzofuran-1,3'-pyrrolidin]-1'-yl]carbonyl}cyclopropyl)pyridin-2-yl]pyrrolidin-3-yl}acetamide This compound was prepared by using procedures analogous to those described in example 163 (steps 1-3). LC/MS: 461.5 (M+FP).

Example 169

(1R)-1'-({1-[6-(1,3-Dihydro-2H-isoindol-2-yl)pyridin-3-yl]cyclopropyl}carbonyl)-3H-spiro[2-benzofuran-1,3'-pyrrolidin]-3-one This compound was prepared by procedures analogous to those described in example 163 (steps 1-3). LC/MS: 452.5 (M+H$^+$).

Example 170

(1R)-1'-({1-[6-(3,4-Dihydroisoquinolin-2(1H)-yl)pyridin-3-yl]cyclopropyl}carbonyl)-3H-spiro[2-benzofuran-1,3'-pyrrolidin]-3-one This compound was prepared by using procedures analogous to those described in example 163 (steps 1-3). LC/MS: 466.5 (M+H$^+$).

Example 171

(1R)-1'-{[1-(6-Morpholin-4-ylpyridin-3-yl)cyclopropyl]carbonyl}-3H-spiro[2-benzofuran-1,3'-pyrrolidin]-3-one This compound was prepared by procedures analogous to those described in example 163 (steps 1-3). LC/MS: 420.1 (M+H$^+$).

Example 172

(1R)-1'-({1-[6-(4-Hydroxypiperidin-1-yl)pyridin-3-yl]cyclopropyl}carbonyl)-3H-spiro[2-benzofuran-1,3'-pyrrolidin]-3-one This compound was prepared by procedures analogous to those described in example 163 (steps 1-3). LC/MS: 434.1 (M+H$^+$).

Example 173

N-{4-[5-(1-{[(1R)-3-Oxo-1'H,3H-spiro[2-benzofuran-1,3'-pyrrolidin]-1'-yl]carbonyl}cyclopropyl)pyridin-2-yl]phenyl}acetamide Step 1. (1R)-1'-{[1-(6-chloropyridin-3-yl)cyclopropyl]carbonyl}-3H-spiro[2-benzofuran-1,3'-pyrrolidin]-3-one 4-Methylmorpholine (790 µL, 0.0072 mol) was added to a mixture of 1-(6-chloropyridin-3-yl)cyclopropanecarboxylic acid (1.8 mmol, 0.0018 mol), [(1R,4S)-7,7-dimethyl-2-oxobicyclo[2.2.1]hept-1-yl]methanesulfonic acid-(1R)-3H-spiro[2-benzofuran-1,3'-pyrrolidin]-3-one (1:1) (760 mg, 0.0018 mol) (prepared by methods described in example 96, steps 1-2), (benzotriazol-1-yloxy)tripyrrolidinophosphonium hexafluorophosphate (984 mg, 0.00189 mol), or benzotriazol-1-yloxytris(dimethylamino)phosphonium hexafluorophosphate (836 mg, 0.00189 mol) in N,N-dimethylformamide (10 mL, 0.1 mol). The reaction mixture was stirred at room temperature for 2 hours. The crude product was purified by prep-LCMS. LC/MS: 369.1 (M+H$^+$).

Step 2

Sodium carbonate (12.7 mg, 0.000120 mol) in water (0.100 mL) was added to a mixture of (1R)-1'-{[1-(6-chloropyridin-3-yl)cyclopropyl]carbonyl}-3H-spiro[2-benzofuran-1,3'-pyrrolidin]-3-one (22.1 mg, 0.0000600 mol), [4-(acetylamino)phenyl]boronic acid (10.7 mg, 0.0000600 mol) and tetrakis(triphenylphosphine)palladium(0) (2.14 mg, 1.86×10$^{-6}$ mol) in toluene (200.00 µL, 0.0018776 mol) and ethanol (100.00 µL, 0.0017127 mol). The resulting mixture was irradiated by microwave at 120° C. for 15 minutes. Ethyl acetate (5 mL) was added and the resulting mixture was washed with water and brine successively. The organic layer was dried over Na$_2$SO$_4$, then filtered, and then concentrated under reduced pressure. The residue was purified by Combi-flash with ethyl acetate/hexane to give the desired product. LC/MS: 468.5 (M+H$^+$).

Example 174

(1R)-1'-({1-[6-(2-Fluorophenyl)pyridin-3-yl]cyclopropyl}carbonyl)-3H-spiro[2-benzofuran-1,3'-pyrrolidin]-3-one This compound was prepared by using a procedure analogous to that described in example 173. LC/MS: 429.1 (M+H⁺).

Example 175

(1R)-1'-({1-[6-(1-Benzothien-3-yl)pyridin-3-yl]cyclopropyl}carbonyl)-3H-spiro[2-benzofuran-1,3'-pyrrolidin]-3-one This compound was prepared by using a procedure analogous to that described in example 173. LC/MS: 467.6 (M+H⁺).

Example 176

(1R)-1'-{[1-(2,3'-Bipyridin-5-yl)cyclopropyl]carbonyl}-3H-spiro[2-benzofuran-1,3'-pyrrolidin]-3-one This compound was prepared by using a procedure analogous to that described in example 173. LC/MS: 412.5 (M+H⁺).

Example 177

(1R)-1'-({1-[6-(1-Methyl-1H-indol-5-yl)pyridine-3-yl]cyclopropyl}carbonyl)-3H-spiro[2-benzofuran-1,3'-pyrrolidin]-3-one This compound was prepared by using a procedure analogous to that described in example 96. LC/MS: 464.5 (M+H⁺).

Example 178

(1R)-1'-[(1-{6-[3-(Trifluoromethoxy)phenyl]pyridine-3-yl}cyclopropyl)carbonyl]-3H-spiro[2-benzofuran-1,3'-pyrrolidin]-3-one This compound was prepared by using a procedure analogous to that described in example 96. LC/MS: 495.5 (M+H⁺).

Example 179

(1R)-1'-({1-[6-(3-Thienyl)pyridine-3-yl]cyclopropyl}carbonyl)-3H-spiro[2-benzofuran-1,3'-pyrrolidin]-3-one This compound was prepared by using a procedure analogous to that described in example 96. LC/MS: 417.5 (M+H⁺).

Example 180

(1R)-1'-[(1-{6-[3-(Trifluoromethyl)phenyl]pyridine-3-yl}cyclopropyl)-carbonyl]-3H-spiro[2-benzofuran-1,3'-pyrrolidin]-3-one This compound was prepared by using a procedure analogous to that described in example 96. LC/MS: 479.5 (M+H⁺).

Example 181

(1R)-1'-({1-[6-(1-Methyl-1H-pyrazol-4-3]pyridine-3-yl]cyclopropyl}carbonyl)-3H-spiro[2-benzofuran-1,3'-pyrrolidin]-3-one This compound was prepared by using a procedure analogous to that described in example 96. LC/MS: 415.5 (M+H⁺).

Example 182

(1R)-1'-{[1-(6-Chloropyridin-3-yl)cyclopropyl]carbonyl}-3H-spiro[2-benzofuran-1,3'-pyrrolidin]-3-one This compound was prepared by using a procedure analogous to that described in example 96 (omitting step 3). LC/MS: 369.5 (M+H⁺).

Example 183

(1R)-1'-({1-[6-(Benzyloxy)pyridin-3-yl]cyclopropyl}carbonyl)-3H-spiro[2-benzofuran-1,3'-pyrrolidin]-3-one The procedure that was outlined for the synthesis of example 96 was followed with the exception that step 3 was omitted and replaced with the following procedure:

Step 3 substitute. 1-[6-(benzyloxy)pyridin-3-yl]cyclopropanecarboxylic acid

A mixture of ethyl 1-(6-chloropyridin-3-yl)cyclopropanecarboxylate (45.1 mg, 0.000200 mol), benzyl alcohol (0.50 mL, 0.0048 mol) and sodium hydride (9.50 mg, 0.000238 mol) was irradiated by microwave at 150° C. for 15 minutes. After cooling, additional sodium hydride (9.5 mg) was added to the mixture. The mixture then was irradiated by microwave at 150° C. for 15 minutes. Ethyl acetate (5 mL) was added and the resulting mixture was washed with water and brine successively. The organic layer was dried over Na₂SO₄, filtered, and concentrated under reduced pressure. The residue was purified by Combiflash with ethyl acetate/hexane to give the desired product.

Following the BOP coupling the desired product, (1R)-1'-({1-[6-(benzyloxy)pyridin-3-yl]cyclopropyl}carbonyl)-3H-spiro[2-benzofuran-1,3'-pyrrolidin]-3-one, was purified by prep-HPLC. LC/MS: 441.2 (M+H⁺).

Example 184

(1R)-1'[(1-Quinolin-3-ylcyclopropyl)carbonyl]-3H-spiro[2-benzofuran-1,3'-pyrrolidin]-3-one This compound was prepared by a procedure analogous to that used for example 173 (step 1). LC/MS: 385.2 (M+h⁺).

Example 185

(1R)-1'-({1-[6-(1-Methyl-1H-pyrazol-4-yl)pyridin-3-yl]cyclopropyl}carbonyl)-3H-spiro[furo[3,4-c]pyridine-1,3'-pyrrolidin]-3-one This compound was prepared by using a procedure analogous to that described in example 96. LC/MS: 416.2 (M+H⁺).

Example 186

(1R)-1'-({1-[6-(Benzyloxy)pyridin-3-yl]cyclopropyl}carbonyl)-3H-spiro[furo[3,4-c]pyridine-1,3'-pyrrolidin]-3-one This compound was prepared by using a procedure analogous to that described in example 183. LC/MS: 442.2 (M+H$^+$).

Example 187

(1R)-1'-{[1-(6-Chloropyridin-3-yl)cyclopropyl]carbonyl}-3H-spiro[furo[3,4-c]pyridine-1,3'-pyrrolidin]-3-one This compound was prepared by using a procedure analogous to that described in example 182. LC/MS: 370.5 (M+H$^+$).

Example 188

(1R)-1'-({1-[6-(3,4-Dihydroisoquinolin-2(1H)-yl)pyridin-3-yl]cyclopropyl}carbonyl)-3H-spiro[furopyridine-1,3'-pyrrolidin]-3-one This compound was prepared by using a procedure analogous to that described in example 170. LC/MS: 467.2 (M+H$^+$).

Example 189

(1R)-1'-({1-[6-(1,3-Dihydro-2H-isoindol-2-yl)pyridin-3-yl]cyclopropyl}carbonyl)-3H-spiro[furo[3,4-c]pyridine-1,3'-pyrrolidin]-3-one This compound was prepared by using a procedure analogous to that described in example 163. LC/MS: 453.2 (M+H$^+$).

Example 190

(1R)-1'-({1-[6-(3,3-Difluoropyrrolidin-1-yl)pyridin-3-yl]cyclopropyl}carbonyl)-3H-spiro[furo[3,4-c]pyridine-1,3'-pyrrolidin]-3-one This compound was prepared by a procedure analogous to the one described in example 163 (steps 1-3). LC/MS: 441.2 (M+H$^+$).

Example 191

(1R)-Isobutyl 4-(5-{1-[(3-oxo-1'H,3H-spiro[furo[3,4-c]pyridine-1,3'-pyrrolidin]-1'-yl)carbonyl]cyclopropyl}pyridin-2-yl)piperazine-1-carboxylate This compound was prepared by a procedure analogous to the one described in example 163. LC/MS: 520.1 (M+H$^+$).

Example 192

(1R)-2-[4-(5-{1-[(3-oxo-1'H,3H-spiro[furo[3,4-c]pyridine-1,3'-pyrrolidin]-1'-yl)carbonyl]cyclopropyl}pyridin-2-yl)piperazin-1-yl]benzonitrile This compound was prepared by a procedure analogous to the one described in example 163 (steps 1-3). LC/MS: 521.1 (M+H$^+$).

Example 193

(1R)-1'-[(1-{6-[4-(4-Fluorophenyl)piperazin-1-yl]pyridin-3-yl}cyclopropyl)carbonyl]-3H-spiro[furo[3,4-c]pyridine-1,3'-pyrrolidin]-3-one This compound was prepared by a procedure analogous to the one described in example 163 (steps 1-3). LC/MS: 514.5 (M+H$^+$).

Example 194

(1R)-1'-[(1-{6-[3-(Trifluoromethyl)phenyl]pyridin-3-yl}cyclopropyl)carbonyl]-3H-spiro[furo[3,4-c]pyridine-1,3'-pyrrolidin]-3-one This compound was prepared by a procedure analogous to the one described in example 96. LC/MS: 480.4 (M+H$^+$).

Example 195

(1R)-1'-[(1-{6-[3-(Trifluoromethoxy)phenyl]pyridin-3-yl}cyclopropyl)carbonyl]-3H-spiro[furo[3,4-c]pyridine-1,3'-pyrrolidin]-3-one This compound was prepared by a procedure analogous to the one described in example 96. LC/MS: 496.1 (M+H$^+$).

Example 196

(1R)-4-(5-{1-[(3-Oxo-1'H,3H-spiro[furo[3,4-c]pyridine-1,3'-pyrrolidin]-1'-yl)carbonyl]cyclopropyl}pyridin-2-yl)benzonitrile This compound was prepared by a procedure analogous to the one described in example 173. LC/MS: 437.2 (M+H$^+$).

Example 197

(1R)-1'-({1-[6-(3-Chloro-4-fluorophenyl)pyridin-3-yl]cyclopropyl}carbonyl)-3H-spiro[furo[3,4-c]pyridine-1,3'-pyrrolidin]-3-one This compound was prepared by a procedure analogous to the one described in example 173. LC/MS: 464.1 (M+H$^+$).

Example 198

(1R)-1'-[(1-{6-[4-(Methoxymethyl)phenyl]pyridin-3-yl}cyclopropyl)carbonyl]-3H-spiro[furo[3,4-c]pyridine-1,3'-pyrrolidin]-3-one This compound was prepared by a procedure analogous to the one described in example 173. LC/MS: 456.2 (M+H$^+$).

Example 199

(1R)—N—[3-(5-{1-[(3-Oxo-1'H,3H-spiro[furo[3,4-c]pyridine-1,3'-pyrrolidin]-1'-yl)carbonyl]cyclopropyl}pyridin-2-yl)phenyl]acetamide This compound was prepared by a procedure analogous to the one described in example 173. LC/MS: 469.2 (M+H$^+$).

Example 200

(1R)-4-(5-{1-[(3-Oxo-1'H,3H-spiro[furo[3,4-c]pyridine-1,3'-pyrrolidin]-2-yl)carbonyl]cyclopropyl}pyridin-2-yl)benzamide This compound was prepared by a procedure analogous to the one described in example 173. LC/MS: 455.2 (M+H$^+$).

Example 201

(1R)-1'-[(1-{6-[4-(Methylsulfonyl)phenyl]pyridin-3-yl}cyclopropyl)carbonyl-3H-spiro[furo[3,4-c]pyridine-1,3'-pyrrolidin]-3-one This compound was prepared by a procedure analogous to the one described in example 173. LC/MS: 490.1 (M+H$^+$).

Example 202

(1R)-1'-({1-[6-(1-Methyl-1H-indol-5-yl)pyridin-3-yl]cyclopropyl}carbonyl)-3H-spiro[furo[3,4-c]pyridine-1,3'-pyrrolidin]-3-one This compound was prepared by a procedure analogous analogous to the one described in example 96. LC/MS: 465.2 (M+H$^+$).

Example 203

(1R)-1'-({1-[6-(1-Benzothien-5-yl)pyridin-3-yl]cyclopropyl}carbonyl)-3H-spiro[furo[3,4-c]pyridine-1,3'-pyrrolidin]-3-one This compound was prepared by a procedure analogous to the one described in example 96. LC/MS: 468.2 (M+H $^+$).

Example 204

(1R)-1'-{[1-(6-Quinolin-3-ylpyridin-3-yl)cyclopropyl]carbonyl}-3H-spiro[furo[3,4-c]pyridine-1,3'-pyrrolidin]-3-one This compound was prepared by a procedure analogous to the one described in example 96. LC/MS: 463.2 (M+H$^+$).

Example 205

(1R)-1'-({1-[6-(3-Thienyl)pyridin-3-yl]cyclopropyl}carbonyl)-3H-spiro[furo[3,4-c]pyridine-1,3'-pyrrolidin]-3-one This compound was prepared by a procedure analogous to the one described in example 96. LC/MS: 418.2 (M+H$^+$).

Example 206

(1R)-1'-({1-[4-(2-Oxo-2,3-dihydro-1H-indol-1-yl)phenyl]cyclopropyl}carbonyl)-3H-spiro[furo[3,4-c]pyridine-1,3'-pyrrolidin]-3-one This compound was prepared by a procedure analogous to the one described in example 129. LC/MS: 466.2 (M+H$^+$).

Example 207

(1R)-1'-({1-[4-(3-Methyl-2-oxo-2,3-dihydro-1H-benzimidazol-1-yl)phenyl]cyclopropyl}carbonyl)-3H-spiro[furo[3,4-c]pyridine-1,3'-pyrrolidin]-3-one Step 1. 1'-({1-[4-(2-oxo-2,3-dihydro-1H-benzimidazol-1-yl)phenyl]cyclopropyl}carbonyl)-3H-spiro[furo[3,4-c]pyridine-1,3'-pyrrolidin]-3-one This compound was prepared by a procedure analogous to the one described in example 129. LC/MS: 467.2 (M+H$^+$).

Step 2

To a solution of (1R)-1'-({1-[4-(2-oxo-2,3-dihydro-1H-benzimidazol-1-yl)phenyl]cyclopropyl}carbonyl)-3H-spiro[furo[3,4-c]pyridine-1,3'-pyrrolidin]-3-one (50 mg, 0.0001 mol) in dimethyl sulfoxide (1 mL, 0.01 mol) were added potassium carbonate (16.3 mg, 0.000118 mol) and methyl iodide (6.67 µL, 0.000107 mol), and the mixture was stirred at room temperature for. 2 hours. The crude product was purified by prep-HPLC.

Example 208

(1R)-4-{1-[(3-Oxo-1'H,3H-spiro[furo[3,4-c]pyridine-1,3'-pyrrolidin]-1'-yl)carbonyl]cyclopropyl}benzonitrile Step 1. Methyl 1-(4-cyanophenyl)cyclopropanecarboxylate A degassed mixture of methyl 1-(4-chlorophenyl)cyclopropanecarboxylate (4.748 g, 0.02254 mol), zinc cyanide (2.701 g, 0.02254 mol), bis(tri-t-butylphosphine)palladium (705 mg, 0.00135 mol) and zinc (265 mg, 0.00406 mol) powder in anhydrous N-methylpyrrolidinone (50.0 mL, 0.518 mol) was heated at 150° C. for 18 hours. The completion of the reaction is determined by LCMS and TLC. The reaction mixture was cooled to rt, diluted with EtOAc, filtered through a pad of celite and the solid was washed with EtOAc. The filtrate was washed with 2 N NH$_4$OH (100 mL) and brine successively, dried over magnesium sulfate, filtered and concentrated in vacuo. The residue was purified by Combiflash with 2-15% EtOAc/hexanes to give the product as a colorless oil (3.434 g, 76% in yield). LC/MS: (M+H)=202.1.

Step 2

The above compound was subjected to the analogous hydrolysis and amide coupling reaction described in step 3 of example 163. LC/MS: 360.1 (M+H$^+$).

Example 209

4-{1-[(3-Oxo-1'H,3H-spiro[furo[3,4-c]pyridine-1,3'-pyrrolidin]-1'-yl)carbonyl]cyclopropyl}benzenecarbothioamide To a microwave vial were added 4-{1-[(3-oxo-1'H,3H-spiro[furo[3,4-c]pyridine-1,3'-pyrrolidin]-1'-yl)carbonyl]cyclopropyl}benzonitrile (0.6085 g, 0.001693 mol), ammonium sulfide in water (7.34 M, 0.461 mL) and methanol (10.00 mL, 0.2469 mol). The resulting solution was microwave irradiated at 100° C. for 30 minutes. The reaction was quenched with 40 mL water, and yellow solid precipitated from the reaction mixture. The precipitated yellow solid was collected by filtration. The filtrate was extracted with ethyl acetate (×3). The combined organic phase was washed with brine, dried over magnesium sulfate, filtered and concentrated. No product was present in the organic layer or aqueous layer. The precipitated yellow solid was identified as the desired product by $^1$H NMR. No purification was required. LC/MS: 394.1 (M+H$^+$).

Example 210

(1R)-1'-(1-{4-[1-(Methylsulfonyl)-1,2,3,6-tetrahydropyridin-4-yl]phenyl}cyclopropyl)carbonyl]-3H-spiro[furo[3,4-c]pyridine-1,3'-pyrrolidin]-3-one Step 1. 1-(4-bromophenyl)cyclopropanecarboxylic acid Sodium hydroxide (50% aqueous solution, 60.0 g, 1.03 mol) was added to a mixture of 4-bromobenzeneacetonitrile (19.6 g, 0.100 mol), benzyltriethylammonium chloride (1.8 g, 0.0079 mol), and 1-bromo-2-chloro-ethane (30.0 g, 0.209 mol) at 50° C. for 5 hours. 1,2-Ethanediol (200.0 mL, 3.588 mol) was added to the mixture and the resulting mixture was heated at 100° C. overnight. The mixture was poured into ice-water (30 mL) and was extracted with ethyl ether (2×10 mL). The aqueous phase was acidified (to pH=2) with 1N HCl and was extracted with ethyl acetate (4×15 mL). The combined organic phases were washed with brine (10 mL), dried over Na$_2$SO$_4$, filtered, and concentrated under reduced pressure. The residue was used in next step reaction without further purification.

Step 2. 1-{4-[1-(tert-butoxycarbonyl)-4-hydroxypiperidin-4-yl]phenyl}cyclopropanecarboxylic acid A solution of 1-(4-bromophenyl)cyclopropanecarboxylic acid (1000.0 mg, 0.0041480 mol) in tetrahydrofuran (30 mL, 0.4 mol) was cooled below −20° C. under a N$_2$ atmosphere and dibutylmagnesium in heptane (1.0 M, 2.2 mL) was slowly added to the solution while the reaction temperature was maintained below −20° C. Then 2.5 M of n-butyllithium in hexane (1.8 mL) was slowly added to the mixture below −20° C. under effective stirring. After stirring below −20° C. for 1 h, a solution of tert-butyl 4-oxo-1-piperidinecarboxylate (0.909 g, 0.00456 mol) in THF (20.0 mL) was added to the mixture below −20° C. After stirring below −20° C. for 1 h, the reaction was quenched with ammonium chloride. The product was extracted with EtOAc and the combined extract was washed with brine, dried over Na$_2$SO$_4$, and filtered. The filtrate was concentrated and then purified by Combiflash, eluting with 5% methanol in methylene chloride.

Step 3. tert-butyl 4-hydroxy-4-(4-{1-[(3-oxo-1'H,3H-spiro[furo[3,4-c]pyridine-1,3'-pyrrolidin]-1'-yl)carbonyl]cyclopropyl}phenyl)piperidine-1-carboxylate To a solution of 1-{4-[1-(tert-butoxycarbonyl)-4-hydroxypiperidin-4-yl]phenyl}cyclopropanecarboxylic acid (230 mg, 0.00064 mol) in methylene chloride (2 mL, 0.03 mol) was added (1R)-3-H-spiro[furo[3,4-c]pyridine-1,3'-pyrrolidin]-3-one dihydrochloride (184 mg, 0.000700 mol). The solution was cooled to 0° C., prior to the addition of BOP. The solution was stirred for 3 minutes and then DIEA was added. Stirring was continued at 0° C. for 20 minutes and then the reaction mixture was allowed to gradually warm to room temperature while stirring overnight. The crude product was purified by Combiflash eluting with 10% methanol in methylene chloride. LC/MS: 534.4 (M+H$^+$).

Step 4. 1'-({1-[4-(1,2,3,6-tetrahydropyridin-4-yl) phenyl]cyclopropyl}carbonyl)-3H-spiro[furo[3,4-c] pyridine-1,3'-pyrrolidin]-3-one To a solution of tert-butyl (1R)-4-hydroxy-4-(4-{1-[(3-oxo-1'H,3H-spiro[furo[3,4-c]pyridine-1,3'-pyrrolidin]-1'-yl) carbonyl]cyclopropyl}phenyl)piperidine-1-carboxylate (140 mg, 0.00026 mol) in methanol (1 mL, 0.02 mol) was added hydrogen chloride in 1,4-dioxane (4 M, 0.9 mL) and the resulting solution was stirred at room temperature for 4 hours. The reaction mixture was then concentrated and TFA (2 mL) was added and the solution was stirred at room temperature overnight. The solvent was removed to afford the desired product. LC/MS: 416.2) (M+H$^+$).

Step 5

To a solution of (1R)-1'-({1-[4-(1,2,3,6-tetrahydropyridin-4-yl)phenyl]cyclopropyl}carbonyl)-3H-spiro[furo[3,4-c]pyridine-1,3'-pyrrolidin]-3-one (22 mg, 0.000053 mol) in acetonitrile (0.5 mL, 0.01 mol) were added triethylamine (16.8 µL, 0.000120 mol) and methane sulfonyl chloride. The reaction mixture was stirred at room temperature overnight. The crude product was purified by prep-HPLC. LC/MS: 494.2 (M+H$^+$).

Example 211

(1R)-1'-[(1-{4-[(E)-2-Pyridin-4-ylvinyl] phenyl}cyclopropyl)carbonyl]-3H-spiro[furo[3,4-c] pyridine-1,3'-pyrrolidin]-3-one This compound was prepared by procedures analogous to those used for the preparation of example 122. LCMS: m/z 438.2 (M+H)$^+$; 460.1 (M+Na)$^+$.

Example 212

(1R)-1'-[(1-{4-[Cyclopentyl(fluoro)methyl] phenyl}cyclopropyl)carbonyl]-3H-spiro[furo[3,4-c] pyridine-1,3'-pyrrolidin]-3-one Step 1. 1-{4-[cyclopentyl(hydroxy)methyl] phenyl}cyclopropanecarbonitrile To a solution of 1-(4-bromophenyl)cyclopropanecarbonitrile (2.01 g, 0.00905 mol) in tetrahydrofuran (30 mL, 0.4 mol) was added 2.5 M of n-butyllithium in hexane (4.0 mL) at −78° C. and the mixture was stirred at −30° C. for 30 minutes. A solution of cyclopentanecarbaldehyde (0.972 g, 0.00990 mol) in THF (2 mL) was added to the above mixture and the resulting mixture was stirred at −78° C. for 2 hours. The reaction was then quenched with a small amount of saturated aqueous NH$_4$Cl solution followed by extraction with ethyl acetate, drying with MgSO$_4$, and concentrating under reduced pressure. The crude product was purified by flash chromatography, eluting with 30% AcOEt in hexanes.

Step 2. 1-{4-[cyclopentyl(fluoro)methyl] phenyl}cyclopropanecarbonitrile

1-{4-[Cyclopentyl(hydroxy)methyl] phenyl}cyclopropanecarbonitrile (600.0 mg, 0.002486 mol) was dissolved in methylene chloride (10 mL, 0.2 mol), cooled to −78° C., and to the solution was added diethylaminosulfur trifluoride (0.328 mL, 0.00249 mol) (DAST). The resulting reaction mixture was warmed to rt and stirred at rt for 18 h. The reaction mixture then was poured into ice-water containing NaHCO$_3$ and the resulting mixture was extracted with CH$_2$Cl$_2$ (3×). The combined organic phase was dried over Na$_2$SO$_4$, and concentrated to afford the product.

Step 3. 1-{4-[cyclopentyl(fluoro)methyl]phenyl}cyclopropanecarboxylic acid

To a mixture of 1-{4-[cyclopentyl(fluoro)methyl]phenyl}cyclopropanecarbonitrile (600.0 mg, 0.002466 mol) and 19.4 M of sodium hydroxide in water (0.51 mL) was added 1,2-ethanediol (5 mL, 0.09 mol), and the mixture was refluxed at 100° C. overnight. After cooling down to rt, the reaction mixture was poured into water and extracted with ether. The aqueous phase then was acidified with HCl and extract with ether. Then the organic phase was washed with brine, dryed over MgSO$_4$, and concentrated to afford the desired product.

Step 4

The BOP coupling was performed under conditions analogous to those outlined in example 95, step B. LC/MS: 435.2 (M+H)$^+$.

Example 213

(1R)-1'-({1-[4-(Tetrahydro-2H-pyran-4-yloxy)phenyl]cyclopropyl}carbonyl)-3H-spiro[furo[3,4-c]pyridine-1,3'-pyrrolidin]-3-one Step 1. 1-(4-hydroxyphenyl)cyclopropanecarboxylic acid A solution of 1-(4-methoxyphenyl)cyclopropanecarboxylic acid (0.70 g, 0.0036 mol) with 1.0 M of L-Selectride® in tetrahydrofuran (18 mL) was microwave irradiated at 120° C. for 2 hours. The completion of the reaction was achieved after LCMS indicated that the starting material was consumed. Then reaction mixture was acidified (pH=2) with concentrated HCl solution. The mixture was concentrated and the residue was diluted with water and stirred at rt to precipitate the white solid product, which was filtered and dried under vacuum to give the desired product. The structure was confirmed by $^1$H NMR.

Step 2. 1'-{[1-(4-hydroxyphenyl)cyclopropyl]carbonyl}-3H-spiro[furo[3,4-c]pyridine-1,3'-pyrrolidin]-3-one A solution of 1-(4-hydroxyphenyl)cyclopropanecarboxylic acid (0.250 g, 0.00140 mol), benzotriazol-1-yloxytris(dimethylamino)phosphonium hexafluorophosphate (0.652 g, 0.00147 mol) in N,N-dimethylformamide (2.0 mL, 0.026 mol) was stirred at rt for 10 minutes. The solution then was cooled to 0° C. and (1R)-3H-spiro[furo[3,4-c]pyridine-1,3'-pyrrolidin]-3-one (0.53 g, 0.0014 mol) was added to the solution followed by N,N-diisopropylethylamine (610 µL, 0.0035 mol). The resulting mixture was stirred at room temperature overnight. After work-up, 0.95 g of the crude product was obtained, which was used without further purification.

Step 3

A mixture of (1R)-1'-{[1-(4-hydroxyphenyl)cyclopropyl]carbonyl}-3H-spiro[furo[3,4-c]pyridine-1,3'-pyrrolidin]-3-one (10 mg, 0.00003 mol), tetrahydro-4H-pyran-4-ol (6.5 µL, 0.000068 mol), diisopropyl azodicarboxylate (13 µL, 0.000068 mol), and triphenylphosphine (18 mg, 0.000068 mol) in tetrahydrofuran (200 µL, 0.002 mol) was stirred at room temperature overnight. It was purified with prep-HPLC to afford 2.3 mg of product. LCMS: m/z 435.1 (M+H)$^+$.

Example 214 tert-Butyl (4-{1-[((1R)-3-oxo-1'H,3H-spiro[furo[3,4-c]pyridine-1,3'-pyrrolidin]-1'-yl)carbonyl]cyclopropyl}phenoxy)acetate This compound was prepared by procedures analogous to those in example 213, with the exception that step 3 in example 213 was replaced with the following procedure: A mixture of 1'-{[1-(4-hydroxyphenyl)cyclopropyl]carbonyl}-3H-spiro[furo[3,4-c]pyridine-1,3'-pyrrolidin]-3-one (30 mg, 0.00004 mol), acetic acid, bromo-, 1,1-dimethylethyl ester (9.5 µL, 0.000064 mol), and cesium carbonate (42 mg, 0.00013 mol) in dimethyl sulfoxide (500 µL, 0.007 mol) was microwave irradiated at 120° C., for 10 minutes. The crude product was purified by prep-HPLC. LCMS: m/z 465.1 (M+H)$^+$; 487.1 (M+Na)$^+$.

Example 215

(4-{1-[((1R)-3-Oxo-1'H,3H-spiro[furo[3,4-c]pyridine-1,3'-pyrrolidin]-1'-yl)carbonyl]cyclopropyl}phenoxy)acetonitrile The title compound was prepared using procedures analogous to those in example 213, with the exception that step 3 was replaced with the following procedure: a mixture of 1'-{[1-(4-hydroxyphenyl)cyclopropyl]carbonyl}-3H-spiro[furo[3,4-c]pyridine-1,3'-pyrrolidin]-3-one (15 mg, 0.000043 mol), bromoacetonitrile (4.3 µL, 0.000064 mol), cesium carbonate (28 mg, 0.000086 mol), and tetra-n-butylammonium iodide (1 mg, 0.000003 mol) in dimethyl sulfoxide (300 µL, 0.004 mol) was stirred at room temperature overnight. The crude product was purified with prep-HPLC. LCMS: m/z 390.1 (M+H)$^+$; 412.1 (M+Na)$^+$.

Example 216

(1R)-1'-[(1-{4-[(5-Methylisoxazol-3-yl)methoxy]phenyl}cyclopropyl)carbonyl]-3H-spiro[furo[3,4-c]pyridine-1,3'-pyrrolidin]-3-one This compound was prepared using procedures analogous to those described for the synthesis of example 215. LCMS: m/z 446.2 (M+H)$^+$; 468.2 (M+Na)$^+$.

Example 217

(1R)-1'-({1-[4-(Cyclopentylmethoxy)phenyl]cyclopropyl}carbonyl)-3H-spiro[furo[3,4-c]pyridine-1,3'-pyrrolidin]-3-one This compound was prepared by using procedures analogous to those described in example 213. LC/MS: m/z 433.1 (M+H)$^+$; 455.1 (M+Na)$^+$.

Example 218

(1R)-1'-({1-[4-(Quinolin-3-ylmethoxy)phenyl]cyclopropyl}carbonyl)-3H-spiro[furo[3,4-c]pyridine-1,3'-pyrrolidin]-3-one This compound was prepared using procedures analogous to those described for the synthesis of example 213. LC/MS: 492.2 (M+H$^+$).

Example 219

(1R)-1'-({1-[4-(Quinolin-4-ylmethoxy)phenyl]cyclopropyl}carbonyl)-3H-spiro[furo[3,4-c]pyridine-1,3'-pyrrolidin]-3-one This compound was prepared using procedures analogous to those described for the synthesis of example 213. LC/MS: 492.2 (M+H$^+$).

Example 220

(1R)-1'-({1-[4-(Quinolin-6-ylmethoxy)phenyl]cyclopropyl}carbonyl)-3H-spiro[furo[3,4-c]pyridine-1,3'-pyrrolidin]-3-one This compound was prepared using procedures analogous to those described for the synthesis of example 213. LC/MS: 492.2 (M+H$^+$).

Example 221

(1R)-1'-({1-[4-(Pyridin-3-ylmethoxy)phenyl]cyclopropyl}carbonyl)-3H-spiro[furo[3,4-c]pyridine-1,3'-pyrrolidin]-3-one This compound was prepared using procedures analogous to those described for the synthesis of example 215. LC/MS: 442.2 (M+H$^+$) and 464.1 (M+Na$^+$).

Example 222

6-(Trifluoromethyl)-1'-({1-[4-(trifluoromethyl)phenyl]cyclopropyl}carbonyl)-3H-spiro[furo[3,4-c]pyridine-1,3'-pyrrolidin]-3-one

Step 1. tert-butyl 3-oxo-6-(trifluoromethyl)-1'H,3H-spiro[furo[3,4-c]pyridine-1,3'-pyrrolidine]-1'-carboxylate To a solution of piperidine, 2,2,6,6-tetramethyl-(0.608 mL, 0.00360 mol) in tetrahydrofuran (15.0 mL, 0.185 mol) at −75° C. was added n-butyllithium in hexane (2.5 M, 2.50 mL). After 15 minutes., a suspension of 6-(trifluoromethyl)nicotinic acid (477.8 mg, 0.002500 mol) in THF (3 mL) was added to the mixture. The mixture was stirred at −55 to −40° C. for 2 hours. tert-Butyl 3-oxopyrrolidine-1-carboxylate (370.4 mg, 0.002000 mol) in THF (2.0 mL) then was added to the above mixture and the reaction temperature was maintained at −40° C. The mixture was stirred at −40° C. for 30 minutes, then slowly warmed up to 0° C. To the mixture was added acetic acid (2.00 mL, 0.0352 mol) at 0° C. and the solution was stirred at room temperature overnight. The reaction mixture was carefully neutralized with NaHCO$_3$ and the resulting mixture was extracted with AcOEt (4×30 mL) The combined organic phase was washed with brine (30 mL), dried over MgSO$_4$, and concentrated. The residue was purified by Combiflash with ethyl acetate/hexane to give the desired product. LC/MS: 359.1 (M−H$^+$)

Step 2. 6-(trifluoromethyl)-3H-spiro[furo[3,4-c]pyridine-1,3'-pyrrolidin]-3-one dihydrochloride tert-Butyl 3-oxo-6-(trifluoromethyl)-1'H,3H-spiro[furo[3,4-c]pyridine-1,3'-pyrrolidine]-1'-carboxylase (0.49 g, 0.0014 mol) was treated with hydrogen chloride in 1,4-dioxane (4.0 M, 2.0 mL) at rt for 1 h. The solvent then was evaporated and the residue was washed with ether and dried to give the desired product. LC/MS: 332.1 (M+H$^+$)

Step 3. 6-(Trifluoromethyl)-1'-({1-[4-(trifluoromethyl)phenyl]cyclopropyl}carbonyl)-3H-spiro[furo[3,4-c]pyridine-1,3'-pyrrolidin]-3-one This compound was prepared using a procedure analogous to the one described in step C of example 94. LC/MS: 471.1 (M+H$^+$).

Example 223

1'-({1-[4-(Trifluoromethoxy)phenyl]cyclopropyl}carbonyl)-6-(trifluoromethyl)-3H-spiro[furo[3,4-c]pyridine-1,3'-pyrrolidin]-3-one This compound was prepared using a procedure analogous to the one described in example 222. LC/MS: 487.1 (M+H$^+$).

Example 224

1'-{[1-(2,4-Difluorophenyl)cyclopropyl]carbonyl}-6-(trifluoromethyl)-3H-spiro[furo[3,4-c]pyridine-1,3'-pyrrolidin]-3-one This compound was prepared using a procedure analogous to the one described in example 222. LC/MS: 439.1 (M+H$^+$).

Example 225

1'-{[1-(1,3-Benzothiazol-2-yl)cyclopropyl]carbonyl}-6-(trifluoromethyl)-3H-spiro[furo[3,4-c]pyridine-1,3'-pyrrolidin]-3-one This compound was prepared using a procedure analogous to the one described in example 222. LC/MS: 460.1 (M+H$^+$).

Example 226

1'-{[1-(4-Chlorophenyl)cyclopropyl]carbonyl}-6-(trifluoromethyl)-3H-spiro[furo[3,4-c]pyridine-1,3'-pyrrolidin]-3-one This compound was prepared using a procedure analogous to the one described in example 222. LC/MS: 437.1 (M+H$^+$).

Example 227

4-Fluoro-1'-[(1-quinolin-4-ylcyclopropyl)carbonyl]-3H-spiro[furo[3,4-c]pyridine-1,3'-pyrrolidin]-3-one

Step 1. tert-butyl 4-fluoro-3-oxo-1'H,3H-spiro[furo[3,4-c]pyridine-1,3'-pyrrolidine]-1'-carboxylate To a solution of piperidine, 2,2,6,6-tetramethyl-(0.984 mL, 0.00583 mol) in tetrahydrofuran (15.0 mL, 0.185 mol) at −75° C. was added 2.50 M of n-butyllithium in hexane (4.00 mL). After 15 minutes, a suspension of 2-fluoronicotinic acid (0.548 g, 0.00389 mol) in THF (5 mL) was added to the mixture. Stirring was continued at −55° C. for 1 h. tert-Butyl 3-oxopyrrolidine-1-carboxylate (0.60 g, 0.0032 mol) in THF (2.0 mL) was added to the above mixture, and the reaction temperature was maintained at −50 to −40° C. The mixture was stirred at −40° C. for 30 min. and then slowly allowed to warm to 0° C. To the mixture was added acetic acid (4.0 mL, 0.070 mol) at 0° C. The mixture was stirred at room temperature overnight and then was carefully neutralized with $NaHCO_3$. The resulting mixture was extracted with AcOEt (4×30 mL). The organic phase was washed with brine (30 mL), dried over $MgSO_4$, and concentrated. The residue was purified by Combiflash with ethyl acetate/hexane to give the desired product 0.41 g. LC/MS: 309.1 (M+H$^+$).

Step 2. 1-quinolin-4-ylcyclopropanecarboxylic acid

A solution of NaOH in water (2 ml, 50%) was added to a mixture of quinolin-4-ylacetonitrile (0.5 g, 0.002 mol), 1-bromo-2-chloro-ethane (1.0 mL, 0.012 mol), and benzyltriethylammonium chloride (0.1 g, 0.0004 mol) at 50° C. After the mixture was stirred at 50° C. for 3 hours, 1,2-ethanediol (5 mL, 0.09 mol) was added. Then the reaction mixture was stirred at 100° C. overnight. The reaction mixture was cooled to room temperature and washed with ether (3×). The aqueous layer was acidified (pH=2), and then extracted with ethyl acetate (3×). The combined organic layer was dried over $MgSO_4$, filtered, and concentrated to afford the desired product. LC/MS: 214.1 (M+H$^+$).

Step 3

HCl in dioxane (4.0 M, 1 mL) was added to tert-butyl 4-fluoro-3-oxo-1'H,3H-spiro[furo[3,4-c]pyridine-1,3'-pyrrolidine]-1'-carboxylate (25.8 mg, 0.0000837 mol). The reaction mixture was stirred at room temperature for 30 minutes before the volatiles was removed to afford the free amine (hydrochloric acid salt), which was subsequently used in the coupling reaction. 4-Methylmorpholine (50 µL, 0.0004 mol) was added to a mixture of 1-quinolin-4-ylcyclopropanecarboxylic acid (17.8 mg, 0.0000837 mol), 4-fluoro-3H-spiro[furo[3,4-c]pyridine-1,3'-pyrrolidin]-3-one dihydrochloride (23.5 mg, 0.0000837 mol), and (benzotriazol-1-yloxy)tripyrrolidinophosphonium hexafluorophosphate (45.7 mg, 0.0000879 mol) in N,N-dimethylformamide (0.5 mL, 0.006 mol). The reaction mixture was stirred at room temperature for 2 hours. The crude product was purified by prep-LCMS. LC/MS: 402.1 (M+H$^+$).

Example 228

1'-{[1-(4-Chlorophenyl)cyclopropyl]carbonyl}-4-fluoro-3H-spiro[furo[3,4-c]pyridine-1,3'-pyrrolidin]-3-one This compound was prepared using procedures analogous to those in example 227. LC/MS: 387.1 (M+H$^+$).

Example 229

7-Fluoro-1'-[(1-{4-[(trifluoromethyl)thio]phenyl}cyclopropyl)carbonyl]-3H-spiro[furo[3,4-c]pyridine-1,3'-pyrrolidin]-3-one Step 1. 1-{4-[(trifluoromethyl)thio]phenyl}cyclopropanecarboxylic acid A mixture of {4-[(trifluoromethyl)thio]phenyl}acetonitrile (1.15 g, 0.00529 mol), 1-bromo-2-chloro-ethane, (880 µL, 0.010 mol), benzyltriethyl ammonium chloride (70 mg, 0.0003 mol) and 1.5 ml of 50% NaOH-water (w/w) solution was kept at 50° C. with stirring for 3 hours. LCMS data supported that the reaction was complete. To the above solution 1,2-ethanediol (10 mL, 0.2 mol) was added. The mixture was heated at 100° C. overnight. After work-up 1.2 g of solid product was obtained. LC/MS: 387.1) (M+H$^+$).

Step 2. tert-butyl 4-fluoro-3-oxo-1'H,3H-spiro[furo[3,4-c]pyridine-1,3'-pyrrolidine]-1'-carboxylate To a solution of 2,2,6,6-tetramethyl-piperidine, (0.984 mL, 0.00583 mol) in tetrahydrofuran (15.0 mL, 0.185 mol) at −75° C. was added n-butyllithium in hexane (2.50 M, 4.00 mL). After 15 min, a suspension of 2-fluoronicotinic acid (0.548 g, 0.00389 mol) in THF (5 mL) was added to the mixture. The mixture was kept at −55° C. with stirring for 1 hour. tert-Butyl 3-oxopyrrolidine-1-carboxylate (0.60 g, 0.0032 mol) in THF (2.0 mL) was added to the above mixture while the reaction temperature was maintained at −50 to −40° C. The mixture was stirred at −40° C. for 30 minutes and then slowly allowed to warm to 0° C. To the mixture was added acetic acid (4.0 mL, 0.070 mol) at 0° C. and the reaction was allowed to gradually warm to room temperature with stirring overnight. The reaction mixture was carefully neutralized with $NaHCO_3$ and the resulting mixture was extracted with AcOEt (4×30 mL). The combined organic phase was washed with brine (30 mL), dried over with $MgSO_4$, and concentrated. The residue was purified by Combiflash with ethyl acetate/hexane to give the desired product (0.41 g). LC/MS: 309.1 (M+H$^+$).

Step 3. 7-Fluoro-1'-[(1-{4-[(trifluoromethyl)thio]phenyl}cyclopropyl)carbonyl]3H-spiro[furo[3,4-c]pyridine-1,3'-pyrrolidin]-3-one The title compound was prepared using a procedure analogous to that described in step 3 of example 227. LC/MS: 453.1 (M+H$^+$).

Example 230

1'-{[1-(4-Bromophenyl)cyclopropyl]carbonyl}-7-fluoro-3H-spiro[furo[3,4-c]pyridine-1,3'-pyrrolidin]-3-one This compound was formed using procedures analogous to those in example 229. LC/MS: 432.1 (M+H$^+$).

Example 231

(1R)-1'-{[1-(1,3-Benzothiazol-2-yl)cyclopropyl]carbonyl}-3H-spiro[furo[3,4-c]pyridine 1,3'-pyrrolidin]-3-one This compound was prepared by using a procedure analogous to that in step B of example 95. The prerequisite 1-(1,3-benzothiazol-2-yl)cyclopropanecarboxylic acid was prepared by using a procedure analogous to that used in step 2 of example 227. LC/MS: 392.1 (M+H$^+$).

Example 232

1'-{[1-(1,3-Benzothiazol-2-yl)cyclopropyl]carbonyl}-6-chloro-3H-spiro[furo[3,4-c]pyridine-1,3'-pyrrolidin]-3-one Step 1. tert-butyl 6-chloro-3-oxo-1'H,3H-spiro[furo[3,4-c]pyridine-1,3'-pyrrolidine]-1'-carboxylate To a solution of 2,2,6,6-tetramethyl-piperidine, (508 mg, 0.00360 mol) in tetrahydrofuran (15.0 mL, 0.185 mol) at −75° C. was added 2.50 M of n-butyllithium in hexane (2.50 mL). After 15 minutes, a suspension of 6-chloronicotinic acid (393.9 mg, 0.002500 mol) in THF (2 mL) was added. The mixture was stirred at −55° C. to −20° C. for 2 hours, then was re-cooled to −20° C. tert-Butyl 3-oxopyrrolidine-1-carboxylate (370.4 mg, 0.002000 mol) in THF (2.0 mL) was added to the above mixture and the reaction temperature was maintained at −40° C. After stirring for 30 minutes, the reaction was allowed to slowly warm up to 0° C. To the mixture was added acetic acid (2.00 mL, 0.0352 mol) at 0° C. and the mixture was stirred at room temperature overnight. The reaction mixture was carefully neutralized with NaHCO$_3$. The resulting mixture was extracted with AcOEt (4×30 mL). The combined organic layer was washed with brine (30 mL), dried over MgSO$_4$, and concentrated. The residue was purified by Combiflash with ethyl acetate/hexane to give the desired product Step 2. 1'-{[1-(1,3-Benzothiazol-2-yl)cyclopropyl]carbonyl}-6-chloro-3H-spiro[furo[3,4-q]pyridine-1,3'-pyrrolidin]-3-one The title compound was prepared by a procedure analogous to that in step 3 of example 227. LC/MS: 426.6 (M+H$^+$).

Example 233

6-Chloro-1'-({1-[4-(trifluoromethoxy)phenyl]cyclopropyl}carbonyl)-3H-spiro[furo[3,4-c]pyridine-1,3'-pyrrolidin]-3-one This compound was prepared by using an analogous procedure to that described above for the synthesis of example 232. LC/MS: 453.6 (M+H$^+$).

Example 234

6-Chloro-1'-{[1-(2-fluorophenyl)cyclopropyl]carbonyl}-3H-spiro[furo[3,4-c]pyridine-1,3'-pyrrolidin]-3-one This compound was prepared by using an analogous procedure to that described above for the synthesis of example 232. LC/MS: 387.6 (M+H$^+$).

Example 235

(1R)-1'-({1-[4-(4-Chlorophenyl)-1,3-thiazol-2-yl]cyclopropyl}carbonyl)-3H-spiro[furo[3,4-c]pyridine-1,3'-pyrrolidin]-3-one This compound was prepared by using an analogous procedure to that described above for the synthesis of example 231. LC/MS: 452.8 (M+H$^+$).

Example 236

4-(1-{[(1R)-3-Oxo-1'H,3H-spiro[2-benzofuran-1,3'-pyrrolidin]-1'-yl]carbonyl}cyclopropyl)benzonitrile A degassed mixture of (1R)-1'-{[1-(4-chlorophenyl)cyclopropyl]carbonyl}-3H-spiro[2-benzofuran-1,3'-pyrrolidin]-3-one (36.0 mg, 0.0000979 mol) (example 83), zinc cyanide (23.4 mg, 0.000196 mol), bis(tri-t-butylphosphine)palladium (31 mg, 0.000059 mol) and zinc (11.5 mg, 0.000176 mol) powder in N-methylpyrrolidinone (1.00 mL, 0.0104 mol) was heated at 150° C. for 16 hours. The reaction mixture was cooled to room temperature, diluted with EtOAc, filtered through a pad of celite and the solid was washed with EtOAc. The filtrate was washed with 2 N NH$_4$OH (20 mL) and brine successively, dried over magnesium sulfate, filtered and concentrated in vacuo. The residue was purified by Combiflash with 10-20% EtOAc/hexanes to give the product. LC/MS: 359.1 (M+H$^+$).

Example 238

(1R)-1'-{[1-(4-Bromophenyl)cyclopropyl]carbonyl}-3H-spiro[2-benzofuran-1,3'-pyrrolidin]-3-one Step 1. 1-(4-bromophenyl)cyclopropanecarboxylic acid Sodium hydroxide, 50% aqueous solution (60.4 mL, 1.58 mol) was added to a mixture of 4-bromobenzeneacetonitrile (30 g, 0.2 mol), benzyltriethylammonium chloride (2.8 g, 0.012 mol), and 1-bromo-2-chloroethane (26.5 mL, 0.320 mol) at 50° C. for 5 hours. 1,2-ethanediol (306.0 mL, 5.491 mol) was added to the mixture and the resulting mixture was heated at 100° C. overnight. The mixture was poured into ice-water (60 mL) and was extracted with ethyl ether (2×150 mL). The aqueous phase was acidified (pH=2) with 1N HCl and was extracted with ethyl acetate (3×50 mL). The combined organic phase was washed with brine (100 mL), dried over MgSO$_4$, filtered, and concentrated under reduced pressure. The residue was the desired product (36.6 g) which was directly used in next step without further purification. $^1$H NMR confirmed the structure of the product.

Step 2

To a stirred solution of 1-(4-bromophenyl)cyclopropanecarboxylic acid (1.616 g, 0.006704 mol) in anhydrous N,N-dimethylformamide (12.0 mL, 0.155 mol) at room temperature was added (7,7-dimethyl-2-oxobicyclo[2.2.1]hept-1-yl)methanesulfonic acid-(1R)-3H-spiro[2-benzofuran-1,3'-pyrrolidin]-3-one (1:1) (2.569 g, 0.006095 mol, example 96, steps 1-2), benzotriazol-1-yloxytris(dimethylamino)phosphonium hexafluorophosphate (3.057 g, 0.006704 mol), followed by N,N-diisopropylethylamine (4.27 mL, 0.0244 mol). The resulting clear solution was stirred at temperature for 17 hours. LCMS showed that the reaction was complete. The reaction was quenched with saturated aqueous NaHCO$_3$ (50 mL), and the reaction miture was extracted with EtOAc (2×). The combined organic layer was washed with brine, dried over magnesium sulfate, filtered and concentrated in vacuo. The residue was purified by Combiflash with 30-70% EtOAc/hexanes to give the product as a colorless solid (2.258 g, 90% in yield). LC/MS (M+H$^+$)=412.1.

Example 239

(1R)-1'-({1-[4-(Pyrrolidin-1-ylcarbonyl)phenyl]cyclopropyl}carbonyl)-3H-spiro[2-benzofuran-1,3'-pyrrolidin]-3-one A mixture of (1R)-1'-{[1-(4-bromophenyl)cyclopropyl]carbonyl}-3H-spiro[2-benzofuran-1,3'-pyrrolidin]-3-one (68.0 mg, 0.000165 mol, example 238), pyrrolidine (42 µL, 0.00049 mol), molybdenum hexacarbonyl (44 mg, 0.00016 mol), trans-di(µ-acetato)bis[o-(di-o-tolylphosphino)benzyl]dipalladium(II) (16 mg, 0.000016 mol) and 1,8-diazabicyclo[5.4.0]undec-7-ene (76 µL, 0.00049 mol) (DBU) in anhydrous tetrahydrofuran (2.0 mL, 0.025 mol) in a microwave vial was irradiated with microwaves to 150° C. for 30 minutes. The reaction mixture was filtered. The filtrate was purified by prep-HPLC to afford the product as a solid (55.9 mg, 79% in yield). LC/MS (M+H$^+$)=431.1.

Example 240

4-(1-{[(1R)-3-Oxo-1'H,3H-spiro[2-benzofuran-1,3'-pyrrolidin]-1'-yl]carbonyl}cyclopropyl)benzohydrazide A mixture of (1R)-1'-{[1-(4-bromophenyl)cyclopropyl]carbonyl}-3H-spiro[2-benzofuran-1,3'-pyrrolidin]-3-one (229 mg, 0.000555 mol, example 238), hydrazine (53 µL, 0.0017 mol), molybdenum hexacarbonyl (0.150 g, 0.000555 mol), trans-di(u-acetato)bis[o-(di-o-tolylphosphino)benzyl]dipalladium (II) (54 mg, 0.000056 mol) and 1,8-diazabicyclo[5.4.0]undec-7-ene (254 µL, 0.00167 mol) (DBU) in anhydrous N-methylpyrrolidinone (2.0 mL, 0.021 mol) and tetrahydrofuran (1.0 mL, 0.012 mol) in a microwave vial was irradiated with microwaves to 170° C. for 30 minutes. The reaction mixture was diluted with MeOH and filtered. The filtrate was purified by prep-HPLC to afford the product as a solid (3.2 mg, 2% in yield for two steps). LC/MS (M+H$^+$)= 392.1.

Example 241

N-Methyl-4-(1-{[(1R)-3-oxo-1'H,3H-spiro[2-benzofuran-1,3'-pyrrolidin]-1'-yl]carbonyl}cyclopropyl) benzamide This compound was prepared by a procedure analogous to that outlined above for the synthesis of example 238. LC/MS (M+H$^+$)=391.2.

Example 242

4-(1-{[(1R)-3-Oxo-1'H,3H-spiro[2-benzofuran-1,3'-pyrrolidin]-1'-yl]carbonyl}cyclopropyl)benzenecarbothioamide A mixture of 4-(1-{[(1R)-3-oxo-1'H,3H-spiro[2-benzofuran-1,3'-pyrrolidin]-1'-yl]carbonyl}cyclopropyl)benzonitrile (126 mg, 0.000352 mol, example 236), 7.34 M of ammonium sulfide in water (145 mL) (50 wt % in water) in methanol (3.5 mL, 0.087 mol) in a microwave vial was irradiated with microwaves at 100° C. for 60 minutes. The reaction was quenched with water (15 mL) and the reaction mixture was extracted with EtOAc (2×). The combined organic layer was washed with brine, dried over magnesium sulfate, filtered and concentrated in vacuo. The residue was purified by Combiflash with 40-90% EtOAc/hexanes to afford the product as a yellow solid (65.5 mg, 48% in yield). (M+H$^+$)=393.1.

Example 243

(1R)-1'-[(1-{4-[2-(Trifluoromethyl)-1H-imidazol-4-yl]phenyl}cyclopropyl)carbonyl]-3H-spiro[2-benzofuran-1,3'-pyrrolidin]-3-one Step 1. methyl 1-phenylcycloprapanecarboxylate Methyl iodide (2.8 mL, 0.045 mol) was added to a mixture of 1-phenylcyclopropane carboxylic acid (4.9 g, 0.030 mol) and potassium carbonate (8.3 g, 0.060 mol) in N,N-dimethylformamide (40 mL, 0.5 mol) at room temperature and then stirred for 1 hour. The mixture was diluted with ether, washed with water (x2) and brine successively, dried and concentrated to give the desired product.

Step 2. methyl 1-[4-(chloroacetyl)phenyl]cyclopropanecarboxylate

Aluminum trichloride (7.9 g, 0.060 mol) was added in portions to a mixture of methyl 1-phenylcyclopropanecarboxylate (3.5 g, 0.020 mol) and chloroacetyl chloride (2.0 mL, 0.026 mol) in carbon disulfide (40 mL, 0.7 mol) at 15-25° C. and then the reaction mixture was stirred at room temperature for 2 hours. The mixture was poured into conc. HCl (10 mL) in ice (100 g) and then extracted with ether. The ether extract was washed with brine, dried and concentrated. The product was purified by CombiFlash using hexane/EtOAc (max.EA 20%). The final product was analyzed by 1H NMR, which showed that the product was a mixture of para and meta substituted isomers with a ratio of 3:2.

Step 3. 1-{4-[2-(trifluoromethyl)-1H-imidazol-4-yl]phenyl}cyclopropanecarboxylic acid A mixture of methyl 1-[4-(chloroacetyl)phenyl]cyclopropanecarboxylate (0.20 g, 0.00079 mol) and 2,2,2-trifluoroethanimidamide (0.18 g, 0.0016 mol) in ethanol (5.0 mL, 0.086 mol) was refluxed for 4 hours. The mixture was diluted with ethyl acetate, washed with sat'd. NaHCO$_3$ and brine successively, dried and concentrated. The residue was triturated with ether and the filtered to provide the methyl ester. LC-MS: 311.1 (M+H)$^+$ The ester was hydrolyzed using lithium hydroxide (6.0 eq.) in methanol/water (3:1) under reflux for 30 minutes. The reaction mixture was then concentrated and the pH was adjusted to 2~3 by adding 1N HCl. The resulting precipitate was filtered and dried to afford the desired product. LC-MS: 297.1 (M+H)$^+$.

Step 4. (1R)-1'-[(1-{4-[2-(Trifluoromethyl)-1H-imidazol-4-yl]phenyl}cyclopropyl)carbonyl]-3H-spiro[2-benzofuran-1,3'-pyrrolidin]-3-one The title compound was prepared using an analogous procedure to that outlined in step 2 of example 238. LC/MS: 468.2 (M+H$^+$).

Example 244

(1R)-1'-({1-[4-(1-Methyl-1H-pyrazol-3-yl)phenyl]cyclopropyl}carbonyl)-3H-spiro[2-benzofuran-1,3'-pyrrolidin]-3-one To a solution of (1R)-1'-{[1-(4-bromophenyl)cyclopropyl]carbonyl}-3H-spiro[2-benzofuran-1,3'-pyrrolidin]-3-one (20 mg, 0.00005 mol, example 238) in tetrahydrofuran (0.2 mL, 0.002 mol) were added tris(dibenzylideneacetone)dipalladium(0) (0.2 mg, 0.0000002 mol), tri-tert-butylphosphine (0.12 mg, 5.8×10$^{-7}$ mol), (1-methyl-1H-pyrazol-3-yl) boronic acid (6.8 mg, 0.0000534 mol). The mixture was heated at 120° C. under microwave for 30 minutes. The reaction mixture then was filtered and the filtrate was diluted with methanol and purified with prep-HPLC to afford the desired product. LC/MS: 414.2 (M+H$^+$).

Example 245

N-Cyclopropyl-4'-(1-{[(1R)-3-oxo-1'H,3H-spiro[2-benzofuran-1,3'-pyrrolidin]-1'-yl]carbonyl}cyclopropyl)biphenyl-4-carboxamide This compound was prepared by using an analogous method to that used for the synthesis of example 244. LC/MS: 493.2 (M+H$^+$).

Example 246

(1R)-1'-[(1-{4-[5-(Trifluoromethyl)-1H-1,2,4-triazol-3-yl]phenyl}cyclopropyl)carbonyl]-3H-spiro[2-benzofuran-1,3'-pyrrolidin]-3-one A mixture of 4-(1-{[(1R)-3-oxo-1'H,3H-spiro[2-benzofuran-1,3'-pyrrolidin]-1'-yl]carbonyl}cyclopropyl)benzenecarbothioamide (39 mg, 0.000099 mol, example 242) and trifluoroacetic acid hydrazide (28 mg, 0.00020 mol) in anhydrous N,N-dimethylformamide (1.0 mL, 0.013 mol) in a microwave vial was irradiated with microwaves at 120° C. for 30 minutes. LCMS showed there was no product formation and some starting material was converted to nitrile. 7.34 M of ammonium sulfide in water (27 μL) and triethylamine (28 μL, 0.00020 mol) then was added. The reaction mixture was irradiated with microwaves at 100° C. for 1.5 hours. The crude reaction mixture was purified by prep-HPLC to give the product as a colorless solid (6.6 mg, 14% in yield) as well as recovered starting material (16.7 mg, 43% recovery of S.M.). LC/MS (M+H$^+$)=469.2

Example 247

(1R)-1'-({1-[4-(1H-tetrazol-5-yl)phenyl]cyclopropyl}carbonyl)-3H-spiro[2-benzofuran-1,3'-pyrrolidin]-3-one A mixture of 4-(1-{[(1R)-3-oxo-1'H,3H-spiro[2-benzofuran-1,3'-pyrrolidin]1'-yl]carbonyl}cyclopropyl)benzonitrile (50.0 mg, 0.000140 mol, example 236), sodium azide (109 mg, 0.00167 mol) and ammonium chloride (89.6 mg, 0.00167 mol) in anhydrous N,N-dimethylformamide (1.4 mL, 0.018 mol) in a microwave vial was irradiated with microwaves to 180° C. for 40 minutes. LCMS showed the reaction was complete. The reaction mixture was filtered and the filtrate was purified by prep-HPLC to give the product as a colorless solid (44.5 mg, 80% in yield). LC/MS (M+H$^+$)=402.1.

Example 248

(1R)-1'-({1-[4-(2-Amino-1,3-oxazol-4-yl)phenyl]cyclopropyl}carbonyl)-3H-spiro[2-benzofuran-1,3'-pyrrolidin]-3-one Step 1. 1-[4-(2-amino-1,3-oxazol-4-yl)phenyl]cyclopropanecarboxylic acid A mixture of methyl 1-[4-(chloroacetyl)phenyl]cyclopropanecarboxylate (0.20 g, 0.00079 mol, example 243, steps 1 & 2) and urea (0.095 g, 0.0016 mol) in ethanol (5.0 mL, 0.086 mol) was refluxed overnight. The mixture was diluted with ethyl acetate and washed with sat'd. NaHCO$_3$, brine, dried and concentrated. The methyl ester was purified by CombiFlash using CH$_2$Cl$_2$/EtOAc (max. EtOAc 100%). The ester was hydrolyzed using lithium hydroxide (6.0 eq.) in methanol/THF and then acidified by adding 1 N HCl. The solvent was removed under vacuum and the crude product was used in the next step. LC-MS: 259.2 (M+H$^+$) methyl eater; 245.2 (M+H$^+$) acid Step 2

The BOP mediated coupling was performed using a procedure analogous to that described in step 2 of example 338.

Example 249

(1R)-1'-{[1-(4-Pyrimidin-5-ylphenyl)cyclopropyl]carbonyl}-3H-spiro[2-benzofuran-1,3'-pyrrolidin]-3-one A mixture of (1R)-1'-{[1-(4-chlorophenyl)cyclopropyl]carbonyl}-3H-spiro[2-benzofuran-1,3'-pyrrolidin]-3-one (15.0 mg, 0.0000408 mol, prepared by a procedure analogous to that in step 1 of example 173), pyrimidin-5-ylboronic acid (5.6 mg, 0.000045 mol), tris(dibenzylidene acetone)dipalladium(0) (2 mg, 0.000002 mol), and tri-tert-butylphosphine (0.8 mg, 0.000004 mol), cesium carbonate (16 mg, 0.000049 mol) in 1,4-dioxane (1.0 mL, 0.013 mol) was microwave irradiated at 90° C. for 30 minutes. The crude product was purified with prep-HPLC. LC/MS: 412.2 (M+H$^+$).

Example 250

(1R)-1'-({1-[4-(6-Fluoropyridin-3-yl)phenyl]cyclopropyl}carbonyl)-3H-spiro[2-benzofuran-1,3'-pyrrolidin]-3-one Step 1. (1R)-1'-({1-[4-(4,4,5,5-tetramethyl-1,3,2-dioxaborolan-2-yl)phenyl]cyclopropyl}carbonyl)-3H-spiro[2-benzofuran-1,3'-pyrrolidin]-3-one To a solution of (1R)-1'-{[1-(4-bromophenyl)cyclopropyl]carbonyl}-3H-spiro[2-benzofuran-1,3'-pyrrolidin]-3-one (0.55 g, 0.0013 mol, example 238) and 4,4,5,5,4',4',5',5'-octamethyl-[2,2']bi[[1,3,2]dioxaborolanyl] (0.37 g, 0.0015 mol) in 1,4-dioxane (8.0 mL, 0.10 mol) were added potassium acetate (0.39 g, 0.0040 mol), 1,1'-bis(diphenylphosphino) ferrocene (40 mg, 0.00007 mol) and [1,1'-bis(diphenylphosphino)ferrocene]dichloropalladium (II), complex with dichloromethane (1:1) (50 mg, 0.00007 mol) under nitrogen and the reaction was stirred at 80° C. overnight. The mixture was filtered through celite and concentrated. The product was purified by CombiFlash using CH$_2$Cl$_2$/EtOAc (max EA 60%). LC-MS: 460.2 (M+H$^+$)

Step 2

To a solution of (1R)-1'-({1-[4-(4,4,5,5-tetramethyl-1,3,2-dioxaborolan-2-yl)phenyl]cyclopropyl}carbonyl)-3H-spiro[2-benzofuran-1,3'-pyrrolidin]-3-one (130 mg, 0.00029 mol) in 1,4-dioxane (1 mL, 0.01 mol) were added 5-bromo-2-fluoropyridine (0.060 mL, 0.00058 mol), tris(dibenzylideneacetone)dipalladium(0) (1 mg, 0.000001 mol), tri-tert-butylphosphine (0.71 mg, 0.0000035 mol) and potassium fluoride (56 mg, 0.00096 mol). The mixture was heated at 110° C. under nitrogen for 30 minutes. The mixture was diluted with ethyl acetate, washed with water and brine successively, dried and concentrated. The product was purified by CombiFlash using CH$_2$Cl$_2$/EtOAc (max. EA 30%). LC-MS: 429.2 (M+H$^+$)

Example 251

(1R)-1'-({1-[4-(6-Pyrrolidin-1-ylpyridin-3-yl)phenyl]cyclopropyl}carbonyl)-3H-spiro[2-benzofuran-1,3'-pyrrolidin]-3-one A mixture of (1R)-1'-({1-[4-(6-fluoropyridin-3-yl)phenyl]cyclopropyl}carbonyl)-3H-spiro[2-benzofuran-1,3'-pyrrolidin]-3-one (20.0 mg, 0.0000467 mol, example 250), pyrrolidine (7.8 µL, 0.000093 mol) in dimethyl sulfoxide (0.5 mL, 0.007 mol) was heated at 100° C. in a sealed tube for 5 hours. The product was purified by prep-HPLC. LC-MS: 480.2 (M+H$^+$)

Example 252

N-Cyclopropyl-5-[4-(1-{[(1R)-3-oxo-1'H,3H-spiro[2-benzofuran-1,3'-pyrrolidin]-1'-yl]carbonyl}cyclopropyl)phenyl]pyridine-2-carboxamide

Step 1. 5-bromopyridine-2-carboxylic acid

Lithium hydroxide, monohydrate (0.39 g, 0.0092 mol) was added to a mixture of 5-bromopyridine-2-carboxylic acid methyl ester (0.25 g, 0.0012 mol) in tetrahydrofuran (4.8 mL, 0.059 mol) and water (2.0 mL) and the reaction mixture was refluxed for 30 minutes. The reaction mixture was concentrated and was adjusted to be acidic (pH=~4) by adding 1 N HCl. The product was extracted with ethyl acetate and the combined extract was concentrated to give the desired product. LC-MS: 202.0/204.0 (M+H$^+$)

Step 2. 5-bromo-N-cyclopropylpyridine-2-carboxamide

N,N-Diisopropylethylamine (0.69 mL, 0.0040 mol) was added to a mixture of 5-bromopyridine-2-carboxylic acid (400 mg, 0.002 mol), cyclopropylamine (0.16 mL, 0.0024 mol) and benzotriazol-1-yloxytris(dimethylamino)phosphonium hexafluorophosphate (1.1 g, 0.0024 mol) in N,N-dimethylformamide (9.4 mL, 0.12 mol) at 0° C. and the mixture was stirred overnight at room temperature. The mixture was diluted with ethyl acetate, washed with water and brine successively, dried over sodium sulfate, filtered and concentrated. The product was purified by CombiFlash eluting with CH$_2$Cl$_2$/EtOAc (max.EtOAc 20%). LC-MS: 241.1/243.1 (M+H$^+$)

Step 3

The title compound was prepared by using a procedure analogous to that described in example 250. LC-MS: 494.2 (M+H$^+$)

Example 253

N-Methyl-5-[4-(1-{[(1R)-3-oxo-1'H,3H-spiro[2-benzofuran-1,3'-pyrrolidin]-1'-yl]carbonyl}cyclopropyl)phenyl]pyridine-2-carboxamide This compound was prepared using an analogous procedure to that outlined above in example 250. LC/MS: 468.2 (M+H$^+$).

Example 254

(1R)-1'-({1-[4-(Methylsulfonyl)phenyl]cyclopropyl}carbonyl)-3H-spiro[2-benzofuran-1,3'-pyrrolidin]-3-one

Step 1. (1R)-1'-({1-[4-(methylthio)phenyl]cyclopropyl}carbonyl)-3H-spiro[2-benzofuran-1,3'-pyrrolidin]-3-one This compound was prepared using a procedure analogous to that used in step 2 of example 238. LC/MS: 380.1 (M+H$^+$).

Step 2

To a solution of (1R)-1'-({1-[4-(methylthio)phenyl]cyclopropyl}carbonyl)-3H-spiro[2-benzofuran-1,3'-pyrrolidin]-3-one (50 mg, 0.00008 mol) and methylene chloride (300 µL, 0.005 mol) was added m-chloroperbenzoic acid (97 mg, 0.00040 mol) in portions. The solution was stirred at room temperature overnight. The product was purified by prep-HPLC to afford the desired product (17.8 mg). LCMS: m/z 412.0 (M+H$^+$); 434.0 (M+Na$^+$).

Example 255

(1R)-1'-[(1-{4-[(Trifluoromethyl)thio]phenyl}cyclopropyl)carbonyl]-3H-spiro[2-benzofuran-1,3'-pyrrolidin]-3-one This compound was prepared using procedures analogous to those used in steps 1-2 of example 238. LCMS: m/z 434.0 (M+H$^+$). 456.0 (M+Na$^+$).

Example 256

(1R)-1'-{[1-(4-Chloro-2-fluorophenyl)cyclopropyl]carbonyl}-3H-spiro[2-benzofuran-1,3'-pyrrolidin]-3-one This compound was prepared using procedures analogous to those used in steps 1-2 of example 238. LCMS: m/z 386.4 (M+H$^+$).

Example 257

(1R)-1'-({1-[4-(2-Oxopyridin-1(2H)-yl)phenyl]cyclopropyl}carbonyl)-3H-spiro[2-benzofuran-1,3'-pyrrolidin]-3-one To a solution of (1R)-1'-{[1-(4-bromophenyl)cyclopropyl]carbonyl}-3H-spiro[2-benzofuran-1,3'-pyrrolidin]-3-one (30.0 mg, 0.0000728 mol, example 238), pyrid-2-one (8.30 mg, 0.0000873 mol) in 1,4-dioxane (2 mL, 0.02 mol) were added (1S,2S)—N,N'-dimethylcyclohexane-1,2-diamine (2.1 mg, 0.000014 mol), copper(I) iodide (1.4 mg, 0.0000073 mol), and potassium carbonate (21.1 mg, 0.000153 mol). The mixture was heated at 160° C. for 60 minutes. The reaction mixture was filtered, and the filtrate was concentrated and purified using prep-HPLC. LC/MS: 427.1 (M+H H⁺).

Example 258

Methyl 4-[4-(1-{[(1R)-3-oxo-1'H,3H-spiro[2-benzofuran-1,3'-pyrrolidin]-1'-yl]carbonyl}cyclopropyl)phenyl]piperazine-1-carboxylate Step 1. tert-butyl 1-(4-bromophenyl)cyclopropanecarboxylate Isobutylene (80.0 mL, 0.847 mol) was passed through a mixture of 1-(4-bromophenyl)cyclopropanecarboxylic acid (10.0 g, 0.0415 mol, example 238, step 1) and sulfuric acid (1.0 mL, 0.019 mol) at −78° C. The mixture was sealed and was stirred at room temperature overnight. The isobutylene was evaporated at room temperature and the residue was dissolved in ethyl acetate (100 mL), and washed with water and brine successively. The organic layer was dried over Na₂SO₄, filtered, and concentrated under reduced pressure to give the desired product.

Step 2. tert-butyl 4-{4-[1-(tert-butoxycarbonyl)cyclopropyl]phenyl}piperazine-1-carboxylate A mixture of tert-butyl 1-(4-bromophenyl)cyclopropanecarboxylate (297.2 mg, 0.001000 mol), tert-butyl piperazine-1-carboxylate (186.2 mg, 0.001000 mol), sodium tert-pentoxide (110.1 mg, 0.001000 mol), [1,1'-bis(diphenylphosphino)ferrocene]dichloropalladium(II), complex with dichloromethane (1:1) (24.5 mg, 0.0000300 mol) and 1,1' bis(diphenylphosphino)ferrocene (16.6 mg, 0.0000300 mol) was deaerated and then charged with nitrogen. To the mixture was added toluene (3.0 mL, 0.028 mol), and the resulting mixture was heated at 100° C. overnight. The mixture was poured into ice-water and was extracted with ethyl acetate (4×10 mL). The combined organic layer was washed with water and brine successively, dried over Na₂SO₄, filtered, and concentrated under reduced pressure. The residue was purified by Combiflash with ethyl acetate/hexane.

Step 3. methyl 4-{4-[1-(tert-butoxycarbonyl)cyclopropyl]phenyl}piperazine-1-carboxylate tert-Butyl 4-{4-[1-(tert-butoxycarbonyl)cyclopropyl]phenyl}piperazine-1-carboxylate (16.0 mg, 0.0000397 mol) was treated with hydrogen chloride in 1,4-dioxane (4.0 M, 0.20 mL) at rt for 30 min. The solvent was evaporated under reduced pressure, and the residue was dissolved in acetonitrile (1.0 mL, 0.019 mol) and was treated with N,N-diisopropylethylamine (20.0 µL, 0.000115 mol) and methyl chloroformate (5.0 µL µL, 0.000065 mol). After 30 min, the solvent was evaporated under reduced pressure and the residue was the desired product, which was directly used in the next step without further purification. LC/MS: 361.2 (M+H⁺).

Step 4

The title compound was prepared using a procedure analogous to that used in step 2 of example 238. LC/MS: 476.4 (M+H⁺).

Example 259

(1R)-1'-[(1-{4-[4-(Methylsulfonyl)-2-oxopiperazin-1-yl]phenyl}cyclopropyl)carbonyl]-3H-spiro[2-benzofuran-1,3'-pyrrolidin]-3-one Step 1. tert-butyl 3-oxo-4-[4-(1-{[(1R)-3-oxo-1'H,3H-spiro[2-benzofuran-1,3'-pyrrolidin]-1'-yl]carbonyl}cyclopropyl)phenyl]piperazine-1-carboxylate This compound was prepared using a procedure analogous to that used above for the synthesis of example 257. LC/MS: 532.2 (M+H⁺).

Step 2. (1R)-1'-({1-[4-(2-oxopiperazin-1-yl)phenyl]cyclopropyl}carbonyl)-3H-spiro[2-benzofuran-1,3'-pyrrolidin]-3-one To a solution of tert-butyl 3-oxo-4-[4-(1-{[(1R)-3-oxo-1'H,3H-spiro[2-benzofuran-1,3'-pyrrolidin]-1'-yl]carbonyl}cyclopropyl)phenyl]piperazine-1-carboxylate (180 mg, 0.00034 mol) in methanol (2 mL, 0.05 mol) was added 4 M of hydrogen chloride in 1,4-dioxane (0.4 mL) and the mixture was stirred at rt for 3 hours and then concentrated. LC/MS: 432.2 (M+H⁺).

Step 3

To a solution of (1R)-1'-({1-[4-(2-oxopiperazin-1-yl)phenyl]cyclopropyl}carbonyl)-3H-spiro[2-benzofuran-1,3'-pyrrolidin]-3-one (36 mg, 0.000083 mol) in acetonitrile (0.5 mL, 0.01 mol) were added triethylamine (29 µL, 0.00021 mol) and methanesulfonyl chloride. After stirring at rt for 3 hours, the crude product was isolated and purified by prep-HPLC. LC/MS: 510.2 (M+H⁺).

Example 260

7-Fluoro-1'-[(1-{4-[3-(trifluoromethyl)-1H-pyrazol-1-yl]phenyl}cyclopropyl)carbonyl]-3H-spiro[2-benzofuran-1,3'-pyrrolidin]-3-one Step 1. 1-(4-bromophenyl)cyclopropanecarbonitrile Sodium hydroxide (50% aqueous solution, 29.3 g, 0.505 mol) was added to a mixture of 4-bromo-benzeneacetonitrile (9.80 g, 0.0500 mol), benzyltriethylammonium chloride (0.90 g, 0.0040 mol), ethane, and 1-bromo-2-chloro-(14.5 g, 0.101 mol) at 50° C. overnight. The mixture was poured into ice-water (80 mL) and was extracted with ethyl ether (4×50 mL). The combined organic phase was washed with HCl aqueous solution (1N, 20 mL) and brine (2×30 mL) successively, dried over Na₂SO₄, filtered, and concentrated under reduced pressure. The residue was the desired product, which was directly used in the next step without further purification.

Step 2. 1-{4-[3-(trifluoromethyl)-1H-pyrazol-1-yl]phenyl}cyclopropanecarbonitrile To a solution of 1-(4-bromophenyl)cyclopropanecarbonitrile (600 mg, 0.003 mol), 3-(trifluoromethyl)-1H-pyrazole (441 mg, 0.00324 mol) in toluene (2 mL, 0.02 mol) and N,N-dimethylformamide (3 mL, 0.04 mol) were added (1S, 2S)—N,N'-dimethylcyclohexane-1,2-diamine (77 mg, 0.00054 mol), copper(I) iodide (51 mg, 0.00027 mol), and potassium carbonate (784 mg, 0.00567 mol). The mixture was microwave irradiated at 200° C. for 60 minutes and then filtered. The filtrate was diluted with methanol, and the product from the filtrate was isolated and purified using prep-HPLC. Additional product could be obtained from the precipitate by dissolving the precipitate in EtOAc, washing with satd. NaHCO$_3$, brine, drying with MgSO$_4$, and concentrating for purification.

Step 3. 1-{4-[3-(trifluoromethyl)-1H-pyrazol-1-yl] phenyl}cyclopropanecarboxylic acid To a solution of sodium hydroxide in water (19.4 M, 0.1 mL) was added 1,2-ethanediol (2 mL, 0.03 mol) and the mixture was refluxed at 120° C. for 20 hours. After cooling to room temperature, the reaction mixture was poured into water and washed with ether. The aqueous solution was acidified with HCl and extracted with ether. The organic phase of the extraction was washed with brine, dried over MgSO$_4$, and concentrated to afford the product.

Step 4

The title compound was prepared using a procedure analogous to that described for the synthesis of example 94.

Example 261

N-[4-(1-{[(1R)-3-Oxo-1'H,3H-spiro[2-benzofuran-1, 3'-pyrrolidin]-1'-yl]carbonyl}cyclopropyl)phenyl] cyclopropanecarboxamide Step 1. tert-butyl 1-{4-[(tert-butoxycarbonyl)amino] phenyl}cyclopropanecarboxylate A mixture of tert-butyl 1-(4-bromophenyl)cyclopropanecarboxylate (320.0 mg, 0.001077 mol, example 258, step 1), t-butyl carbamate (180.0 mg, 0.001536 mol), sodium benzylate (175.01 mg, 0.0015075 mol), tris(dibenzylideneacetone) dipalladium(0) (16.5 mg, 0.0000180 mol) and tri-tert-butylphosphine (18.8 mg, 0.0000929 mol) in toluene (3.0 mL, 0.028 mol) was deaerated and then charged with nitrogen. The resulting mixture was heated at 100° C. overnight. After cooling, the mixture was filtered through a pad of celite and washed with ethyl acetate. The filtrate was concentrated and the residue was purified by Combiflash with ethyl acetate/hexane to give the desired product.

Step 2. 1-(4-aminophenyl)cyclopropanecarboxylic acid 4.0 M HCl in dioxane was added to tert-butyl 1-{4-[(tert-butoxycarbonyl)amino]phenyl}cyclopropanecarboxylate (160 mg, 0.00048 mol). After stirring at rt for 2 h, the volatiles were removed in-vacuo and the resulting residue was used in the next step without further purification.

Step 3. (1S)-1'-{[1-(4-aminophenyl)cyclopropyl] carbonyl}-3H-spiro[2-benzofuran-1,3'-pyrrolidin]-3-one 4-Methylmorpholine (260 µL, 0.0024 mol) was added to a mixture of 1-(4-aminophenyl)cyclopropanecarboxylic acid (0.48 mmol, 0.00048 mol), [(1R,4S)-7,7-dimethyl-2-oxobicyclo[2.2.1]hept-1-yl]methanesulfonic acid-(1S)-3H-spiro [2-benzofuran-1,3'-pyrrolidin]-3-one (1:1) (2.0×10$^{-2}$ mg, 0.00048 mol), (benzotriazol-1-yloxy)tripyrrolidino phosphonium hexafluorophosphate (261 mg, 0.000502 mol), or benzotriazol-1-yloxytris(dimethylamino)phosphonium hexafluorophosphate (222 mg, 0.000502 mol) in N,N-dimethylformamide (1.5 mL, 0.019 mol). The reaction mixture was stirred at rt for 2 h. The crude product was purified by prep-LCMS. LC/MS: 349.0 (M+H$^+$).

Step 4. N-[4-(1-{[(1R)-3-oxo-1'H,3H-spiro[2-benzofuran-1,3'-pyrrolidin]-1'-yl]carbonyl}cyclopropyl) phenyl]cyclopropanecarboxamide Benzotriazol-1-yloxytris(dimethylamino)phosphonium hexafluorophosphate (17 mg, 0.000038 mol) was added into a solution of (1R)-1'-{[1-(4-aminophenyl)cyclopropyl]carbonyl}-3H-spiro[2-benzofuran-1,3'-pyrrolidin]-3-one (12 mg, 0.000034 mol), cyclopropanecarboxylic acid (3.0 µL, 0.000038 mol) and 4-methylmorpholine (15 µL, 0.00014 mol) in N,N-dimethylformamide (0.5 mL, 0.006 mol). The reaction mixture was stirred at rt for 2 h. It was purified by prep-LCMS. LC/MS: 417.2 (M+H$^+$).

Example 262

N-[4-(1-{[(1R)-3-Oxo-1'H,3H-spiro[2-benzofuran-1, 3'-pyrrolidin]-1'-yl]carbonyl}cyclopropyl)phenyl] benzenesulfonamide This compound was prepared by using procedures analogous to those were described in step 1 of example 202, and in steps 2-3 of example 261. LC/MS: 489.2 (M+H$^+$).

Example 263

Methyl allyl[4-(1-{[(1R)-3-oxo-1'H,3H-spiro[2-benzofuran-1,3'-pyrrolidin]-1'-yl]carbonyl}cyclopropyl) phenyl]carbamate Step 1. tert-butyl 1-[4-(allylamino)phenyl]cyclopropanecarboxylate This compound was prepared from the N-2-propenyl-2-propen-1-amine using the coupling protocol outlined in example 258, step 2. The other major product was tert-butyl 1-[4-(diallylamino)phenyl]cyclopropanecarboxylate.

Step 2. 1-{4-[allyl(methoxycarbonyl)amino] phenyl}cyclopropanecarboxylic acid

Methyl chloroformate (34 µL, 0.00044 mol) was added to a mixture of tert-butyl 1-[4-(allylamino)phenyl]cyclopropanecarboxylate (6.0×10$^{-1}$ mg, 0.00022 mol) and triethylamine (92 µL, 0.00066 mol) in acetonitrile (1.0 mL, 0.019 mol) at rt. The reaction mixture was stirred at rt for 30 minutes, then was washed with water, and then extracted with EtOAc (3×). The organic layers were combined and concentrated. To the residue was added 4.0M HCl in dioxane and the reaction was stirred at rt for 2 h. The solvent was removed in-vacuo and used in the following step. LC/MS: 276.2 (M+H$^+$).

Step 3

The title compound was prepared by using a procedure analogous to that in step 3 of example 261. LC/MS: 447.2 (M+H$^+$).

Example 264

(1R)-1'-({1-[4-(1H-1,2,4-Triazol-1-yl)phenyl]cyclopropyl}carbonyl)-3H-spiro[2-benzofuran-1,3'-pyrrolidin]-3-one This compound was prepared by using a procedure similar to that outlined for the synthesis of example 257. LC/MS: 401.1 (M+H$^+$).

Example 265

(1R)-1'-[(1-Quinolin-6-ylcyclopropyl)carbonyl]-3H-spiro[2-benzofuran-1,3'-pyrrolidin]-3-one This compound was prepared by using a procedure similar to that outlined for the synthesis of example 238. LC/MS: 385.2 (M+H$^+$).

Example 266

(1R)-1'-[(1-Pyridin-4-ylcyclopropyl)carbonyl]-3H-spiro[2-benzofuran-1,3'-pyrrolidin]-3-one This compound was prepared by using a method similar to that outlined in the synthesis of example 238, beginning with ethyl 1-pyridin-4-ylcyclopropanecarboxylate. LC/MS: 335.1 (M+H$^+$).

Example 267

(1R)-1'-[(1-Quinolin-4-ylcyclopropyl)carbonyl]-3H-spiro[2-benzofuran-1,3'-pyrrolidin]-3-one This compound was prepared by using a method similar to that outlined in the synthesis of example 238. LC/MS:385.1 (M+H$^+$).

Example 268

(1R)-1'[(1-Quinolin-2-ylcyclopropyl)carbonyl]-3H-spiro[2-benzofuran-1,3'-pyrrolidin]-3-one This compound was prepared by using a method similar to that outlined in the synthesis of example 238. LC/MS:385.2 (M+H$^+$).

Example 269

(1R)-1'-[(1-Pyridin-2-ylcyclopropyl)carbonyl]-3H-spiro[2-benzofuran-1,3'-pyrrolidin]-3-one This compound was prepared by using a method similar to that outlined in the synthesis of example 238, beginning with methyl 1-pyridin-2-ylcyclopropanecarboxylate. LC/MS: 335.1 (M+H$^+$).

Example 270

(1R)-1'-{[1-(1,3-Benzothiazol-2-yl)cyclopropyl]carbonyl}-3H-spiro[2-benzofuran-1,3'-pyrrolidin]-3-one This compound was prepared by using a method similar to that outlined in the synthesis of example 238. LC/MS: 391.1 (M+H$^+$).

Example 271

2-(1-{[1-(4-Chlorophenyl)cyclopropyl]carbonyl}pyrrolidine-3-yl)-1,3-thiazole

Step 1. tert-butyl 3-hydroxy-3-(1,3-thiazol-2-yl)pyrrolidine-1-carboxylate 1.600 M of n-Butyllithium in hexane (1.0×10$^{-1}$ mL) was added to 1,3-thiazole (0.958 mL, 0.0135 mol) in THF (20 mL) at −78° C. After 30 minutes, tert-butyl 3-oxopyrrolidine-1-carboxylate (2.50 g, 0.0135 mol) in THF (10 mL) was added, and the mixture was slowly warmed to room temperature overnight. The reaction was quenched with water, and the reaction mixture was extracted with ethyl acetate, dried with MgSO$_4$, filtered and concentrated. The residue was purified by flash column (50% EtOAc/hexanes to pure EtOAc) to give the desired product (2.57 g, 70%).

Step 2. 2-(2,5-dihydro-1H-pyrrol-3-yl)-1,3-thiazole trifluoroacetate tert-Butyl 3-hydroxy-3-(1,3-thiazol-2-yl)pyrrolidine-1-carboxylate (1.0 g, 0.0037 mol) was dissolved in trifluoroacetic acid (10.0 mL, 0.130 mol) under N$_2$ at rt. The reaction flask was wrapped with aluminum foil and the mixture was stirred under reflux for 3 h. After cooling to rt the reaction mixture was concentrated in vacuo and used directly for the next step without further purification.

Step 3. 2-pyrrolidin-3-yl-1,3-thiazole trifluoroacetate

To a solution of 2-(2,5-dihydro-1H-pyrrol-3-yl)-1,3-thiazole trifluoroacetate (2.49 g, 0.00936 mol) in methanol (100.0 mL, 2.469 mol) was added platinum dioxide (320 mg, 0.0014 mol) and the resulting mixture was hydrogenated on par shaker at 56 psi for 3 h. After filtration, the filtrate was concentrated in vacuo and dried under high vacuum to give the desired product as a solid. LC-MS (M+H) 155.2 (base).

Step 4

The title compound was prepared using the BOP coupling method that was outlined in the synthesis of example 1. LC/MS (M+H) 333.2 (base).

Example 272

1'-{[1-(4-Methylphenyl)cyclopropyl]carbonyl}spiro[pyrido[3,4-d][1,3]oxazine-4,3'-pyrrolidin]-2(1H)-one Step 1. benzyl 3-{3-[(tert-butoxycarbonyl)amino]pyridin-4-yl}-3-hydroxypyrrolidine-1-carboxylate To a flame-dried round bottomed flask with thermometer side-arm, equipped with a stir bar, was added tert-butyl pyridin-3-ylcarbamate (1.104 g, 0.005684 mol) in 75 mL THF under inert atmosphere. The solution was cooled to −78° C. and then 1.7 M of tert-butyllithium in pentane (7.4 mL) was added dropwise. The resulting solution was stirred for 2 h at −78° C., followed by the addition of benzyl 3-oxopyrrolidine-1-carboxylate (1.038 g, 0.004736 mol) in 75 mL THF. The reaction was allowed to warm to rt and stirred for 5 hrs. The reaction mixture was quenched with saturated ammonium chloride, diluted with water and extracted with ethyl acetate. The combined organic phases were treated with brine and then magnesium sulfate, filtered, and concentrated. The crude product was purified by combiflash using 50-80% ethyl acetate/hexane to recover the starting material (0.9 g) and then 100% ethyl acetate to obtain the product (0.5 g). The product was verified by LCMS and NMR data.

Step 2. benzyl 3-(3-aminopyridin-4-yl)-3-hydroxy-pyrrolidine-1-carboxylate bis(trifluoroacetate) (salt)

To a stirred solution of benzyl 3-{3-[(tert-butoxycarbonyl)amino]pyridin-4-yl}-3-hydroxypyrrolidine-1-carboxylate (4.38 g, 0.0106 mol) in methylene chloride (12.00 mL, 0.1872 mol) at rt was added trifluoroacetic acid (10.00 mL, 0.1298 mol) and the reaction mixture was stirred at rt for 4 h. LCMS (m+1, 314.2) indicated that the reaction was complete. The volatiles were removed and NMR data supported the formation of the desired product.

Step 3. benzyl 2-oxo-1,2-dihydro-PH-spiro[pyrido[3,4-d][1,3]oxazine-4,3'-pyrrolidine]-1'-carboxylate To a solution of benzyl 3-(3-aminopyridin-4-yl)-3-hydroxypyrrolidine-1-carboxylate bis(trifluoroacetate) (salt) (0.4239 g, 0.0007830 mol) in 4 mL THF was added triethylamine (0.4365 mL, 0.003132 mol) at 0° C. Then a solution of triphosgene (0.2323 g, 0.0007830 mol) in 3 mL THF was added rapidly. The mixture was stirred and monitored by LCMS for 45 min at 0° C. After 4 h the reaction was quenched with saturated sodium bicarbonate and the product was extracted with ethyl acetate. The combined organic phases were treated with brine and then magnesium sulfate, filtered, and concentrated. The crude product was purified by Combiflash.

Step 4. spiro[pyrido[3,4-d][1,3]oxazine-4,3'-pyrrolidin]-2(1H)-one

To a solution of benzyl 2-oxo-1,2-dihydro-1'H-spiro[pyrido[3,4-d][1,3]oxazine-4,3'-pyrrolidine]-1'-carboxylate (461.00 mg, 0.0013585 mol) in dichloromethane (10.00 mL, 0.1560 mol) and methanol (10 mL, 0.2 mol) was added palladium (92 mg, 0.00086 mol). The reaction was stirred under a hydrogen atmosphere using a balloon for 2 h. The reaction mixture was filtered and concentrated to afford the product (quantitative yield).

Step 5

The title compound was prepared by a BOP mediated coupling reaction analogous to that outlined in the synthesis of example 1.

Example 273

1-{[1-(4-Chlorophenyl)cyclopropyl]carbonyl}-3-pyridin-4-ylpyrrolidin-3-ol

Step 1. tert-butyl 3-hydroxy-3-pyridin-4-ylpyrrolidine-1-carboxylate 1.600 M of n-Butyllithium in hexane (0.810 mL) was added to a solution of 4-bromopyridine hydrochloride (210 mg, 1.1 mmol) in ether (5 mL, 0.05 mol) at −78° C. The solution was stirred at −78° C. for 30 min. and then tert-butyl 3-oxopyrrolidine-1-carboxylate (200 mg, 0.001 mol) was added and the temperature was maintained at −78° C. for 3 hours. The reaction mixture was quenched with water, extracted with AcOEt. The organic layer was dried with $MgSO_4$, and concentrated to afford the desired product.

Step 2. 3-pyridin-4-ylpyrrolidin-3-ol

To the above compound was added hydrogen chloride in 1,4-dioxane (4M, 1 mL) and. The mixture was stirred at rt for 2 hours and then concentrated to afford the product.

Step 3

The title compound was prepared using a BOP mediated coupling procedure analogous to that described for the synthesis of example 1.

Example 274

1-{[1-(4-Chlorophenyl)cyclopropyl]carbonyl}-3-(3-fluoropyridin-4-yl)pyrrolidin-3-ol This compound was prepared by using an analogous procedure to that outlined above for the synthesis of example 273. LC/MS (M+H) 361.7.

Example 275

1-{[1-(4-Chlorophenyl)cyclopropyl]carbonyl}-3-(2-fluorophenyl)pyrrolidin-3-61

This compound was prepared by using an analogous procedure to that outlined above for the synthesis of example 273. LC/MS (M+H) 360.7.

Example 276

1-{[1-(4-Chlorophenyl)cyclopropyl]carbonyl}-3-[2-(hydroxymethyl)phenyl]pyrrolidin-3-ol This compound was prepared by using an analogous procedure to that outlined above for the synthesis of example 273. LC/MS (M+H) 372.7.

Example 277

1-{[1-(4-Chlorophenyl)cyclopropyl]carbonyl}-3-pyridin-2-ylpyrrolidin-3-ol

This compound was prepared by using an analogous procedure to that outlined above for the synthesis of example 273.

Example 278

(1R)-1'-({1-[4-(Pyrrolidin-1-ylmethyl)phenyl]cyclopropyl}carbonyl)-3H-spiro[2-benzofuran-1,3'-pyrrolidin]-3-one Step 1. 1-(4-vinylphenyl)cyclopropanecarbonitrile A mixture of (4-vinylphenyl)acetonitrile (2.1 g, 0.015 mol), 1-bromo-2-chloro-ethane (1.4 mL, 0.016 mol) and benzyltriethylammonium chloride (0.2 g, 0.0008 mol) in aqueous sodium hydroxide solution (20m, 6 mL) was stirred at 70° C. for 1 h. The reaction mixture was cooled, diluted with water and extracted with ethyl ether. The combined ether layers were washed with water and brine, dried and concentrated to afford the product.

Step 2. 1-(4-formylphenyl)cyclopropanecarbonitrile

Ozone was bubbled through a solution of 1-(4-vinylphenyl)cyclopropanecarbonitrile (1.8 g, 0.011 mol) in methylene chloride (40 mL, 0.6 mol) at −78° C. until a blue color appeared and then nitrogen was bubbled through the solution for 10 minutes. Methyl sulfide was added and the mixture was stirred overnight. The mixture was washed with water and brine successively, dried, and concentrated to give the desired product.

Step 3. 1-[4-(pyrrolidin-1-ylmethyl)phenyl]cyclopropanecarbonitrile

A mixture of 1-(4-formylphenyl)cyclopropanecarbonitrile (0.30 g, 0.0018 mol), pyrrolidine (0.18 mL, 0.0021 mol) and sodium triacetoxyborohydride (0.74 g, 0.0035 mol) in methanol (5.0 mL, 0.12 mol) was stirred at rt for 1 h. The reaction was adjusted to be basic (pH=12) and extracted with ethyl acetate. The combined extract was washed with brine, dried, and concentrated to provide the desired product. LC-MS: 227.1 (M+H)+

Step 4. 1-[4-(pyrrolidin-1-ylmethyl)phenyl]cyclopropanecarboxylic acid

A solution of 1-[4-(pyrrolidin-1-ylmethyl)phenyl]cyclopropanecarbonitrile (100 mg, 0.0004 mol) in ethanol (5 mL, 0.08 mol) and 50% NaOH (aq. 4 ml) and water (2 ml) was stirred at 100 celsius overnight. The mixture was then carefully adjusted to be slightly acidic (pH=6) and the precipitate formed was filtered and dried to afford the product. LC-MS: 246.1 (M+H)+

Step 5

The title compound was prepared using a procedure analogous to that used for the synthesis of example 173.

Example 280

6-Chloro-1'-({1-[4-(Trifluoromethyl)phenyl]cyclopropyl}carbonyl)-3H-spiro[furo[3,4-c]pyridine-1,3'-pyrrolidin]-3-one This compound was prepared by using an analogous procedure to that described above for the synthesis of example 232. LC/MS: 437.6 (M+H+).

Example 281

6-Chloro-1'-{[1-(4-methylphenyl)cyclopropyl]carbonyl}-3H-spiro[furo[3,4-c]pyridine-1,3'-pyrrolidin]-3-one This compound was prepared by using an analogous procedure to that described above for the synthesis of example 232. LC/MS: 383.6 (M+H+).

Example 282

(1R)-1'-({1-[4-(3-Thienyl)phenyl]cyclopropyl}carbonyl)-3'-spiro[2-benzofuran-1,3'-pyrrolidin]-3-one This compound was prepared by using an analogous procedure to that described above for the synthesis of example 116. LC/MS: 416.3 (M+H+).

Example 283

1-{[1-(4-Chlorophenyl)cyclopropyl]carbonyl}-3-(1,3-thiazol-2-yl)pyrrolidin-3-ol This compound was prepared by using analogous procedures to those outlined above in steps 1 and 4 of example 269. LC/MS (M+H) 349.1 alcohol.

Example 284

(1R)-1'-{[1-(2-Naphthyl)cyclopropyl]carbonyl}-3H-spiro[furo[3,4-c]pyridine-1,3'-pyrrolidin]-3-one

Step 1. 1-(2-naphthyl)cyclopropanecarboxylic acid

Sodium hydroxide (50% aqueous solution, 3.20 g, 0.0552 mol) was added to a mixture of 2-naphthylacetonitrile (0.913 g, 0.00546 mol), benzyltriethylammonium chloride (0.09 g, 0.0004 mol), and 1-bromo-2-chloro-ethane (1.58 g, 0.0110 mol) at 50 celsius for 5 h. Then 1,2-ethanediol (10.0 mL, 0.179 mol) was added and the mixture was heated at 100° C. overnight. The mixture was poured into ice-water (30 mL) and was extracted with ethyl ether (2×10 mL). The aqueous phase was acidified (pH=2) with 1N HCl and was extracted with ethyl acetate (4×15 mL). The combined organic phase was washed with brine (10 mL), dried over $Na_2SO_4$, filtered, and concentrated under reduced pressure. The residue was the desired product, which was directly used in next step reaction without further purification.

Step 2

The title compound was prepared by using an analogous procedure to that used for the synthesis in step B of example 95. LC/MS: 385.1 (M+H+).

Example 285

(1R)-1'-({1-[4-(Pyridin-4-ylmethoxy)phenyl]cyclopropyl}carbonyl)-3H-spiro[furo[3,4-c]pyridine-1,3'-pyrrolidin]-3-one This compound was prepared using a procedure analogous to that described for the synthesis of example 215. LC/MS: 442.2 (M+H+) and 464.1 (M+Na+).

Example 286

(3aR,7aS)-2-{[1-(4-Chlorophenyl)cyclopropyl]carbonyl}octahydro-1H-isoindole This compound was prepared using an analogous procedure to that used for the synthesis of example 1. LC/MS (M+H) 304.1.

Example 287

1'-{[1-(4-Chlorophenyl)cyclopropyl]carbonyl}spiro[isochromene-3,3'-pyrrolidin]-1(4H)-one

Step 1. Benzyl 1-oxo-1,4-dihydro-1'H-spiro[isochromene-3,3'-pyrrolidine]-1'-carboxylate Into a 1-neck round-bottom flask were added N,N-diethyl-2-methylbenzamide (200 mg, 0.001 mol) and anhydrous THF (ca. 20 mL) and the solution was cooled to −78° C. prior to the dropwise addition of 1.8 M of lithium diisopropylamide in heptane (630 µL). The color changed to purple, which is characteristic of laterally lithiated species due to the ortho-quinodimethane structure. The laterally lithiated species was allowed to form for 40 min. and then a solution of benzyl 3-oxopyrrolidine-1-carboxylate (210 mg, 0.00095 mol) in anhydrous THF (2 mL) was added dropwise via cannula. The color remained indicating that there was excess lithiated species. After stirring for 2 h, the reaction was quenched by addition of sat'd. NH$_4$Cl and the reaction mixture was allowed to gradually warm to rt. The mixture was diluted with H$_2$O (5 mL) and the product was extracted with EtOAc (3×5 mL). The combined organic phase was washed with H$_2$O (5 mL) and brine (5 mL) successively, dried (over Na$_2$SO$_4$), filtered, and concentrated in-vacuo. The LC/MS data suggested that a mixture of cyclized and uncyclized products was formed. The crude product was dissolved in toluene and refluxed overnight in the presence of a catalytic amount of p-Toluenesulfonic acid monohydrate (159 mg, 0.000836 mol) LC/MS: 411.1 (M+H$^+$). The product was purified using Combiflash eluting with 30 to 50% EtOAc/hexanes. LC/MS: 360.1 (M+Na$^+$).

Step 2. Cbz Deprotection

Benzyl 1-oxo-1,4-dihydro-1'H-spiro[isochromene-3,3'-pyrrolidine]-1'-carboxylate (10 mg, 0.00003 mol) was dissolved in MeOH. To this solution was added Pd/C Palladium (10 mg, 0.000009 mol) and the reaction vessel was sealed and flushed with N$_2$ (g) followed by H$_2$ (g) and then placed under a H$_2$ (g) balloon for 1 h. The palladium was filtered off and the solvent was removed from the filtrate. The crude material was used directly in the next step. LC/MS: 204.3 (M+H$^+$).

Step 3

The title compound was prepared using an analogous procedure to that described for the synthesis of example 1. LC/MS: 382.0 (M+H$^+$).

Example 288

N-(tert-Butyl)-2-(1-{[1-(4-chlorophenyl)cyclopropyl]carbonyl}-3-hydroxypyrrolidin-3-yl)benzenesulfonamide Step 1. 1-{[1-(4-chlorophenyl)cyclopropyl]carbonyl}pyrrolidin-3-ol 3-Pyrrolidinol (1.81 g, 0.0208 mol) was added to a mixture of 1-(4-chlorophenyl)cyclopropanecarboxylic acid (3.93 g, 0.0200 mol), benzotriazol-1-yloxytris(dimethylamino)phosphonium hexafluorophosphate (8.84 g, 0.0200 mol) and 4-methylmorpholine (9.00 mL, 0.0819 mol) in N,N-dimethylformamide (20.0 mL, 0.258 mol). The mixture was stirred at rt overnight. The mixture was diluted with ethyl acetate (100 mL) and was washed with NaHCO$_3$ (7.5%, 3×30 mL). The organic layer was dried over Na$_2$SO$_4$, filtered and concentrated under reduced pressure. The residue was used directly in the next step without further purification.

Step 2. 1-{[1-(4-chlorophenyl)cyclopropyl]carbonyl}pyrrolidin-3-one

To a solution of 1-{[1-(4-chlorophenyl)cyclopropyl]carbonyl}pyrrolidin-3-ol (2.70 g, 0.0102 mol) in acetone (50 mL, 0.7 mol) was added Jone's oxidant in water (8.00M, 1.90 mL) at 0° C. The solution was stirred at rt for 1 hour and then filtered, concentrated. The residue was dissolved in AcOEt, and the solution was washed with water and brine successively, dried over MgSO$_4$, and concentrated. The crude product was purified using Combiflash eluting with 50% AcOEt in hexanes.

Step 3

To a solution of N-(tert-butyl)benzenesulfonamide (569 mg, 0.00267 mol) in ether (10 mL, 0.1 mol) was added 1.7 M of tert-butyllithium in pentane (4.7 mL) under nitrogen at −78° C. The mixture was stirred at −78° C. for 15 minutes, then at 0° C. for 1 hour. The reaction mixture then was cooled down to −78° C. again and a solution of 1-{[1-(4-chlorophenyl)cyclopropyl]carbonyl}pyrrolidin-3-one (640 mg, 0.0024 mol) in ether was added. After stirring for 2 hours, the reaction mixture was quenched with saturated NH$_4$Cl aqueous solution and then extracted with EtOAc. The combined organic layer was washed with brine, dried over MgSO$_4$ and concentrated. The crude product was purified using Combiflash eluting with 30% AcOEt in hexanes to afford the desired product. LC/MS (M+H$^+$) 478.0.

Example 289

2-[(1-{[1-(4-Chlorophenyl)cyclopropyl]carbonyl}-3-hydroxypyrrolidin-3-yl)methyl]nicotinic acid To a solution of 2,2,6,6-tetramethyl-piperidine (0.123 g, 0.000872 mol) in tetrahydrofuran (3.00 mL, 0.0370 mol) at −75° C. was added 2.50 M of n-butyllithium in hexane (0.500 mL). After stirring for 15 min., a suspension of 2-methylnicotinic acid (120.5 mg, 0.0008787 mol) in THF (5.0 mL) was added at −55° C. The mixture was stirred at −55° C. for 1 h. 1-{[1-(4-Chlorophenyl)cyclopropyl]carbonyl}pyrrolidin-3-one (100.0 mg, 0.0003792 mol, prepared in steps 1 and 2 of example 288) was added to the above mixture and the reaction temperature was maintained at −50 to −40° C. The mixture was stirred at −40° C. for 30 minutes, then slowly warmed up to 0° C. To the mixture was added acetic acid (0.50 mL, 0.0088 mol) at 0° C. and the reaction mixture was stirred overnight while gradually warming to rt. The reaction mixture was carefully neutralized with NaHCO$_3$ and the resulting mixture was extracted with AcOEt (4×30 mL). The combined organic layer was washed with brine (30 mL), dried over MgSO$_4$, and concentrated. The residue was purified by Combiflash with ethyl acetate/hexane to give the desired product. LC/MS (M+H$^+$) 401.7.

Example 290

1-{[1-(4-Chlorophenyl)cyclopropyl]carbonyl}-3-phenylpyrrolidine-3,4-diol

To a solution of 1-{[1-(4-chlorophenyl)cyclopropyl]carbonyl}-3-phenyl-2,5-dihydro-1H-pyrrole (80 mg, 0.0002 mol, prepared using a procedure analogous to that described in example 1) in acetone (500 µL, 0.007 mol), water (1250 µL, 0.0694 mol), and tert-butyl alcohol (250 µL, 0.0026 mol), was added osmium tetraoxide (80 mg, 0.00001 mol) followed by 4-methylmorpholine 4-oxide (29 mg, 0.00025 mol). The mixture was heated at 70° C. for 1 hour. After cooling, it was filtered and the filtrate was purified with prep-HPLC to afford the product (36.5 mg). LCMS: m/z 358.0 (M+H)$^+$; 379.9 (M+Na$^+$).

Example 291

(1R)-1'-{[1-(2-Fluoro-4-pyridin-4-ylphenyl)cyclopropyl]carbonyl}-3H-spiro[2-benzofuran-1,3'-pyrrolidin]-3-one To a solution of (1R)-1'-{[1-(4-bromo-2-fluorophenyl)cyclopropyl]carbonyl}-3H-spiro[2-benzofuran-1,3'-pyrrolidin]-3-one (30 mg, 0.00007 mol, this compound was prepared by using a method that was analogous to that used for the synthesis of 238) in tetrahydrofuran (0.2 mL, 0.002 mol) were added tris(dibenzylideneacetone)dipalladium(0) (3 mg, 0.000003 mol), tri-tert-butylphosphine (1.7 mg, 0.0000083 mol), 4-(tributylstannyl)pyridine (30.7 mg, 0.0000835 mol), and the mixture was heated to 120° C. under microwave for 30 minutes. The reaction mixture was then filtered and the filtrate was diluted with methanol, and the product was isolated and purified by prep-HPLC. LC/MS (M+H$^+$) 429.2.

Example 292

5-Methoxy-1'-{[1-(4-methylphenyl)cyclopropyl]carbonyl}-3H-spiro[2-benzofuran-1,3'-pyrrolidin]-3-one

Step 1. tert-butyl 5-methoxy-3-oxo-1'H,3H-spiro[2-benzofuran-1,3'-pyrrolidine]-1'-carboxylate A solution of 2-bromo-5-methoxybenzoic acid (1.85 g, 0.00801 mol) in tetrahydrofuran (50 mL, 0.6 mol) was cooled below −20° C. under N$_2$ atmosphere and dibutylmagnesium in heptane (1.0 M, 4.2 mL) was slowly added to the solution. Then to the mixture was added slowly n-butyllithium in hexane (2.5 M, 3.5 mL). After stirring below at −15° C. for 1 hour, a solution of tert-butyl 3-oxopyrrolidine-1-carboxylate (1.50 g, 0.00810 mol) in THF (20.0 mL) was added. After stirring below −20° C. for 1 hour, the reaction was quenched with acetic acid (10 mL). The resulting mixture was stirred at rt overnight. The mixture was neutralized and extracted with EtOAc. The organic layer was washed with NaHCO$_3$ solution, water and brine successively, dried over Na$_2$SO$_4$, and filtered. The filtrate was concentrated to afford the desired product. LC/MS (M+H$^+$) 320.1.

Step 2

A mixture of tert-butyl 5-methoxy-3-oxo-1'H,3H-spiro[2-benzofuran-1,3'-pyrrolidine]-1'-carboxylate (80.0 mg, 0.000250 mol) and 4M HCl in dioxane was stirred for 2 hours and then concentrated. To a solution of 1-(4-methylphenyl)cyclopropanecarboxylic acid (44.1 mg, 0.000250 mol) in dichloromethane (2 mL, 0.03 mol) was added the above residue. The solution was cooled to 0° C. and BOP was added. The solution was stirred for 3 min and then DIEA was added. The solution was stirred at 0° C. for 20 min and then gradually allowed to warm to rt with stirring overnight. The crude product was purified using prep-HPLC. LC/MS (M+H$^+$) 378.1.

Example 293

1'-{[1-(4-Methylphenyl)cyclopropyl]carbonyl}-3-oxo-3H-spiro[2-benzofuran-1,3'-pyrrolidine]-5-carbonitrile This compound was prepared by using an analogous procedure to that used for the synthesis of example 292. LC/MS (M+H$^+$) 373.1.

Example 294

(1R)-1'-({1-[3'-(Hydroxymethyl)biphenyl-4-yl]cyclopropyl}carbonyl)-3H-spiro[2-benzofuran-1,3'-pyrrolidin]-3-one This compound was prepared by using a procedure analogous to that outlined for the synthesis of example 250. LC/MS: 440.2 (M+H$^+$).

Example 295

(1R)-1'-({1-[2'(Methylthio)biphenyl-4-yl]cyclopropyl}carbonyl)-3H-spiro[2-benzofuran-1,3'-pyrrolidin]-3-one This compound was prepared by using a procedure analogous to that outlined for the synthesis of example 250. LC/MS: 456.2 (M+H$^+$).

Example 296

1'-{[1-(1,3-Benzothiazol-2-yl)cyclopropyl]carbonyl}-7H-spiro[furo[3,4-b]pyridine-5,3'-pyrrolidin]-7-one The starting material 1-(1,3-benzothiazol-2-yl)cyclopropanecarboxylic acid was prepared by using a procedure analogous to that in step 1 of example 238. The starting material 7H-spiro[furo[3,4-b]pyridine-5,3'-pyrrolidin]-7-one hydrochloride was prepared by using a procedure analogous to that used in step 1 of example 90. The amine and carboxylic acid were subjected to BOP mediated coupling conditions analogous to those described in step 5 of example 82. LC/MS: 392.1 (M+H$^+$).

Example 297

1'-{[1-(2-Naphthyl)cyclopropyl]carbonyl}-7H-spiro[furo[3,4-b]pyridine-5,3'-pyrrolidin]-7-one The starting material 1-(2-naphthyl)cyclopropanecarboxylic acid was prepared by using a procedure analogous to that used in step 1 of example 238. The starting material 7H-spiro[furo[3, 4-b]pyridine-5,3'-pyrrolidin]-7-one hydrochloride was prepared by using a procedure analogous to that in step 1 of example 90. The amine and carboxylic acid were subjected to BOP mediated coupling conditions analogous to those described in step 5 of example 82. LC/MS: 385.1 (M+H$^+$).

Example 298

1'-({1-[4-(Difluoromethoxy)phenyl]cyclopropyl}carbonyl)-7H-spiro[furo[3,4-b]pyridine-5,3'-pyrrolidin]-7-one The starting material 1-[4-(difluoromethoxy)phenyl]cyclopropanecarboxylic acid was prepared by using a procedure analogous to that in step 1 of example 238. The starting material 7H-spiro[furo[3,4-b]pyridine-5,3'-pyrrolidin]-7-one hydrochloride was prepared by using a procedure analogous to that in step 1 of example 90. The amine and carboxylic acid were subjected to BOP mediated coupling conditions analogous to those described in step 5 of example 82. LC/MS: 401.1 (M+H$^+$).

Example 299

(1R)-1'-{[1-(4-{[4-(Trifluoromethoxy)benzyl]oxy}phenyl)cyclopropyl]carbonyl}-3H-spiro[furo[3,4-c]pyridine-1,3'-pyrrolidin]-3-one This compound was prepared using a procedure analogous to that described in steps 1 & 2 of example 104. LC/MS: 525.2 (M+H⁺).

Example 300

(1R)-1'-[(1-{4-[1-(4-Bromophenyl)ethoxy]phenyl}cyclopropyl)carbonyl]-3H-spiro[furo[3,4-c]pyridine-1,3'-pyrrolidin]-3-one This compound was prepared using a procedure analogous to that described in example 105. LC/MS: 534.1 (M+H⁺).

Example 301

(1R)-1'-{[1-(4-Pyridin-3-ylphenyl)cyclopropyl]carbonyl}-3H-spiro[furo[3,4-c]pyridine-1,3'-pyrrolidin]-3-one This compound was prepared using a procedure that was analogous to that described in steps 1 & 2 of example 250. LC/MS: 412.2 (M+H⁺).

Example 302

(1R)-[4-(4-{1-[(3-Oxo-1'H,3H-spiro[furo[3,4-c]pyridine-1,3'-pyrrolidin]-1'-yl)carbonyl]cyclopropyl}phenyl)-1,3-thiazol-2-yl]acetonitrile This compound was prepared using a procedure that was analogous to that in steps 1-5 of example 142 (replacing thiourea with 2-cyanoethanethioamide in step 3). LC/MS: 457.1 (M+H H⁺).

Example 303

(1R)-1'-({1-[4-(2-Pyridin-3-yl-1,3-thiazol-4-yl)phenyl]cyclopropyl}carbonyl)-3H-spiro[furo[3,4-c]pyridine-1,3'-pyrrolidin]-3-one This compound was prepared using a procedure that was analogous to that described in steps 1-5 of example 142 (replacing thiourea with pyridine-3-carbothioamide in step 3). LC/MS: 495.2 (M+H⁺).

Example 304

(1R)-1'-({1-[4-(1-Propionyl-1,2,3,6-tetrahydropyridin-4-yl)phenyl]cyclopropyl}carbonyl)-3H-spiro[furo[3,4-c]pyridine-1,3'-pyrrolidin]-3-one This compound was prepared using a procedure that was analogous to that described in steps 1-6 of example 210. LC/MS: 472.2 (M+H⁺).

Example 305

Ethyl 4-[4-(1-{[(1R)-3-oxo-1'H,3H-spiro[furo[3,4-c]pyridine-1,3'-pyrrolidin]-1'-yl]carbonyl}cyclopropyl)phenyl]-3,6-dihydropyridine-1(2H)-carboxylate This compound was prepared using a procedure that was analogous to that described in steps 1-6 of example 210. LC/MS: 488.2 (M+H⁺).

Example 306

(1R)-4-[(E)-2-(4-{1-[(3-Oxo-1'H,3H-spiro[furo[3,4-c]pyridine-1,3'-pyrrolidin]-1'-yl)carbonyl]cyclopropyl}phenyl)vinyl]benzonitrile This compound was prepared using a procedure that was analogous to that described in example 122. LC/MS: 462.2 (M+H⁺).

Example 307

(1R)-1'-{[1-(2-Fluoro-4-pyridin-4-ylphenyl)cyclopropyl]carbonyl}-3H-spiro[furo[3,4-c]pyridine-1,3'-pyrrolidin]-3-one This compound was prepared using a procedure that was analogous to that described in example 291. LC/MS: 430.2 (M+H⁺).

Example 308

(1R)-1'-[(1-{2-Fluoro-4-[3-(trifluoromethyl)-1H-pyrazol-1-yl]phenyl}cyclopropyl)carbonyl]-3H-spiro[furo[3,4-c]pyridine-1,3'-pyrrolidin]-3-one This compound was prepared using a procedure that was analogous to that described in example 126. LC/MS: 487.2 (M+H⁺).

Example 309

(1R)-1'-({1-[4-(2H-Indazol-2-yl)phenyl]cyclopropyl}carbonyl)-3H-spiro[furo[3,4-c]pyridine-1,3'-pyrrolidin]-3-one This compound was prepared using a procedure that was analogous to that described in example 129. LC/MS: 451.2 (M+H⁺).

Example 310

(1R)-1'-({1-[4-(3,3-Difluoropyrrolidin-1-yl)phenyl]cyclopropyl}carbonyl)-3H-spiro[furo[3,4-c]pyridine-1,3'-pyrrolidin]-3-one This compound was prepared by using a procedure analogous to that described in example 98, with the exception that the coupling steps were reversed, i.e., (1R)-1'-{[1-(4-bromophenyl)cyclopropyl]carbonyl}-3H-spiro[furo[3,4-c]pyridine-1,3'-pyrrolidin]-3-one was prepared first by the BOP mediated coupling reaction and then subsequently coupled in the presence of Pd(dppf) to 3,3-difluoropyrrolidine hydrochloride. LC/MS: 440.2 (M+H⁺).

Example 311

(1R)-1'-({1-[2-Fluoro-4-(2-oxopyrrolidin-1-yl)phenyl]cyclopropyl}carbonyl)-3H-spiro[furo[3,4-c]pyridine-1,3'-pyrrolidin]-3-one Step 1. 1'-{[1-(4-bromo-2-fluorophenyl)cyclopropyl]carbonyl}-3H-spiro[furo[3,4-c]pyridine-1,3'-pyrrolidin]-3-one This compound was prepared using a procedure analogous to that described in steps 1-2 of example 95. LC/MS:430.1 & 432.1 (M+H⁺).

Step 2

The title compound was prepared by using a copper (I) mediated coupling reaction analogous to that described in step 1 of example 102. LC/MS: 436.2 (M+H⁺).

Example 312

(1R)-1'-({1-[4-(2-Oxopyrrolidin-1-yl)phenyl]cyclopropyl}carbonyl)-3H-spiro[furo[3,4-c]pyridine-1,3'-pyrrolidin]-3-one This compound was prepared using a procedure analogous to that described in example 98. LC/MS: 418.1 (M+H⁺).

Example 313

(1R)-1'-({1-[4-(2-Oxo-1,3-oxazolidin-3-yl)phenyl]cyclopropyl}carbonyl)-3H-spiro[furo[3,4-c]pyridine-1,3% pyrrolidin]-3-one This compound was prepared using a procedure analogous to that described in example 102. LC/MS: 420.1 (M+H⁺).

Example 314

(1R)-1'-[(1-{4-[(4S)-4-Isopropyl-2-oxo-1,3-oxazolidin-3-yl]phenyl}cyclopropyl) carbonyl]-3H-spiro[furo[3,4-c]pyridine-1,3'-pyrrolidin]-3-one To a solution of (1R)-1'-([144-bromophenyl)cyclopropyl]carbonyl)-3H-spiro[2-benzofuran-1,3'-pyrrolidin]-3-one (20.0 mg, 0.0000485 mol, prepared by using a procedure analogous to that used in example 238) and (4S)-4-isopropyl-1,3-oxazolidin-2-one (18.8 mg, 0.000146 mol) in freshly distilled toluene (0.34 mL, 0.0032 mol) were added tris(dibenzylideneacetone)dipalladium(0) (4.4 mg, 0.0000048 mol), tri-tert-butylphosphine (2.0 mg, 0.0000097 mol) and cesium carbonate (15.8 mg, 0.0000485 mol), and the mixture was heated to at 50° C. overnight. The reaction mixture was then cooled to rt, filtered over celite and concentrated under reduced pressure. The crude product was purified by prep-HPLC separation. LC/MS: 462.2 (M+H⁺).

Example 315

(1R)-1'-({1-[4-(2-Oxoimidazolidin-1-yl)phenyl]cyclopropyl}carbonyl)-3H-spiro[furo[3,4-c]pyridine-1,3'-pyrrolidin]-3-one This compound was prepared by using a procedure analogous to that outlined for the synthesis of example 314. LC/MS: 419.2 (M+H⁺).

Example 316

(1R)-1'-({1-[4-(2-Oxoimidazolidin-1-yl)phenyl]cyclopropyl}carbonyl)-3H-spiro[2-benzofuran-1,3'-pyrrolidin]-3-one This compound was prepared by using a procedure analogous to that outlined for the synthesis of example 314. LC/MS: 418.2 (M+H⁺).

Example 317

(1R)-1'-[(1-{4-[(45)-4-Isopropyl-2-oxo-1,3-oxazolidin-3-yl]phenyl}cyclopropyl)carbonyl]-3H-spiro[2-benzofuran-1,3'-pyrrolidin]-3-one This compound was prepared by using a procedure analogous to that outlined for the synthesis of example 314. LC/MS: 461.2 (M+H⁺).

Example 318

(1R)-1'-({1-[2-Fluoro-4-(2-oxopyrrolidin-1-yl)phenyl]cyclopropyl}carbonyl)-3H-spiro[2-benzofuran-1,3'-pyrrolidin]-3-one A mixture of (1R)-1'-{[1-(4-bromo-2-fluorophenyl)cyclopropyl]carbonyl}-3H-spiro[2-benzofuran-1,3'-pyrrolidin]-3-one (10 mg, 0.00002 mol, prepared by methods analogous to those used for the synthesis of example 238), 2-pyrrolidinone (2.4 mg, 0.000028 mol), copper(I) iodide (0.2 mg, 0.000001 mol), trans-1,2-cyclohexanediamine (0.28 µL, 0.0000023 mol), and potassium carbonate (6.4 mg, 0.000046 mol) in toluene (0.5 mL) and N,N-dimethylformamide (0.5 mL) was microwave irradiated at 110° C. for 30 minutes. The crude product was purified with prep-HPLC. LCMS: m/z 435.2 (M+H⁺); 457.1 (M+Na⁺).

Example 319

(1R)-1'-({1-[2-Fluoro-4-(2-oxo-1,3-oxazolidin-3-yl)phenyl]cyclopropyl}carbonyl)-3H-spiro[2-benzofuran-1,3'-pyrrolidin]-3-one This compound was prepared by using a procedure analogous to that outlined for the synthesis in example 318. LC/MS: 437.1 (M+H⁺).

Example 320

Methyl 3-oxo-4-[4-(1-{[(1R)-3-oxo-1'H,3H-spiro[2-benzofuran-1,3'-pyrrolidin]-1'-yl]carbonyl}cyclopropyl)phenyl]piperazine-1-carboxylate This compound was prepared by using a procedure analogous to that outlined for the synthesis in example 259. LC/MS: 490.2 (M+H⁺).

Example 321

(1R)-1'-[(1-{6-[4-(Cyclopropylcarbonyl)piperazin-1-yl]pyridin-3-yl}cyclopropyl) carbonyl]-3H-spiro[2-benzofuran-1,3'-pyrrolidin]-3-one 4-Methylmorpholine ($2.0 \times 10^{-1}$ μL, 0.00018 mol) was added to a mixture of (1R)-1'-{[1-(6-piperazin-1-ylpyridin-3-yl)cyclopropyl]carbonyl}-3H-spiro[2-benzofuran-1,3'-pyrrolidin]-3-one (15 mg, 0.000036 mol, this compound was prepared in a way similar to that described in example 163), cyclopropanecarboxylic acid (3.4 μL, 0.000043 mol) and benzotriazol-1-yloxytris(dimethylamino)phosphonium hexafluorophosphate (19 mg, 0.000043 mol) in acetonitrile (0.7 mL, 0.01 mol). The reaction mixture was stirred at room temperature overnight. The crude product was purified by prep-LCMS. LC/MS: 487.3 (M+H$^+$).

Example 322

(1R)-1'-[(1-{6-[4-(Pyridin-4-yloxy)piperidin-1-yl]pyridin-3-yl}cyclopropyl)carbonyl]-3H-spiro[2-benzofuran-1,3'-pyrrolidin]-3-one Diethyl azodicarboxylate ($3.0 \times 10^{-1}$ μL, 0.00019 mol) was added to a mixture of (1R)-1'-({1-[6-(4-hydroxypiperidin-1-yl)pyridin-3-yl]cyclopropyl}carbonyl)-3H-spiro[2-benzofuran-1,3'-pyrrolidin]-3-one trifluoroacetate (salt) (42 mg, 0.000077 mol, example 172), 4-pyridinol (18 mg, 0.00019 mol) and triphenylphosphine ($5.0 \times 10^{-1}$ mg, 0.00019 mol) in tetrahydrofuran (1.0 mL, 0.012 mol). The reaction mixture was stirred at room temperature overnight. The crude product was purified by prep-LCMS. LC/MS: 511.2 (M+H$^+$).

Example 323

(1R)-1'-[(1-{6-[(3R)-3-(Pyridin-4-yloxy)pyrrolidin-1-yl]pyridin-3-yl}cyclopropyl)carbonyl]-3H-spiro[2-benzofuran-1,3'-pyrrolidin]-3-one This compound was prepared by using a procedure analogous to that outlined in example 322 using (1R)-1'-[(1-{6-[(3S)-3-hydroxypyrrolidin-1-yl]pyridin-3-yl}cyclopropyl)carbonyl]-3H-spiro[2-benzofuran-1,3'-pyrrolidin]-3-one trifluoroacetate (salt), as the starting material. LC/MS: 497.2 (M+H$^+$).

Example 324

(1R)-1'-({1-[4-(6-Methoxypyridin-3-yl)phenyl]cyclopropyl}carbonyl)-3H-spiro[2-benzofuran-1,3'-pyrrolidin]-3-one This compound was prepared by using a procedure analogous to that outlined in example 123. LC/MS: 441.2 (M+H$^+$).

Example 325

[4'-(1-{[(1R)-3-Oxo-1'H,3H-spiro[2-benzofuran-1,3'-pyrrolidin]-1'-yl]carbonyl}cyclopropyl)biphenyl-3-yl]acetonitrile This compound was prepared by using a procedure analogous to that outlined for the synthesis of example 123. LC/MS: 449.2 (M+H$^+$).

Example 326

(1R)-1'-({1-[4-(6-Aminopyridin-3-yl)phenyl]cyclopropyl}carbonyl)-3H-spiro[2-benzofuran-1,3'-pyrrolidin]-3-one This compound was prepared by using a procedure analogous to that outlined for the synthesis of example 250. LC/MS: 426.1 (M+H$^+$).

Example 327

(1R)-1'-({1-[4-(6-Hydroxypyridin-3-yl)phenyl]cyclopropyl}carbonyl)-3H-spiro[2-benzofuran-1,3'-pyrrolidin]-3-one A mixture of (1R)-1'-({1-[4-(6-fluoropyridin-3-yl)phenyl]cyclopropyl}carbonyl)-3H-spiro[2-benzofuran-1,3'-pyrrolidin]-3-one (20.0 mg, 0.0000467 mol, see example 250 for the preparation), and ammonium acetate (0.0216 g, 0.000280 mol) in dimethyl sulfoxide (0.5 mL, 0.007 mol) and water (0.1 mL) was heated at 100° C. in a sealed tube overnight. The major product was the phenol rather than the aniline derivative. The product was isolated and purified by prep-HPLC. LC-MS: 427.2 (M+H$^+$)

Example 328

(1R)-1'-({1-[4-(5-Methylpyridin-2-yl)phenyl]cyclopropyl}carbonyl)-3H-spiro[2-benzofuran-1,3'-pyrrolidin]-3-one To a solution of (1R)-1'-{[1-(4-bromophenyl)cyclopropyl]carbonyl}-3H-spiro[2-benzofuran-1,3'-pyrrolidin]-3-one (20 mg, 0.00005 mol, prepared as example 238) in 1,4-dioxane (0.2 mL, 0.002 mol) were added tris(dibenzylideneacetone)dipalladium(0) (0.2 mg, 0.0000002 mol), tri-tert-butylphosphine (0.12 mg, $5.8 \times 10^{-7}$ mol), potassium fluoride (9.3 mg, 0.00016 mol) and 2-bromo-5-methylpyridine (0.012 g, 0.000073 mol), and the mixture was heated at 110° C. for 30 minutes. The reaction mixture was filtered and the filtrate was diluted with methanol. The product was isolated and purified with prep-HPLC. LC-MS: 425.2 (M+H$^+$).

Example 329

(1R)-1'-[(1-{4-[(Pyridin-2-yloxy)methyl]phenyl}cyclopropyl)carbonyl]-3H-spiro[2-benzofuran-1,3'-pyrrolidin]-3-one To a mixture of (1R)-1'-({1-[4-(hydroxymethyl)phenyl]cyclopropyl}carbonyl)-3H-spiro[2-benzofuran-1,3'-pyrrolidin]-3-one (16.0 mg, 0.0000440 mol, prepared in example 237), triphenylphosphine (17 mg, 0.000066 mol), and 2-hydroxypyridine (4.0 mg) in tetrahydrofuran (2 mL, 0.02 mol) was added diisopropyl azodicarboxylate (14 μL, 0.000070 mol) at room temperature, and the mixture was stirred overnight. The product was isolated and purified by prep-HPLC. LC-MS: 441.2 (M+H$^+$)

Example 330

(1R)-1'-[(1-{4-[(Pyridin-3-yloxy)methyl]phenyl}cyclopropyl)carbonyl]-3H-spiro[2-benzofuran-1,3'-pyrrolidin]-3-one This compound was prepared by using a procedure analogous to that outlined for the synthesis of example 329. LC/MS: 441.2 (M+H$^+$).

Example 331

(1R)-1'-[(1-{4-[(Pyridin-4-yloxy)methyl]phenyl}cyclopropyl)carbonyl]-3H-spiro[2-benzofuran-1,3'-pyrrolidin]-3-one

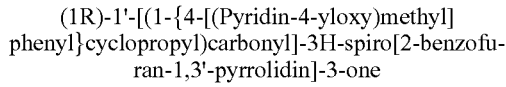

This compound was prepared by using a procedure analogous to that outlined for the synthesis of example 329. LC/MS: 441.2 (M+H⁺).

Example 332

3-(1-{[(1R)-3-Oxo-1'H,3H-spiro[2-benzofuran-1,3'-pyrrolidin]-1'-yl]carbonyl}cyclopropyl)benzonitrile

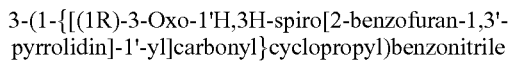

A mixture of (1R)-1'-{[1-(3-bromophenyl)cyclopropyl]carbonyl}-3H-spiro[2-benzofuran-1,3'-pyrrolidin]-3-one (30 mg, 0.00007 mol, prepared by using a procedure that was analogous to that used for the synthesis of example 238), zinc cyanide (8.5 mg, 0.000073 mol), and tetra-N-butylammonium bromide (5.9 mg, 0.000018 mol) in N,N-dimethylformamide (0.5 mL, 0.006 mol) was microwave irradiated (at 170° C.) for 5 minutes. The crude product was isolated and purified with prep-HPLC. LCMS: m/z 359.1 (M+H⁺).

Example 333

(1R)-1'-[(1-Biphenyl-3-ylcyclopropyl)carbonyl]-3H-spiro[2-benzofuran-1,3'-pyrrolidin]-3-one This compound was prepared by using a procedure analogous to that outlined for the synthesis of example 244. LC/MS: 410.1 (M+H⁺) & 432.1 (M+Na⁺).

Example 334

(1R)-1'-{[1-(1-Naphthyl)cyclopropyl]carbonyl}-3H-spiro[2-benzofuran-1,3'-pyrrolidin]-3-one

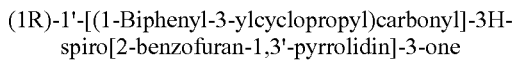

This compound was prepared by using a procedure analogous to that outlined in example 238, starting with methyl-1-naphthaleneacetate. LC/MS: 384.1 (M+H⁺)

Example 335

(1R)-1'-[(1-Quinolin-6-ylcyclopropyl)carbonyl]-3H-spiro[2-benzofuran-1,3'-pyrrolidin]-3-one

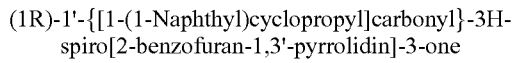

This compound was prepared by using a procedure analogous to that outlined for the synthesis of example 238. LC/MS: 385.2 (M+H⁺).

Example 336

(1R)-1'-[(1-{4-[(5-Methylisoxazol-3-yl)methoxy]phenyl}cyclopropyl)carbonyl]-3H-spiro[2-benzofuran-1,3'-pyrrolidin]-3-one

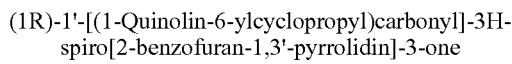

This compound was prepared by using a procedure analogous to that outlined for the synthesis of example 114. LCMS: m/z 445.2 (M+H)+; 467.2 (M+Na)+

Example 337

(1R)-1'-({1-[4-(2-Pyridin-3-yl-1,3-thiazol-4-yl)phenyl]cyclopropyl}carbonyl)-3H-spiro[2-benzofuran-1,3'-pyrrolidin]-3-one

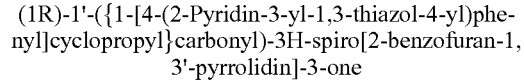

This compound was prepared by using a procedure analogous to that outlined for the synthesis of example 142. LCMS: m/z 494.2 (M+H)+

Example 338

(1R)-1'-[(1-({4-[5-(Trifluoromethyl)-1,3,4-oxadiazol-2-yl]phenyl}cyclopropyl)carbonyl]-3H-spiro[2-benzofuran-1,3'-pyrrolidin]-3-one

Step 1. (1R)-1'-({1-[4-(1H-tetrazol-5-yl)phenyl]cyclopropyl}carbonyl)-3H-spiro[2-benzofuran-1,3'-pyrrolidin]-3-one

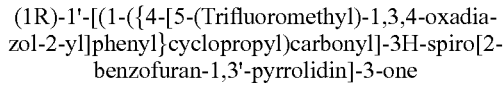

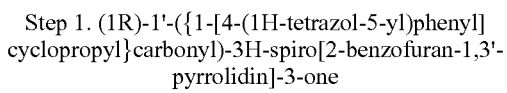

A mixture of 4-(1-{[(1R)-3-oxo-1'H,3H-spiro[2-benzofuran-1,3'-pyrrolidin]-1'-yl]carbonyl}cyclopropyl)benzonitrile (50.0 mg, 0.000140 mol, example 236), sodium azide (109 mg, 0.00167 mol) and ammonium chloride (89.6 mg, 0.00167 mol) in anhydrous N,N-dimethylformamide (1.4 mL, 0.018 mol) in a microwave vial was irradiated with microwaves to 150° C. for 30 minutes. LCMS showed about 60% conversion. The reaction mixture was then irradiated with microwaves to 180° C. for 20 minutes. LCMS showed the reaction was complete. The reaction mixture was filtered. The filtrate was in prep-HPLC to give the product as a colorless solid (44.5 mg, 80% in yield). (M+H⁺)=402.1.

Step 2

A suspension of (1R)-1'-({1-[4-(1H-tetrazol-5-yl)phenyl]cyclopropyl}carbonyl)-3H-spiro[2-benzofuran-1,3'-pyrrolidin]-3-one (30.0 mg, 0.0000747 mol) in trifluoroacetic anhydride (0.50 mL, 0.0035 mol) in a sealed tube was heated at 100° C. for 1 hour with stirring. LCMS showed the reaction was complete. The product from the reaction mixture was isolated and purified by prep-HPLC as a colorless solid (24.0 mg, 68% in yield). (M+H⁺)=470.1.

Example 339

(1R)-1'-{[1-(4-tert-Butyl-1,3-thiazol-2-yl)cyclopropyl]carbonyl}-3H-spiro[2-benzofuran-1,3'-pyrrolidin]-3-one

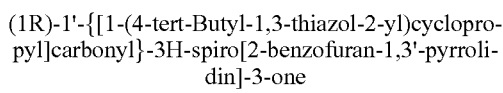

This compound was prepared by using a procedure analogous to that outlined for the synthesis of example 238. LCMS: m/z 397.1 (M+H⁺)

Example 340

(1R)-1'-({1-[4-(4-Chlorophenyl)-1,3-thiazol-2-yl]cyclopropyl}carbonyl)-3H-spiro[2-benzofuran-1,3'-pyrrolidin]-3-one

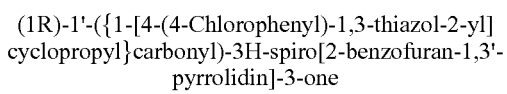

This compound was prepared by using a procedure analogous to that outlined for the synthesis of example 238. LCMS: m/z 451.0 (M H⁺)

Example 341

1',1'''-[1,4-Phenylenebis(cyclopropane-1,1-diylcarbonyl)]bis(3H-spiro[2-benzofuran-1,3'-pyrrolidin]-3-one)

This compound was prepared by using a procedure analogous to that outlined in example 238.

Example 342

4-Hydroxy-1'-[(1-quinolin-4-ylcyclopropyl)carbonyl]-3H-spiro[furo[3,4-c]pyridine-1,3'-pyrrolidin]-3-one This compound was prepared by using a procedure analogous to that outlined for the synthesis of example 95. LCMS: m/z 402.1 (M+H$^+$)

Example 343

4-Methoxy-1'-[(1-quinolin-4-ylcyclopropyl)carbonyl]-3H-spiro[furo[3,4-c]pyridine-1,3'-pyrrolidin]-3-one This compound was prepared by using a procedure analogous to that outlined in example 95. LCMS: m/z 416.1 (M+H$^+$)

Example 344

(1R)-1'-[(1-Pyridin-3-ylcyclobutyl)carbonyl]-3H-spiro[2-benzofuran-1,3'-pyrrolidin]-3-one This compound was prepared by using a procedure analogous to that outlined in example 161. LCMS: m/z 349.1 (M+H$^+$)

Example 345

(1R)-1'-{[1-(4-Chlorophenyl)cyclobutyl]carbonyl}-3H-spiro[2-benzofuran-1,3'-pyrrolidin]-3-one This compound was prepared by using a procedure analogous to that outlined for the synthesis of example 83. LCMS: m/z 382.4 (M+H$^+$)

Example 346

(5R)-1'-{[1-(4-Chlorophenyl)cyclobutyl]carbonyl}-7H-spiro[furo[3,4-b]pyridine-5,3'-pyrrolidin]-7-one This compound was prepared by using a procedure analogous to that outlined for the synthesis of example 156. LCMS: m/z 383.1 (M+H$^+$)

Example 347

1-{[1-(4-Chlorophenyl)cyclopropyl]carbonyl}-4-phenylpyrrolidin-3-61

Step 1. benzyl 3-hydroxy-4-phenylpyrrolidine-1-carboxylate

To a solution of benzyl 3-oxo-4-phenylpyrrolidine-1-carboxylate (200 mg, 0.0007 mol) in tetrahydrofuran (2.0 mL, 0.025 mol) under a N$_2$ atmosphere at −78° C. was added L-Selectride® in tetrahydrofuran (1M, 4.1 mL) with stirring. The mixture was stirred at this temperature for 1.5 hours. LCMS indicated that the starting material was consumed and the reaction was quenched with water. The solution was adjusted to pH ~6 to 7 and was extracted with EtOAc. The organic extract was washed with brine, dried over Na$_2$SO$_4$, filtered and the filtrate was concentrated. The resulting residue was purified with Combiflash, eluting with EtOAc/hexane to afford the product (125 mg). LCMS: m/z 298.0 (M+H$^+$); 320.0 (M+Na$^+$).

Step 2. 4-phenylpyrrolidin-3-ol

A mixture of benzyl 3-hydroxy-4-phenylpyrrolidine-1-carboxylate (125 mg, 0.000420 mol), palladium (25 mg, 0.000023 mol) in methanol (10 mL, 0.2 mol) was stirred under a H$_2$ atmosphere (balloon with H$_2$) over 2 hours. LCMS indicated that the starting material was consumed. The reaction mixture was filtered and the filtrate was concentrated to yield the product (62 mg). LCMS: m/z 163.9 (M+H$^+$).

Step 3

The title compound was prepared by using a procedure analogous to that outlined in example 4. LCMS: m/z 342.1 (M+H$^+$); 364.1 (M+Na$^+$); 707.2 (2M+Na$^+$) (trans-isomer).

Example 348

6-{[1-(4-Chlorophenyl)cyclopropyl]carbonyl}-1,3,3-trimethyl-6-azabicyclo[3.2.1]octane This compound was prepared by using a procedure analogous to that outlined for the synthesis in example 4. LCMS: m/z 332.6 (M+H)$^+$

Example 349

((2S,3R)-1-{[1-(4-Chlorophenyl)cyclopropyl]carbonyl}-3-phenylpyrrolidin-2-yl)methanol Step 1. [(2S,3R)-3-phenylpyrrolidin-2-yl]methanol Borane in tetrahydrofuran (1.0 M, 1.0 mL) was added to (2S,3R)-3-phenylpyrrolidine-2-carboxylic acid (30.0 mg, 0.000157 mol) in tetrahydrofuran (1.0 mL, 0.012 mol) at rt. After stirring for 1 h the solvent was evaporated under reduced pressure and the residue was azeotroped with methanol (3×2 mL) to afford the desired product, which was directly used in next step reaction without further purification.

Step 2

The title compound was prepared by using a procedure analogous to that outlined for the synthesis in example 4. LCMS: m/z 356.6 (M+H)$^+$

Example 350

((2S,4S)-1-{[1-(4-Chlorophenyl)cyclopropyl]carbonyl}-4-phenylpyrrolidin-2-yl)methanol This compound was prepared by using a procedure analogous to that outlined for the synthesis in example 4. LCMS: m/z 356.6 (M+H)$^+$

Example 351

((2S,4R)-1-{[1-(4-Chlorophenyl)cyclopropyl]carbonyl}-4-phenylpyrrolidin-2-yl)methanol

Step 1. Methyl (2S,4R)—N-tert-Butoxycarbonyl-4-hydroxy-2-pyrrolidinecarboxylate To a suspension of methyl (2S,4R)-4-hydroxypyrrolidine-2-carboxylate hydrochloride (10.00 g, 0.05506 mol) in methylene chloride (50 mL, 0.8 mol) was added triethylamine (20 mL, 0.1 mol) at ambient temperature. The reaction mixture was stirred for 15 minutes and then cooled to 0° C. 4-Dimethylaminopyridine (0.8 g, 0.007 mol) and di-tert-butyldicarbonate (22.00 g, 0.1008 mol) were added sequentially and the reaction was allowed to warm slowly to ambient temperature with stirring. The reaction mixture was filtered to remove the solid and the filtrate was then concentrated in vacuo. The residue was dissolved in EtOAc (50 mL) and the solution was washed with 1N HCl (20 mL) and then NaHCO$_3$ (10 mL) and finally brine. The organic layer was then dried over MgSO$_4$ and concentrated in vacuo. The $^1$H NMR confirmed the product was formed.

Step 2. 1-tert-butyl 2-methyl (2S)-4-oxopyrrolidine-1,2-dicarboxylate

Methyl (2S,4R)—N-tert-butoxycarbonyl-4-hydroxy-2-pyrrolidinecarboxylate (2.00 g, 0.00815 mol) was dissolved in acetone (50.0 mL, 0.681 mol) and ether (50 mL). To the solution with stirring, was added a solution of chromium(VI) oxide (1.90 g, 0.0190 mol) in water (5.50 mL, 0.305 mol) and sulfuric acid (1.60 mL, 0.0294 mol) over 15 minutes with the presence of an ice-water bath to maintain the reaction temperature at about room temperature. The mixture was stirred at rt for 10 minutes and then iso-propanol (10 mL) was added. The mixture was stirred for an additional 5 min. The mixture was filtered through a pad of silica gel plus potassium carbonate. The filtrated was concentrated and the residue was purified by Combiflash with ethyl acetate/hexane (25%) to give the desired product (1.12 g).

Step 3. 1-tert-butyl 2-methyl (2S)-4-hydroxy-4-phenylpyrrolidine-1,2-dicarboxylate Phenylmagnesium bromide in ether (3.00M, 0.400 mL) was added to a solution of 1-tert-butyl 2-methyl (2S)-4-oxopyrrolidine-1,2-dicarboxylate (243.0 mg, 0.0009989 mol) in tetrahydrofuran (5.00 mL, 0.0616 mol) at −40° C. The reaction mixture was stirred at between −40° C. and −10° C. for 2 h and then was quenched with ammonium chloride solution (5 mL). The organic phase was separated and the aqueous phase was extracted with ethyl acetate (2×5 mL). The combined organic layers were washed with brine, dried over Na$_2$SO$_4$, filtered, and concentrated under reduced pressure. The residue was used directly in the next step without further purification.

Step 4. methyl (2S,4R)-4-phenylpyrrolidine-2-carboxylate 1-tert-Butyl 2-methyl (2S)-4-hydroxy-4-phenylpyrrolidine-1,2-dicarboxylate (0.32 g, 0.0010 mol) was treated with trifluoroacetic acid (1.00 mL, 0.0130 mol) and methylene chloride (1.00 mL, 0.0156 mol) at rt for 4 h. The solvents were evaporated and the residue was dissolved in methanol (5.0 mL, 0.12 mol). Palladium (50.0 mg, 0.000470 mol) was added under nitrogen and the resulting mixture was hydrogenized with a hydrogen-gas-filled-balloon for 3 h. The mixture was filtered and the filtrate was concentrated to give the desired product, which was directly used in the next step without further purification.

Step 5. [(2S,4R)-4-phenylpyrrolidin-2-yl]methanol

Lithium tetrahydroaluminate in tetrahydrofuran (1.00 M, 1.00 mL) was added to methyl (2S,4R)-4-phenylpyrrolidine-2-carboxylate (103.0 mg, 0.0005018 mol) in tetrahydrofuran (3.00 mL, 0.0370 mol) at 0° C. Then the ice-water bath was removed and the reaction mixture was stirred at rt for 1 h and was quenched with brine (1 mL). The resulting mixture was extracted with ethyl acetate (2×2 mL). The combined organic layer was washed with brine, dried over Na$_2$SO$_4$, filtered, and concentrated under reduced pressure to give the desired product which was directly used in the next step without further purification.

Step 6

The title compound was prepared by using a procedure analogous to that outlined for the synthesis in example 4. LCMS: m/z 356.6 (M+H)$^+$

Example 352

1-{[1-(4-Chlorophenyl)cyclopropyl]carbonyl}pyrrolidine

This compound was prepared by using a procedure analogous to that outlined for the synthesis in example 4. LCMS: m/z 250.4 (M+H)$^+$

Example 353

1-{[1-(4-Chlorophenyl)cyclopentyl]carbonyl}azepane

This compound was prepared by using a procedure analogous to that outlined for the synthesis in example 4. LCMS: m/z 306.5 (M+H)$^+$

Example 354

3-Chloro-N-((3S)-1-{[1-(4-chlorophenyl)cyclopropyl]carbonyl}pyrrolidin-3-yl)-2-methylbenzenesulfonamide

Step 1. tert-butyl ((3S)-1-{[1-(4-chlorophenyl)cyclopropyl]carbonyl}pyrrolidin-3-yl)carbamate This compound was prepared by using a procedure analogous to that outlined for the synthesis in example 4. LCMS: m/z 365.5 (M+H)$^+$

Step 2 tert-Butyl ((3S)-1-{[1-(4-chlorophenyl)cyclopropyl]carbonyl}pyrrolidin-3-yl)carbamate (7.30 mg, 0.0000200 mol) was treated with hydrogen chloride in 1,4-dioxane (4.0 M, 0.50 mL) at rt for 30 minutes. The solvent was evaporated under reduced pressure and acetonitrile (1.0 mL, 0.019 mol) was added. The mixture was then treated with N,N-diisopropylethylamine (20.0 µL, 0.000115 mol), followed by the addition of 3-chloro-2-methylbenzenesulfonyl chloride (4.50 mg, 0.0000200 mol) at rt. The reaction mixture was stirred at rt for 1 h and then acidified (pH 2.0) with TFA. The solution was diluted with methanol (0.80 mL) and was submitted for purification by prep-HPLC to give the desired product. LCMS: m/z 454.1 (M+H)$^+$ Example 355

(3S,4R)-1-{[1-(4-Chlorophenyl)cyclopropyl]carbonyl}-4-phenylpyrrolidine-3-carboxylic acid To a solution of methyl (3S,4R)-1-{[1-(4-chlorophenyl)cyclopropyl]carbonyl}-4-phenylpyrrolidine-3-carboxylate (50 mg, 0.0001 mol, example 39) in tetrahydrofuran (2 mL, 0.02 mol) was added lithium hydroxide (9.4 mg, 0.00039 mol) and water (0.5 mL, 0.03 mol) and the solution was stirred at rt for 1 h. The reaction mixture was then acidified (pH ~2) and was extracted with AcOEt. The organic layer was dried (over MgSO$_4$), and concentrated to afford the product. LCMS: m/z 370.4 (M+H)$^+$ Example 356

((3S,4R)-1-{[1-(4-Chlorophenyl)cyclopropyl]carbonyl}-4-phenylpyrrolidin-3-yl)methanol To a solution of (3S,4R)-1-{[1-(4-chlorophenyl)cyclopropyl]carbonyl}-4-phenylpyrrolidine-3-carboxylic acid (80 mg, 0.0002 mol, example 355) in tetrahydrofuran (2 mL, 0.02 mol) were added triethylamine (0.0316 mL, 0.000227 mol) and methyl chloroformate (20.0 μL, 0.000260 mol) at −15° C. The mixture was stirred at −15° C. for 20 minutes. To the above mixture was added sodium borohydride (16.4 mg, 0.000433 mol) in THF and the resulting mixture was stirred at 0° C. for 1 h. The reaction mixture was quenched by water and then was extracted with AcOEt. The organic layer was dried over MgSO$_4$, and concentrated to afford the product. The product was purified with Combiflash eluting with 60% AcOEt in hexanes. LCMS: m/z 356.4 (M+H)$^+$ Example 357

2-[1-{[1-(4-Chlorophenyl)cyclopropyl]carbonyl}-4-(hydroxymethyl)pyrrolidin-3-yl]phenol Step 1. N-Benzyl-N-(trimethylsilyl)methylamine Into a round bottom 3-neck flask equipped with a nitrogen flow, a magnetic stirrer, and a fried richs condenser was added (chloromethyl)trimethylsilane (0.100 mol). To the flask was added benzylamine (0.300 mol), with stirring, and the resulting solution heated at 200° C. for 2.5 hours. Sodium hydroxide aqueous solution (0.1N) was added in order to hydrolyze the white organic salt that had formed. The mixture was extracted with ether and the ether layer was dried over magnesium sulfate and concentrated under reduced pressure through a Vigreux column to give the product at b.p. 68-72° C./0.7-0.8 mm.

Step 2. N-Benzyl-N-methoxymethyl-N-(trimethylsilyl)methylamine

Into a round bottom 3-neck flask equipped with a nitrogen flow and a magnetic stirrer was added formaldehyde (74.000 mmol, 7.4000×10$^{-2}$ mol) (as a 37% aqueous solution). The flask was cooled to 0° C. and N-benzyl-N-(trimethylsilyl) methylamine (10.000 g, 5.1716790×10$^{-2}$ mol) was added dropwise with stirring. After stirring for 10 minutes at 0° C., methanol (6.000 mL, 0.14811874 mol) was added in one portion. Potassium carbonate (4.000 g, 2.8942408×10$^{-2}$ mol) was added to the mixture to absorb the aqueous phase. The mixture was stirred for one hour, then the nonaqueous phase decanted, and then potassium carbonate (2.000 g, 1.4471204×10$^{-2}$ mol) was added. The mixture was stirred at 25° C. for 12 hours. Ether is added to the mixture and the solution was dried over potassium carbonate, filterd and concentrated under reduced pressure. The residue is distilled at reduced pressure to give the product as a colorless liquid.

Step 4. 2-benzyl-2,3,3a,9b-tetrahydrochromeno[3,4-c]pyrrol-4(1H)-one

N-Benzyl-N-methoxymethyl-N-(trimethylsilyl)methylamine (1.54 mL, 0.00600 mol) in methylene chloride (0.50 mL) was added to a mixture of coumarin (0.731 g, 0.00500 mol) and of trifluoroacetic acid in DCM (1M, 10 mL) at rt. The resulting mixture was stirred at rt for 1 h and was then washed with NaHCO$_3$ (2 mL) and brine (2 mL) successively. The organic phase was dried (over Na$_2$SO$_4$), filtered, and concentrated. The residue was purified by CombiFlash (ethyl acetate/hexane 20%) to give the desired product (0.99 g).

Step 5. 2-[1-benzyl-4-(hydroxymethyl)pyrrolidin-3-yl]phenol

Lithium tetrahydroaluminate in tetrahydrofuran (1.00 M, 1.50 mL) was added to a solution of 2-benzyl-2,3,3a,9b-tetrahydrochromeno[3,4-c]pyrrol-4(1H)-one (188.0 mg, 0.0006730 mol) in THF (2.0 mL) at 0° C. The mixture was stirred at 0° C. for 1 h and then quenched with acetone. Ethyl acetate (10 mL) was added and the resulting mixture was treated with NaOH (1N, 3 mL) and then was filtered through a pad of celite. The filtrate was washed with brine (2×5 mL) and the organic layer was dried over Na$_2$SO$_4$, filtered, and concentrated under reduced pressure to give the desired product.

Step 6.
(cis)-2-[4-(hydroxymethyl)pyrrolidin-3-yl]phenol

A mixture of 2-[1-benzyl-4-(hydroxymethyl)pyrrolidin-3-yl]phenol (101.4 mg, 0.0003580 mol) and palladium (10% on carbon, 75 mg) in methanol (5.0 mL, 0.12 mol) was stirred under hydrogen (balloon) overnight. The mixture was filtered and the filtrate was concentrated. The residue was used in next step without further purification.

Step 7

The title compound was prepared by using a procedure analogous to that outlined for the synthesis in example 4. LCMS: m/z 372.5 (M+H$^+$)$^+$ Example 358

2-{[1-(4-Chlorophenyl)cyclopropyl]carbonyl}-1,2,3,3a,4,9b-hexahydrochromeno[3,4-c]pyrrole A mixture of 2-[1-{[1-(4-chlorophenyl)cyclopropyl]carbonyl}-4-(hydroxymethyl)pyrrolidin-3-yl]phenol (13.0 mg, 0.0000350 mol), triphenylphosphine (20.0 mg, 0.0000762 mol) and diisopropyl azodicarboxylate (15.0 μL, 0.0000762 mol) in tetrahydrofuran (1.0 mL, 0.012 mol) was stirred at rt for 4 h. The mixture was diluted with methanol (0.80 mL) and the desired product from the mixture was isolated and purified by prep-HPLC. LCMS: m/z 354.5 (M+H)$^+$

Example 359

2-{[1-(4-Chlorophenyl)cyclopropyl]carbonyl}-8-(methylsulfonyl)-2,8-diazaspiro[4.5]decane Step 1. tert-butyl 8-(methylsulfonyl)-2,8-diazaspiro[4.5]decane-2-carboxylate N,N-Diisopropylethylamine (30.0 µL, 0.000172 mol) was added to tert-butyl 2,8-diazaspiro[4.5]decane-2-carboxylate hydrochloride (18.5 mg, 0.0000668 mol) in acetonitrile (1.0 mL, 0.019 mol), followed by methanesulfonyl chloride (10.0 µL, 0.000129 mol). After stirring for 1 h the solvent was evaporated, and the residue was dried under high vacuum and was used in the next step without further purification.

Step 2. 8-(methylsulfonyl)-2,8-diazaspiro[4.5]decane hydrochloride

Hydrogen chloride in 1,4-dioxane (4.0M, 0.50 mL) was added to tert-butyl 8-(methylsulfonyl)-2,8-diazaspiro[4.5]decane-2-carboxylate (21.0 mg, 0.0000659 mol) at rt. The mixture was stirred at rt for 1 h and then the solvent was evaporated. and the residue was dried under high vacuum to afford the desired product. LCMS: m/z 255.5 (M+H)$^+$ Step 3

The title compound was prepared by using a procedure analogous to that outlined for the synthesis in example 4. LCMS: m/z 397.5 (M+H)$^+$

Example 360

8-Acetyl-2-{[1-(4-chlorophenyl)cyclopropyl]carbonyl}-2,8-diazaspiro[4.5]decane

This compound was prepared by using a procedure analogous to that outlined for the synthesis in example 359. LCMS: m/z 361.5 (M+H)$^+$

Example 361

3-(1-{[1-(4-Chlorophenyl)cyclopropyl]carbonyl}pyrrolidin-3-yl)pyridine

This compound was prepared by using a procedure analogous to that outlined for the synthesis in example 4. LCMS: m/z 327.5 (M+H)$^+$

Example 362

3-(1-{[1-(4-Phenoxyphenyl)cyclopropyl]carbonyl}pyrrolidin-3-yl)pyridine

Step 1. 4-{1-[(3-pyridin-3-ylpyrrolidin-1-yl)carbonyl]cyclopropyl}

This compound was prepared by using a procedure analogous to that outlined for the synthesis in example 4. LCMS: m/z 309.1 (M+H)$^+$ Step 2

To a solution of 4-{1-[(3-pyridin-3-ylpyrrolidin-1-yl)carbonyl]cyclopropyl}phenol (40.0 mg, 0.000130 mol) in methylene chloride (1 mL, 0.02 mol) were added phenylboronic acid (15.8 mg, 0.000130 mol), copper(II) diacetate (0.0236 g, 0.000130 mol) and molecular sieves at rt. Triethylamine (0.0904 mL, 0.000648 mol) was then added and the reaction mixture was stirred at rt overnight. The reaction mixture was filtered and the filtrate was concentrated. The desired product from the residue was isolated and purified by prep-HPLC. LCMS: m/z 385.1 (M+H)$^+$

Example 363

3-[1-({1-[4-(Cyclopentyloxy)phenyl]cyclopropyl}carbonyl)pyrrolidin-3-yl]pyridine This compound was prepared by using a procedure analogous to that outlined for the synthesis in example 4. LCMS: m/z 309.1 (M+H)$^+$ Step 2

To a solution of 4-{1-[(3-pyridin-3-ylpyrrolidin-1-yl)carbonyl]cyclopropyl}phenol (40.0 mg, 0.000130 mol) in tetrahydrofuran were added cyclopentanol (29.4 µL, 0.000324 mol) diethyl azodicarboxylate (0.0511 mL, 0.000324 mol), and triphenylphosphine (85.0 mg, 0.000324 mol) at room temperature, and the reaction mixture was stirred overnight. The crude product was purified by prep-HPLC. LCMS: m/z 377.1 (M+H)$^+$

Example 364 tert-Butyl 4-(5-{1-[(3-pyridin-3-ylpyrrolidin-1-yl)carbonyl]cyclopropyl}pyridine-2-yl)piperazine-1-carboxylate This compound was prepared by using a procedure analogous to that outlined in steps 1-3 of example 163. LCMS: m/z 478.1 (M+H)$^+$

Example 365

1-{[1-(4-Chlorophenyl)cyclopropyl]carbonyl}-3-isopropylpyrrolidine

Step 1. tert-butyl 3-hydroxy-3-isopropenylpyrrolidine-1-carboxylate

To a solution of tert-butyl 3-oxopyrrolidine-1-carboxylate (2.0 g, 0.011 mol) in tetrahydrofuran (15.4 mL, 0.190 mol) was added dropwise a 0.5 M in THF solution of bromo(isopropenyl)magnesium (1.80 g, 0.0124 mol) (24.8 mL) at rt under N$_2$. After the addition was complete, the reaction mixture was heated to reflux for 15 minutes and then cooled to rt. The crude mixture was poured into saturated NH$_4$Cl, extracted with ether (3×) The combined organic phase was dried over MgSO$_4$, concentrated in vacuo. The crude product was purified by flash chromatography eluting with 0-40% EA-hexanes to afford pure product as a white solid (1.4 g). The product was confirmed by $^1$H NMR & LC/MS (M+H-Boc) 128.1 (base), [(M+Na) 250.0].

Step 2. 3-isopropenyl-2,5-dihydro-1H-pyrrole trifluoroacetate tert-Butyl 3-hydroxy-3-isopropenylpyrrolidine-1-carboxylate (1.51 g, 0.00664 mol) was dissolved in trifluoroacetic acid (10.0 mL, 0.130 mol) under N$_2$ at rt. The reaction flask was wrapped with aluminum foil and the mixture was stirred overnight. The reaction mixture was then concentrated in vacuo and the residue was used directly in the next step without further purification.

Step 3. 3-isopropylpyrrolidine trifluoroacetate

To a solution of 3-isopropenyl-2,5-dihydro-1H-pyrrole trifluoroacetate (2.09 g, 0.00936 mol) in methanol (100.0 mL, 2.469 mol) was added 1.3 g of Pd (10% wt. on activated carbon), then the mixture was hydrogenated on par shaker at 43 psi for 3 h. The mixture was filtered and the filtrate was concentrated in vacuo. The residue was dried under high vacuum to afford the product as a white solid. LC-MS (M+H) 114.2 (base) [M+H) 130.1 base, for the corresponding alcohol].

Step 4

The title compound was prepared by using a procedure analogous to that outlined for the synthesis in example 4.

Example 366

Methyl 3-(1-{[1-(4-chlorophenyl)cyclopropyl]carbonyl}pyrrolidin-3-yl)benzoate

Step 1. methyl 3-[1-(phenoxyacetyl)-2,3-dihydro-1H-pyrrol-3-yl]benzoate

A solution of benzyl 2,5-dihydro-1H-pyrrole-1-carboxylate (0.626 mL, 0.00349 mol), methyl 3-bromo-benzoate (300 mg, 0.001 mol), palladium(II) diacetate (14 mg, 0.000063 mol), potassium acetate (356 mg, 0.00363 mol), and tetra-N-butylammonium bromide (4.50×10$^{-2}$ mg, 0.00140 mol) in N,N-dimethylformamide (5 mL, 0.06 mol) was stirred under nitrogen at 40° C. for 4 days. The reaction mixture was diluted with AcOEt and water. The organic layer was separated and the aqueous layer was extracted with AcOEt. The combined organic layer was washed with brine, dried with MgSO$_4$, and concentrated to afford the crude product. The crude product was purified by flash chromatography, eluting with 30% AcOEt in hexanes.

Step 2. methyl 3-pyrrolidin-3-ylbenzoate

To a solution of methyl 3-[1-(phenoxyacetyl)-2,3-dihydro-1H-pyrrol-3-yl]benzoate (0.5 g, 0.001 mol) in methanol (15 mL, 0.37 mol) was added 10% Pd/C (80 mg), and the resulting suspension was stirred under 1 atm of H, (balloon) for 5 h. The mixture was filtered and the filtrate was concentrated to afford the desired product.

Step 3

The title compound was prepared by using a procedure analogous to that outlined for the synthesis in example 4. LCMS: m/z 384.4 (M+H)$^+$ Example 367

1-{[1-(4-Chlorophenyl)cyclopropyl]carbonyl}-3-(2-methylphenyl)pyrrolidine

Step 1. 1-{[1-(4-chlorophenyl)cyclopropyl]carbonyl}-3-(2-methylphenyl)-2,5-dihydro-1H-pyrrole This compound was prepared by using a procedure analogous to that outlined for the synthesis in example 4. LCMS: m/z 338.4 (M+H)$^+$ Step 2

To a solution of 1-{[1-(4-chlorophenyl)cyclopropyl]carbonyl}-3-(2-methylphenyl)-2,5-dihydro-1H-pyrrole (5 mg, 0.00001 mol) in methanol (1 mL, 0.02 mol) was added Pd/BaSO$_4$ (reduced) and the mixture was stirred under an atmosphere of hydrogen at rt for 1 h. The crude product was purified using prep-HPLC. LCMS: m/z 340.4 (M+H)$^+$ Example 368

1-{[1-(4-Chlorophenyl)cyclopropyl]carbonyl}-3-(2-methoxyphenyl)pyrrolidine

This compound was prepared by using a procedure analogous to that outlined for the synthesis in example 367. LCMS: m/z 356.4 (M+H)$^+$ Example 369

1-{[1-(4-Chlorophenyl)cyclopropyl]carbonyl}-3-(2,6-dimethylphenyl)pyrrolidine

This compound was prepared by using a procedure analogous to that outlined for the synthesis in example 4. LCMS: m/z 354.4 (M+H)$^+$ Example 370

1-(4-{1-[(3-Pyridin-4-ylpyrrolidin-1-yl)carbonyl]cyclopropyl}phenyl)pyrrolidin-2-one This compound was prepared by coupling the title compound in example 23 with 2-pyrrolidinone using a copper mediated procedure analogous to that outlined in step 1 of example 102. LCMS: m/z 376.3 (M+H$^+$); 398.3 (M+Na$^+$).

Example 371

3-(4-{1-[(3-Pyridin-4-ylpyrrolidin-1-yl)carbonyl]cyclopropyl}phenyl)-1,3-oxazolidin-2-one This compound was prepared by using a procedure analogous to that outlined for the synthesis in example 370. LCMS: m/z 378.2 (M+H)$^+$ Example 372

4-{1-[(3-Pyridin-4-ylpyrrolidin-1-yl)carbonyl]cyclopropyl}phenol

This compound was prepared by using a procedure analogous to that outlined for the synthesis in example 4. LCMS: m/z 309.0 (M+H)$^+$ Example 373

4-[1-({1-[4-(Benzyloxy)phenyl]cyclopropyl}carbonyl)pyrrolidin-3-yl]pyridine

A mixture of 4-{1-[(3-pyridin-4-ylpyrrolidin-1-yl)-carbonyl]cyclopropyl}phenol (20 mg, 0.00006 mol, example 372), benzyl bromide (7.7 µL, 0.000065 mol), and potassium carbonate (18 mg, 0.00013 mol) in N,N-dimethylformamide (200 µL, 0.002 mol) was stirred at room temperature over night. The crude product was purified with prep-HPLC to afford the product (10.3 mg). LCMS: m/z 399.0 (M+H⁺).

Example 374

4-[1-({1-[4-(Allyloxy)phenyl]cyclopropyl}carbonyl)pyrrolidin-3-yl]pyridine

This compound was prepared by using a procedure analogous to that outlined for the synthesis in example 373. LCMS: m/z 349.1 (M+H)⁺.

Example 375

4-[1-({1-[4-(Pyridin-4-yloxy)phenyl]cyclopropyl}carbonyl)pyrrolidin-3-yl]pyridine This compound was prepared by using a procedure analogous to that outlined for the synthesis in example 362. LCMS: m/z 386.1 (M+H)⁺.

Example 377

4-[1-({1-[4-(Cyclopentyloxy)phenyl]cyclopropyl}carbonyl)pyrrolidine-3-yl]pyridine This compound was prepared by using a procedure analogous to that outlined for the synthesis in example 373. LCMS: m/z 377.1 (M+H)⁺, 399.0 (M+Na)⁺.

Example 378

4-[1-({1-[4-(Cyclohex-2-en-1-yloxy)phenyl]cyclopropyl}carbonyl)pyrrolidine-3-yl]pyridine This compound was prepared by using a procedure analogous to that outlined for the synthesis in example 373. LCMS: m/z 411.0 (M+Na)⁺.

Example 379

3-[(4-{1-[(3-Pyridin-4-ylpyrrolidin-1-yl)carbonyl]cyclopropyl}phenoxy)methyl]pyridine This compound was prepared by using a procedure analogous to that outlined for the synthesis in example 373. LCMS: m/z 400.1 (M+H)⁺, 422.1 (M+Na)⁺.

Example 380

2-[(4-{1-[(3-Pyridin-4-ylpyrrolidin-1-yl)carbonyl]cyclopropyl}phenoxy)methyl]pyridine This compound was prepared by using a procedure analogous to that outlined for the synthesis in example 373. LCMS: m/z 400.1 (M+H)⁺, 422.1 (M+Na)⁺.

Example 381

4-[2-(4-{1-[(3-Pyridin-4-ylpyrrolidin-1-yl)carbonyl]cyclopropyl}phenoxy)ethyl]morpholine This compound was prepared by using a procedure analogous to that outlined for the synthesis in example 214. LCMS: m/z 422.1 (M+H)⁺.

Example 382

4-((3S)-1-{[1-(4-Chlorophenyl)cyclopropyl]carbonyl}pyrrolidin-3-yl)pyridine 1-oxide 4-((3S)-1-{[1-(4-Chlorophenyl)cyclopropyl]carbonyl}pyrrolidin-3-yl)pyridine (20 mg, 0.00006 mol, example 24) was dissolved in dichloromethane (1 mL, 0.02 mol) and to this solution was added m-chloroperbenzoic acid (44 mg, 0.00015 mol). The reaction mixture was stirred at 25° C. for 2.5 h. The reaction mixture then was concentrated and the residue was diluted with NaHCO₃ and methanol. The crude product was purified by prep-HPLC. LCMS: m/z 343.4 (M+H)⁺.

Example 383

4-(1-{[1-(4-Chlorophenyl)cyclopropyl]carbonyl}pyrrolidin-3-yl)-3-fluoropyridine

This compound was prepared by using a procedure analogous to that outlined for the synthesis in example 4. LCMS: m/z 345.4 (M+H)⁺.

Example 384

1-{[1-(4-Chlorophenyl)cyclopropyl]carbonyl}-3-isopropylpyrrolidin-3-ol

This compound was prepared by using a procedure analogous to that outlined for the synthesis in example 365. LCMS: m/z 308.1 (M+H)⁺.

Example 385

3-tert-Butyl-1-{[1-(4-chlorophenyl)cyclopropyl]carbonyl}pyrrolidine-3-ol

Step 1. tert-butyl 3-tert-butyl-3-hydroxypyrrolidine-1-carboxylate

To a solution of tert-butyl 3-oxopyrrolidine-1-carboxylate (500.0 mg, 0.002699 mol) in tetrahydrofuran (3.85 mL, 0.0475 mol) was added dropwise a 1.7 M in pentane solution of tert-butyllithium (198.8 mg, 0.003104 mol) (1.8 mL) at −78° C. under N₂. After the addition was complete, the reaction mixture was warmed to rt. After stirring for 1 h, the reaction mixture was poured into a saturated NH₄Cl aqueous solution and the resulting mixture was extracted with ether (3×). The combined organic layer was dried over MgSO₄, and concentrated in vacuo. The crude product was purified by Combiflash eluting with 0-40% EtAc-hexanes to afford the product as a white solid (0.451 g). LC MS (M+H-Boc) 144.1

Step 2. 3-tert-butylpyrrolidin-3-ol hydrochloride tert-Butyl 3-tert-butyl-3-hydroxypyrrolidine-1-carboxylate (0.60 g, 0.0025 mol) was dissolved in a solution of hydrogen chloride in 1,4-dioxane (4N, 0.30 mL, 0.0099 mol) under N₂ at rt. The reaction mixture was stirred for 3 h at rt, then concentrated in vacuo. The crude product was used directly in the next step without further purification. (M+H) 144.1

Step 3

The title compound was prepared by using a procedure analogous to that outlined for the synthesis in example 4. LCMS: m/z 322.2 (M+H)+.

Example 386

1-{[1-(4-Chlorophenyl)cyclopropyl]carbonyl}-3-(2-methylphenyl)pyrrolidin-3-61

This compound was prepared by using a procedure analogous to that outlined for the synthesis in example 273. LCMS: m/z 356.4 (M+H)+.

Example 387

Methyl [(1-{[1-(4-chlorophenyl)cyclopropyl]carbonyl}-3-phenylpyrrolidin-3-yl)oxy]acetate

Step 1. tert-butyl 3-hydroxy-3-phenylpyrrolidine-1-carboxylate

To a solution of tert-butyl 3-oxopyrrolidine-1-carboxylate (1.0 g, 0.0054 mol) in ether (20.000 mL, 0.19050 mol) was added dropwise a solution of phenylmagnesium bromide (1.12 g, 0.00621 mol) in ether (10.3 mL) at rt under $N_2$. After the addition was complete, the reaction mixture was heated to reflux for 15 min. and then cooled to rt. The reaction mixture was poured into saturated $NH_4Cl$ and extracted with ether (3×). The combined organic layers were dried over $Na_2SO_4$ and concentrated in vacuo. The product was purified by Combiflash eluting with 0-40% EtOAc-hexanes. The product was confirmed by $^1H$ NMR and LC/MS: m/z 286.0 (M+Na)+.

Step 2. tert-butyl 3-(2-methoxy-2-oxoethoxy)-3-phenylpyrrolidine-1-carboxylate To a solution of tert-butyl 3-hydroxy-3-phenylpyrrolidine-1-carboxylate (480 mg, 0.0018 mol) in toluene (20 mL, 0.2 mol) was added sodium hydride (80.2 mg, 0.00200 mol) and the solution was refluxed for 1 hour. Methyl bromoacetate (0.190 mL, 0.00200 mol) was then added and the mixture continued to be stirred under reflux overnight. The reaction mixture was allowed to cool to rt and the product was extracted with EtOAc. The combined organic layers were washed with water, dried with $MgSO_4$, and concentrated in-vacuo. LC/MS: m/z 336.1 (M+H)+.

Step 3. Methyl [(3-phenylpyrrolidin-3-yl)oxy]acetate

To tert-butyl 3-(2-methoxy-2-oxoethoxy)-3-phenylpyrrolidine-1-carboxylate (160 mg, 0.00048 mol) was added 4 M of hydrogen chloride in 1,4-dioxane (1 mL) and the resulting solution was stirred for 1 h. The reaction mixture was then concentrated in-vacuo and the crude product was used directly in the next step.

Step 4. Methyl [(1-{[1-(4-chlorophenyl)cyclopropyl]carbonyl}-3-phenylpyrrolidin-3-yl)oxy]acetate The title compound was prepared by using a procedure analogous to that outlined for the synthesis of example 4. LCMS: m/z 414.4 (M+H)+.

Example 388

[(1-{[1-(4-Chlorophenyl)cyclopropyl]carbonyl}-3-phenylpyrrolidin-3-yl)oxy]acetic acid To a solution of methyl [(1-{[1-(4-chlorophenyl)cyclopropyl]carbonyl}-3-phenylpyrrolidin-3-yl)oxy]acetate (40.0 mg, 0.0000966 mol, example 387) in tetrahydrofuran (1 mL, 0.01 mol) was added lithium hydroxide hydrate (4.87 mg, 0.000116 mol) in water (0.5 mL, 0.03 mol). The solution was stirred at rt for 2 hours and then acidified with 1N HCl (aq.). The product was purified by prep-HPLC. LCMS: m/z 400.4 (M+H)+.

Example 389

1-{[1-(4-Chlorophenyl)cyclopropyl]carbonyl}-3-(3-chloropyridin-4-yl)pyrrolidine-3-ol This compound was prepared by using a procedure analogous to that outlined in example 273. LCMS: m/z 378.1 (M+H)+.

Example 390

1'-{[1-(4-Chlorophenyl)cyclopropyl]carbonyl}-spiro[pyrido[3,4-d][1,3]oxazine-4,3'-pyrrolidin]-2(1H)-one This compound was prepared by using a procedure analogous to that outlined in example 272.

Example 391

1'-{[1-(2,4-Dichlorophenyl)cyclopropyl]carbonyl}spiro[pyrido[3,4-d][1,3]oxazine-4,3'-pyrrolidin]-2(1H)-one This compound was prepared by using a procedure analogous to that outlined in example 272.

Example 392

1'-{[1-(4-Bromophenyl)cyclopropyl]carbonyl}spiro[pyrido[3,4-d][1,3]oxazine-4,3'-pyrrolidin]-2(1H)-one This compound was prepared by using a procedure analogous to that outlined in example 272.

Example 393

1'-{[1-(4-Methoxyphenyl)cyclopropyl]carbonyl}spiro[pyrido[3,4-d][1,3]oxazine-4,3'-pyrrolidin]-2(1H)-one This compound was prepared by using a procedure analogous to that outlined in example 272.

Example 394

1'-{[1-(4-Phenoxyphenyl)cyclopropyl]carbonyl}spiro[pyrido[3,4-d][1,3]oxazine-4,3'-pyrrolidin]-2(1H)-one This compound was prepared by using a procedure analogous to that outlined in example 272.

Example 395

1'-[(1-{4-[(Trifluoromethyl)thio]phenyl}cyclopropyl)carbonyl]spiro[pyrido[3,4-d][1,3]oxazine-4,3'-pyrrolidin]-2(1H)-one This compound was prepared by using a procedure analogous to that outlined in example 272.

Example 396

1'-{[1-(3-Bromophenyl)cyclopropyl]carbonyl}spiro[pyrido[3,4-c][1,3]oxazine-4,3'-pyrrolidin]-2(1H)-one This compound was prepared by using a procedure analogous to that outlined in example 272.

Example 397

1'-{[1-(3-Methoxyphenyl)cyclopropyl]carbonyl}spiro[pyrido[3,4-d][1,3]oxazine-4,3'-pyrrolidin]-2(1H)-one This compound was prepared by using a procedure analogous to that outlined in example 272.

Example 398

1'-{[1-(6-Chloropyridin-3-yl)cyclopropyl]carbonyl}-7H-spiro[furo[3,4-b]pyridine-5,3'-pyrrolidin]-7-one This compound was prepared by using a procedure analogous to that outlined in example 90 using 1-(6-chloropyridin-3-yl)cyclopropanecarboxylic acid, which was obtained by following a procedure analogous to that outlined in steps 1 & 3 of example 162. LCMS: m/z 370.1 (M+H)⁺.

Example 399

1'-{[1-(4-Methylphenyl)cyclopropyl]carbonyl}-7H-spiro[furo[3,4-b]pyridine-5,3'-pyrrolidin]-7-one This compound was prepared by using a procedure analogous to that outlined in example 90. LCMS: m/z 349.1 (M+H)⁺.

Example 400

1'-({1-[4-(Trifluoromethyl)phenyl]cyclopropyl}carbonyl)-7H-spiro[furo[3,4-b]pyridine-5,3'-pyrrolidin]-7-one This compound was prepared by using a procedure analogous to that outlined in example 298. LCMS: mix 403.1 (M+H)⁺.

Example 401

1'-{[1-(4-Methoxyphenyl)cyclopropyl]carbonyl}-7H-spiro[furo[3,4-b]pyridine-5,3'-pyrrolidin]-7-one This compound was prepared by using a procedure analogous to that outlined in example 298. LCMS: m/z 365.1 (M+H)⁺.

Example 402

1'-({1-[4-(Trifluoromethoxy)phenyl]cyclopropyl}carbonyl)-7H-spiro[furo[3,4-b]pyridine-5,3'-pyrrolidin]-7-one This compound was prepared by using a procedure analogous to that outlined in example 298. LCMS: m/z 419.0 (M+H)⁺.

Example 403

1'-{[1-(4-Fluorophenyl)cyclopropyl]carbonyl}-7H-spiro[furo[3,4-b]pyridine-5,3'-pyrrolidin]-7-one This compound was prepared by using a procedure analogous to that outlined in example 298. LCMS: m/z 353.1 (M+H)⁺.

Example 404

1'-{[1-(2-Chloro-4-fluorophenyl)cyclopropyl]carbonyl}-7H-spiro[furo[3,4-b]pyridine-5,3'-pyrrolidin]-7-one This compound was prepared by using a procedure analogous to that outlined in example 298. LCMS: m/z 387.0 (M+H)⁺.

Example 405

1'-{[1-(2,4-Difluorophenyl)cyclopropyl]carbonyl}-7H-spiro[furo[3,4-b]pyridine-5,3'-pyrrolidin]-7-one This compound was prepared by using a procedure analogous to that outlined in example 298. LCMS: m/z 371.0 (M+H)⁺.

Example 406

1'-{[1-(3-Chlorophenyl)cyclopropyl]carbonyl}-7H-spiro[furo[3,4-b]pyridine-5,3'-pyrrolidin]-7-one This compound was prepared by using a procedure analogous to that outlined in example 298. LCMS: m/z 369.0 (M+H)⁺.

Example 407

1'-{[1-(3,4-Dichlorophenyl)cyclopropyl]carbonyl}-7H-spiro[furo[3,4-b]pyridine-5,3'-pyrrolidin]-7-one This compound was prepared by using a procedure analogous to that outlined in example 298. LCMS: m/z 403.0 & 405.0 (M+H)⁺.

Example 408

1'-{[1-(2,3-Difluorophenyl)cyclopropyl]carbonyl}-7H-spiro[furo[3,4-b]pyridine-5,3'-pyrrolidin]-7-one This compound was prepared by using a procedure analogous to that outlined in example 298. LCMS: m/z 371.0 (M+H)⁺.

Example 409

1'-{[1-(2,4-Dichlorophenyl)cyclopropyl]carbonyl}-7H-spiro[furo[3,4-b]pyridine-5,3'-pyrrolidin]-7-one This compound was prepared by using a procedure analogous to that outlined in example 90. LCMS: m/z 403.0 & 405.0 (M+H)$^+$.

Example 410

Ethyl 4-[5-(1-{[(1R)-3-oxo-1'H,3H-spiro[2-benzofuran-1,3'-pyrrolidin]-1'-yl]carbonyl}cyclopropyl)pyridin-2-yl]piperazine-1-carboxylate tert-Butyl 4-[5-(1-{[(1R)-3-oxo-1'H,3H-spiro[2-benzofuran-1,3'-pyrrolidin]-1'-yl]carbonyl}cyclopropyl)pyridin-2-yl]piperazine-1-carboxylate (10.4 mg, 0.0000200 mol, prepared by a procedure similar to that in steps 1-3 of example 163) was treated with hydrogen chloride in 1,4-dioxane (4.0 M, 20.0 µL) at rt for 1 h. The solvent was evaporated and acetonitrile (1.00 mL, 0.0191 mol) was added to the residue followed by N,N-diisopropylethylamine (20.0 µL, 0.000115 mol) and ethyl chloroformate (5.0 µL, 0.000052 mol). The mixture was stirred at rt for 30 min, and adjusted to be acidic (pH=2.0) with TFA, and diluted with metanol (0.8 mL). The desired product from the resulting solution was isolated and purified by prep-HPLC. LCMS: m/z 491.2 (M+H)$^+$.

Example 411

(1R)-1'-[(1-{6-[4-(ethylsulfonyl)piperazin-1-yl]pyridin-3-yl}cyclopropyl)carbonyl]-3H-spiro[2-benzofuran-1,3'-pyrrolidin]-3-one This compound was prepared by using a procedure analogous to that outlined in example 164. LCMS: m/z 511.2 (M+H)$^+$.

Example 412

(1R)-1'-({1-[6-(4-Methylpiperazin-1-yl)pyridin-3-yl]cyclopropyl}carbonyl)-3H-spiro[2-benzofuran-1,3'-pyrrolidin]-3-one This compound was prepared by using a procedure analogous to that outlined in steps 1-4 of example 163, with the exception that in step 4 the free amine compound underwent a reductive alkylation outlined below instead of being reacted with a carbamoyl chloride, as outlined below.
N,N-Diisopropylethylamine (8.3 µL, 0.000048 mol) was added to (1R)-1'-{[1-(6-piperazin-1-ylpyridin-3-yl)cyclopropyl]carbonyl}-3H-spiro[2-benzofuran-1,3'-pyrrolidin]-3-one (10.0 mg, 0.0000239 mol) and formaldehyde (8.90 µL, 0.000119 mol) in tetrahydrofuran (0.5 mL, 0.006 mol) and acetonitrile (0.5 mL, 0.01 mol). To this solution was added sodium triacetoxyborohydride (25 mg, 0.00012 mol) and the reaction was stirred at room temperature overnight. LCMS: m/z 433.2 (M+H)$^+$.

Example 413

(1R)-1'-({1-[6-(4-Phenylpiperazin-1-yl)pyridin-3-yl]cyclopropyl}carbonyl)-3H-spiro[2-benzofuran-1,3'-pyrrolidin]-3-one This compound was prepared by using a procedure analogous to that outlined in steps 1-3 of example 163. LCMS: m/z 495.1 (M+H)$^+$.

Example 414

(1R)-1'-[(1-{6-[4-(3-Methylbutanoyl)piperazin-1-yl]pyridin-3-yl}cyclopropyl)carbonyl]-3H-spiro[2-benzofuran-1,3'-pyrrolidin]-3-one This compound was prepared by using a procedure analogous to that outlined in steps 1-4 of example 163, with the exception that in step 4 the amide was formed by BOP mediated coupling as outlined below.
4-Methylmorpholine (2.0×10$^{-1}$ µL, 0.00018 mol) was added to a mixture of (1R)-1'-{[1-(6-piperazin-1-ylpyridin-3-yl)cyclopropyl]carbonyl}-3H-spiro[2-benzofuran-1,3'-pyrrolidin]-3-one (15 mg, 0.000036 mol), butanoic acid, 3-methyl-(4.4 mg, 0.000043 mol) and benzotriazol-1-yloxytris(dimethylamino)phosphonium hexafluorophosphate (19 mg, 0.000043 mol) in acetonitrile (0.7 mL, 0.01 mol). The reaction mixture was stirred at room temperature overnight. The crude product was purified by prep-LCMS. LCMS: m/z 503.3 (M+H)$^+$.

Example 415

(1R)-1'-[(1-{6-[4-(Cyclopropylmethyl)piperazin-1-yl]pyridin-3-yl}cyclopropyl)carbonyl]-3H-spiro[2-benzofuran-1,3'-pyrrolidin]-3-one This compound was prepared by using a procedure analogous to that outlined in steps 1-4 of example 163, with the exception that in step 4 the free amine was alkylated by a reductive alkylation outlined below.
N,N-Diisopropylethylamine (8.3 µL, 0.000048 mol) was added to (1R)-1'-{[1-(6-piperazin-1-ylpyridin-3-yl)cyclopropyl]carbonyl}-3H-spiro[2-benzofuran-1,3'-pyrrolidin]-3-one (10.0 mg, 0.0000239 mol) and cyclopropanecarboxaldehyde (8.93 µL, 0.000119 mol) in tetrahydrofuran (0.5 mL, 0.006 mol) and acetonitrile (0.5 mL, 0.01 mol) followed by sodium triacetoxyborohydride (25 mg, 0.00012 mol). The reaction mixture was stirred at room temperature overnight. LCMS: m/z 473.2 (M+H)$^+$.

Example 416

(1R)-1'-({1-[6-(2,5-Dihydro-1H-pyrrol-1-yl)pyridin-3-yl]cyclopropyl}carbonyl)-3H-spiro[2-benzofuran-1,3'-pyrrolidin]-3-one This compound was prepared by using a procedure analogous to that outlined in steps 1-3 of example 163. LCMS: m/z 402.2 (M+H)$^+$.

Example 417

(1R)-1'-{[1-(6-Piperidin-1-ylpyridin-3-yl)cyclopropyl]carbonyl}-3H-spiro[2-benzofuran-1,3'-pyrrolidin]-3-one This compound was prepared by using a procedure analogous to that outlined in steps 1-3 of example 163. LCMS: m/z 418.1 (M+H)$^+$.

Example 418

(1R)-1'-({1-[4-(4-Methyl-2-oxopiperazin-1-yl)phenyl]cyclopropyl}carbonyl)-3H-spiro[2-benzofuran-1,3'-pyrrolidin]-3-one This compound was prepared by using a procedure analogous to that outlined in steps 1-2 of example 259, followed by a reductive amination of the resulting free amine by using a procedure that was analogous to that used in example 415. LCMS: m/z 446.1 (M+H)$^+$.

Example 419

(1R)-1'-({1-[4-(4-Acetyl-2-oxopiperazin-1-yl)phenyl]cyclopropyl}carbonyl)-3H-spiro[2-benzofuran-1,3'-pyrrolidin]-3-one This compound was prepared by using a procedure analogous to that outlined in example 259, steps 1-3.

Example 420 tert-Butyl 4-[4-(1-{[(1R)-3-oxo-1'H,3H-spiro[2-benzofuran-1,3'-pyrrolidin]-1'-yl]carbonyl}cyclopropyl)phenyl]piperazine-1-carboxylate A mixture of (1R)-1'-{[1-(4-chlorophenyl)cyclopropyl]carbonyl}-3H-spiro[2-benzofuran-1,3'-pyrrolidin]-3-one (0.50 g, 0.0014 mol, see steps 1 & 2 of example 96), tert-butyl piperazine-1-carboxylate (0.30 g, 0.0016 mol), sodium tert-butoxide (0.31 g, 0.0033 mol), palladium acetate (9 mg, 0.00004 mol) and 2-(di-t-butylphosphino)biphenyl (10 mg, 0.00004 mol) was degassed and then charged with nitrogen. To the mixture was added 1,4-dioxane (10.0 mL, 0.128 mol) and the resulting mixture was refluxed for 1 h.

Example 421

(1R)-1'-({1-[4-(4-Isobutyrylpiperazin-1-yl)-phenyl]cyclopropyl}carbonyl)-3H-spiro[2-benzofuran-1,3'-pyrrolidin]-3-one Step 1. (1R)-1'-{[1-(4-piperazin-1-ylphenyl)cyclopropyl]carbonyl}-3H-spiro[2-benzofuran-1,3'-pyrrolidin]-3-one tert-Butyl 4-[4-(1-{[(1R)-3-oxo-1'H,3H-spiro[2-benzofuran-1,3'-pyrrolidin]-1'-yl]carbonyl}cyclopropyl)phenyl]piperazine-1-carboxylate (0.65 g, 0.0012 mol, see example 420) was dissolved in methylene chloride (2.0 mL, 0.031 mol) and to this solution was added hydrogen chloride in 1,4-dioxane (4.0 M, 5.0 mL) and the reaction mixture was stirred at rt for 2 h. The mixture was diluted with ether and precipitate formed was filtered and dried to give the desired product. LC-MS: 418.2 (M+H)$^+$ Step 2

Propanoyl chloride (5.0 µL, 0.000057 mol) was added to a solution of (1R)-1'-{[1-(4-piperazin-1-ylphenyl)cyclopropyl]carbonyl}-3H-spiro[2-benzofuran-1,3'-pyrrolidin]-3-one (20.0 mg, 0.0000478 mol) and N,N-diisopropylethylamine (27 µL, 0.00016 mol) in methylene chloride (1.0 mL, 0.016 mol) and the mixture was stirred for 1 h. The solvent was removed and the crude product was purified by prep-HPLC. LC-MS: 488.2 (M+H)$^+$

Example 422

(1R)-1'-[(1-{4-[4-(Cyclopropylcarbonyl)piperazin-1-yl]phenyl}cyclopropyl)carbonyl]-3H-spiro[2-benzofuran-1,3'-pyrrolidin]-3-one This compound was prepared by using a procedure analogous to that outlined in steps 1 & 2 of example 421. LCMS: m/z 486.2 (M+H)$^+$.

Example 423

(1R)-1'-[(1-{4-[4-(Methylsulfonyl)piperazin-1-yl]phenyl}cyclopropyl)carbonyl]-3H-spiro[2-benzofuran-1,3'-pyrrolidin]-3-one This compound was prepared by using a procedure analogous to that outlined in steps 1 & 2 of example 421.

Example 424

(1R)-1'-({1-[4-(4-Methylpiperazin-1-yl)phenyl]cyclopropyl}carbonyl)-3H-spiro[2-benzofuran-1,3'-pyrrolidin]-3-one Formaldehyde (10.0 mg, 0.000333 mol) was added to a solution of (1R)-1'-{[1-(4-piperazin-1-ylphenyl)cyclopropyl]carbonyl}-3H-spiro[2-benzofuran-1,3'-pyrrolidin]-3-one (0.13 g, 0.00032 mol, example 421, step 1) in methanol (1.0 mL, 0.025 mol) followed by sodium triacetoxyborohydride (0.20 g, 0.00095 mol), and the mixture was stirred for 1 h. The crude product was purified by prep-HPLC. LC-MS: 432.3 (M+H)+

Example 425

N-Methyl-N-[4-(1-{[(1R)-3-oxo-1'H,3H-spiro[2-benzofuran-1,3'-pyrrolidin]-1'-yl]carbonyl}cyclopropyl)phenyl]cyclopropanecarboxamide This compound was prepared by using a procedure analogous to a combination of step 1 of example 102 and steps 3-4 of example 258. LCMS: m/z 431.1 (M+H)$^+$.

Example 426

N-[4-(1-{[(1R)-3-Oxo-1'H,3H-spiro[2-benzofuran-1,3'-pyrrolidin]-1'-yl]carbonyl}cyclopropyl)phenyl]acetamide This compound was prepared by using a procedure analogous to that outlined in steps 1-4 of example 261. LCMS: m/z 391.2 (M+H)$^+$.

Example 427

(1R)-1-({1-[4-(2-Oxopyrrolidin-1-yl)phenyl]cyclopropyl}carbonyl)-3H-spiro[2-benzofuran-1,3'-pyrrolidin]-3-one This compound was prepared by using a procedure analogous to that outlined in example 257. LCMS: m/z 417.2 (M+H)$^+$.

Example 428

(1R)-1'-({1-[4-(2-Oxo-1,3-oxazolidin-3-yl)phenyl]cyclopropyl}carbonyl)-3H-spiro[2-benzofuran-1,3'-pyrrolidin]-3-one This compound was prepared by using a procedure analogous to that outlined for the synthesis of example 257. LCMS: m/z 419.2 (M+H)$^+$.

Example 429

(1R)-1'-({1-[4-(1H-Pyrazol-1-yl)phenyl]
cyclopropyl}carbonyl)-3H-spiro[2-benzofuran-1,3'-
pyrrolidin]-3-one This compound was prepared by using a procedure analogous to that outlined for the synthesis of example 102. LCMS: m/z 400.1 (M+H)+.

Example 430

(1R)-1'-({1-[4-(2-Oxopiperidin-1-yl)phenyl]
cyclopropyl}carbonyl)-3H-spiro[2-benzofuran-1,3'-
pyrrolidin]-3-one This compound was prepared by using a procedure analogous to that outlined for the synthesis of example 257. LCMS: m/z 431.2 (M+H)+.

Example 431

1-Methyl-3-[4-(1-{[(1R)-3-oxo-1'H,3H-spiro[2-benzofuran-1,3'-pyrrolidin]-1'-yl]carbonyl}cyclopropyl)
phenyl]imidazolidine-2,4-dione This compound was prepared by using a procedure analogous to that outlined for the synthesis of example 257. LCMS: m/z 446.2 (M+H)+.

Example 432

(1R)-1'-{[1-(4-Morpholin-4-ylphenyl)cyclopropyl]
carbonyl}-3H-spiro[2-benzofuran-1,3'-pyrrolidin]-3-
one A mixture of (1R)-1'-{[1-(4-chlorophenyl)cyclopropyl]carbonyl}-3H-spiro[2-benzofuran-1,3'-pyrrolidin]-3-one (30.0 mg, 0.0000816 mol, example 83), morpholine (8.5 μL, 0.000098 mol), sodium tert-butoxide (19 mg, 0.00020 mol), palladium acetate (0.5 mg, 0.000002 mol) and 2-(di-t-butylphosphino)biphenyl (0.7 mg, 0.000002 mol) was degassed and charged with nitrogen. To the mixture was added 1,4-dioxane (1.0 mL, 0.013 mol). The resulting mixture was refluxed overnight. The crude product was purified prep-HPLC. LC-MS: 419.2 (M+H)+

Example 433

1-[4-(1-{[3-Phenylpyrrolidin-1-yl]
carbonyl}cyclopropyl)phenyl]pyrrolidine-2-one This compound was prepared by using a procedure analogous to that outlined in step 1 of example 102, starting with (3R)-1-{[1-(4-chlorophenyl)cyclopropyl]carbonyl}-3-phenylpyrrolidine (example 29). LCMS: m/z 375.2 (M+H)+.

Example 434

3-[4-(1-{[3-Phenylpyrrolidin-1-yl]
carbonyl}cyclopropyl)phenyl]-1,3-oxazolidin-2-one This compound was prepared by using a procedure analogous to that outlined for the synthesis of example 102, step 1, starting with (3R)-1-{[1-(4-chlorophenyl)cyclopropyl]carbonyl}-3-phenylpyrrolidine (example 29). LCMS: m/z 377.2 (M+H)+.

Example 435

Methyl 4-(4-{1-[(3-phenylpyrrolidin-1-yl)carbonyl]
cyclopropyl}phenyl)piperazine-1-carboxylate This compound was prepared by using a procedure analogous to that outlined for the synthesis of example 258. LCMS: m/z 434.2 (M+H)+.

Example 436

Ethyl 4-(4-{1-[(3-phenylpyrrolidin-1-yl)carbonyl]
cyclopropyl}phenyl)piperazine-1-carboxylate This compound was prepared by using a procedure analogous to that outlined for the synthesis of example 258.

Example 437

1-Isobutyryl-4-(4-{1-[(3-phenylpyrrolidin-1-yl)carbonyl]cyclopropyl}phenyl)piperazine This compound was prepared by using a procedure analogous to that outlined for the synthesis of example 258. LCMS: m/z 446.3 (M+H)+.

Example 438

1-Acetyl-4-(4-{1-[(3-phenylpyrrolidin-1-yl)carbonyl]cyclopropyl}phenyl)piperazine This compound was prepared by using a procedure analogous to that outlined for the synthesis of example 258. LCMS: m/z 418.3 (M+H)+.

Example 439

1-(Cyclopropylcarbonyl)-4-(4-{1-[(3-phenylpyrrolidin-1-yl)carbonyl]cyclopropyl}phenyl)piperazine This compound was prepared by using a procedure analogous to that outlined for the synthesis of example 258. LCMS: m/z 444.3 (M+H)+.

Example 440

1-Isobutyryl-4-(5-{1-[(3-phenylpyrrolidin-1-yl)carbonyl]cyclopropyl}pyridin-2-yl)piperazine This compound was prepared by using a procedure analogous to that outlined for the synthesis of example 163. LCMS: m/z 447.3 (M+H)+.

Example 441

1-(Cyclopropylcarbonyl)-4-(5-{1-[(3-phenylpyrrolidin-1-yl)carbonyl]cyclopropyl}pyridin-2-yl)piperazine This compound was prepared by using a procedure analogous to that outlined for the synthesis of example 163. LCMS: m/z 445.3 (M+H)+.

Example 442

(1R)-1'-[(1-Pyridin-3-ylcyclopropyl)carbonyl]-3H-spiro[2-benzofuran-1,3'-pyrrolidin]-3-one This compound was prepared by using a procedure analogous to that outlined in steps 1-2 and 4 of example 96. LCMS: m/z 335.1 (M+H)$^+$.

Example 443

N-Methyl-4-[5-(1-{[(1R)-3-oxo-1'H,3H-spiro[2-benzofuran-1,3'-pyrrolidin]-1'-yl]carbonyl}cyclopropyl)pyridin-2-yl]benzamide Step 1. 4-[5-(1-{[(1R)-3-oxo-1'H,3H-spiro[2-benzofuran-1,3'-pyrrolidin]-1'-yl]carbonyl}cyclopropyl)pyridin-2-yl]benzoic acid This compound was prepared by using a procedure analogous to that outlined in steps 1-2 of example 173. LCMS: m/z 455.2 (M+H)$^+$.

Step 2

4-Methylmorpholine (12 µL, 0.00011 mol) was added to a mixture of 4-[5-(1-{[(1R)-3-oxo-1'H,3H-spiro[2-benzofuran-1,3'-pyrrolidin]-1'-yl]carbonyl}cyclopropyl)pyridin-2-yl]benzoic acid (13 mg, 0.000029 mol), methylammonium chloride (2.9 mg, 0.000043 mol), and benzotriazol-1-yloxy-tris(dimethylamino)phosphonium hexafluorophosphate (14 mg, 0.000031 mol) in N,N-dimethylformamide (0.5 mL, 0.006 mol), and the resulting mixture was stirred at rt for 2 h. The crude product was purified by prep-LCMS. LCMS: m/z 468.2 (M+H)$^+$.

Example 444

N,N-Dimethyl-4-[5-(1-{[(1R)-3-oxo-1'H,3H-spiro[2-benzofuran-1,3'-pyrrolidin]-1'-yl]carbonyl}cyclopropyl)pyridin-2-yl]benzamide This compound was prepared by using a procedure analogous to that outlined in steps 1-2 of example 443. LCMS: m/z 482.2 (M+H)$^+$.

Example 445

(1R)-1'-[(1-{6-[4-(Methylsulfonyl)phenyl]pyridin-3-yl}cyclopropyl)carbonyl]-3H-spiro[2-benzofuran-1,3'-pyrrolidin]-3-one This compound was prepared by using a procedure analogous to that outlined in steps 1-2 of example 173. LCMS: m/z 489.1 (M+H)$^+$.

Example 446

(1R)-1'-{[1-(4-Methoxyphenyl)cyclopropyl]carbonyl}-3H-spiro[2-benzofuran-1,3'-pyrrolidin]-3-one This compound was prepared by using a procedure analogous to that outlined in steps 1-2 and 4 of example 96. LCMS: m/z 364.2 (M+H)$^+$.

Example 447

(1R)-1'-({1-[4-(Pyridin-2-yloxy)phenyl]cyclopropyl}carbonyl)-3H-spiro[2-benzofuran-1,3'-pyrrolidin]-3-one This compound was prepared by using a procedure analogous to that outlined in steps 1-2 of example 114. LCMS: m/z 427.1 (M+H)$^+$ 449.1 (M+Na)$^+$.

Example 448

(1R)-1'-({1-[4-(Pyridin-3-ylmethoxy)phenyl]cyclopropyl}carbonyl)-3H-spiro[2-benzofuran-1,3'-pyrrolidin]-3-one This compound was prepared by using a procedure analogous to that outlined in steps 1-2 of example 114. LCMS: m/z 441.1 (M+H)$^+$ 463.1 (M+Na)$^+$.

Example 449

(1R)-1'-({1-[4-(Isoquinolin-1-ylmethoxy)phenyl]cyclopropyl}carbonyl)-3H-spiro[2-benzofuran-1,3'-pyrrolidin]-3-one This compound was prepared by using a procedure analogous to that outlined in steps 1-2 of example 114. LCMS: m/z 491.2 (M+H)$^+$.

Example 450

1'-{[1-(4-Vinylphenyl)cyclopropyl]carbonyl}-3H-spiro[2-benzofuran-1,3'-pyrrolidin]-3-one This compound was prepared by using a procedure analogous to that outlined in example 119. LCMS: m/z 360.1 (M+H)$^+$ 382.0 (M+Na)$^+$.

Example 451

Methyl 4-[4-(1-{[(1R)-3-oxo-1'H,3H-spiro[2-benzofuran-1,3'-pyrrolidin]-1'-yl]carbonyl}cyclopropyl)phenyl]-3,6-dihydropyridine-1(2H)-carboxylate Step 1. 1-{4-[1-(tert-butoxycarbonyl)-1,2,3,6-tetrahydropyridin-4-yl]phenyl}cyclopropane carboxylic acid A mixture of 1-{4-[1-(tert-butoxycarbonyl)-4-hydroxypiperidin-4-yl]phenyl}cyclopropanecarboxylic acid (300 mg, prepared as described in example 210, steps 1 & 2) and trifluoroacetic acid 2 mL was stirred at rt for 5 h. The reaction mixture was then concentrated. The crude product was dissolved in tetrahydrofuran (4 mL, 0.05 mol) and to this was added di-tert-butyldicarbonate (333 mg, 0.00152 mol) and N,N-diisopropylethylamine (6.0×10$^{-2}$ µL, 0.0035 mol). The mixture was stirred at rt for 5 h and then diluted with AcOEt, washed with saturated NaHCO$_3$ aqueous solution and 1M HCl successively, dried with MgSO$_4$, and concentrated in-vacuo to afford the desired product.

Step 2. Methyl 4-[4-(1-{[(1R)-3-oxo-1H,3H-spiro[2-benzofuran-1,3'-pyrrolidin]-1'-yl]carbonyl}cyclopropyl)phenyl]-3,6-dihydropyridine-1(2H)-carboxylate The title compound was prepared using a procedure analogous to that in steps 3-4 of example 163, with the omission of the LiOH-promoted-hydrolysis. LCMS: m/z 473.3 (M+H)+.

Example 452

Ethyl 4-[4-(1-{[(1R)-3-oxo-1'H,3H-spiro[2-benzofuran-1,3'-pyrrolidin]-1'-yl]carbonyl}cyclopropyl)phenyl]-3,6-dihydropyridine-1(2H)-carboxylate This compound was prepared by using a procedure analogous to that outlined in steps 1-2 of example 451. LCMS: m/z 487.3 (M+H)+.

Example 453

(1R)-1'-({1-[4-(1-Acetyl-1,2,3,6-tetrahydropyridin-4-yl)phenyl]cyclopropyl}carbonyl)-3H-spiro[2-benzofuran-1,3'-pyrrolidin]-3-one This compound was prepared by using a procedure analogous to that outlined in steps 1 & 2 of example 451. LCMS: m/z 457.3 (M+H)+.

Example 454

(1R)-1'-[(1-{4-[1-(3-Methylbutanoyl)-1,2,3,6-tetrahydropyridin-4-yl]phenyl}cyclopropyl)carbonyl]-3H-spiro[2-benzofuran-1,3'-pyrrolidin]-3-one This compound was prepared by using a procedure analogous to that outlined in steps 1 & 2 of example 451, with the exception that for the last step the acid chloride was replaced by the corresponding carboxylic acid as described below: A mixture of 3-methyl butanoic acid (16 mg, 0.00015 mol), benzotriazol-1-yloxytris(dimethylamino) phosphonium hexafluorophosphate (38 mg, 0.000085 mol), and N,N-diisopropylethylamine (4.0×10⁻¹ μL, 0.00023 mol) dissolved in N,N-dimethylformamide (0.5 mL, 0.006 mol) was stirred at rt for 2 h. The reaction mixture was then diluted with MeOH and the crude product was purified by prep-HPLC to afford the desired product. LCMS: m/z 499.3 (M+H)+.

Example 455

5-Hydroxy-1'-{[1-(4-methylphenyl)cyclopropyl]carbonyl}-3H-spiro[2-benzofuran-1,3'-pyrrolidin]-3-one To a solution of 5-methoxy-1'-{[1-(4-methylphenyl)cyclopropyl]carbonyl}-3H-spiro[2-benzofuran-1,3'-pyrrolidin]-3-one (40 mg, 0.0001 mol) in tetrahydrofuran (2 mL, 0.02 mol) was added L-Selectride® in tetrahydrofuran (1.0 M, 0.53 mL) and the resulting solution was heated to 120° C. for 50 minutes using microwave irradiation. To the reaction mixture was added a few drops of water to quench the reaction. Then the reaction mixture was concentrated and about. 3 mL of concentrated HCl aqueous solution was added to dissolve the residue. The resulting solution was stirred at rt for 2 h. The crude product was purified using prep-HPLC. LCMS: m/z 364.2 (M+H)+.

Example 455a

1'-{[1-(4-Methylphenyl)cyclopropyl]carbonyl}-3H-spiro[2-benzofuran-1,3'-pyrrolidin]-5-ol This compound was prepared by using a procedure analogous to that outlined in example 454. LCMS: m/z 350.2 (M+H)+.

Example 456

(1R)-1'-({1-[4-(Pyrrolidin-1-ylmethyl)phenyl]cyclopropyl}carbonyl)-3H-spiro[2-benzofuran-1,3'-pyrrolidin]-3-one Step 1. 1-[4-(pyrrolidin-1-ylmethyl)phenyl]cyclopropanecarbonitrile A mixture of 1-(4-formylphenyl)cyclopropanecarbonitrile (0.30 g, 0.0018 mol), pyrrolidine (0.18 mL, 0.0021 mol) and sodium triacetoxyborohydride (0.74 g, 0.0035 mol) in methanol (5.0 mL, 0.12 mol) was stirred at rt for 1 h. The reaction mixture was adjusted to be basic (pH=12) and extracted with ethyl acetate. The combined organic extract was washed with brine, dried and concentrated to provide the desired product. LC-MS: 227.1 (M+H)+

Step 2

The title compound was prepared by using a procedure analogous to that outlined in steps 1, 2 and 4 of example 96.

Example 457

(1R)-1'-{[1-(6-Pyrrolidin-1-ylpyridin-3-yl)cyclopropyl]carbonyl}-3H-spiro[furo[3,4-c]pyridine-1,3'-pyrrolidin]-3-one This compound was prepared by using a procedure analogous to that outlined in steps 1-3 of example 163. LCMS: m/z 405.1 (M+H)+.

Example 458

(1R)-1'-({1-[6-(4-Phenylpiperazin-1-yl)pyridin-3-yl]cycle propyl}carbonyl)-3H-spiro[furo[3,4-c]pyridine-1,3'-pyrrolidin]-3-one This compound was prepared by using a procedure analogous to that outlined in steps 1-3 of example 163. LCMS: m/z 496.2 (M+H)+.

Example 459

Methyl 4-[5-(1-{[(1R)-3-oxo-1'H,3H-spiro[furo[3,4-c]pyridine-1,3'-pyrrolidin]-1'-yl]carbonyl}cyclopropyl)pyridin-2-yl]piperazine-1-carboxylate This compound was prepared by using a procedure analogous to that outlined in steps 1-4 of example 163. LCMS: m/z 478.2 (M+H)+.

Example 460

Ethyl 4-(5-{1-[(3-oxo-1'H,3H-spiro[furo[3,4-c]pyridine-1,3'-pyrrolidin]-1'-yl)carbonyl]cyclopropyl}pyridin-2-yl)piperazine-1-carboxylate This compound was prepared by using a procedure analogous to that outlined in steps 1-4 of example 163.

Example 461

Isopropyl 4-(5-{1-[(3-oxo-1'H,3H-spiro[furo[3,4-c]pyridine-1,3'-pyrrolidin]-1'-yl)carbonyl]cyclopropyl}pyridin-2-yl)piperazine-1-carboxylate This compound was prepared by using a procedure analogous to that outlined in steps 1-4 of example 163. LCMS: m/z 506.2 (M−H)$^+$.

Example 462

1'-({1-[6-(4-Chloro phenyl)pyridin-3-yl]cyclopropyl}carbonyl)-3H-spiro[furo[3,4-c]pyridine-1,3'-pyrrolidin]-3-one This compound was prepared by using a procedure analogous to that outlined in steps 1-2 of example 173. LCMS: m/z 446.1 & 448.1 (M+H)$^+$.

Example 463

1'-({1-[6-(4-Fluorophenyl)pyridin-3-yl]cyclopropyl}carbonyl)-3H-spiro[furo[3,4-c]pyridine-1,3'-pyrrolidin]-3-one This compound was prepared by using a procedure analogous to that outlined in steps 1-2 of example 173. LCMS: m/z 430.2 (M+H)$^+$.

Example 464

1'-({1-[6-(4-Fluoro-2-methylphenyl)pyridin-3-yl]cyclopropyl}carbonyl)-3H-spiro[furo[3,4-c]pyridine-1,3'-pyrrolidin]-3-one This compound was prepared by using a procedure analogous to that outlined in steps 1-2 of example 173. LCMS: m/z 444.2 (M+H)$^+$.

Example 465

1'-[(1-Quinolin-4-ylcyclopropyl)carbonyl]-3H-spiro[furo[3,4-c]pyridine-1,3'-pyrrolidin]-3-one This compound was prepared by using a procedure analogous to that outlined in steps A & B of example 95. LCMS: m/z 386.1 (M+H)$^+$.

Example 466

4-Chloro-1'-[(1-quinolin-4-ylcyclopropyl)carbonyl]-3H-spiro[furo[3,4-c]pyridine-1,3'-pyrrolidin]-3-one This compound was prepared by using a procedure analogous to that outlined in steps 1-3 of example 227. LCMS: m/z 420.0 & 422.0 (M+H)$^+$.

Example 467

4-Hydroxy-1'-[(1-quinolin-4-ylcyclopropyl)carbonyl]-3H-spiro[furo[3,4-c]pyridine-1,3'-pyrrolidin]-3-one This compound was prepared by using a procedure analogous to that outlined in steps 1-3 of example 227. LCMS: m/z 402.1 (M+H)$^+$.

Example 468

4-Methoxy-1'-[(1-quinolin-4-ylcyclopropyl)carbonyl]-3H-spiro[furo[3,4-c]pyridine-1,3'-pyrrolidin]-3-one This compound was prepared by using a procedure analogous to that outlined in steps 1-3 of example 227. LCMS: m/z 416.1 (M+H)$^+$.

Example 469

1'-[(1-{4-[(4-Fluorobenzyl)oxy]phenyl}cyclopropyl)carbonyl]-3H-spiro[furo[3,4-c]pyridine-1,3'-pyrrolidin]-3-one This compound was prepared by using a procedure analogous to that outlined in steps 1 & 2 of example 104. LCMS: m/z 459.2 (M+H)$^+$.

Example 470

1'-{[1-(4-{[4-(Trifluoromethyl)benzyl]oxy}phenyl)cyclopropyl]carbonyl}-3H-spiro[furo[3,4-c]pyridine-1,3'-pyrrolidin]-3-one This compound was prepared by using a procedure analogous to that outlined in steps 1 & 2 of example 104. LCMS: m/z 509.2 (M+H)$^+$.

Example 471

1'-[(1-{4-[(2-Chloro-4-fluorobenzyl)oxy]phenyl}cyclopropyl)carbonyl]-3H-spiro[furo[3,4-c]pyridine-1,3'-pyrrolidin]-3-one This compound was prepared by using a procedure analogous to that outlined in steps 1 & 2 of example 104.

Example 472

1'-[(1-{4[(4-Bromo-2-fluorobenzyl)oxy]phenyl}cyclopropyl)carbonyl]-3H-spiro[furo[3,4-c]pyridine-1,3'-pyrrolidin]-3-one This compound was prepared by using a procedure analogous to that outlined in steps 1 & 2 of example 104. LCMS: m/z 537.1 (M+H)$^+$ 559.1 (M+Na)$^+$.

Example 473

3-Fluoro-4-[(4-{1-[(3-oxo-1'H,3H-spiro[furo[3,4-c]pyridine-1,3'-pyrrolidin]-1'-yl)carbonyl]cyclopropyl}phenoxy)methyl]benzonitrile A mixture of 1'-[(1-{4-[(4-bromo-2-fluorobenzyl)oxy]phenyl}cyclopropyl)carbonyl]-3H-spiro[furo[3,4-c]pyridine-1,3'-pyrrolidin]-3-one (18 mg, 0.000033 mol, example 474), zinc cyanide (3.9 mg, 0.000033 mol), tetrakis(triphenylphosphine)palladium(0) (2 mg, 0.000002 mol), and tetra-N-butylammonium bromide (2.7 mg, 0.0000084 mol) in N,N-dimethylformamide (0.5 mL, 0.006 mol) was microwave irradiated at 170° C. for 5 min. After cooling, the crude product was purified with prep-hplc to afford 12.4 mg of pure product. LCMS: m/z 484.2 (M+H)$^+$.

Example 474

1'-[(1-{4-[1-(2-Fluorophenyl)ethoxy]phenyl}cyclopropyl)carbonyl]-3H-spiro[furo[3,4-c]pyridine-1,3'-pyrrolidin]-3-one This compound was prepared by using a procedure analogous to that outlined for the synthesis in example 105. LCMS: m/z 473.2 (M+H)$^+$.

Example 475

4-[1-(4-{1-[(3-oxo-1'H,3H-spiro[furo[3,4-c]pyridine-1,3'-pyrrolidin]-1'-yl)carbonyl]cyclopropyl}phenoxy)ethyl]benzonitrile This compound was prepared by using a procedure analogous to that outlined in example 473, using the title compound of example 300 as the benzyl bromide starting material. LCMS: m/z 480.2 (M+H)$^+$.

Example 476

1'-({1-[4-(Quinolin-2-ylmethoxy)phenyl]cyclopropyl}carbonyl)-3H-spiro[furo[3,4-c]pyridine-1,3'-pyrrolidin]-3-one This compound was prepared by using a procedure analogous to that outlined in steps 1-2 of example 104. LCMS: m/z 492.2 (M+H)$^+$ Example 477

1'-{[1-(4-Methoxyphenyl)cyclopropyl]carbonyl}-3H-spiro[furo[3,4-c]pyridine-1,3'-pyrrolidin]-3-one This compound was prepared by using a procedure analogous to that outlined in step B of example 95. LCMS: m/z 365.1 (M+H)$^+$ Example 478

6-Chloro-1'-{[1-(4-methoxyphenyl)cyclopropyl]carbonyl}-3H-spiro[furo[3,4-c]pyridine-1,3'-pyrrolidin]-3-one This compound was prepared by using a procedure analogous to that outlined for the synthesis in example 232. LCMS: m/z 399.4 (M+H)$^+$ Example 479

1'-{[1-(4-Methoxyphenyl)cyclopropyl]carbonyl}-6-(trifluoromethyl)-3H-spiro[furo[3,4-c]pyridine-1,3'-pyrrolidin]-3-one This compound was prepared by using a procedure analogous to that outlined for the synthesis in example 222. LCMS: m/z 433.1 (M+H)$^+$ Example 480

1'-({1-[4-(Cyclopentyloxy)phenyl]cyclopropyl}carbonyl)-3H-spiro[furo[3,4-c]pyridine-1,3'-pyrrolidin]-3-one This compound was prepared by using a procedure analogous to that outlined in steps 1-3 of example 213. LCMS: m/z 419.2 (M+H)$^+$ 441.1 (M+Na)$^+$.

Example 481

1'-({1-[4-(Allyloxy)phenyl]cyclopropyl}carbonyl)-3H-spiro[furo[3,4-c]pyridine-1,3'-pyrrolidin]-3-one This compound was prepared by using a procedure analogous to that outlined for the synthesis in example 215. LCMS: m/z 391.3 (M+H)$^+$ 413.2 (M+Na)$^+$.

Example 482

1'-({1-[4-(2-Methoxyethoxy)phenyl]cyclopropyl}carbonyl)-3H-spiro[furo[3,4-c]pyridine-1,3'-pyrrolidin]-3-one This compound was prepared by using a procedure analogous to that outlined in steps 1-3 of example 213. LCMS: m/z 409.2 (M+H)$^+$ 431.2 (M+Na)$^+$.

Example 483

1'-({1-[4-(Cyclopropylmethoxy)phenyl]cyclopropyl}carbonyl)-3H-spiro[furo[3,4-c]pyridine-1,3'-pyrrolidin]-3-one This compound was prepared by using a procedure analogous to that outlined for the synthesis in example 215. LCMS: m/z 405.1 (M+H)$^+$ 427.1 (M+Na)$^+$.

Example 484

1'-{[1-(4-Methylphenyl)cyclopropyl]carbonyl}-6-(trifluoromethyl)-3H-spiro[furo[3,4-c]pyridine-1,3'-pyrrolidin]-3-one This compound was prepared by using a procedure analogous to that outlined for the synthesis in example 222. LCMS: m/z 417.1 (M+H)$^+$ Example 485

1'-{[1-(4-Methylphenyl)cyclopropyl]carbonyl}-3H-spiro[furo[3,4-c]pyridine-1,3'-pyrrolidin]-3-one This compound was prepared by using a procedure analogous to that outlined in step B of example 95.

Example 486

1'-({1-[4-(Trifluoromethyl)phenyl]cyclopropyl}carbonyl)-3H-spiro[furo[3,4-c]pyridine-1,3'-pyrrolidin]-3-one This compound was prepared by using a procedure analogous to that outlined in steps A & B of example 95. LCMS: m/z 403.1 (M+H)$^+$

Example 487

1'-{[1-(4-Vinylphenyl)cyclopropyl]carbonyl}-3H-spiro[furo[3,4-c]pyridine-1,3'-pyrrolidin]-3-one This compound was prepared by using a procedure analogous to that outlined for the synthesis in example 123. LCMS: m/z 361.0 (M+H)$^+$ 383.1 (M+Na)$^+$.

Example 488

1'-[(1-{4-[(E)-2-Pyridin-2-ylvinyl]phenyl}cyclopropyl)carbonyl]-3H-spiro[furo[3,4-c]pyridine-1,3'-pyrrolidin]-3-one This compound was prepared by using a procedure analogous to that outlined for the synthesis in example 122. LCMS: m/z 438.2 (M+H)$^+$ 460.1 (M+Na)$^+$.

Example 489

1'-({1-[4-(1-Isobutyryl-1,2,3,6-tetrahydropyridin-4-yl)phenyl]cyclopropyl}carbonyl)-3H-spiro[furo[3,4-c]pyridine-1,3'-pyrrolidin]-3-one This compound was prepared by using a procedure analogous to that outlined in steps 1-50f example 210. LCMS: m/z 486.2 (M+H)$^+$.

Example 490

1'-({1-[4-(1-Acetylpiperidin-4-yl)phenyl]cyclopropyl}carbonyl)-3H-spiro[furo[3,4-c]pyridine-1,3'-pyrrolidin]-3-one This compound was prepared by using a procedure analogous to that outlined in steps 1 and 2 of example 451 with the exception that step 1 was modified by an addition of 20 equivalent of triethylsilane during the dehydration by treatment with TFA. LCMS: m/z 460.2 (M+H)$^+$.

Example 491

Ethyl 4-(4-{1-[(3-oxo-1'H,3H-spiro[furo[3,4-c]pyridine-1,3'-pyrrolidin]-1'-yl)carbonyl]cyclopropyl}phenyl)piperidine-1-carboxylate This compound was prepared by using a procedure analogous to that outlined for the synthesis in example 490. LCMS: m/z 490.2 (M+H)$^+$.

Example 492

1'-({1-[4-(1-Isobutyrylpiperidin-4-yl)phenyl]cyclopropyl}carbonyl)-3H-spiro[furo[3,4-c]pyridine-1,3'-pyrrolidin]-3-one This compound was prepared by using a procedure analogous to that outlined for the synthesis in example 454, with the exception that step 1 of example 451 was modified by an addition of 20 equivalent of triethylsilane during the dehydration with TFA.

Example 493

1'-({1-[4-(1-Propionylpiperidin-4-yl)phenyl]cyclopropyl}carbonyl)-3H-spiro[furo[3,4-c]pyridine-1,3'-pyrrolidin]-3-one This compound was prepared by using a procedure analogous to that outlined for the synthesis in example 492. LCMS: m/z 474.2 (M+H)$^+$.

Example 494

1'-[(1-{4-[1-(3-Methylbutanoyl)piperidin-4-yl]phenyl}cyclopropyl)carbonyl]-3H-spiro[furo[3,4-c]pyridine-1,3'-pyrrolidin]-3-one This compound was prepared by using a procedure analogous to that outlined for the synthesis in example 492. LCMS: m/z 502.3 (M+H)$^+$.

Example 495

1'-({1-[4-(2-Isopropyl-1,3-thiazol-4-yl)phenyl]cyclopropyl}carbonyl)-3H-spiro[furo[3,4-c]pyridine-1,3'-pyrrolidin]-3-one This compound was prepared by using a procedure analogous to that outlined for the synthesis in example 142. LCMS: m/z 460.2 (M+H)$^+$.

Example 496

1'-[(1-{4-[2-(Dimethylamino)-1,3-thiazol-4-yl]phenyl}cyclopropyl)carbonyl]-3H-spiro[furo[3,4-c]pyridine-1,3'-pyrrolidin]-3-one This compound was prepared by using a procedure analogous to that outlined for the synthesis in example 142. LCMS: m/z 461.2 (M+H)$^+$.

Example 497

1'-({1-[4-(2-Amino-1,3-thiazol-4-yl)phenyl]cyclopropyl}carbonyl)-3H-spiro[furo[3,4-c]pyridine-1,3'-pyrrolidin]-3-one This compound was prepared by using a procedure analogous to that outlined for the synthesis in example 142. LCMS: m/z 433.2 (M+H)$^+$.

Example 498

3-Fluoro-4-{1-[(3-oxo-1'H,3H-spiro[furo[3,4-c]pyridine-1,3'-pyrrolidin]-1'-yl)carbonyl]cyclopropyl}benzonitrile This compound was prepared by using a procedure analogous to that outlined for the synthesis in example 208. LCMS: m/z 378.1 (M+H)$^+$.

Example 499

1'-({1-[2-Fluoro-4-(4-methyl-1,3-thiazol-2-yl)phenyl]cyclopropyl}carbonyl)-3H-spiro[furo[3,4-c]pyridine-1,3'-pyrrolidin]-3-one Into a microwave vial was added 3-fluoro-4-{1-[(3-oxo-1'H,3H-spiro[furo[3,4-c]pyridine-1,3'-pyrrolidin]-1'-yl)carbonyl]cyclopropyl}benzenecarbothioamide (35 mg, 0.000085 mol, prepared by subjecting the title compound in example 498 to analogous reaction conditions outlined in example 209) in ethanol (0.300 mL, 0.00514 mol) and N,N-dimethylformamide (0.75 mL, 0.0097 mol). To this solution was added chloroacetone (0.2 mL, 0.002 mol) and the tube was sealed and heated at 80° C. for 4 h using an oil bath. After ~3 h the mixture became homogeneous. LCMS indicated that the reaction was complete. The crude product was purified by prep-LCMS. LCMS: m/z 450.2 (M+H)$^+$.

Example 500

(1R)-1'-[(1-{4-[5-(Trifluoromethyl)-1,3,4-oxadiazol-2-yl]phenyl}cyclopropyl)carbonyl]-3H-spiro[furo[3,4-c]pyridine-1,3'-pyrrolidin]-3-one This compound was prepared by using a procedure analogous to that outlined in example 338. LCMS: m/z 471.1 (M+H)$^+$.

Example 501

1'-({1-[4-(3-Methylisoxazol-4-yl)phenyl]cyclopropyl}carbonyl)-3H-spiro[furo[3,4-c]pyridine-1,3'-pyrrolidin]-3-one Step 1. 1-(4-ethynylphenyl)cyclopropanecarbonitrile A mixture of (4-ethynylphenyl)acetonitrile (1.0 g, 0.0071 mol), 1-bromo-2-chloro-ethane (1200 μL, 0.014 mol), benzyltriethylammonium chloride (0.1 g, 0.0004 mol) and 1 ml of 50% NaOH water (w/v) was heated at 50° C. for 4 hours. The product was extracted with EtOAc and the combined organic phases were washed with water and brine successively, dried over Na$_2$SO$_4$, filtered, and concentrated in-vacuo to afford 1.1 g of the desired product, which was used in the following step without further purification.

Step 2. 1-[4-(3-methylisoxazol-4-yl)phenyl]cyclopropanecarbonitrile

To a mixture of 1-(4-ethynylphenyl)cyclopropanecarbonitrile (200 mg, 0.001 mol) acetaldoxime (71 mg, 0.0012 mol) in tetrahydrofuran (5.0 mL, 0.062 mol) was added N-chlorosuccinimide (160 mg, 0.0012 mol) in portions with stirring. After the addition was complete, triethylamine (170 μL, 0.0012 mol) was added. The mixture was stirred at rt for 2 days. The reaction mixture was diluted with ethyl acetate and washed with water and brine successively, dried over MgSO$_4$ and filtered. The filtrate was concentrated to afford the desired product in quantitative yield.

Step 3

The title compound was prepared by using a procedure analogous to that outlined for the synthesis of example 212, steps 3 & 4. LCMS: m/z 416.1 (M+H)$^+$.

Example 502

(1R)-1'-({1-[4-(2-Pyridin-2-ylethyl)phenyl]cyclopropyl}carbonyl)-3H-spiro[furo[3,4-c]pyridine-1,3'-pyrrolidin]-3-one A mixture of (1R)-1'-[(1-{4-[(E)-2-pyridin-2-ylvinyl]phenyl}cyclopropyl)carbonyl]-3H-spiro[furo[3,4-c]pyridine-1,3'-pyrrolidin]-3-one (20 mg, 0.00004 mol, example 488), 10% Pd—C in methanol (1 mL, 0.02 mol) was stirred under a hydrogen atmosphere (balloon) for 1.5 h. The reaction mixture was then filtered and concentrated to afford the desired product. LCMS: m/z 440.2 (M+H)+; 462.2 (M+Na)+.

Example 503

1'-({1-[2-Fluoro-4-(1H-pyrazol-1-yl)phenyl]cyclopropyl}carbonyl)-3H-spiro[furo[3,4-c]pyridine-1,3'-pyrrolidin]-3-one This compound was prepared by using a procedure analogous to that outlined in example 126.

Example 504

1'-({1-[2-Fluoro-4-(3-methyl-1H-pyrazol-1-yl)phenyl]cyclopropyl}carbonyl)-3H-spiro[furo[3,4-c]pyridine-1,3'-pyrrolidin]-3-one This compound was prepared by using a procedure analogous to that outlined in example 126.

Example 505

1'-({1-[4-(3-Amino-1H-pyrazol-1-yl)phenyl]cyclopropyl}carbonyl)-3H-spiro[furo[3,4-c]pyridine-1,3'-pyrrolidin]-3-one This compound was prepared by using a procedure analogous to that outlined in example 126. LCMS: m/z 416.1 (M+H)$^+$.

Example 506

1'-({1-[4-(1H-Benzimidazol-1-yl)-2-fluorophenyl]cyclopropyl}carbonyl)-3H-spiro[furo[3,4-c]pyridine-1,3'-pyrrolidin]-3-one This compound was prepared by using a procedure analogous to that outlined in example 130.

Example 507

1'-[(1-{2-Fluoro-4-[2-(trifluoromethyl)-1H-benzimidazol-1-yl]phenyl}cyclopropyl)-carbonyl]-3H-spiro[furo[3,4-c]pyridine-1,3'-pyrrolidin]-3-one This compound was prepared by using a procedure analogous to that outlined in example 130.

Example 508

1'-({1-[4-(2-Methoxy-H1-benzimidazol-1-yl)phenyl]cyclopropyl}carbonyl)-3H-spiro[furo[3,4-c]pyridine-1,3'-pyrrolidin]-3-one This compound was prepared by using a procedure analogous to that outlined in example 207. LCMS: m/z 481.2 (M+H)$^+$.

Example 509

Ethyl 4-(4-{1-[(3-oxo-1'H,3H-spiro[furo[3,4-c]pyridine-1,3'-pyrrolidin]-1'-yl)carbonyl]cyclopropyl}phenyl)piperazine-1-carboxylate This compound was prepared by using a procedure analogous to that outlined in steps 1-4 of example 163, with the exception that step 2 was replaced by the following protocol: A mixture of methyl 1-(4-bromophenyl)cyclopropanecarboxylate (0.53 g, 0.0021 mol), tert-butyl piperazine-1-carboxylate (0.42 g, 0.0023 mol), potassium phosphate (0.66 g, 0.0031 mol), tris(dibenzylideneacetone)dipalladium(0) (57.0 mg, 0.0000622 mol) and o-(dicyclohexylphosphino)biphenyl (21.8 mg, 0.0000622 mol) was degassed and then charged with nitrogen. To the mixture was added toluene (8.0 mL, 0.075 mol) and the resulting mixture was heated at 100° C. overnight. The mixture was filtered through a short silica gel pad and the solvent was removed under reduced pressure. The crude product was purified by CombiFlash eluting with hexane/EtOAc (max. EtOAc 20%). LC-MS: 361.2 (M+H)$^+$, 305.2 (M+H-56)+

Example 510

Isopropyl 4-[4-(1-{[(1R)-3-oxo-1'H,3H-spiro[furo[3,4-c]pyridine-1,3'-pyrrolidin]-1'-yl]carbonyl}cyclopropyl)phenyl]piperazine-1-carboxylate This compound was prepared by using a procedure analogous to that outlined in example 509. LCMS: m/z 505.2 (M+H)$^+$.

Example 511

(1R)-1'-({1-[4-(4-Propionylpiperazin-1-yl)phenyl]cyclopropyl}carbonyl)-3H-spiro[furo[3,4-c]pyridine-1,3'-pyrrolidin]-3-one This compound was prepared by using a procedure analogous to that outlined in example 509. LCMS: m/z 475.2 (M+H)$^+$.

Example 512

(1R)-1'-({1-[4-(4-Isobutyrylpiperazin-1-yl)phenyl]cyclopropyl}carbonyl)-3H-spiro[furo[3,4-c]pyridine-1,3'-pyrrolidin]-3-one This compound was prepared by using a procedure analogous to that outlined in example 509. LCMS: m/z 489.2 (M+H)$^+$.

Example 513

(1R)-1'-[(1-{4-[4-(Cyclopropylcarbonyl)piperazin-1-yl]phenyl}cyclopropyl)carbonyl]-3H-spiro[furo[3,4-c]pyridine-1,3'-pyrrolidin]-3-one This compound was prepared by using a procedure analogous to that outlined for the synthesis of example 509. LCMS: m/z 487.3 (M+H)$^+$.

Example 514

1'-[(1-{4-[4-(Methylsulfonyl)piperazin-1-yl]phenyl}cyclopropyl)carbonyl]-3H-spiro[furo[3,4-c]pyridine-1,3'-pyrrolidin]-3-one This compound was prepared by using a procedure analogous to that outlined for the synthesis of example 509. LCMS: m/z 497.2 (M+H)$^+$.

Example 515

1'-({1-[4-(2-Oxopyridin-1(2H)-yl)phenyl]cyclopropyl}carbonyl)-3H-spiro[furo[3,4-c]pyridine-1,3'-pyrrolidin]-3-one This compound was prepared by using a procedure analogous to that outlined for the synthesis of example 257. LCMS: m/z 428.2 (M+H)$^+$.

Example 516

Methyl [4-(1-{[(1R)-3-oxo-1'H,3H-spiro[furo[3,4-c]pyridine-1,3'-pyrrolidin]-1'-yl]carbonyl}cyclopropyl)phenyl]carbamate This compound was prepared by using a procedure analogous to a combination of steps 1-3 of example 261 and step 2 of example 263. LCMS: m/z 408.1 (M+H)$^+$.

Example 517

N-[4-(1-{[(1R)-3-Oxo-1'H,3H-spiro[furo[3,4-c]pyridine-1,3'-pyrrolidin]-1'-yl]carbonyl}cyclopropyl)phenyl]methanesulfonamide This compound was prepared by using a procedure analogous to that outlined for the synthesis of example 262. LCMS: m/z 428.1 (M+H)$^+$.

Example 518

(1R)-1'-{[1-(2-Fluorophenyl)cyclopropyl]carbonyl}-3H-spiro[furo[3,4-c]pyridine-1,3'-pyrrolidin]-3-one This compound was prepared by using a procedure analogous to that outlined for the synthesis of example 95. LCMS: m/z 353.1 (M+H)$^+$.

Example 519

1'-{[1-(2-Chlorophenyl)cyclopropyl]carbonyl}-3H-spiro[furo[3,4-c]pyridine-1,3'-pyrrolidin]-3-one This compound was prepared by using a procedure analogous to that outlined for the synthesis of example 95. LCMS: m/z 369.5 (M+H)$^+$.

Example 520

1'-{[1-(2-Bromophenyl)cyclopropyl]carbonyl}-3H-spiro[furo[3,4-c]pyridine-1,3'-pyrrolidin]-3-one This compound was prepared by using a procedure analogous to that outlined for the synthesis of example 95. LCMS: m/z 414.1 (M+H)$^+$.

Example 521

1'-({1-[2-(Trifluoromethyl)phenyl]cyclopropyl}carbonyl)-3H-spiro[furo[3,4-c]pyridine-1,3'-pyrrolidin]-3-one This compound was prepared by using a procedure analogous to that outlined for the synthesis of example 95. LCMS: m/z 403.1 (M+H)$^+$.

Example 522

1'-{[1-(2-Methoxyphenyl)cyclopropyl]carbonyl)-3H-spiro[furo[3,4-e]pyridine-1,3'-pyrrolidin]-3-one This compound was prepared by using a procedure analogous to that outlined for the synthesis of example 95. LCMS: m/z 365.1 (M+H)$^+$.

Example 523

1'-{[1-(2-Methylphenyl)cyclopropyl]carbonyl}-3H-spiro[furo[3,4-c]pyridine-1,3'-pyrrolidin]-3-one This compound was prepared by using a procedure analogous to that outlined for the synthesis of example 95. LCMS: m/z 349.1 (M+H)$^+$.

Example 524

(1R)-1'-{[1-(2,3-Difluorophenyl)cyclopropyl]carbonyl}-3H-spiro[furo[3,4-c]pyridine-1,3'-pyrrolidin]-3-one This compound was prepared by using a procedure analogous to that outlined for the synthesis of example 95. LCMS: m/z 371.1 (M+H)$^+$.

Example 525

1'-{[1-(2-Chloro-6-fluorophenyl)cyclopropyl]carbonyl}-3H-spiro[furo[3,4-c]pyridine-1,3'-pyrrolidin]-3-one This compound was prepared by using a procedure analogous to that outlined for the synthesis of example 95. LCMS: m/z 387.4 (M+H)$^+$.

Example 526

1'-{[1-(1-Naphthyl)cyclopropyl]carbonyl}-3H-spiro[furo[3,4-c]pyridine-1,3'-pyrrolidin]-3-one This compound was prepared by using a procedure analogous to that outlined for the synthesis of example 95. LCMS: m/z 385.1 (M+H)$^+$.

Example 527

1'-{[1-(2-Fluorophenyl)cyclopropyl]carbonyl}-6-(trifluoromethyl)-3H-spiro[furo[3,4-c]pyridine-1,3'-pyrrolidin]-3-one This compound was prepared by using a procedure analogous to that outlined for the synthesis of example 222. LCMS: m/z 421.1 (M+H)$^+$.

Example 528

6-Chloro-1'-{[1-(4-methylphenyl)cyclopropyl]carbonyl}-3H-spiro[furo[3,4-c]pyridine-1,3'-pyrrolidin]-3-one This compound was prepared by using a procedure analogous to that outlined for the synthesis of example 232. LCMS: m/z 383.5 (M+H)$^+$.

Example 529

6-Chloro-1'-({1-[4-(trifluoromethyl)phenyl]cyclopropyl}carbonyl)-3H-spiro[furo[3,4-c]pyridine-1,3'-pyrrolidin]-3-one This compound was prepared by using a procedure analogous to that outlined for the synthesis of example 232. LCMS: m/z 436.3 (M+H)$^+$.

Example 530

6-Chloro-1'-{[1-(2,4-difluorophenyl)cyclopropyl]carbonyl}-3H-spiro[furo[3,4-c]pyridine-1,3'-pyrrolidin]-3-one This compound was prepared by using a procedure analogous to that outlined for the synthesis of example 232. LCMS: m/z 404.3 (M+H)$^+$.

Example 531

6-Chloro-1'-({1-[3-(difluoromethoxy)phenyl]cyclopropyl}carbonyl)-3H-spiro[furo[3,4-c]pyridine-1,3'-pyrrolidin]-3-one This compound was prepared by using a procedure analogous to that outlined for the synthesis of example 95. LCMS: m/z 435.4 (M+H)$^+$.

Example 532

1'-{[1-(2,4-Dichlorophenyl)cyclopropyl]carbonyl}-3H-spiro[furo[3,4-c]pyridine-1,3'-pyrrolidin]-3-one

Step 1. 1-{[1-(2,4-dichlorophenyl)cyclopropyl]carbonyl}pyrrolidin-3-ol

To a solution of 3-pyrrolidinol (0.861 mL, 0.0106 mol) in N,N-dimethylformamide (5 mL, 0.06 mol) were added 1-(2,4-dichlorophenyl)cyclopropanecarboxylic acid and BOP. After the mixture was stirred for 3 min, DIEA was added. After the reaction mixture was stirred for 3 h, the solution was diluted with AcOEt, washed with sat'd. NaHCO$_3$ aq. (×3), water and brine successively, dried with MgSO$_4$, and concentrated in-vacuo.

Step 2. 1-{[1-(2,4-dichlorophenyl)cyclopropyl]carbonyl}pyrrolidin-3-one

To a solution of 1-{[1-(2,4-dichlorophenyl)cyclopropyl]carbonyl}pyrrolidin-3-ol (3.05 g, 0.0102 mol) in acetone (50 mL, 0.7 mol) was added Jones oxidant in water (8.00 M, 2.54 mL) at 0 degrees celsius and the resulting solution was stirred at rt for 1 hour. The mixture was filtered through celite and the filtrate was concentrated. The resulting residue was dissolved in AcOEt, washed with water and brine successively, dried with MgSO$_4$, and concentrated in-vacuo. The crude product was purified by Combiflash eluting with 40% AcOEt in hexanes.

Step 3

To a solution of 2,2,6,6-tetramethyl-piperidine, (1.18 mL, 0.00700 mol) in tetrahydrofuran (30 mL, 0.4 mol) at −78° C. was added n-butyllithium in hexane (2.5 M, 3.7 mL). After stirring for 15 min., a suspension of niacin (0.287 g, 0.00233 mol) in THF was added and the mixture was stirred at −78° C. for 10 min. The reaction mixture was then warmed to −55° C. for 60 min. A solution of 1-{[1-(2,4-dichlorophenyl)cyclopropyl]carbonyl}pyrrolidin-3-one (580 mg, 0.0019 mol) in THF (2 mL) was added to the above mixture and stirring was continued at −55 degrees celsius for 20 min. The reaction mixture was then allowed to warm to rt for 1 h and then acidified (pH ~1) using 6M HCl aq. solution. The reaction mixture was stirred at rt overnight and then neutralized (pH ~7). The product from the mixture was extracted with AcOEt. The organic extract was washed with brine, dried with MgSO$_4$, and concentrated in-vacuo. The crude product was purified by Combiflash followed by separation of the enantiomers using a chiral column. LCMS: m/z 402.0 & 404.0 (M+H)$^+$.

Example 533

1'-{[1-(4-Chlorophenyl)cyclopropyl]carbonyl}-4-methoxy-3H-spiro[furo[3,4-c]pyridine-1,3'-pyrrolidin]-3-one This compound was prepared by using a procedure analogous to that outlined in steps 1-3 of example 227. LCMS: m/z 399.4 (M+H)$^+$.

Example 534

1'-{[1-(4-Chlorophenyl)cyclopropyl]carbonyl}-4-hydroxy-3H-spiro[furo[3,4-c]pyridine-1,3'-pyrrolidin]-3-one This compound was prepared by using a procedure analogous to that outlined in steps 1-3 of example 227. LCMS: m/z 385.4 (M+H)$^+$.

Example 535

6-Chloro-1'-{[1-(3,4-dichlorophenyl)cyclopropyl]carbonyl}-3H-spiro[furo[3,4-c]pyridine-1,3'-pyrrolidin]-3-one This compound was prepared by using a procedure analogous to that outlined in steps 1-2 of example 232. LCMS: m/z 438.4 (M+H)$^+$.

Example 536

1'-{[1-(4-Chloro-2-fluorophenyl)cyclopropyl]carbonyl}-3H-spiro[furo[3,4-c]pyridine-1,3'-pyrrolidin]-3-one This compound was prepared by using a procedure analogous to that outlined in steps 1-2 of example 95. LCMS: m/z 387.0 (M+H)$^+$409.0 (M+Na)$^+$.

Example 537

6-Chloro-1'-{[1-(2,4-difluorophenyl)cyclopropy]carbonyl}-3H-spiro[furo[3,4-c]pyridine-1,3'-pyrrolidin]-3-one This compound was prepared by using a procedure analogous to that outlined for the synthesis of example 232. LCMS: m/z 405.0 (M+H)$^+$.

Example 538

1'-{[1-(2-Chloro-4-fluorophenyl)cyclopropyl]carbonyl}-3H-spiro[furo[3,4-c]pyridine-1,3'-pyrrolidin]-3-one This compound was prepared by using a procedure analogous to that outlined for the synthesis of example 95. LCMS: m/z 387.3 (M+H)$^+$.

Example 539

1'-{[1-(2,4-Difluorophenyl)cyclopropyl]carbonyl}-3H-spiro[furo[3,4-c]pyridine-1,3'-pyrrolidin]-3-one This compound was prepared by using a procedure analogous to that outlined for the synthesis of example 95. LCMS: m/z 371.1 (M+H)$^+$.

Example 540

1'-({1-[4-(Methylthio)phenyl]cyclopropyl}carbonyl)-3H-spiro[furo[3,4-c]pyridine-1,3'-pyrrolidin]-3-one This compound was prepared by using a procedure analogous to that outlined for the synthesis of example 95. LCMS: m/z 381.2 (M+H)$^+$403.2 (M+Na)$^+$.

Example 541

1'-[(1-{4-[(Trifluoromethyl)thio]phenyl}cyclopropyl)carbonyl]-3H-spiro[furo[3,4-c]pyridine-1,3'-pyrrolidin]-3-one This compound was prepared by using a procedure analogous to that outlined for the synthesis of example 95. LCMS: m/z 435.0 (M+H)$^+$437.0 (M+Na)$^+$.

Example 542

(1R)-1'-{[144-Chlorophenyl)cyclopentyl]carbonyl}-3H-spiro[2-benzofuran-1,3'-pyrrolidin]-3-one This compound was prepared by using a procedure analogous to that outlined for the synthesis of example 4. LCMS: m/z 396.5 (M+H)$^+$.

Example 543

1-{[1-(4-Chlorophenyl)cyclohexyl]carbonyl}azepane

This compound was prepared by using a procedure analogous to that outlined for the synthesis of example 4. LCMS: m/z 320.1 (M+H)$^+$.

Example 544

Methyl 4-[5-(1-{[(1R)-3-oxo-1'H,3H-spiro[2-benzofuran-1,3'-pyrrolidin]-1'-yl]carbonyl}cyclopropyl)pyridin-2-yl]piperazine-1-carboxylate This compound was prepared by using a procedure analogous to that outlined for the synthesis of example 410. LCMS: m/z 477.2 (M+H)$^+$.

Example 545

N,N-Dimethyl-4-[4-(1-{[(1R)-3-oxo-1'H,3H-spiro[2-benzofuran-1,3'-pyrrolidin]-1'-yl]carbonyl}cyclopropyl)phenyl]piperazine-1-carboxamide This compound was prepared by using a procedure analogous to that described for the synthesis of example 421. LCMS: m/z 489.3 (M+H)$^+$.

Example 546

Methyl 4-[3-fluoro-4-(1-{[(1R)-3-oxo-1'H,3H-spiro[2-benzofuran-1,3'-pyrrolidin]-1'-yl]carbonyl}cyclopropyl)phenyl]piperazine-1-carboxylate This compound was prepared by using a procedure analogous to that described for the synthesis of example 421. LCMS: m/z 494.3 (M+H)$^+$.

Example 547

(1R)-1'-({1-[2-Fluoro-4-(4-propionylpiperazin-1-yl)phenyl]cyclopropyl}carbonyl)-3H-spiro[2-benzofuran-1,3'-pyrrolidin]-3-one This compound was prepared by using a procedure analogous to that described for the synthesis of example 421. LCMS: m/z 492.3 (M+H)$^+$.

Example 548

(1R)-1'-({1-[2-Fluoro-4-(4-isobutyrylpiperazin-1-yl)phenyl]cyclopropyl}carbonyl)-3H-spiro[2-benzofuran-1,3'-pyrrolidin]-3-one This compound was prepared by using a procedure analogous to that described for the synthesis of example 421. LCMS: m/z 506.2 (M+H)$^+$.

Example 549

(1R)-1'-[(1-{4-[4-(Cyclopropylcarbonyl)piperazin-1-yl]-2-fluorophenyl}cyclopropyl)carbonyl]-3H-spiro[2-benzofuran-1,3'-pyrrolidin]-3-one This compound was prepared by using a procedure analogous to that described for the synthesis of example 421. LCMS: m/z 504.2 (M+H)$^+$.

Example 550

(1R)-1'-({1-[4-(4-Acetylpiperazin-1-yl)-2-fluorophenyl]cyclopropyl}carbonyl)-3H-spiro[2-benzofuran-1,3'-pyrrolidin]-3-one This compound was prepared by using a procedure analogous to that described for the synthesis of example 421. LCMS: m/z 478.3 (M+H)$^+$.

Example 551

4-[3-Fluoro-4-(1-{[(1R)-3-oxo-1'H,3H-spiro[2-benzofuran-1,3'-pyrrolidin]-1'-yl]carbonyl}cyclopropyl)phenyl]-N,N-dimethylpiperazine-1-carboxamide This compound was prepared by using a procedure analogous to that described for the synthesis of example 421. LCMS: m/z 507.3 (M+H)$^+$.

Example 552

(1R)-1'-({1-[4-(4-Hydroxypiperidin-1-yl)phenyl]cyclopropyl}carbonyl)-3H-spiro[2-benzofuran-1,3'-pyrrolidin]-3-one This compound was prepared by using a procedure analogous to that described for the synthesis of example 420. LCMS: m/z 433.2 (M+H)$^+$.

Example 553

N,N-Dimethyl-1-[4-(1-{[(1R)-3-oxo-1'H,3H-spiro[2-benzofuran-1,3'-pyrrolidin]-1'-yl]carbonyl}cyclopropyl)phenyl]piperidine-4-carboxamide Step 1.
1-[(Benzyloxy)carbonyl]piperidine-4-carboxylic acid Sodium carbonate (1.59 g, 0.0150 mol) was added to a solution of piperidine-4-carboxylic acid (0.970 g, 0.00751 mol) in water (15 mL). After the solid was dissolved, benzyl chloroformate (1.54 g, 0.00901 mol) was added dropwise. The mixture was stirred at rt for 3 h. The mixture was carefully acidified (pH=4) with 2N HCl, and then was extracted with DCM (4×10 mL). The combined organic layer was dried over Na2SO4, filtered, and concentrated under reduced pressure to give the desired product.

Step 2. benzyl 4-[(dimethylamino)carbonyl]piperidine-1-carboxylate

Benzotriazol-1-yloxytris(dimethylamino)phosphonium hexafluorophosphate (0.442 g, 0.00100 mol) was added to a solution of 1-[(benzyloxy)carbonyl]piperidine-4-carboxylic acid (0.263 g, 0.00100 mol) in methylene chloride (3.00 mL, 0.0468 mol), followed by 4-methylmorpholine (0.440 mL, 0.00400 mol) and dimethylamine in tetrahydrofuran (2.00 M, 0.750 mL). The mixture was stirred at rt for 1 h and was diluted with ethyl acetate (20 mL). The solution was washed with NaHCO$_3$ (7.5%, 3×5 mL) and with brine (5 mL) successively. The organic layer was dried over Na$_2$SO4, filtered, and concentrated under reduced pressure. The residue was purified by Combiflash eluting with ethyl acetate/hexane to give the desired product.

Step 3. N,N-dimethylpiperidine-4-carboxamide

Palladium (10.0 mg, 9.40E-6 mol) was added to a solution of benzyl 4-[(dimethylamino)carbonyl]piperidine-1-carboxylate (190.0 mg, 0.0006544 mol) in methanol (5.0 mL, 0.12 mol) under nitrogen. The mixture was hydrogenised with a balloon filled with hydrogen for 3 h. The mixture was filtered and the filtrate was concentrated to give the desired product.

Step 4. N,N-Dimethyl-1-[4-(1-{[(1R)-3-oxo-1'H,3H-spiro[2-benzofuran-1,3'-pyrrolidin]-1'-yl]carbonyl}cyclopropyl)phenyl]piperidine-4-carboxamide The title compound was prepared by using a procedure analogous to that described for the synthesis of example 420. LCMS: m/z 488.2 (M+H)+.

Example 554

Methyl 4-[4-(1-{[(1R)-3-oxo-1'H,3H-spiro[2-benzofuran-1,3'-pyrrolidin]-1'-yl]carbonyl}cyclopropyl)phenyl]piperidine-1-carboxylate This compound was prepared by using a procedure analogous to that described for the synthesis of example 490. LCMS: m/z 475.1 (M+H)+.

Example 555

Ethyl 4-[4-(1-{[(1R)-3-oxo-1'H,3H-spiro[2-benzofuran-1,3'-pyrrolidin]-1'-yl]carbonyl}cyclopropyl)phenyl]piperidine-1-carboxylate This compound was prepared by using a procedure analogous to that described for the synthesis of example 490. LCMS: m/z 489.1 (M+H)+.

Example 556

(1R)-1'-({1-[4-(1-Acetylpiperidin-4-yl)phenyl]cyclopropyl}carbonyl)-3H-spiro[2-benzofuran-1,3'-pyrrolidin]-3-one This compound was prepared by using a procedure analogous to that described for the synthesis of example 490. LCMS: m/z 459.2 (M+H)+.

Example 557

(1R)-1'-({1-[4-(1-Isobutyrylpiperidin-4-yl)phenyl]cyclopropyl}carbonyl)-3H-spiro[2-benzofuran-1,3'-pyrrolidin]-3-one This compound was prepared by using a procedure analogous to that described for the synthesis of example 492. LCMS: m/z 487.2 (M+H)+.

Example 558

(1R)-1'-({1-[4-(1-Propionylpiperidin-4-yl)phenyl]cyclopropyl}carbonyl)-3H-spiro[2-benzofuran-1,3'-pyrrolidin]-3-one This compound was prepared by using a procedure analogous to that described for the synthesis of example 490.

Example 559

(1R)-1'-[(1-{4-[1-(3-Methylbutanoyl)piperidin-4-yl]phenyl}cyclopropyl)carbonyl]-3H-spiro[2-benzofuran-1,3'-pyrrolidin]-3-one This compound was prepared by using a procedure analogous to that described for the synthesis of example 492.

Example 560

(1R)-1'-({1-[4-(1-Acetylpiperidin-4-yl)phenyl]cyclopropyl}carbonyl)-3H-spiro[furo[3,4-c]pyridine-1,3'-pyrrolidin]-3-one This compound was prepared by using a procedure analogous to that described for the synthesis of example 490. LCMS: m/z 460.2 (M+H)+.

Example 561

(1R)-1'-({1-[4-(1-Isobutyrylpiperidin-4-yl)phenyl]cyclopropyl}carbonyl)-3H-spiro[furo[3,4-c]pyridine-1,3'-pyrrolidin]-3-one This compound was prepared by using a procedure analogous to that described for the synthesis of example 492. LCMS: m/z 488.2 (M+H)+.

Example 562

(1R)-1'-({1-[4-(1-Propionylpiperidin-4-yl)phenyl]cyclopropyl}carbonyl)-3H-spiro[furo[3,4-c]pyridine-1,3'-pyrrolidin]-3-one This compound was prepared by using a procedure analogous to that described for the synthesis of example 492. LCMS: m/z 474.2 (M+H)+.

Example 563

(1R)-1'-[(1-{4-[1-(3-Methylbutanoyl)piperidin-4-yl]phenyl}cyclopropyl)carbonyl]-3H-spiro[furo[3,4-e]pyridin e-1,3'-pyrrolidin]-3-one This compound was prepared by using a procedure analogous to that described for the synthesis of example 492. LCMS: m/z 502.2 (M+H)+.

Example 564

Methyl 4-[4-(1-{[(1R)-3-oxo-1'H,3H-spiro[furo[3,4-c]pyridine-1,3'-pyrrolidin]-1'-yl]carbonyl}cyclopropyl)phenyl]piperidine-1-carboxylate This compound was prepared by using a procedure analogous to that described for the synthesis of example 490. LCMS: m/z 476.2 (M+H)+.

Example 565

Ethyl 4-[4-(1-{[(1R)-3-oxo-1'H,3H-spiro[furo[3,4-c]pyridine-1,3'-pyrrolidin]-1'-yl]carbonyl}cyclopropyl)phenyl]piperidine-1-carboxylate This compound was prepared by using a procedure analogous to that described for the synthesis of example 490.

Example 566

Isopropyl 4-[4-(1-{[(1R)-3-oxo-1'H,3H-spiro[furo[3,4-c]pyridine-1,3'-pyrrolidin]-1'-yl]carbonyl}cyclopropyl)phenyl]piperidine-1-carboxylate This compound was prepared by using a procedure analogous to that described for the synthesis of example 490. LCMS: m/z 504.3 (M+H)+.

Example 567

Methyl 4-hydroxy-4-[4-(1-{[(1R)-3-oxo-1'H,3H-spiro[2-benzofuran-1,3'-pyrrolidin]-1'-yl]carbonyl}cyclopropyl)phenyl]piperidine-1-carboxylate This compound was prepared by using a procedure analogous to that described in steps 1-5 of example 210, with the exception that the TFA mediated dehydration in step 4 was omitted. LCMS: m/z 491.2 (M+H)$^+$.

Example 568

Ethyl 4-hydroxy-4-[4-(1-{[(1R)-3-oxo-1'H,3H-spiro[2-benzofuran-1,3'-pyrrolidin]-1'-yl]carbonyl}cyclopropyl)phenyl]piperidine-1-carboxylate This compound was prepared by using a procedure analogous to that described in steps 1-5 of example 210, with the exception that the TFA mediated dehydration in step 4 was omitted. LCMS: m/z 505.3 (M+H)$^+$.

Example 569

Methyl 4-(5-{1-[(3-pyridin-3-ylpyrrolidin-1-yl)carbonyl]cyclopropyl}pyridin-2-yl)piperazine-1-carboxylate This compound was prepared by using a procedure analogous to that described in steps 1-4 of example 163. LCMS: m/z 436.2 (M+H)$^+$.

Example 570

Ethyl 4-(5-{1-[(3-pyridin-3-ylpyrrolidin-1-yl)carbonyl]cyclopropyl}pyridin-2-yl)piperazine-1-carboxylate This compound was prepared by using a procedure analogous to that described in steps 1-4 of example 163.

Example 571

1-Acetyl-4-(5-{1-[(3-pyridin-3-ylpyrrolidin-1-yl)carbonyl]cyclopropyl}pyridin-2-yl)piperazine This compound was prepared by using a procedure analogous to that described in steps 1-4 of example 163. LCMS: m/z 420.2 (M+H)$^+$.

Example 572

1-Isobutyryl-4-(5-{1-[(3-pyridin-3-ylpyrrolidin-1-yl)carbonyl]cyclopropyl}pyridin-2-yl)piperazine This compound was prepared by using a procedure analogous to that described for the synthesis of example 321. LCMS: m/z 448.3 (M+H)$^+$.

Example 573

1-(Cyclopropylcarbonyl)-4-(5-{1-[(3-pyridin-3-ylpyrrolidin-1-yl)carbonyl]cyclopropyl}pyridin-2-yl)piperazine This compound was prepared by using a procedure analogous to that described for the synthesis of example 321. LCMS: m/z 446.3 (M+H$^+$)$^+$.

Example 574

Isopropyl 4-[4-(1-{[(1R)-3-oxo-1'H,3H-spiro[2-benzofuran-1,3'-pyrrolidin]-1'-yl]carbonyl}cyclopropyl)phenyl]piperazine-1-carboxylate This compound was prepared by using a procedure analogous to that described for the synthesis of example 421. LCMS: m/z 504.3 (M+H)$^+$.

Example 575

(1R)-1'-[(1-{4-[6-(Pyrrolidin-1-ylcarbonyl)pyridin-3-yl]phenyl}cyclopropyl)carbonyl]-3H-spiro[2-benzofuran-1,3'-pyrrolidin]-3-one This compound was prepared by using a procedure analogous to that described for the synthesis of example 250. LCMS: m/z 508.2 (M+H)$^+$.

Example 576

N-Ethyl-N-methyl-5-[4-(1-{[(1R)-3-oxo-1'H,3H-spiro[2-benzofuran-1,3'-pyrrolidin]-1'-yl]carbonyl}cyclopropyl)phenyl]pyridine-2-carboxamide This compound was prepared by using a procedure analogous to that described for the synthesis of example 250. LCMS: m/z 496.6 (M+H)$^+$.

Example 577

N,N-Diethyl-5-[4-(1-{[(1R)-3-oxo-1'H,3H-spiro[2-benzofuran-1,3'-pyrrolidin]-1'-yl]carbonyl}cyclopropyl)phenyl]pyridine-2-carboxamide This compound was prepared by using a procedure analogous to that described for the synthesis of example 250. LCMS: m/z 510.2 (M+H)$^+$.

Example 578 tert-Butyl {4-[5-(1-{[(1R)-3-oxo-1'H,3H-spiro[2-benzofuran-1,3'-pyrrolidin]-1'-yl]carbonyl}cyclopropyl)pyridin-2-yl]phenyl}carbamate This compound was prepared by using a procedure analogous to that described for the synthesis of example 173. LCMS: m/z 526.2 (M+H)$^+$.

Example 579

N,N-Dimethyl-1-[5-(1-{[(1R)-3-oxo-1'H,3H-spiro[2-benzofuran-1,3'-pyrrolidin]-1'-yl]carbonyl}cyclopropyl)pyridin-2-yl]piperidine-4-carboxamide This compound was prepared by using a procedure analogous to that described for the synthesis of example 163, steps 1-3.

Example 580

(1R)-1'-{[1-(6-Piperidin-1-ylpyridin-3-yl)cyclopropyl]carbonyl}-3H-spiro[furo[3,4-c]pyridine-1,3'-pyrrolidin]-3-one This compound was prepared by using a procedure analogous to that described for the synthesis of example 163, steps 1-3. LCMS: m/z 419.2 (M+H)$^+$.

Example 581

(1R)-1'-({1-[2-Fluoro-4-(2-oxopyrrolidin-1-yl)phenyl]cyclopropyl}carbonyl)-3H-spiro[2-benzofuran-1,3'-pyrrolidin]-3-one This compound was prepared by using a procedure analogous to that described for the synthesis of example 257. LCMS: m/z 435.2 (M+H)$^+$; 457.1 (M+Na)$^+$.

Example 582

(1R)-1'-({1-[2-Fluoro-4-(2-oxo-1,3-oxazolidin-3-yl)phenyl]cyclopropyl}carbonyl)-3H-spiro[furo[3,4-c]pyridine-1,3'-pyrrolidin]-3-one This compound was prepared by using a procedure analogous to that described for the synthesis of example 257. LCMS: m/z 438.1 (M+H)$^+$.

Example 583

(112)-1'-({1-[4-(2-Oxoazetidin-1-yl)phenyl]cyclopropyl}carbonyl)-3H-spiro[2-benzofuran-1,3'-pyrrolidin]-3-one This compound was prepared by using a procedure analogous to that described for the synthesis of example 257. LCMS: m/z 403.2 (M+H)$^+$.

Example 584

(1R)-1'-({1-[2-Fluoro-4-(2-oxoazetidin-1-yl)phenyl]cyclopropyl}carbonyl)-3H-spiro[2-benzofuran-1,3'-pyrrolidin]-3-one This compound was prepared by using a procedure analogous to that described for the synthesis of example 257. LCMS: m/z 421.1 (M+H)$^+$.

Example 585

1'-({1-[4-(2-Oxoazetidin-1-yl)phenyl]cyclopropyl}carbonyl)-3H-spiro[furo[3,4-c]pyridine-1,3'-pyrrolidin]-3-one This compound was prepared by using a procedure analogous to that described for the synthesis of example 257. LCMS: m/z 404.2 (M+H)$^+$.

Example 586

(1R)-1'-({1-[2-Fluoro-4-(2-oxoazetidin-1-yl)phenyl]cyclopropyl}carbonyl)-3H-spiro[furo[3,4-c]pyridine-1,3'-pyrrolidin]-3-one This compound was prepared by using a procedure analogous to that described for the synthesis of example 257. LCMS: m/z 422.2 (M+H)$^+$.

Example 587

Propyl 4-[5-(1-{[(1R)-3-oxo-1'H,3H-spiro[2-benzofuran-1,3'-pyrrolidin]-1'-yl]carbonyl}cyclopropyl)pyridin-2-yl]piperazine-1-carboxylate This compound was prepared by using a procedure analogous to that described for the synthesis of example 410. LCMS: m/z 505.2 (M+H$^+$)$^+$.

Example 588

Isobutyl 4-[5-(1-{[1R)-3-oxo-1'H,3H-spiro[2-benzofuran-1,3'-pyrrolidin]-1'-yl]carbonyl}cyclopropyl)pyridin-2-yl]piperazine-1-carboxylate This compound was prepared by using a procedure analogous to that described for the synthesis of example 410. LCMS: m/z 519.3 (M+H)$^+$.

Example 589

Isopropyl 4-[5-(1-{[(1R)-3-oxo-1'H,3H-spiro[2-benzofuran-1,3'-pyrrolidin]-1'-yl]carbonyl}cyclopropyl)pyridin-2-yl]piperazine-1-carboxylate This compound was prepared by using a procedure analogous to that described for the synthesis of example 410. LCMS: m/z 505.3 (M+H)$^+$.

Example 590

Ethyl 4-[4-({[(1R)-3-oxo-1'H,3H-spiro[2-benzofuran-1,3'-pyrrolidin]-1'-yl]carbonyl}cyclopropyl)phenyl]piperazine-1-carboxylate This compound was prepared by using a procedure analogous to that described for the synthesis of example 421. LCMS: m/z 490.3 (M+H)$^+$.

Example 591

Propyl 4-[4-(1-{[(1R)-3-oxo-1'H,3H-spiro[2-benzofuran-1,3'-pyrrolidin]-1'-yl]carbonyl}cyclopropyl)phenyl]piperazine-1-carboxylate This compound was prepared by using a procedure analogous to that described for the synthesis of example 421. LCMS: m/z 504.3 (M+H)$^+$.

Example 592

Isobutyl 4-[4-(1-{[(1R)-3-oxo-1'H,3H-spiro[2-benzofuran-1,3'-pyrrolidin]-1'-yl]carbonyl}cyclopropyl)phenyl]piperazine-1-carboxylate This compound was prepared by using a procedure analogous to that described for the synthesis of example 421. LCMS: m/z 518.3 (M+H)+.

Example 593

(1R)-1'[(1-{4-[4-(Cyclopropylacetyl)piperazin-1-yl]phenyl}cyclopropyl)carbonyl]-3H-spiro[2-benzofuran-1,3'-pyrrolidin]-3-one This compound was prepared by using a procedure analogous to that described in step 1 of example 421, followed by the BOP mediated coupling that was outlined in example 414. LCMS: m/z 500.3 (M+H)+.

Example 594

(1R)-1'-[(1-{4-[4-(Cyclopropylacetyl)piperazin-1-yl]-2-fluorophenyl}cyclopropyl) carbonyl]-3H-spiro[2-benzofuran-1,3'-pyrrolidin]-3-one This compound was prepared by using a procedure analogous to that described in step 1 of example 421, followed by the BOP mediated coupling that was outlined in example 414. LCMS: m/z 518.2 (M+H)+.

Example 595

(1R)-1'-[(1-{4-[4-(3-Methylbutanoyl)piperazin-1-yl]phenyl}cyclopropyl)carbonyl]-3H-spiro[2-benzofuran-1,3'-pyrrolidin]-3-one This compound was prepared by using a procedure that was analogous to that described in step 1 of example 421, followed by the BOP mediated coupling that was outlined in example 414. LCMS: m/z 502.3 (M+H)+.

Example 596

(1R)-1'-[1-{2-Fluoro-4-[4-(3-methylbutanoyl)piperazin-1-yl]phenyl}cyclopropyl)carbonyl]-3H-spiro[2-benzofuran-1,3'-pyrrolidin]-3-one This compound was prepared by using a procedure analogous to that described in step 1 of example 421, followed by the BOP mediated coupling that was outlined in example 414. LCMS: m/z 520.3 (M+H)+.

Example 597

(1R)-1'-[(1-{4-[4-(Tetrahydro-2H-pyran-4-ylcarbonyl)piperazin-1-yl]phenyl}cyclopropyl)carbonyl]-3H-spiro[2-benzofuran-1,3'-pyrrolidin]-3-one This compound was prepared by using a procedure analogous to that described in step 1 of example 421, followed by the BOP mediated coupling that was outlined in example 414. LCMS: m/z 530.3 (M+H)+.

Example 598

Ethyl 4-[3-fluoro-4-(1-{[(1R)-3-oxo-1'H,3H-spiro[2-benzofuran-1,3'-pyrrolidin]-1'-yl]carbonyl}cyclopropyl)phenyl]piperazine-1-carboxylate This compound was prepared by using a procedure analogous to that described in steps 1-2 of example 421. LCMS: m/z 508.3 (M+H)+.

Example 599

Propyl 4-[3-fluoro-4-(1-{[(1R)-3-oxo-1'H,3H-spiro[2-benzofuran-1,3'-pyrrolidin]-1'-yl]carbonyl}cyclopropyl)phenyl]piperazine-1-carboxylate This compound was prepared by using a procedure analogous to that described in steps 1 & 2 of example 421. LCMS: m/z 522.3 (M+H)+.

Example 600

4-[3-Fluoro-4-(1-{[(1R)-3-oxo-1'H,3H-spiro[2-benzofuran-1,3'-pyrrolidin]-1'-yl]carbonyl}cyclopropyl)phenyl]-N-methylpiperazine-1-carboxamide This compound was prepared by using a procedure analogous to that described in steps 1 & 2 of example 421. LCMS: m/z 493.1 (M+H)+.

Example 601

(1R)-1'-[(1-{2-Fluoro-4-[4-(3-methylbutanoyl)piperazin-1-yl]phenyl}cyclopropyl)carbonyl]-3H-spiro[2-benzofuran-1,3'-pyrrolidin]-3-one This compound was prepared by using a procedure analogous to that described in step 1 of example 421, followed by the BOP mediated coupling that was outlined in example 414. LCMS: m/z 520.3 (M+H)+.

Example 602

(1R)-1'-[(1-{4-[4-(Cyclopropylacetyl)piperazin-1-yl]-2-fluorophenyl}cyclopropyl)carbonyl]-3H-spiro[2-benzofuran-1,3'-pyrrolidin]-3-one This compound was prepared by using a procedure analogous to that described in step 1 of example 421, followed by the BOP mediated coupling that was outlined in example 414. LCMS: m/z 518.2 (M+H)+.

Example 603

Methyl 4-[3-fluoro-4-(1-{[(1R)-3-oxo-1'H,3H-spiro[furo[3,4-c]pyridine-1,3'-pyrrolidin]-1'-yl]carbonyl}cyclopropyl)phenyl]piperazine-1-carboxylate This compound was prepared by using a procedure analogous to that described in steps 1 & 2 of example 421. LCMS: m/z 495.2 (M+H)+.

Example 604

Ethyl 4-[3-fluoro-4-(1-{[(1R)-3-oxo-1'H,3H-spiro [furo[3,4-c]pyridine-1,3'-pyrrolidin]-1'-yl] carbonyl}cyclopropyl)phenyl]piperazine-1-carboxylate This compound was prepared by using a procedure analogous to that described in steps 1 & 2 of example 421. LCMS: m/z 509.2 (M+H)$^+$.

Example 605

Propyl 4-[3-fluoro-4-(1-{[(1R)-3-oxo-1'H,3H-spiro [furo[3,4-c]pyridine-1,3'-pyrrolidin]-1'-yl] carbonyl}cyclopropyl)phenyl]piperazine-1-carboxylate This compound was prepared by using a procedure analogous to that described in steps 1 & 2 of example 421.

Example 606 i-Propyl 4-[3-fluoro-4-(1-{[(1R)-3-oxo-1'H,3H-spiro [furo[3,4-c]pyridine-1,3'-pyrrolidin]-1'-yl] carbonyl}cyclopropyl)phenyl]piperazine-1-carboxylate This compound was prepared by using a procedure analogous to that described in steps 1 & 2 of example 421.

Example 607 i-Butyl 4-[3-fluoro-4-(1-{[(1R)-3-oxo-1'H,3H-spiro [furo[3,4-c]pyridine-1,3'-pyrrolidin]-1'-yl] carbonyl}cyclopropyl)phenyl]piperazine-1-carboxylate This compound was prepared by using a procedure analogous to that described in steps 1 & 2 of example 421. LCMS: m/z 537.1 (M+H$^+$)'.

Example 608

(1R)-1'[(1-{4-[4-(Cyclopropylcarbonyl)piperazine-1-yl]-2-fluorophenyl}cyclopropyl) carbonyl]-3H-spiro [furo[3,4-c]pyridine-1,3'-pyrrolidin]-3-one This compound was prepared by using a procedure analogous to that described in step 1 of example 421, followed by the BOP mediated coupling that was outlined in example 414.

Example 609

(1R)-1'-[(1-{2-Fluoro-4-[4-(3-methylbutanoyl)piperazin-1-yl]phenyl}cyclopropyl) carbonyl]-3H-spiro [furo[3,4-c]pyridine-1,3'-pyrrolidin]-3-one This compound was prepared by using a procedure analogous to that described in step 1 of example 421, followed by the BOP mediated coupling that was outlined in example 414. LCMS: m/z 521.3 (M+H)$^+$.

Example 610

N,N-Dimethyl-5-[4-(1-{[(1R)-3-oxo-1'H,3H-spiro[2-benzofuran-1,3'-pyrrolidin]-1'-yl] carbonyl}cyclopropyl)phenyl]pyridine-2-carboxamide This compound was prepared by using a procedure analogous to that described in steps 1 & 2 of example 250. LCMS: m/z 482.2 (M+H)$^+$.

Example 611

N-Ethyl-5-[4-(1-{[(1R)-3-oxo-1'H,3H-spiro[2-benzofuran-1,3'-pyrrolidin]-1'-yl]carbonyl}cyclopropyl) phenyl]pyridine-2-carboxamide This compound was prepared by using a procedure analogous to that described in steps 1 & 2 of example 250. LCMS: m/z 482.2 (M+H)$^+$.

Example 612

N-Isopropyl-5-[4-(1-{[(1R)-3-oxo-1'H,3H-spiro[2-benzofuran-1,3'-pyrrolidin]-1'-yl] carbonyl}cyclopropyl)phenyl]pyridine-2-carboxamide This compound was prepared by using a procedure analogous to that described in steps 1 & 2 of example 250. LCMS: m/z 496.2 (M+H)$^+$.

Example 613

5-[3-Fluoro-4-(1-{[(1R)-3-oxo-1'H,3H-spiro[2-benzofuran-1,3'-pyrrolidin]-1'-yl]carbonyl}cyclopropyl) phenyl]-N-methylpyridine-2-carboxamide This compound was prepared by using a procedure analogous to that described in steps 1 & 2 of example 250. LCMS: m/z 486.2 (M+H)$^+$.

Example 614

5-[3-Fluoro-4-(1-{[(1R)-3-oxo-1'H,3H-spiro[2-benzofuran-1,3'-pyrrolidin]-1'-yl]carbonyl}cyclopropyl) phenyl]-N-ethylpyridine-2-carboxamide This compound was prepared by using a procedure analogous to that described in steps 1 & 2 of example 250. LCMS: m/z 500.2 (M+H)$^+$.

Example 615

5-[3-Fluoro-4-(1-{[(1R)-3-oxo-1'H,3H-spiro[2-benzofuran-1,3'-pyrrolidin]-1'-yl]carbonyl}cyclopropyl) phenyl]-N-i-propylpyridine-2-carboxamide This compound was prepared by using a procedure analogous to that described in steps 1 & 2 of example 250. LCMS: m/z 514.2 (M+H)$^+$.

Example 616

5-[3-Fluoro-4-(1-{[(1R)-3-oxo-1'H,3H-spiro[2-benzofuran-1,3'-pyrrolidin]-1'-yl]carbonyl}cyclopropyl)phenyl]-N,N-dimethylpyridine-2-carboxamide This compound was prepared by using a procedure analogous to that described in steps 1 & 2 of example 250. LCMS: m/z 500.2 (M+H)$^+$.

Example 617

5-[3-Fluoro-4-(1-{[(1R)-3-oxo-1'H,3H-spiro[furo[3,4-c]pyridine-1,3'-pyrrolidin]-1'-yl]carbonyl}cyclopropyl)phenyl]-N-methylpyridine-2-carboxamide This compound was prepared by using a procedure analogous to that described in steps 1 & 2 of example 250. LCMS: m/z 487.2 (M+H)$^+$.

Example 618

N-Ethyl-5-[3-fluoro-4-(1-{[(1R)-3-oxo-1'H,3H-spiro[furo[3,4-c]pyridine-1,3'-pyrrolidin]-1'-yl]carbonyl}cyclopropyl)phenyl]pyridine-2-carboxamide This compound was prepared by using a procedure analogous to that described in steps 1 & 2 of example 250. LCMS: m/z 501.2 (M+H)$^+$.

Example 619

5-[3-Fluoro-4-(1-{[(1R)-3-oxo-1'H,3H-spiro[furo[3,4-c]pyridine-1,3'-pyrrolidin]-1'-yl]carbonyl}cyclopropyl)phenyl]-N-isopropylpyridine-2-carboxamide This compound was prepared by using a procedure analogous to that described in steps 1 & 2 of example 250. LCMS: m/z 515.2 (M+H)$^+$.

Example 620

5-[3-Fluoro-4-(1-{[(1R)-3-oxo-1'H,3H-spiro[furo[3,4-c]pyridine-1,3'-pyrrolidin]-1'-yl]carbonyl}cyclopropyl)phenyl]-N,N-dimethylpyridine-2-carboxamide This compound was prepared by using a procedure analogous to that described in steps 1 & 2 of example 250. LCMS: m/z 501.2 (M+H)$^+$.

Example 621

6-[3-Fluoro-4-(1-{[(1R)-3-oxo-1'H,3R-spiro[2-benzofuran-1,3'-pyrrolidin]-1'-yl]carbonyl}cyclopropyl)phenyl]-N-methylnicotinamide This compound was prepared by using a procedure analogous to that described in steps 1 & 2 of example 250. LCMS: m/z 486.1 (M+H)$^+$.

Example 622

6-[3-Fluoro-4-(1-{[(1R)-3-oxo-1'H,3H-spiro[2-benzofuran-1,3'-pyrrolidin]-1'-yl]carbonyl}cyclopropyl)phenyl]-N,N-dimethylnicotinamide This compound was prepared by using a procedure analogous to that described in steps 1 & 2 of example 250. LCMS: m/z 500.2 (M+H$^+$)'.

Example 623

N-Methyl-6-[4-(1-{[(1R)-3-oxo-1'H,3H-spiro[2-benzofuran-1,3'-pyrrolidin]-1'-yl]carbonyl}cyclopropyl)phenyl]nicotinamide This compound was prepared by using a procedure analogous to that described in steps 1 & 2 of example 250. LCMS: m/z 468.2 (M+H)$^+$.

Example 624

N,N-Dimethyl-6-[4-(1-{[(1R)-3-oxo-1'H,3H-spiro[2-benzofuran-1,3'-pyrrolidin]-1'-yl]carbonyl}cyclopropyl)phenyl]nicotinamide This compound was prepared by using a procedure analogous to that described in steps 1 & 2 of example 250. LCMS: m/z 482.2 (M+H)$^+$.

Example 625

(1R)-1'-({1-[4-(1-Isobutyryl-1,2,3,6-tetrahydropyridin-4-yl)phenyl]cyclopropyl}carbonyl)-3H-spiro[2-benzofuran-1,3'-pyrrolidin]-3-one This compound was prepared by using a procedure that was analogous to that described for the synthesis of example 454. LCMS: m/z 485.3 (M+H)$^+$.

Example 626

(1R)-1'-({1-[4-(1-Propionyl-1,2,3,6-tetrahydropyridin-4-yl)phenyl]cyclopropyl}carbonyl)-3H-spiro[2-benzofuran-1,3'-pyrrolidin]-3-one This compound was prepared by using a procedure that was analogous to that described for the synthesis of example 454. LCMS: m/z 471.3 (M+H)$^+$.

Example 627

(1R)-1'-({1-[3-Fluoro-4-(3-methyl-1H-pyrazol-1-yl)phenyl]cyclopropyl}carbonyl)-3H-spiro[furo[3,4-c]pyridine-1,3'-pyrrolidin]-3-one This compound was prepared by using a procedure that was analogous to that described for the synthesis of example 94. LCMS: m/z 433.1 (M+H)$^+$.

Example 628

Methyl 4-(4-{1-[(4,4-dimethyl-2-oxo-1-oxa-7-azaspiro[4.4]non-7-yl)carbonyl]cyclopropyl}-3-fluorophenyl)piperazine-1-carboxylate Step 1. tert-butyl 3-(1,1-dimethylprop-2-en-1-yl)-3-hydroxypyrrolidine-1-carboxylate To a suspension of tert-butyl 3-oxopyrrolidine-1-carboxylate (2.40 g, 0.0130 mol), 4-bromo-2-methyl-2-butene (3.00 mL, 0.0260 mol) in 15.0 mL sat'd. ammonium chloride and tetrahydrofuran (3.00 mL, 0.0370 mol) was added zinc (1.70 g, 0.0260 mol) at rt. Soon after stirring was started, gas and heat were released. After 30 to 45 min., the resulting light grey mixture was filtered through celite. The filtration was extracted with EtOAc. The organic layers were combined, washed with brine, dried (NaSO4) and concentrated in-vacuo. The residue was purified on silica gel, eluting with 0 to 40% EtOAc in hexane, to give the desired product. LCMS (M+Na) 278.2.

Step 2. tert-butyl 4,4-dimethyl-2-oxo-1-oxa-7-azaspiro[4,4]nonane-7-carboxylate

To a solution of borane-dimethyl sulfide complex (0.409 mL, 0.00460 mol) in methylene chloride (6.00 mL, 0.0936 mol) was slowly added a solution of tert-butyl 3-(1,1-dimethylprop-2-en-1-yl)-3-hydroxypyrrolidine-1-carboxylate (3.20 g, 0.0125 mol) in methylene chloride (6.00 mL, 0.0936 mol) with stirring at rt. After 2 h, the reaction mixture was slowly added to a solution of chromium(VI) oxide (7.52 g, 0.0752 mol)in acetic acid (45.00 mL, 0.7915 mol), and water (5.00 mL, 0.278 mol) at 5° C. After stirring the reaction mixture at rt for 12 h, water (60 mL) and methylene chloride (30 mL) were added. The organic layer was separated and the aqueous layer was further extracted with methylene chloride (2×30 mL). The organic layers were combined, washed with brine (2×30 mL), dried and concentrated. The residue was purified on silica gel, eluting with 0 to 50% EtOAc in hexane, to give the product. LCMS (M+Na) 292.2.

Step 3. 4,4-dimethyl-1-oxa-7-azaspiro[4.4]nonan-2-one hydrochloride tert-Butyl 4,4-dimethyl-2-oxo-1-oxa-7-azaspiro[4.4] nonane-7-carboxylate (0.20 g, 0.00074 mol) was treated with hydrogen chloride in 1,4-dioxane (4.00 M, 5.00 mL) at rt for 2 h. The volatiles were removed in-vacuo and the resultant HCl salt was used directly in the next step without further purification. LCMS (M+H) 170.2.

Step 4. 1-(4-bromo-2-fluorophenyl)cyclopropanecarboxylic acid

This compound was prepared by using a procedure analogous to that described in step 1 of example 238. NMR analysis confirmed the formation of the desired product, which was used in the next step without further purification.

Step 5. tert-butyl 4-(4-{1-[(4,4-dimethyl-2-oxo-1-oxa-7-azaspiro[4.4]non-7-yl)carbonyl]cyclopropyl}-3-fluorophenyl)piperazine-1-carboxylate To a mixture of 4,4-dimethyl-1-oxa-7-azaspiro[4.4]nonan-2-one hydrochloride (20.3 mg, 0.0000988 mol) and 1-{4-[4-(tert-butoxycarbonyl)piperazin-1-yl]-2-fluorophenyl}cyclopropanecarboxylic acid (36.0 mg, 0.0000988 mol) in N,N-dimethylformamide (0.30 mL, 0.0039 mol) was added benzotriazol-1-yloxytris(dimethylamino)phosphonium hexafluorophosphate (48.1 mg, 0.000109 mol) followed by N,N-diisopropylethylamine (0.0206 mL, 0.000118 mol). After stirring at rt for 1 h, the reaction mixture was quenched with water and extracted with EtOAc. The organic layers were combined, washed with brine, and dried. The crude residue was used directly in the next step without further purification. LCMS (M+H) 516.3. (M+Na) 538.3.

Step 6. methyl 4-(4-{1-[(4,4-dimethyl-2-oxo-1-oxa-7-azaspiro[4.4]non-7-yl)carbonyl]cyclopropyl}-3-fluorophenyl)piperazine-1-carboxylate tert-Butyl 4-(4-{1-[(4,4-dimethyl-2-oxo-1-oxa-7-azaspiro [4.4]non-7-yl)carbonyl]cyclopropyl}-3-fluorophenyl)piperazine-1-carboxylate (25.0 mg, 0.0000485 mol) was treated with TFA. After stirring at rt for 30 min, the volatiles were removed in-vacuo and the residue was dried on high vacuum. The resultant TFA salt was dissolved in methylene chloride (0.25 mL, 0.0039 mol) and to this was added triethylamine (0.0203 mL, 0.000145 mol) followed by methyl chloroformate (0.00749 mL, 0.0000970 mol). The reaction mixture was stirred at rt for 1 h and then the volatiles were removed in-vacuo. The residue was diluted with methanol and applied directly on RP-HPLC to yield the desired product. LCMS (M+H) 474.2.

Example 629

Ethyl 4-(4-{1-[(4,4-dimethyl-2-oxo-1-oxa-7-azaspiro [4.4]non-7-yl)carbonyl]cyclopropyl}-3-fluorophenyl)piperazine-1-carboxylate This compound was prepared by using a procedure analogous to that described in steps 1-6 of example 628. LCMS: m/z 488.3 (M+H)$^+$.

Example 630

7-{[1-(4-Chlorophenyl)cyclopropyl]carbonyl}-4,4-dimethyl-1-oxa-7-azaspiro[4.4]nonan-2-one This compound was prepared by using a procedure analogous to that described in steps 1-3 and 5 of example 628. LCMS: m/z 348.2 (M+H)$^+$.

Example 631

Methyl 4-(3-fluoro-4-{1-[3-pyridin-3-ylpyrrolidin-1-yl)carbonyl]cyclopropyl}phenyl)piperazine-1-carboxylate This compound was prepared by using a procedure analogous to that described for the synthesis of example 421. LCMS: m/z 453.2 (M+H)$^+$.

Example 632

Methyl 4-(5-{1-[(3-pyridin-3-ylpyrrolidin-1-yl)carbonyl]cyclopropyl}pyridin-2-yl)piperazine-1-carboxylate This compound was prepared by using a procedure analogous to that described in steps 1-4 of example 163. LCMS: m/z 436.2 (M+H)$^+$.

Example 633

Ethyl 4-(5-{1-[(3-pyridin-3-ylpyrrolidin-1-yl)carbonyl]cyclopropyl}pyridin-2-yl)piperazine-1-carboxylate This compound was prepared by using a procedure analogous to that described in steps 1-4 of example 163. LCMS: m/z 450.3 (M+H)$^+$.

Example 634

1-Acetyl-4-(5-{1-[(3-pyridin-3-ylpyrrolidin-1-yl)carbonyl]cyclopropyl}pyridin-2-yl)piperazine This compound was prepared by using a procedure analogous to that described in steps 1-4 of example 163. LCMS: m/z 420.2 (M+H)$^+$; 442.3 (M+Na)$^+$.

Example 635

1-(3-Methylbutanoyl)-4-(5-{1-[(3-pyridin-3-ylpyrrolidin-1-yl)carbonyl]cyclopropyl}pyridin-2-yl)piperazine This compound was prepared by using a procedure analogous to that described in steps 1-4 of example 163.

Example 636

1-(Cyclopropylcarbonyl)-4-(5-{1-[(3-pyridin-3-ylpyrrolidin-1-yl)carbonyl]cyclopropyl}pyridin-2-yl)piperazine This compound was prepared by using a procedure analogous to that described in steps 1-4 of example 163. LCMS: m/z 446.3 (M+H)$^+$; 468.2 (M+Na)$^+$.

Example 637

Methyl 4-(3-fluoro-4-{1-[(1,3,3-trimethyl-6-azabicyclo[3.2.1]oet-6-yl)-carbonyl]cyclopropyl}phenyl)piperazine-1-carboxylate This compound was prepared by using a procedure that was analogous to that described for the synthesis of example 421. LCMS: m/z 458.2 (M+H)$^+$.

Example 638

(1R)-1'-{[1-(6-Azetidin-1-ylpyridin-3-yl)cyclopropyl]carbonyl}-3H-spiro[furo[3,4-c]pyridine-1,3'-pyrrolidin]-3-one

Step 1. 1-(6-chloropyridin-3-yl)cyclopropanecarbonitrile

To a stirred mixture of the (6-chloropyridin-3-yl)acetonitrile (8.00 g, 0.0524 mol), benzyltriethylammonium chloride (0.8 g, 0.004 mol), and 1-bromo-2-chloro-ethane (8.69 mL, 0.105 mol) was added dropwise sodium hydroxide, 50% aqueous solution (16.1 mL, 0.419 mol) at 50° C. After stirring for 2 h, the reaction mixture was diluted with water and the resulting layers were separated. The aqueous layer was extracted with dichloromethane. The combined organic layers were washed with 1N HCl and brine successively, dried with magnesium sulfate, filtered, and concentrated in-vacuo. The crude product was purified by combiflash to obtain 2.5 g of pure product as a white solid.

Step 2. 1-(6-azetidin-1-ylpyridin-3-yl)cyclopropanecarbonitrile

To a solution of 1-(6-chloropyridin-3-yl)cyclopropanecarbonitrile (200.0 mg, 0.001120 mol) in 1,4-dioxane (8.00 mL, 0.102 mol) at rt were added azetidine hydrochloride (128.3 mg, 0.001344 mol), palladium acetate (25.2 mg, 0.000112 mol), and sodium tert-butoxide (288 mg, 0.00291 mol). The reaction mixture was degassed and then microwave irradiated at 150° C. for 40 min. The reaction mixture was quenched with water and extracted with ethyl acetate and dichloromethane. The crude product was purified by combiflash. LCMS: m/z 200.2 (M+H)$^+$.

Step 3. 1-(6-azetidin-1-ylpyridin-3-yl)cyclopropanecarboxylic acid dihydrochloride Into a microwave vial was transferred 1-(6-azetidin-1-ylpyridin-3-yl)cyclopropanecarbonitrile (42.00 mg, 0.0002108 mol) and hydrogen chloride (1.00 mL, 0.0326 mol). The mixture was stirred at 100 degrees for 2 h. Upon completion the crude product was azeotroped with toluene 3× and used in the next step without further purification.

Step 4. 1-(6-azetidin-1-ylpyridin-3-yl)cyclopropanecarbonyl chloride dihydrochloride To 1-(6-azetidin-1-ylpyridin-3-yl)cyclopropanecarboxylic acid dihydrochloride (61.00 mg, 0.0002095 mol) were added thionyl chloride (1.00 mL, 0.0137 mol) at 0° C. and the resulting solution was stirred at rt for 1 hr. Upon completion, the reaction mixture was azeotroped with toluene (3×) and then used in the next step without further purification.

Step 5. (1R)-1'-{[1-(6-azetidin-1-ylpyridin-3-yl)cyclopropyl]carbonyl}-3H-spiro[furo[3,4-c]pyridine-1,3'-pyrrolidin]-3-one To a solution of 1-(6-azetidin-1-ylpyridin-3-yl)cyclopropanecarbonyl chloride dihydrochloride (64.00 mg, 0.0002067 mol) and (7,7-dimethyl-2-oxobicyclo[2.2.1]hept-1-yl)methanesulfonic acid-(1R)-3H-spiro[furo[3,4-c]pyridine-1,3'-pyrrolidin]-3-one (1:1) (87.3 mg, 0.000207 mol) in methylene chloride (1.00 mL, 0.0156 mol) was added N,N-diisopropylethylamine (0.144 mL, 0.000827 mol) at 0° C. The reaction mixture was stirred at rt for 1-2 h. Upon completion the reaction mixture was diluted with ethyl acetate and washed with water and brine successively, dried with sodium sulfate, filtered, and concentrated. The crude product was purified by prep-LCMS twice to obtain the product as a TFA salt. LCMS: m/z 391.2 (M+H)$^+$.

Example 639

(1R)-1'-({1-[6-(2-Oxoazetidin-1-yl)pyridin-3-yl]cyclopropyl}carbonyl)-3H-spiro[2-benzofuran-1,3'-pyrrolidin]-3-one This compound was prepared by using a procedure analogous to that described for the synthesis of example 257. LCMS: m/z 404.2 (M+H)$^+$.

Example 640

Methyl [3-fluoro-4-(1-{[(1R)-3-oxo-1'H,3H-spiro[furo[3,4-c]pyridine-1,3'-pyrrolidin]-1'yl]carbonyl}cyclopropyl)phenyl]carbamate This compound was prepared by using a procedure analogous to that described for the synthesis of example 257. LCMS: m/z 426.2 (M+Hr.

Example 641

Methyl [3-fluoro-4-(1-{[(1R)-3-oxo-1'H,3H-spiro[2-benzofuran-1,3'-pyrrolidin]-1'-yl]carbonyl}cyclopropyl)phenyl]carbamate This compound was prepared by using a procedure analogous to that described for the synthesis of example 257. LCMS: m/z 425.2 (M+H)+.

Example 642

(1R)-1'-({1-[4-(2-Oxopyrrolidin-1-yl)phenyl]cyclopropyl}carbonyl)-3H-spiro[furo[3,4-c]pyridine-1,3'-pyrrolidin]-3-one This compound was prepared by using a procedure analogous to that described for the synthesis of example 257. LCMS: m/z 418.2 (M+H)+.

Example 643

(1R)-1'-[(1-{4-[4-(Cyclopropylcarbonyl)piperazin-1-yl]phenyl}cyclobutyl)carbonyl]-3H-spiro[2-benzofuran-1,3'-pyrrolidin]-3-one This compound was prepared by using a procedure analogous to that described for the synthesis of example 163. LCMS: m/z 500.2 (M+H)+.

Example 644

Ethyl 4-[4-(1-{[(1R)-3-oxo-1'H,3H-spiro[furo[3,4-c]pyridine-1,3'-pyrrolidin]-1'-yl]carbonyl}cyclopropyl)phenyl]piperazine-1-carboxylate This compound was prepared by using a procedure analogous to that described for the synthesis of example 163. LCMS: m/z 491.2 (M+H)+.

Example 645

1-{[1-(4-Chlorophenyl)cyclopropyl]carbonyl}-3-(1,1-dimethylpropyl)pyrrolidin-3-ol Step 1. benzyl 3-(1,1-dimethylprop-2-en-1-yl)-3-hydroxypyrrolidine-1-carboxylate To a suspension of benzyl 3-oxopyrrolidine-1-carboxylate (4.50 g, 0.0205 mol) and 4-bromo-2-methyl-2-butene (4.75 mL, 0.0412 mol) in 25.0 mL of saturated ammonium chloride and tetrahydrofuran (4.75 mL, 0.0586 mol) was added zinc (2.70 g, 0.0412 mol) at rt. Soon after stirring was started, gas and heat were evolved. After 45 min., the resulting light grey mixture was filtered through celite. Layers of the filtrate were separated and the aqueous layer of the filtrate was extracted with EtOAc. The organic layers were combined, washed with brine, dried and evaporated in-vacuo. The residue was purified on silica gel, eluting with 0 to 40% EtOAc in hexane, to give the desired product. LCMS (M+Na) 290.2.

Step 2. 3-(1,1-dimethylpropyl)pyrrolidin-3-ol

Benzyl 3-(1,1-dimethylprop-2-en-1-yl)-3-hydroxypyrrolidine-1-carboxylate (56 mg, 0.00019 mol) was dissolved in methanol and to this solution was added Pd/C (10% dry, 10 mg). The reaction vessel was purged with hydrogen and allowed to stir for 3 h with a hydrogen balloon. The catalyst was filtered off and the filtrate was concentrated in-vauo to afford the desired product. LCMS (M+H)=158.

Step 3. 1-{[1-(4-chlorophenyl)cyclopropyl]carbonyl}-3-(1,1-dimethylpropyl)pyrrolidin-3-ol 3-(1,1-Dimethylpropyl)pyrrolidin-3-ol (29.5 mg, 0.000188 mol) was dissolved in DMF and to this solution were added 1-(4-chlorophenyl)cyclopropanecarboxylic acid (44.3 mg, 0.000225 mol), benzotriazol-1-yloxytris(dimethylamino)phosphonium hexafluorophosphate (99.6 mg, 0.000225 mol) and N,N-diisopropylethylamine (49 μL, 0.00028 mol), and the resulting solution was stirred at rt overnight. The product was purified by prep-HPLC. LCMS (M+H)=336

Example 646

7-{[1-(4-Chlorophenyl)cyclopropyl]carbonyl}-4,4-dimethyl-1-oxa-7-azaspiro[4.4]nonane Step 1. tert-butyl 3-iodo-4,4-dimethyl-1-oxa-7-azaspiro[4.4]nonane-7-carboxylate To a solution of tert-butyl 3-(1,1-dimethylprop-2-en-1-yl)-3-hydroxypyrrolidine-1-carboxylate (1.00 g, 0.00392 mol) in anhydrous acetonitrile (20.00 mL, 0.3829 mol) were added sodium bicarbonate (0.658 g, 0.00783 mol) and iodine (2.98 g, 0.0117 mol). The resulting mixture was protected from light and stirred at rt for 24 h. The mixture was cooled to 0° C. and sodium thiosulfate was carefully added until the dark iodine color disappeared. Layers of the reaction mixture were separated and the aqueous layer was extracted with EtOAc. The organic layers were combined, dried and the concentrated in vacuo. The crude ether was purified by CombiFlash, eluting with 0 to 30% EtOAc in hexane, to provide the iodo ether as a mixture of diastereoisomers. LCMS (M+Na) 404.1.

Step 2. tert-butyl 4,4-dimethyl-1-oxa-7-azaspiro[4.4]nonane-7-carboxylate

A mixture of tert-butyl 3-iodo-4,4-dimethyl-1-oxa-7-azaspiro[4.4]nonane-7-carboxylate (0.47 g, 0.0012 mol), tris(trimethylsilyl)silane (0.456 mL, 0.00148 mol) and 2,2'-azobis-isobutyronitrile (0.002 g, 0.00001 mol) in toluene (10.00 mL, 0.09388 mol) was heated at 90° C. overnight. The volatiles were removed in-vacuo and the residue was purified by CombiFlash, eluting with 0 to 30% EtOAc in hexane, to provide the THF compound. LCMS (M+Na) 278.2.

Step 3. 7-{[1-(4-chlorophenyl)cyclopropyl]carbonyl}-4,4-dimethyl-1-oxa-7-azaspiro[4.4]nonane A mixture of tert-butyl 2,3,3-trimethyl-1-oxa-6-azaspiro[3.4]octane-6-carboxylate (25.0 mg, 0.0000979 mol) and tert-butyl 4,4-dimethyl-1-oxa-7-azaspiro[4.4]nonane-7-carboxylate (25.0 mg, 0.0000979 mol) was treated with 1 mL of TFA at rt for 30 min. The volatiles were removed in-vacuo and the resultant TFA salt was used directly in next step. To a mixture of the above made TFA salt in N,N-dimethylformamide (0.50 mL, 0.0064 mol) were added 1-(4-chlorophenyl)cyclopropanecarboxylic acid (38.5 mg, 0.000196 mol) and benzotriazol-1-yloxytris(dimethylamino)phosphonium hexafluorophosphate (104 mg, 0.000235 mol), followed by N,N-diisopropylethylamine (0.0853 mL, 0.000490 mol). The mixture was stirred at rt for 2 h and then the product was isolated and purified by RP-HPLC. LCMS (M+H) 334.2.

Example 647

Methyl 4-(4-{1-[(3-tert-butyl-3-hydroxypyrrolidin-1-yl)carbonyl]cyclopropyl}-3-fluorophenyl)piperazine-1-carboxylate This compound was prepared by using a procedure analogous to that described in steps 1 & 3-6 of example 628. LCMS: m/z 448.1 (M+H)$^+$ and 470.1 (M+Na)$^+$.

Example 648

N,N-Diethyl-5-[3-fluoro-4-(1-{[(1R)-3-oxo-1'H,3H-spiro[2-benzofuran-1,3'-pyrrolidin]-1'-yl]carbonyl}cyclopropyl)phenyl]pyridine-2-carboxamide This compound was prepared by using a procedure analogous to that described in steps 1 & 2 of example 250. LCMS: m/z 528.2 (M+H)$^+$.

Example 649

(1S)-1'-({1-[4-(2-Oxopyrrolidin-1-yl)phenyl]cyclopropyl}carbonyl)-3H-spiro[2-benzofuran-1,3'-pyrrolidin]-3-one This compound was prepared by using a procedure analogous to that described for the synthesis of example 103.

Example 650

(1R)-1'-({1-[2-Fluoro-4-(1H-1,2,3-triazol-1-yl)phenyl]cyclopropyl}carbonyl)-3H-spiro[2-benzofuran-1,3'-pyrrolidin]-3-one This compound was prepared by using a procedure analogous to that described for the synthesis of example 118. LCMS: m/z 419.1 (M+H)$^+$.

Example 651

(1R)-1'-({1-[2-Fluoro-4-(2H-1,2,3-triazol-2-yl)phenyl]cyclopropyl}carbonyl)-3H-spiro[2-benzofuran-1,3'-pyrrolidin]-3-one This compound was prepared by using a procedure analogous to that described for the synthesis of example 118. LCMS: m/z 419.1 (M+H)$^+$.

Example 652

(1R)-1'-({1-[2-Fluoro-4-(1H-1,2,4-triazol-1-yl)phenyl]cyclopropyl}carbonyl)-3H-spiro[2-benzofuran-1,3'-pyrrolidin]-3-one This compound was prepared by using a procedure analogous to that described for the synthesis of example 118. LCMS: m/z 419.1 (M+H)$^+$.

Example 653

(1R)-1'-({1-[2-Fluoro-4-(4H-1,2,4-triazol-4-yl)phenyl]cyclopropyl}carbonyl)-3H-spiro[2-benzofuran-1,3'-pyrrolidin]-3-one This compound was prepared by using a procedure analogous to that described for the synthesis of example 118. LCMS: m/z 419.1 (M+H)$^+$.

Example 654

N-Ethyl-5-[3-fluoro-4-(1-{[(1R)-3-oxo-1'H,3H-spiro[2-benzofuran-1,3'-pyrrolidin]-1'-yl]carbonyl}cyclopropyl)phenyl]pyridine-2-carboxamide This compound was prepared by using a procedure analogous to that described in steps 1 & 2 of example 250. LCMS: m/z 500.2 (M+H)$^+$.

Example 655

5-[3-Fluoro-4-(1-{[(1R)-3-oxo-1'H,3H-spiro[2-benzofuran-1,3'-pyrrolidin]-1'-yl]carbonyl}cyclopropyl)phenyl]-N-isopropylpyridine-2-carboxamide This compound was prepared by using a procedure analogous to that described in steps 1 & 2 of example 250. LCMS: m/z 514.2 (M+H)$^+$.

Example A

Enzymatic Assay of 11βHSD1

All in vitro assays were performed with clarified lysates as the source of 11βHSD1 activity. HEK-293 transient transfectants expressing an epitope-tagged version of full-length human 11βHSD1 were harvested by centrifugation. Roughly 2×10$^7$ cells were resuspended in 40 mL of lysis buffer (25 mM Tris-HCl, pH 7.5, 0.1 M NaCl, 1 mM MgCl$_2$ and 250 mM sucrose) and lysed in a microfluidizer. Lysates were clarified by centrifugation and the supernatants were aliquoted and frozen.

Inhibition of 11βHSD1 by test compounds was assessed in vitro by a Scintillation Proximity Assay (SPA). Dry test compounds were dissolved at 5 mM in DMSO. These were diluted in DMSO to suitable concentrations for the SPA assay. 0.8 μL of 2-fold serial dilutions of compounds were dotted on 384 well plates in DMSO such that 3 logs of compound concentration were covered. 20 μL, of clarified lysate was added to each well. Reactions were initiated by addition of 20 μL of substrate-cofactor mix in assay buffer (25 mM Tris-HCl, pH 7.5, 0.1 M NaCl, 1 mM MgCl$_2$) to final concentrations of 400 μM NADPH, 25 nM $^3$H-cortisone and 0.007% Triton X-100. Plates were incubated at 37° C. for one hour. Reactions were quenched by addition of 40 μL of anti-mouse coated SPA beads that had been pre-incubated with 10 μM carbenoxolone and a cortisol-specific monoclonal antibody. Quenched plates were incubated for a minimum of 30 minutes at RT prior to reading on a Topcount scintillation counter. Controls with no lysate, inhibited lysate, and with no mAb were run routinely. Roughly 30% of input cortisone is reduced by 11βHSD1 in the uninhibited reaction under these conditions.

Test compounds having an IC$_{50}$ value less than about 20 μM according to this assay were considered active.

Example B

Cell-Based Assays for HSD Activity

Peripheral blood mononuclear cells (PBMCs) were isolated from normal human volunteers by Ficoll density centrifugation. Cells were plated at 4×10$^5$ cells/well in 200 µL of AIM V (Gibco-BRL) media in 96 well plates. The cells were stimulated overnight with 50 ng/ml recombinant human IL-4 (R&D Systems). The following morning, 200 nM cortisone (Sigma) was added in the presence or absence of various concentrations of compound. The cells were incubated for 48 hours and then supernatants were harvested. Conversion of cortisone to cortisol was determined by a commercially available ELISA (Assay Design).

Test compounds having an IC$_{50}$ value less than about 20 µM according to this assay were considered active.

Example C

Cellular Assay to Evaluate MR Antagonism

Assays for MR antagonism were performed essentially as described (Jausons-Loffreda et al. J Biolumin and Chemilumin, 1994, 9: 217-221). Briefly, HEK293/MSR cells (Invitrogen Corp.) were co-transfected with three plasmids: 1) one designed to express a fusion protein of the GAL4 DNA binding domain and the mineralocorticoid receptor ligand binding domain, 2) one containing the GAL4 upstream activation sequence positioned upstream of a firefly luciferase reporter gene (pFR-LUC, Stratagene, Inc.), and 3) one containing the Renilla luciferase reporter gene cloned downstream of a thymidine kinase promoter (Promega). Transfections were performed using the FuGENE6 reagent (Roche). Transfected cells were ready for use in subsequent assays 24 hours post-transfection.

In order to evaluate a compound's ability to antagonize the MR, test compounds are diluted in cell culture medium (E-MEM, 10% charcoal-stripped FBS, 2 mM L-glutamine) supplemented with 1 nM aldosterone and applied to the transfected cells for 16-18 hours. After the incubation of the cells with the test compound and aldosterone, the activity of firefly luciferase (indicative of MR agonism by aldosterone) and Renilla luciferase (normalization control) were determined using the Dual-Glo Luciferae Assay System (Promega). Antagonism of the mineralocorticoid receptor was determined by monitoring the ability of a test compound to attenuate the aldosterone-induced firefly luciferase activity.

Compounds having an IC$_{50}$ of 100 µM or less were considered active.

Various modifications of the invention, in addition to those described herein, will be apparent to those skilled in the art from the foregoing description. Such modifications are also intended to fall within the scope of the appended claims. Each reference, including all patent, patent applications, and publications, cited in the present application is incorporated herein by reference in its entirety.

What is claimed is:

1. A compound of Formula VIII:

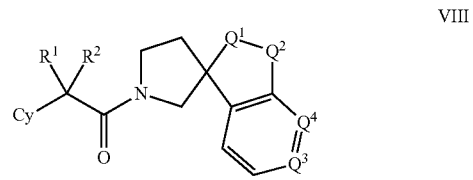

or a pharmaceutically acceptable salt thereof, wherein:

Cy is aryl, heteroaryl, cycloalkyl or heterocycloalkyl, each optionally substituted by 1, 2, 3, 4 or 5-W—X—Y—Z;

$R^1$ and $R^2$ together with the C atom to which they are attached form a 3-, 4-, 5-, 6- or 7-membered cycloalkyl group or a 3-, 4-, 5-, 6- or 7-membered heterocycloalkyl group, each optionally substituted by 1, 2 or 3 $R^5$;

$R^5$ is halo, $C_{1-6}$ alkyl, $C_{2-6}$ alkenyl, $C_{2-6}$ alkynyl, $C_{1-4}$ haloalkyl, aryl, cycloalkyl, heteroaryl, heterocycloalkyl, CN, NO$_2$, OR$^a$, SR$^a$, C(O)R$^b$, C(O)NR$^c$R$^d$, C(O)OR$^a$, OC(O)R$^b$, OC(O)NR$^c$R$^d$, NR$^c$R$^d$, NR$^c$C(O)R$^d$, NR$^c$C(O)OR$^a$, S(O)R$^b$, S(O)NR$^c$R$^d$, S(O)$_2$R$^b$, or S(O)$_2$NR$^c$R$^d$;

one of $Q^1$ and $Q^2$ is CO and the other is O, NH, or CH$_2$;

$Q^3$ is CH or N;

$Q^4$ is CH or N;

W is absent, $C_{1-6}$ alkylenyl, $C_{1-6}$ alkenylenyl, $C_{2-6}$ alkynylenyl, O, S, NR$^e$, CO, CS, COO, CONR$^e$, OCONR$^e$, SO, SO$_2$, SONR$^e$, or NR$^e$CONR$^f$, wherein said $C_{1-6}$ alkylenyl, $C_{2-6}$ alkenylenyl, $C_{2-6}$ alkynylenyl are each optionally substituted by 1, 2 or 3 halo, OH, $C_{1-4}$ alkoxy, $C_{1-4}$ haloalkoxy, amino, $C_{1-4}$ alkylamino or $C_{2-8}$ dialkylamino;

X is absent, $C_{1-8}$ alkylenyl, $C_{2-8}$ alkenylenyl, $C_{2-8}$ alkynylenyl, aryl, cycloalkyl, heteroaryl, heterocycloalkyl, arylalkyl, cycloalkylalkyl, heteroarylalkyl, heterocycloalkylalkyl, arylalkenyl, cycloalkylalkenyl, heteroarylalkenyl, heterocycloalkylalkenyl, arylalkynyl, cycloalkylalkynyl, heteroarylalkynyl, heterocycloalkylalkynyl, each of which is optionally substituted by one or more halo, CN, NO$_2$, OH, $C_{1-4}$ alkoxy, $C_{1-4}$ haloalkoxy, amino, $C_{1-4}$ alkylamino or $C_{2-4}$ dialkylamino;

Y is absent, $C_{1-6}$ alkylenyl, $C_{2-6}$ alkenylenyl, $C_{2-6}$ alkynylenyl, O, S, NR$^e$, CO, CS, COO, CONR$^e$, OCONR$^e$, SO, SO$_2$, SONR$^e$, or NR$^e$CONR$^f$, wherein said $C_{1-6}$ alkylenyl, $C_{2-6}$ alkenylenyl, $C_{2-6}$ alkynylenyl are each optionally substituted by 1, 2 or 3 halo, OH, $C_{1-4}$ alkoxy, $C_{1-4}$ haloalkoxy, amino, $C_{1-4}$ alkylamino or $C_{2-8}$ dialkylamino;

Z is H, halo, CN, NO$_2$, OH, $C_{1-4}$ alkoxy, $C_{1-4}$ haloalkoxy, amino, $C_{1-4}$ alkylamino or $C_{2-4}$ dialkylamino, $C_{1-6}$ alkyl, $C_{2-6}$ alkenyl, $C_{2-6}$ alkynyl, aryl, cycloalkyl, heteroaryl or heterocycloalkyl, wherein said $C_{1-6}$ alkyl, $C_{2-6}$ alkenyl, $C_{2-6}$ alkynyl, aryl, cycloalkyl, heteroaryl or heterocycloalkyl is optionally substituted by 1, 2 or 3 substituents independently selected from halo, $C_{1-6}$ alkyl, $C_{2-6}$ alkenyl, $C_{2-6}$ alkynyl, $C_{1-4}$ haloalkyl, aryl, cycloalkyl, heteroaryl, heterocycloalkyl, CN, NO$_2$, OR$^a$, SR$^a$, C(O)R$^b$, C(O)NR$^c$R$^d$, C(O)OR$^a$, OC(O)R$^b$, OC(O)NR$^c$R$^d$, NR$^c$R$^d$, NR$^c$C(O)R$^d$, NR$^c$C(O)OR$^a$, S(O)R$^b$, S(O)NR$^c$R$^d$, S(O)$_2$R$^b$, and S(O)$_2$NR$^c$R$^d$;

wherein —W—X—Y—Z is other than H;

R$^a$ is H, C$_{1-6}$ alkyl, C$_{1-6}$ haloalkyl, C$_{2-6}$ alkenyl, (C$_{1-6}$ alkoxy)-C$_{1-6}$ alkyl, C$_{2-6}$ alkynyl, aryl, cycloalkyl, heteroaryl or heterocycloalkyl;

R$^b$ is H, C$_{1-6}$ alkyl, C$_{1-6}$ haloalkyl, C$_{2-6}$ alkenyl, C$_{2-6}$ alkynyl, aryl, cycloalkyl, heteroaryl or heterocycloalkyl;

R$^c$ and R$^d$ are each, independently, H, C$_{1-6}$ alkyl, C$_{1-6}$ haloalkyl, C$_{2-6}$ alkenyl, C$_{2-6}$ alkynyl, aryl, cycloalkyl, arylalkyl, or cycloalkylalkyl;

or R$^c$ and R$^d$ together with the N atom to which they are attached form a 4-, 5-, 6- or 7-membered heterocycloalkyl group; and R$^e$ and R$^f$ are each, independently, H, C$_{1-6}$ alkyl, C$_{1-6}$ haloalkyl, C$_{2-6}$ alkenyl, C$_{2-6}$ alkynyl, aryl, cycloalkyl, arylalkyl, or cycloalkylalkyl;

or R$^e$ and R$^f$ together with the N atom to which they are attached form a 4-, 5-, 6- or 7-membered heterocycloalkyl group.

2. The compound of claim 1, or a pharmaceutically acceptable salt thereof, wherein Cy is aryl or heteroaryl, each optionally substituted by 1, 2, 3, 4 or 5-W—X—Y—Z.

3. The compound of claim 1, or a pharmaceutically acceptable salt thereof; wherein Cy is aryl optionally substituted by 1, 2, 3, 4 or 5-W—X—Y—Z.

4. The compound of claim 1, or a pharmaceutically acceptable salt thereof, wherein Cy is aryl optionally substituted by 1, 2 or 3 halo, C$_{1-4}$ alkyl, C$_{1-4}$ alkoxy, C$_{1-4}$ haloalkyl, or C$_{1-4}$ haloalkoxy.

5. The compound of claim 1, or a pharmaceutically acceptable salt thereof, wherein Cy is phenyl optionally substituted by 1, 2 or 3 halo, C$_{1-4}$ alkyl, C$_{1-4}$ alkoxy, C$_{1-4}$ haloalkyl, or C$_{1-4}$ haloalkoxy.

6. The compound of claim 1, or a pharmaceutically acceptable salt thereof, wherein R$^1$ and R$^2$ together with the C atom to which they are attached form a 3-, 4-, 5-, 6- or 7-membered cycloalkyl group.

7. The compound of claim 1, or a pharmaceutically acceptable salt thereof, wherein R$^1$ and R$^2$ together with the C atom to which they are attached form a cyclopropyl group.

8. The compound of claim 1, or a pharmaceutically acceptable salt thereof, wherein —W—X—Y—Z is halo, cyano, C$_{1-4}$ cyanoalkyl, nitro, C$_{1-8}$ alkyl, C$_{2-8}$ alkenyl, C$_{1-8}$ haloalkyl, C$_{1-4}$ alkylthio, C$_{1-4}$ haloalkylthio, C$_{1-8}$ alkoxy, C$_{2-8}$ alkenyloxy, C$_{1-4}$ haloalkoxy, OH, (C$_{1-4}$ alkoxy)-C$_{1-4}$ alkyl, amino, C$_{1-4}$ alkylamino, C$_{2-8}$ dialkylamino, OC(O)NR$^c$R$^d$, NR$^c$C(O)R$^d$, NR$^c$C(O)OR$^a$, NR$^c$S(O)$_2$R$^d$, C(O)OR$^a$, C(O)R$^a$, C(O)NR$^a$NR$^c$R$^d$, S(O)$_2$R$^d$, SR$^d$, C(O)NR$^c$R$^d$, C(S)NR$^c$R$^d$, aryloxy, heteroaryloxy, cycloalkyloxy, cycloalkenyloxy, heterocycloalkyloxy, arylalkyloxy, heteroarylalkyloxy, cycloalkylalkyloxy, heterocycloalkylalkyloxy, heteroaryloxyalkyl, aryloxyalkyl, aryl, heteroaryl, cycloalkyl, heterocycloalkyl, arylalkyl, arylalkenyl, arylalkynyl, heteroarylalkyl, heteroarylalkenyl, heteroarylalkynyl, cycloalkylalkyl, or heterocycloalkylalkyl;

wherein each of said C$_{1-8}$ alkyl, C$_{2-8}$ alkenyl, C$_{1-8}$ haloalkyl, C$_{1-4}$ alkylthio, C$_{1-4}$ haloalkylthio, C$_{1-8}$ alkoxy, aryloxy, heteroaryloxy, arylalkyloxy, heteroarylalkyloxy, heteroaryloxyalkyl, aryloxy, heteroaryloxy, cycloalkyloxy, cycloalkenyloxy, heterocycloalkyloxy, arylalkyloxy, heteroarylalkyloxy, cycloalkylalkyloxy, heterocycloalkylalkyloxy, heteroaryloxyalkyl, aryloxyalkyl, aryl, heteroaryl, cycloalkyl, heterocycloalkyl, arylalkyl, arylalkenyl, arylalkynyl, heteroarylalkyl, heteroarylalkenyl, heteroarylalkynyl, cycloalkylalkyl, or heterocycloalkylalkyl is optionally substituted by 1, 2 or 3 substituents independently selected from halo, cyano, nitro, hydroxyl-(C$_{1-6}$ alkyl), aminoalkyl, dialkylaminoalkyl, C$_{1-4}$ alkyl, C$_{1-4}$ haloalkyl, C$_{1-4}$ cyanoalkyl, C$_{1-4}$ alkoxy, C$_{1-4}$ haloalkoxy, OH, OR$^a$, (C$_{1-4}$ alkoxy)-C$_{1-4}$ alkyl, amino, C$_{1-4}$ alkylamino, C$_{2-8}$ dialkylamino, C(O)NR$^c$R$^d$, C(O)OR$^a$, C(O)R$^a$, (cyclocalkylalkyl)-C(O)—, NR$^c$C(O)R$^d$, NR$^c$C(O)OR$^a$, NR$^c$S(O)$_2$R$^d$, C(S)NR$^c$R$^d$, S(O)$_2$R$^d$, (C$_{1-4}$ alkyl)sulfonyl, arylsulfonyl, aryl optionally substituted by halo, heteroaryl, cycloalkylalkyl, cycloalkyl, and heterocycloalkyl.

9. The compound of claim 1, or a pharmaceutically acceptable salt thereof, wherein —W—X—Y—Z is halo, cyano, C$_{1-4}$ cyanoalkyl, nitro, C$_{1-8}$ alkyl, C$_{1-8}$ alkenyl, C$_{1-8}$ haloalkyl, C$_{1-10}$ alkoxy, C$_{1-4}$ haloalkoxy, OH, C$_{1-8}$ alkoxyalkyl, amino, C$_{1-4}$ alkylamino, C$_{2-8}$ dialkylamino, OC(O)NR$^c$R$^d$, NR$^c$C(O)R$^d$, NR$^c$C(O)OR$^a$, aryloxy, heteroaryloxy, arylalkyloxy, heteroarylalkyloxy, heteroaryloxyalkyl, aryloxyalkyl, aryl, heteroaryl, cycloalkyl, heterocycloalkyl, arylalkyl, arylalkenyl, arylalkynyl, heteroarylalkyl, heteroarylalkenyl, heteroarylalkynyl, cycloalkylalkyl, or heterocycloalkylalkyl;

wherein each of said C$_{1-8}$ alkyl, C$_{1-8}$ alkenyl, C$_{1-8}$ haloalkyl, C$_{1-8}$ alkoxy, aryloxy, heteroaryloxy, arylalkyloxy, heteroarylalkyloxy, heteroaryloxyalkyl, aryloxyalkyl, aryl, heteroaryl, cycloalkyl, heterocycloalkyl, arylalkyl, arylalkenyl, arylalkynyl, heteroarylalkyl, heteroarylalkenyl, heteroarylalkynyl, cycloalkylalkyl, or heterocycloalkylalkyl is optionally substituted by 1, 2, or 3 substituents independently selected from halo, cyano, nitro, hydroxyl-(C$_{1-6}$ alkyl), aminoalkyl, dialkylaminoalkyl, C$_{1-4}$ alkyl, C$_{1-4}$ haloalkyl, C$_{1-4}$ alkoxy, C$_{1-4}$ haloalkoxy, OH, C$_{1-8}$ alkoxyalkyl, amino, C$_{1-4}$ alkylamino, C$_{2-8}$ dialkylamino, C(O)NR$^c$R$^d$, C(O)OR$^a$, NR$^c$C(O)R$^d$, NR$^c$S(O)$_2$R$^d$, (C$_{1-4}$ alkyl)sulfonyl, arylsulfonyl, aryl, heteroaryl, cycloalkyl, and heterocycloalkyl.

10. The compound of claim 1, or a pharmaceutically acceptable salt thereof; wherein —W—X—Y—Z is halo, cyano, C$_{1-4}$ cyanoalkyl, nitro, C$_{1-4}$ nitroalkyl, C$_{1-4}$ alkyl, C$_{1-4}$ haloalkyl, C$_{1-4}$ alkoxy, C$_{1-4}$ haloalkoxy, OH, (C$_{1-4}$ alkoxy)-C$_{1-4}$ alkyl, amino, C$_{1-4}$ alkylamino, C$_{2-8}$ dialkylamino, aryl, heteroaryl, cycloalkyl, heterocycloalkyl, arylalkyl, heteroarylalkyl, cycloalkylalkyl, or heterocycloalkylalkyl.

11. The compound of claim 1, or a pharmaceutically acceptable salt thereof; wherein —W—X—Y—Z is halo, C$_{1-4}$ alkyl, or C$_{1-4}$ alkoxy.

12. A compound of claim 1 selected from:

1'-{[1-(4-chlorophenyl)cyclopropyl]carbonyl}-1-methyl-spiro[indole-3,4'-piperidin]-2(1H)-one;

1'-{[1-(4-Chlorophenyl)cyclopropyl]carbonyl}-3H-spiro[2-benzofuran-1,3'-pyrrolidin]-3-one;

1'-({1-[4-(Pyridin-2-yloxy)phenyl]cyclopropyl}carbonyl)-3H-spiro[2-benzofuran-1,3'-pyrrolidin]-3-one;

1'-{[1-(4-Chlorophenyl)cyclobutyl]carbonyl}-3H-spiro[2-benzofuran-1,3'-pyrrolidin]-3-one;

1'-{[1-(4-Methylphenyl)cyclopropyl]carbonyl}-3H-spiro[2-benzofuran-1,3'-pyrrolidin]-3-one;

1'-{[1-(4-Methoxyphenyl)cyclopropyl]carbonyl}-3H-spiro[2-benzofuran-1,3'-pyrrolidin]-3-one;

1'-{[1-(2,4-Dichlorophenyl)cyclopropyl]carbonyl}-3H-spiro[2-benzofuran-1,3'-pyrrolidin]-3-one;

1'-{[1-(4-Chlorophenyl)cyclopropyl]carbonyl}-7H-spiro[furo[3,4-b]pyridine-5,3'-pyrrolidin]-7-one;

1'-{[1-(4-Chlorophenyl)cyclopropyl]carbonyl}-3H-spiro[furo[3,4-c]pyridine-1,3'-pyrrolidin]-3-one;

1'-{[1-(4-Chlorophenyl)cyclopropyl]carbonyl}spiro[indole-3,3'-pyrrolidin]-2(1H)-one;

1'-({1-[4-(1H-Pyrazol-1-yl)phenyl]cyclopropyl}carbonyl)-3H-spiro[furo[3,4-c]pyridine-1,3'-pyrrolidin]-3-one;

1'-({1-[4-(Difluoromethoxy)phenyl]
cyclopropyl}carbonyl)-3H-spiro[furo[3,4-c]pyridine-
1,3'-pyrrolidin]-3-one;

1'-{[1-(6-Phenylpyridin-3-yl)cyclopropyl]carbonyl}-3H-
spiro[2-benzofuran-1,3'-pyrrolidin]-3-one;

1'-{[1-(6-Phenylpyridin-3-yl)cyclopropyl]carbonyl}-3H-
spiro[furo[3,4-c]pyridine-1,3'-pyrrolidin]-3-one;

1'-{[1-(4-Pyrrolidin-1-ylphenyl)cyclopropyl]carbonyl}-
3H-spiro[furo[3,4-c]pyridine-1,3'-pyrrolidin]-3-one;

1'-{[1-(4-Pyrrolidin-1-ylphenyl)cyclopropyl]carbonyl}-3,
4-spiro[2-benzofuran-1,3'-pyrrolidin]-3-one; and 1'-{[1-(6-Pyrrolidin-1-ylpyridin-3-yl)cyclopropyl]carbo-
nyl}-3H-spiro[furo[3,4-c]pyridine-1,3'-pyrrolidin]-3-
one, or a pharmaceutically acceptable salt thereof.

13. A compound of claim 1 selected from:

1'-{[1-(6-Pyrrolidin-1-ylpyridin-3-yl)cyclopropyl]carbo-
nyl}-3H-spiro[2-benzofuran-1,3'-pyrrolidin]-3-one;

1'-({1-[4-(2-oxo-1,3-oxazolidin-3-yl)phenyl]
cyclopropyl}carbonyl)-3H-spiro[2-benzofuran-1,3'-
pyrrolidin]-3-one;

1'-({1-[4-(2-oxopyrrolidin-1-yl)phenyl]
cyclopropyl}carbonyl)-3H-spiro[2-benzofuran-1,3'-
pyrrolidin]-3-one;

1'-({1-[4-(2-Phenylethoxy)phenyl]
cyclopropyl}carbonyl)-3H-spiro[furo[3,4-c]pyridine-
1,3'-pyrrolidin]-3-one;

1'-[(1-{4-[(1-Methylcyclopropyl)methoxy]
phenyl}cyclopropyl)-carbonyl]-3H-spiro[furo[3,4-c]
pyridine-1,3'-pyrrolidin]-3-one;

1'-[(1-{4-[(2-Fluorobenzyl)oxy]phenyl}cyclopropyl)car-
bonyl]-3H-spiro[furo[3,4-c]pyridine-1,3'-pyrrolidin]-
3-one;

1'-({1-[4-(Quinolin-2-ylmethoxy)phenyl}cyclopropyl)
carbonyl]-3H-spiro[furo[3,4-c]pyridine-1,3'-pyrroli-
din]-3-one;

1'-[(1-{4-[(3-Fluorobenzyl)oxy]phenyl}cyclopropyl)car-
bonyl]-3H-spiro[furo[3,4-c]pyridine-1,3'-pyrrolidin]-
3-one;

1'-({1-[4-(1,3-Benzothiazol-2-ylmethoxy)phenyl]cyclo-
propyl}-carbonyl)-3H-spiro[furo[3,4-c]pyridine-1,3'-
pyrrolidin]-3-one;

1'-{[1-(4-{[3,5-Bis(trifluoromethyl)benzyl]oxy}phenyl)-
cyclopropyl]carbonyl}-3 H-spiro[furo[3,4-c]pyridine-
1,3'-pyrrolidin]-3-one;

1'-[(1-{4-[2-(4-Fluorophenyl)ethoxy]
phenyl}cyclopropyl)-carbonyl]-3H-spiro[furo[3,4-c]
pyridine-1,3'-pyrrolidin]-3-one;

4-[(4-{1-[(3-oxo-1'H,3H-spiro[furo[3,4-c]pyridine-1,3'-
pyrrolidin]-1'-yl)carbonyl]cyclopropyl}phenoxy)me-
thyl]benzonitrile;

1'-{[1-(4-Phenoxyphenyl)cyclopropyl]carbonyl}-3H-
spiro[furo[3,4-c]pyridine-1,3'-pyrrolidin]-3-one;

1'-({1-[4-(Pyridin-4-ylmethoxy)phenyl]cyclopropyl}-
carbonyl)-3H-spiro[2-benzofuran-1,3'-pyrrolidin]-3-
one;

1'-({1-[4-(Pyridin-2-ylmethoxy)phenyl]cyclopropyl}-
carbonyl)-3H-spiro[2-benzofuran-1,3'-pyrrolidin]-3-
one;

1'-{[1-(4-Pyridin-4-ylphenyl)cyclopropyl]carbonyl}-3H-
spiro[2-benzofuran-1,3'-pyrrolidin]-3-one;

1'-{[1-(4-Cyclopropylphenyl)cyclopropyl]carbonyl}-3H-
spiro[2-benzofuran-1,3'-pyrrolidin]-3-one;

1'-{[1-(2-Fluoro-4-pyridin-2-ylphenyl)cyclopropyl]-car-
bonyl}-3H-spiro[2-benzofuran-1,3'-pyrrolidin]-3-one;

1'-[(1-{4-[(E)-2-(4-Methylphenyl)vinyl]phenyl}-cyclo-
propyl)carbonyl]-3H-spiro[2-benzofuran-1,3'-pyrroli-
din]-3-one;

1'-({1-[4-(2-Pyridin-2-ylethoxy)phenyl]cyclopropyl}-
carbonyl)-3H-spiro[2-benzofuran-1,3'-pyrrolidin]-3-
one;

1'-({1-[4-(2-Pyridin-2-ylethoxy)phenyl]
cyclopropyl}carbonyl)-3H-spiro[furo[3,4-c]pyridine-
1,3'-pyrrolidin]-3-one;

1'-[(1-{4-[(E)-2-Pyridin-4-ylvinyl]phenyl}cyclopropyl)-
carbonyl]-3H-spiro[2-benzofuran-1,3'-pyrrolidin]-3-
one;

1'-({1-[4-(3,5-Dimethylisoxazol-4-yl)phenyl]
cyclopropyl}carbonyl)-3H-spiro[2-benzofuran-1,3'-
pyrrolidin]-3-one;

1'-({1-[4-(1-Methyl-1H-pyrazol-4-yl)phenyl]
cyclopropyl}carbonyl)-3H-spiro[2-benzofuran-1,3'-
pyrrolidin]-3-one;

1'-({1-[4'-(Methylsulfonyl)biphenyl-4-yl]
cyclopropyl}carbonyl)-3H-spiro[2-benzofuran-1,3'-
pyrrolidin]-3-one;

1'-({1-{4-[3-Methyl-1H-pyrazol-1-yl)phenyl]
cyclopropyl}carbonyl)-3H-spiro[furo[3,4-c]pyridine-
1,3'-pyrrolidin]-3-one;

1'-[(1-{4-[3-(Trifluoromethyl)-1H-pyrazol-1-yl]phenyl]
cyclopropyl}carbonyl]-3H-spiro[furo[3,4-c]pyridine-
1,3'-pyrrolidin]-3-one;

1'-({1-[4-(4-Methyl-1H-pyrazol-1-yl)phenyl]
cyclopropyl}carbonyl)-3H-spiro[furo[3,4-c]pyridine-
1,3'-pyrrolidin]-3-one;

1'-({1-[4-(2H-Indazol-2-yl)phenyl]
cyclopropyl}carbonyl)-3H-spiro[furo[3,4-c]pyridine-
1,3'-pyrrolidin]-3-one;

1'-({1-[4-(1H-Benzimidazol-1-yl)phenyl]
cyclopropyl}carbonyl)-3H-spiro[furo[3,4-c]pyridine-
1,3'-pyrrolidin]-3-one;

1'-({1-[4-(2-Methyl-1H-imidazol-1-yl)phenyl]
cyclopropyl}carbonyl)-3H-spiro[furo[3,4-c]pyridine-
1,3'-pyrrolidin]-3-one;

1'-({1-[4-(1H-1,2,4-Triazol-1-yl)phenyl]
cyclopropyl}carbonyl)-3H-spiro[2-benzofuran-1,3'-
pyrrolidin]-3-one;

1'-({1-[4-(1-Hydroxycyclopentyl)phenyl]
cyclopropyl}carbonyl)-3H-spiro[2-benzofuran-1,3'-
pyrrolidin]-3-one;

1'-{[1-(4-Cyclopentylphenyl)cyclopropyl]carbonyl}-3H-
spiro[furo[3,4-c]pyridine-1,3'-pyrrolidin]-3-one;

1'-({1-[4-(1-Hydroxycyclopentyl)phenyl]
cyclopropyl}carbonyl)-3H-spiro[furo[3,4-c]pyridine-
1,3'-pyrrolidin]-3-one;

1'-({1-[4-(1-Hydroxycyclobutyl)phenyl]
cyclopropyl}carbonyl)-3H-spiro[2-benzofuran-1,3'-
pyrrolidin]-3-one;

1'-({1-[4-(1-Hydroxycyclobutyl)phenyl]
cyclopropyl}carbonyl)-3H-spiro[furo[3,4-c]pyridine-
1,3'-pyrrolidin]-3-one;

1'-({1-[4-(Tetrahydro-2H-pyran-4-yl)phenyl]
cyclopropyl}carbonyl)-3H-spiro[furo[3,4-c]pyridine-
1,3'-pyrrolidin]-3-one;

1'-{[1-(4-Cyclobutylphenyl)cyclopropyl]carbonyl}-3H-
spiro[furo[3,4-c]pyridine-1,3'-pyrrolidin]-3-one;

1'-({1-[4-(4-Hydroxytetrahydro-2H-pyran-4-yl)phenyl]
cyclopropyl}carbonyl)-3 H-spiro[2-benzofuran-1,3'-
pyrrolidin]-3-one;

1'-({1-[4-(4-Hydroxytetrahydro-2H-pyran-4-yl)phenyl]
cyclopropyl}carbonyl)-3 H-spiro[furo[3,4-c]pyridine-
1,3'-pyrrolidin]-3-one;

1'-({1-[4-(2-Amino-1,3-thiazol-4-yl)phenyl]cyclopropyl}carbonyl)-3H-spiro[2-benzofuran-1,3'-pyrrolidin]-3-one;
1'-({1-[4-(2-Methyl-1,3-thiazol-4-yl)phenyl]cyclopropyl}carbonyl)-3H-spiro[2-benzofuran-1,3'-pyrrolidin]-3-one;
1'-({1-[4-(2-Ethyl-1,3-thiazol-4-yl)phenyl]cyclopropyl}carbonyl)-3H-spiro[2-benzofuran-1,3'-pyrrolidin]-3-one;
1'-({1-[4-(2-Amino-1,3-thiazol-4-yl)phenyl]cyclopropyl}carbonyl)-3H-spiro[furo[3,4-c]pyridine-1,3'-pyrrolidin]-3-one;
1'-({1-[4-(2-Methyl-1,3-thiazol-4-yl)phenyl]cyclopropyl}carbonyl)-3H-spiro[furo[3,4-c]pyridine-1,3'-pyrrolidin]-3-one;
1'-({1-[4-(1,3-Thiazol-4-yl)phenyl]cyclopropyl}carbonyl)-3H-spiro[2-benzofuran-1,3'-pyrrolidin]-3-one;
1'-{[trans-1-(4-Chlorophenyl)-3-hydroxycyclobutyl]carbonyl}-3H-spiro[2-benzofuran-1,3'-pyrrolidin]-3-one;
1'-{[cis-1-(4-Chlorophenyl)-3-fluorocyclobutyl]carbonyl}-3H-spiro[2-benzofuran-1,3'-pyrrolidin]-3-one;
1'-{[cis-1-(4-Chlorophenyl)-3-fluorocyclobutyl]carbonyl}-3H-spiro[furo[3,4-c]pyridine-1,3'-pyrrolidin]-3-one;
1'-{[cis-1-(4-Chlorophenyl)-3-fluorocyclobutyl]carbonyl}-7H-spiro[furo[3,4-b]pyridine-5,3'-pyrrolidin]-7-one;
1'-{[1-(4-Chlorophenyl)cyclobutyl]carbonyl}-7H-spiro[furo[3,4-b]pyridine-5,3'-pyrrolidin]-7-one;
1'-({1-[4-(1H-Indazol-1-yl)phenyl]cyclobutyl}carbonyl)-3H-spiro[furo[3,4-c]pyridine-1,3'-pyrrolidin]-3-one;
1'-[(1-{4-[3-(Trifluoromethyl)-1H-pyrazol-1-yl]phenyl}cyclobutyl)carbonyl]-3H-spiro[furo[3,4-c]pyridine-1,3'-pyrrolidin]-3-one;
1'-({1-[4-(1H-Benzimidazol-1-yl)phenyl]cyclobutyl}carbonyl)-3H-spiro[furo[3,4-c]pyridine-1,3'-pyrrolidin]-3-one;
1'-({1-[4-(2-oxo-1,3-oxazolidin-3-yl)phenyl]cyclobutyl}carbonyl)-3H-spiro[2-benzofuran-1,3'-pyrrolidin]-3-one;
1'-[(1-Pyridin-4-ylcyclobutyl)carbonyl]-3H-spiro[2-benzofuran-1,3'-pyrrolidin]-3-one;
1'-{[1-(4-Pyridin-4-ylphenyl)cyclobutyl]carbonyl}-3H-spiro[2-benzofuran-1,3'-pyrrolidin]-3-one;
N,N-Dimethyl-4-[5-(1-{[3-oxo-1'H,3H-spiro[2-benzofuran-1,3'-pyrrolidin]-1'-yl]carbonyl}cyclopropyl)pyridin-2-yl]piperazine-1-carboxamide;
1'-[(1-{6-[4-(Methylsulfonyl)piperazin-1-yl]pyridin-3-yl}cyclopropyl)carbonyl]-3H-spiro[2-benzofuran-1,3'-pyrrolidin]-3-one;
1'-[(1-{6-[4-(2-Fluorophenyl)piperazin-1-yl]pyridin-3-yl}cyclopropyl)carbonyl]-3H-spiro[2-benzofuran-1,3'-pyrrolidin]-3-one;
1'-({1-[6-(3,3-Difluoropyrrolidin-1-yl)pyridin-3-yl]cyclopropyl}carbonyl)-3H-spiro[2-benzofuran-1,3'-pyrrolidin]-3-one;
1'-[(1-{6-[3-Hydroxypyrrolidin-1-yl]pyridin-3-yl}cyclopropyl)carbonyl]-3H-spiro[2-benzofuran-1,3'-pyrrolidin]-3-one;
N-{1-[5-(1-{[3-Oxo-1'H,3H-spiro[2-benzofuran-1,3'-pyrrolidin]-yl]carbonyl}cyclopropyl)pyridin-2-yl]pyrrolidin-3-yl}acetamide;
1'-({1-[6-(1,3-Dihydro-2H-isoindol-2-yl)pyridin-3-yl]cyclopropyl}carbonyl)-3H-spiro[2-benzofuran-1,3'-pyrrolidin]-3-one;
1'-({1-[6-(3,4-Dihydro-isoquinolin-2(1H)-yl)pyridin-3-yl]cyclopropyl}carbonyl)-3H-spiro[2-benzofuran-1,3'-pyrrolidin]-3-one;
1'-{[1-(6-Morpholin-4-ylpyridin-3-yl)cyclopropyl]carbonyl}-3H-spiro[2-benzofuran-1,3'-pyrrolidin]-3-one;
1'({1-[6-(4-Hydroxypiperidin-1-yl)pyridin-3-yl]cyclopropyl}carbonyl)-3H-spiro[2-benzofuran-1,3'-pyrrolidin]-3-one;
N-{4-[5-(1-{[3-Oxo-1'H,3H-spiro[2-benzofuran-1,3'-pyrrolidin]-1'yl]carbonyl}cyclopropyl)pyridin-2-yl]phenyl}acetamide;
1'-({1-[6-(2-Fluorophenyl)pyridin-3-yl]cyclopropyl}carbonyl)-3H-spiro[2-benzofuran-1,3'-pyrrolidin]-3-one;
1'-({1-[6-(1-Benzothien-3-yl)pyridin-3-yl]cyclopropyl}carbonyl)-3H-spiro[2-benzofuran-1,3'-pyrrolidin]-3-one;
1'-({[1-(2,3'-Bipyridin-5-yl)cyclopropyl]carbonyl}-3H-spiro[2-benzofuran-1,3'-pyrrolidin]-3-one;
1'-({1-[6-(1-Methyl-1H-indol-5-yl)pyridine-3-yl]cyclopropyl}carbonyl)-3H-spiro[2-benzofuran-1,3'-pyrrolidin]-3-one;
1'-[(1-{6-[3-(Trifluoromethoxy)phenyl]pyridine-3-yl}cyclopropyl)carbonyl]-3H-spiro[2-benzofuran-1,3'-pyrrolidin]-3-one;
1'-({1-[6-(3-Thienyl)pyridine-3-yl]cyclopropyl}carbonyl)-3H-spiro[2-benzofuran-1,3'-pyrrolidin]-3-one;
1'-[(1-{6-[3-(Trifluoromethyl)phenyl]pyridine-3-yl}cyclopropyl)carbonyl]-3H-spiro[2-benzofuran-1,3'-pyrrolidin]-3-one;
1'-({1-[6-(1-Methyl-1H-pyrazol-4-yl)pyridine-3-yl]cyclopropyl}carbonyl)-3H-spiro[2-benzofuran-1,3'-pyrrolidin]-3-one;
1'-{[1-(6-Chloropyridin-3-yl)cyclopropyl]carbonyl}-3H-spiro[2-benzofuran-1,3'-pyrrolidin]-3-one;
1'-({1-[6-(Benzyloxy)pyridin-3-yl]cyclopropyl}carbonyl)-3H-spiro[2-benzofuran-1,3'-pyrrolidin]-3-one;
1'-[(1-Quinolin-3-ylcyclopropyl)carbonyl]-3H-spiro[2-benzofuran-1,3'-pyrrolidin]-3-one;
1'-({1-[6-(1-Methyl-1H-pyrazol-4-yl)pyridin-3-yl]cyclopropyl}carbonyl)-3H-spiro[furo[3,4-c]pyridine-1,3'-pyrrolidin]-3-one;
1'-({1-[6-(Benzyloxy)pyridin-3-yl]cyclopropyl}carbonyl)-3H-spiro[furo[3,4-c]pyridine-1,3'-pyrrolidin]-3-one;
1'-{[1-(6-Chloropyridin-3-yl)cyclopropyl]carbonyl}-3H-spiro[furo[3,4-c]pyridine-1,3'-pyrrolidin]-3-one;
1'-({1-[6-(3,4-Dihydroisoquinolin-2(1H)-yl)pyridin-3-yl]cyclopropyl}carbonyl)-3 H-spiro[furo[3,4-c]pyridine-1,3'-pyrrolidin]-3-one;
1'-({1-[6-(1,3-Dihydro-2H-isoindol-2-yl)pyridin-3-yl]cyclopropyl}carbonyl)-3H-spiro[furo[3,4-c]pyridine-1,3'-pyrrolidin]-3-one;
1'-({1-[6-(3,3-Difluoropyrrolidin-1-yl)pyridin-3-yl]cyclopropyl}carbonyl)-3H-spiro[furo[3,4-c]pyridine-1,3'-pyrrolidin]-3-one;
Isobutyl 4-(5-{1-[(3-oxo-1'H,3H-spiro[furo[3,4-c]pyridine-1,3'-pyrrolidin]-1'-yl)carbonyl]cyclopropyl}pyridin-2-yl)piperazine-1-carboxylate;
2-[4-(5-{1-[(3-oxo-1'H,3H-spiro[furo[3,4-c]pyridine-1,3'-pyrrolidin]-1'-yl)carbonyl]cyclopropyl}pyridin-2-yl)piperazin-1-yl]benzonitrile;
1'-[(1-{6-[4-(4-Fluorophenyl)piperazin-1-yl]pyridin-3-yl}cyclopropyl)carbonyl]-3H-spiro[furo[3,4-c]pyridine-1,3'-pyrrolidin]-3-one;

1'-[(1-{6-[3-(Trifluoromethyl)phenyl]pyridin-3-yl}cyclopropyl)carbonyl]-3H-spiro[furo[3,4-c]pyridine-1,3'-pyrrolidin]-3-one;
1'-[(1-{6-[3-(Trifluoromethoxy)phenyl]pyridin-3-yl}cyclopropyl)carbonyl]-3H-spiro[furo[3,4-c]pyridine-1,3'-pyrrolidin]-3-one;
4-(5-{1-[(3-oxo-1'H,3H-spiro[furo[3,4-c]pyridine-1,3'-pyrrolidin]-1'-yl)carbonyl]cyclopropyl}pyridin-2-yl)benzonitrile;
1'-({1-[6-(3-Chloro-4-fluorophenyl)pyridin-3-yl]cyclopropyl}carbonyl)-3H-spiro[furo[3,4-c]pyridine-1,3'-pyrrolidin]-3-one;
1'-[(1-{6-[4-(Methoxymethyl)phenyl]pyridin-3-yl}cyclopropyl)carbonyl]-3H-spiro[furo[3,4-c]pyridine-1,3'-pyrrolidin]-3-one;
N-[3-(5-{1-[(3-Oxo-1'H,3H-spiro[furo[3,4-c]pyridine-1,3'-pyrrolidin]-1'-yl)carbonyl]cyclopropyl}pyridin-2-yl)phenyl]acetamide; and
4-(5-{1-[(3-oxo-1'H,3H-spiro[furo[3,4-c]pyridine-1,3'-pyrrolidin]-1'-yl)carbonyl]cyclopropyl}pyridin-2-yl)benzamide,
or a pharmaceutically acceptable salt thereof.

14. A compound of claim 1 selected from:
1'-[(1-{6-[4-(Methylsulfonyl)phenyl]pyridin-3-yl}cyclopropyl)carbonyl]-3H-spiro[furo[3,4-c]pyridine-1,3'-pyrrolidin]-3-one;
1'-({1-[6-(1-Methyl-1H-indol-5-yl)pyridin-3-yl]cyclopropyl}carbonyl)-3H-spiro[furo[3,4-c]pyridine-1,3'-pyrrolidin]-3-one;
1'-({1-[6-(1-Benzothien-5-yl)pyridin-3-yl]cyclopropyl}carbonyl)-3H-spiro[furo[3,4-c]pyridine-1,3'-pyrrolidin]-3-one;
1'-{[1-(6-Quinolin-3-ylpyridin-3-yl)cyclopropyl]carbonyl}-3H-spiro[furo[3,4-c]pyridine-1,3'-pyrrolidin]-3-one;
1'-({1-[6-(3-Thienyl)pyridin-3-yl]cyclopropyl}carbonyl)-3H-spiro[furo[3,4-c]pyridine-1,3'-pyrrolidin]-3-one;
1'-({1-[4-(2-Oxo-2,3-dihydro-1H-indol-1-yl)phenyl]cyclopropyl}carbonyl)-3H-spiro[furo[3,4-c]pyridine-1,3'-pyrrolidin]-3-one;
1'-({1-[4-(3-Methyl-2-oxo-2,3-dihydro-1H-benzimidazol-1-yl)-phenyl]cyclopropyl}carbonyl)-3H-spiro[furo[3,4-c]pyridine-1,3'-pyrrolidin]-3-one;
4-{1-[(3-Oxo-1'H,3H-spiro[furo[3,4-c]pyridine-1,3'-pyrrolidin]-1'-yl)carbonyl]cyclopropyl}benzonitrile;
4-{1-[(3-Oxo-1'H,3H-spiro[furo[3,4-c]pyridine-1,3'-pyrrolidin]-1'-yl)carbonyl]cyclopropyl}benzenecarbothioamide;
1'-[(1-{4-[1-(Methylsulfonyl)-1,2,3,6-tetrahydropyridin-4-yl]phenyl}cyclopropyl)carbonyl]-3H-spiro[furo[3,4-c]pyridine-1,3'-pyrrolidin]-3-one;
1'-[(1-{4-[(E)-2-Pyridin-4-ylvinyl]phenyl}cyclopropyl)carbonyl]-3H-spiro[furo[3,4-c]pyridine-1,3'-pyrrolidin]-3-one;
1'-[(1-{4-[Cyclopentyl(fluoro)methyl]phenyl}cyclopropyl)carbonyl]-3H-spiro[furo[3,4-c]pyridine-1,3'-pyrrolidin]-3-one;
1'-({1-[4-(Tetrahydro-2H-pyran-4-yloxy)phenyl]cyclopropyl}carbonyl)-3H-spiro[furo[3,4-c]pyridine-1,3'-pyrrolidin]-3-one;
tert-Butyl (4-{1-[(3-oxo-1'H,3H-spiro[furo[3,4-c]pyridine-1,3'-pyrrolidin]-1'-yl)carbonyl]cyclopropyl}phenoxy)acetate;
(4-{1-[(3-Oxo-1'H,3H-spiro[furo[3,4-c]pyridine-1,3'-pyrrolidin]-1'-yl)carbonyl]cyclopropyl}phenoxy)acetonitrile;
1'-[(1-{4-[(5-Methylisoxazol-3-yl)methoxy]phenyl}cyclopropyl)-carbonyl]-3H-spiro[furo[3,4-c]pyridine-1,3'-pyrrolidin]-3-one;
1'-({1-[4-(Cyclopentylmethoxy)phenyl]cyclopropyl}carbonyl)-3H-spiro[furo[3,4-c]pyridine-1,3'-pyrrolidin]-3-one;
1'-({1-[4-(Quinolin-3-ylmethoxy)phenyl]cyclopropyl}carbonyl)-3H-spiro[furo[3,4-c]pyridine-1,3'-pyrrolidin]-3-one;
1'-({1-[4-(Quinolin-4-ylmethoxy)phenyl]cyclopropyl}carbonyl)-3H-spiro[furo[3,4-c]pyridine-1,3'-pyrrolidin]-3-one;
1'-({1-[4-(Quinolin-6-ylmethoxy)phenyl]cyclopropyl}carbonyl)-3H-spiro[furo[3,4-c]pyridine-1,3'-pyrrolidin]-3-one;
1'-({1-[4-(Pyridin-3-ylmethoxy)phenyl]cyclopropyl}carbonyl)-3H-spiro[furo[3,4-c]pyridine-1,3'-pyrrolidin]-3-one;
1'-{[1-(1,3-Benzothiazol-2-yl)cyclopropyl]carbonyl}-3H-spiro[furo[3,4-c]pyridine-1,3'-pyrrolidin]-3-one;
1'-({1-[4-(4-Chlorophenyl)-1,3-thiazol-2-yl]cyclopropyl}carbonyl)-3H-spiro[furo[3,4-c]pyridine-1,3'-pyrrolidin]-3-one;
4-(1-{[3-Oxo-1'H,3H-spiro[2-benzofuran-1,3'-pyrrolidin]-1'-yl]carbonyl}cyclopropyl)benzonitrile;
1'-{[1-(4-Bromophenyl)cyclopropyl]carbonyl}-3H-spiro[2-benzofuran-1,3'-pyrrolidin]-3-one;
1'-({1-[4-(Pyrrolidin-1-ylcarbonyl)phenyl]cyclopropyl}carbonyl)-3H-spiro[2-benzofuran-1,3'-pyrrolidin]-3-one;
4-(1-{[3-Oxo-1'H,3H-spiro[2-benzofuran-1,3'-pyrrolidin]-1'-yl]carbonyl}cyclopropyl)benzohydrazide;
N-Methyl-4-(1-{[3-oxo-1'H,3H-spiro[2-benzofuran-1,3'-pyrrolidin]-yl]carbonyl}cyclopropyl)benzamide;
4-(1-{[3-Oxo-1'H,3H-spiro[2-benzofuran-1,3'-pyrrolidin]-1'-yl]carbonyl}cyclopropyl)benzenecarbothioamide;
1'-[(1-{4-[2-(Trifluoromethyl)-1H-imidazol-4-yl]phenyl}cyclopropyl)carbonyl]-3H-spiro[2-benzofuran-1,3'-pyrrolidin]-3-one;
1'-({1-[4-(1-Methyl-1H-pyrazol-3-yl)phenyl]cyclopropyl}carbonyl)-3H-spiro[2-benzofuran-1,3'-pyrrolidin]-3-one;
N-Cyclopropyl-4'-(1-{[3-oxo-1'H,3H-spiro[2-benzofuran-1,3'-pyrrolidin]-1'-yl]carbonyl}cyclopropyl)biphenyl-4-carboxamide;
1'-[(1-{4-[5-(Trifluoromethyl)-1H-1,2,4-triazol-3-yl]phenyl}cyclopropyl)carbonyl]-3H-spiro[2-benzofuran-1,3'-pyrrolidin]-3-one;
1'-({1-[4-(1-Methyl-1H-tetrazol-5-yl)phenyl]cyclopropyl}carbonyl)-3H-spiro[2-benzofuran-1,3'-pyrrolidin]-3-one;
1'-({1-[4-(2-Amino-1,3-oxazol-4-yl)phenyl]cyclopropyl}carbonyl)-3H-spiro[2-benzofuran-1,3'-pyrrolidin]-3-one;
1'-{[1-(4-Pyrimidin-5-ylphenyl)cyclopropyl]carbonyl}-3H-spiro[2-benzofuran-1,3'-pyrrolidin]-3-one;
1'-({1-[4-(6-Fluoropyridin-3-yl)phenyl]cyclopropyl}carbonyl)-3H-spiro[2-benzofuran-1,3'-pyrrolidin]-3-one;
1'-({1-[4-(6-Pyrrolidin-1-ylpyridin-3-yl)phenyl]cyclopropyl}carbonyl)-3H-spiro[2-benzofuran-1,3'-pyrrolidin]-3-one;
N-Cyclopropyl-5-[4-(1-{[3-oxo-1'H,3H-spiro[2-benzofuran-1,3'-pyrrolidin]-yl]carbonyl}cyclopropyl)phenyl]pyridine-2-carboxamide;

N-Methyl-5-[4-(1-{[3-oxo-1'H,3'H-spiro[2-benzofuran-1,
3'-pyrrolidin]-1'-yl]carbonyl}cyclopropyl)phenyl]pyridine-2-carboxamide;
1'-({1-[4-(Methylsulfonyl)phenyl]
cyclopropyl}carbonyl)-3H-spiro[2-benzofuran-1,3'-pyrrolidin]-3-one;
1'-[(1-{4-[(Trifluoromethyl)thio]phenyl}cyclopropyl)carbonyl]-3H-spiro[2-benzofuran-1,3'-pyrrolidin]-3-one;
1'-{[1-(4-Chloro-2-fluorophenyl)cyclopropyl]carbonyl}-3H-spiro[2-benzofuran-1,3'-pyrrolidin]-3-one;
1'-({1-[4-(2-Oxopyridin-1(2H)-yl)phenyl]
cyclopropyl}carbonyl)-3H-spiro[2-benzofuran-1,3'-pyrrolidin]-3-one;
Methyl 4-[4-(1-{[3-oxo-1'H,3'H-spiro[2-benzofuran-1,3'-pyrrolidin]-1'-yl]carbonyl}cyclopropyl)phenyl]piperazine-1-carboxylate;
1'-[(1-{4-[4-(Methylsulfonyl)-2-oxopiperazin-1-yl]
phenyl}cyclopropyl)carbonyl]-3H-spiro[2-benzofuran-1,3'-pyrrolidin]-3-one;
N-[4-(1-{[3-Oxo-1'H,3'H-spiro[2-benzofuran-1,3'-pyrrolidin]-1'-yl]carbonyl}cyclopropyl)phenyl]cyclopropanecarboxamide;
N-[4-(1-{[3-Oxo-1'H,3'H-spiro[2-benzofuran-1,3'-pyrrolidin]-1'-yl]carbonyl}cyclopropyl)phenyl]benzenesulfonamide;
Methyl allyl[4-(1-{[3-oxo-1'H,3'H-spiro[2-benzofuran-1,3'-pyrrolidin]-1'-yl]carbonyl}cyclopropyl)phenyl]carbamate;
1'-({1-[4-(1H-1,2,4-Triazol-1-yl)phenyl]
cyclopropyl}carbonyl)-3H-spiro[2-benzofuran-1,3'-pyrrolidin]-3-one;
1'-[(1-Quinolin-6-ylcyclopropyl)carbonyl]-3H-spiro[2-benzofuran-1,3'-pyrrolidin]-3-one;
1'-[(1-Pyridin-4-ylcyclopropyl)carbonyl]-3H-spiro[2-benzofuran-1,3'-pyrrolidin]-3-one;
1'-[(1-Quinolin-4-ylcyclopropyl)carbonyl]-3H-spiro[2-benzofuran-1,3'-pyrrolidin]-3-one;
1'-[(1-Quinolin-2-ylcyclopropyl)carbonyl]-3H-spiro[2-benzofuran-1,3'-pyrrolidin]-3-one;
1'[(1-Pyridin-2-ylcyclopropyl)carbonyl]-3H-spiro[2-benzofuran-1,3'-pyrrolidin]-3-one;
1-{[1-(1,3-Benzothiazol-2-yl)cyclopropyl]carbonyl}-3H-spiro[2-benzofuran-1,3'-pyrrolidin]-3-one;
1'-({1-[4-(Pyrrolidin-1-ylmethyl)phenyl]
cyclopropyl}carbonyl)-3H-spiro[2-benzofuran-1,3'-pyrrolidin]-3-one;
1'-({1-[4-(3-Thienyl)phenyl]cyclopropyl}carbonyl)-3H-spiro[2-benzofuran-1,3'-pyrrolidin]-3-one;
1'-{[1-(2-Naphthyl)cyclopropyl]carbonyl}-3H-spiro[furo[3,4-c]pyridine-1,3'-pyrrolidin]-3-one;
1'-({1-[4-(Pyridin-4-ylmethoxy)phenyl]
cyclopropyl}carbonyl)-3H-spiro[furo[3,4-c]pyridine-1,3'-pyrrolidin]-3-one;
1'-{[1-(2-Fluoro-4-pyridin-4-ylphenyl)cyclopropyl]carbonyl}-3H-spiro[2-benzofuran-1,3'-pyrrolidin]-3-one;
1'-({1-[3'-(Hydroxymethyl)biphenyl-4-yl]
cyclopropyl}carbonyl)-3H-spiro[2-benzofuran-1,3'-pyrrolidin]-3-one;
1'-({1-[2'-(Methylthio)biphenyl-4-yl]
cyclopropyl}carbonyl)-3H-spiro[2-benzofuran-1,3'-pyrrolidin]-3-one;
1'-{[1-(1,3-Benzothiazol-2-yl)cyclopropyl]carbonyl}-7H-spiro[furo[3,4-b]pyridine-5,3'-pyrrolidin]-7-one;
1'-{[1-(2-Naphthyl)cyclopropyl]carbonyl}-7H-spiro[furo[3,4-b]pyridine-5,3'-pyrrolidin]-7-one;
1'-({1-[4-(Difluoromethoxy)phenyl]
cyclopropyl}carbonyl)-7H-spiro[furo[3,4-b]pyridine-5,3'-pyrrolidin]-7-one;
1'-{[1-(4-{[4-(Trifluoromethoxy)benzyl]oxy}phenyl)cyclopropyl]carbonyl}-3H-spiro[furo[3,4-c]pyridine-1,3'-pyrrolidin]-3-one; and
1'-[(1-{4-[1-(4-Bromophenyl)ethoxy]
phenyl}cyclopropyl)carbonyl]-3H-spiro[furo[3,4-c]pyridine-1,3'-pyrrolidin]-3-one,
or a pharmaceutically acceptable salt thereof.
15. A compound of claim 1 selected from:
1'-{[1-(4-Pyridin-3-ylphenyl)cyclopropyl]carbonyl}-3H-spiro[furo[3,4-c]pyridine-1,3'-pyrrolidin]-3-one;
[4-(4-{1-[(3-Oxo-1'H,3'H-spiro[furo[3,4-c]pyridine-1,3'-pyrrolidin]-1'-yl)carbonyl]cyclopropyl}phenyl)-1,3-thiazol-2-yl]acetonitrile;
1'-({1-[4-(2-Pyridin-3-yl-1,3-thiazol-4-yl)phenyl]
cyclopropyl}carbonyl)-3H-spiro[furo[3,4-c]pyridine-1,3'-pyrrolidin]-3-one;
1'-({1-[4-(1-Propionyl-1,2,3,6-tetrahydropyridin-4-yl)
phenyl]cyclopropyl}carbonyl)-3H-spiro[furo[3,4-c]pyridine-1,3'-pyrrolidin]-3-one;
Ethyl 4-[4-(1-{[3-oxo-1'H,3'H-spiro[furo[3,4-c]pyridine-1,3'-pyrrolidin]-1'-yl]carbonyl}cyclopropyl)phenyl]-3,6-dihydropyridine-1(2H)-carboxylate;
4-[(E)-2-(4-{1-[(3-Oxo-1'H,3'H-spiro[furo[3,4-c]pyridine-1,3'-pyrrolidin]-1'-yl)carbonyl]
cyclopropyl}phenyl)vinyl]benzonitrile;
1'-{[1-(2-Fluoro-4-pyridin-4-ylphenyl)cyclopropyl]carbonyl}-3H-spiro[furo[3,4-c]pyridine-1,3'-pyrrolidin]-3-one;
1'-[(1-{2-Fluoro-4-[3-(trifluoromethyl)-1H-pyrazol-1-yl]
phenyl}cyclopropyl)carbonyl]-3H-spiro[furo[3,4-c]pyridine-1,3'-pyrrolidin]-3-one;
1'-({1-[4-(2H-Indazol-2-yl)phenyl]
cyclopropyl}carbonyl)-3H-spiro[furo[3,4-c]pyridine-1,3'-pyrrolidin]-3-one;
1'-({1-[4-(3,3-Difluoropyrrolidin-1-yl)phenyl]
cyclopropyl}carbonyl)-3H-spiro[furo[3,4-c]pyridine-1,3'-pyrrolidin]-3-one;
1'-({1-[2-Fluoro-4-(2-oxopyrrolidin-1-yl)phenyl]
cyclopropyl}carbonyl)-3H-spiro[furo[3,4-c]pyridine-1,3'-pyrrolidin]-3-one;
1'-({1-[4-(2-Oxopyrrolidin-1-yl)phenyl]
cyclopropyl}carbonyl)-3H-spiro[furo[3,4-c]pyridine-1,3'-pyrrolidin]-3-one;
1'-({1-[4-(2-Oxo-1,3-oxazolidin-3-yl)phenyl]
cyclopropyl}carbonyl)-3H-spiro[furo[3,4-c]pyridine-1,3'-pyrrolidin]-3-one;
1'-[(1-{4-[4-Isopropyl-2-oxo-1,3-oxazolidin-3-yl]
phenyl}cyclopropyl)carbonyl]-3H-spiro[furo[3,4-c]pyridine-1,3'-pyrrolidin]-3-one;
1'-({1-[4-(2-Oxoimidazolidin-1-yl)phenyl]
cyclopropyl}carbonyl)-3H-spiro[furo[3,4-c]pyridine-1,3'-pyrrolidin]-3-one;
1'-({1-[4-(2-Oxoimidazolidin-1-yl)phenyl]
cyclopropyl}carbonyl)-3H-spiro[2-benzofuran-1,3'-pyrrolidin]-3-one;
1'-[(1-{4-[4-Isopropyl-2-oxo-1,3-oxazolidin-3-yl]
phenyl}cyclopropyl)carbonyl]-3H-spiro[2-benzofuran-1,3'-pyrrolidin]-3-one;
1'-({1-[2-Fluoro-4-(2-oxopyrrolidin-1-yl)phenyl]
cyclopropyl}carbonyl)-3H-spiro[2-benzofuran-1,3'-pyrrolidin]-3-one;
1'-({1-[2-Fluoro-4-(2-oxo-1,3-oxazolidin-3-yl)phenyl]
cyclopropyl}carbonyl)-3H-spiro[2-benzofuran-1,3'-pyrrolidin]-3-one;

Methyl 3-oxo-4-[4-(1-{[3-oxo-1'H,3H-spiro[2-benzofuran-1,3'-pyrrolidin]-1'-yl]carbonyl}cyclopropyl)phenyl]piperazine-1-carboxylate;

1'-[(1-{6-[4-(Cyclopropylcarbonyl)piperazin-1-yl]pyridin-3-yl}cyclopropyl)carbonyl]-3H-spiro[2-benzofuran-1,3'-pyrrolidin]-3-one;

1'-[(1-{6-[4-(Pyridin-4-yloxy)piperidin-1-yl]pyridin-3-yl}cyclopropyl)carbonyl]-3H-spiro[2-benzofuran-1,3'-pyrrolidin]-3-one;

1'-[(1-{6-[3-(Pyridin-4-yloxy)pyrrolidin-1-yl]pyridin-3-yl}cyclopropyl)carbonyl]-3H-spiro[2-benzofuran-1,3'-pyrrolidin]-3-one;

1'-({1-[4-(6-Methoxypyridin-3-yl)phenyl]cyclopropyl}carbonyl)-3H-spiro[2-benzofuran-1,3'-pyrrolidin]-3-one;

[4'-(1-{[3-Oxo-1'H,3H-spiro[2-benzofuran-1,3'-pyrrolidin]-1'-yl]carbonyl}cyclopropyl)biphenyl-3-yl]acetonitrile;

1'-({1-[4-(6-Aminopyridin-3-yl)phenyl]cyclopropyl}carbonyl)-3H-spiro[2-benzofuran-1,3'-pyrrolidin]-3-one;

1'-({1-[4-(6-Hydroxypyridin-3-yl)phenyl]cyclopropyl}carbonyl)-3H-spiro[2-benzofuran-1,3'-pyrrolidin]-3-one;

1'-({1-[4-(5-Methylpyridin-2-yl)phenyl]cyclopropyl}carbonyl)-3H-spiro[2-benzofuran-1,3'-pyrrolidin]-3-one;

1'-[(1-{4-[(Pyridin-2-yloxy)methyl]phenyl}cyclopropyl)carbonyl]-3H-spiro[2-benzofuran-1,3'-pyrrolidin]-3-one;

1'-[(1-{4-[(Pyridin-3-yloxy)methyl]phenyl}cyclopropyl)carbonyl]-3H-spiro[2-benzofuran-1,3'-pyrrolidin]-3-one;

1'-[(1-{4-[(Pyridin-4-yloxy)methyl]phenyl}cyclopropyl)carbonyl]-3H-spiro[2-benzofuran-1,3'-pyrrolidin]-3-one;

3-(1-{[3-Oxo-1'H,3H-spiro[2-benzofuran-1,3'-pyrrolidin]-1'-yl]carbonyl}cyclopropyl)benzonitrile;

1'-[(1-Biphenyl-3-ylcyclopropyl)carbonyl]-3H-spiro[2-benzofuran-1,3'-pyrrolidin]-3-one;

1'-{[1-(1-Naphthyl)cyclopropyl]carbonyl}-3H-spiro[2-benzofuran-1,3'-pyrrolidin]-3-one;

1'-[(1-Quinolin-6-ylcyclopropyl)carbonyl]-3H-spiro[2-benzofuran-1,3'-pyrrolidin]-3-one;

1'-[(1-{4-[(5-Methylisoxazol-3-yl)methoxy]phenyl}cyclopropyl)carbonyl]-3H-spiro[2-benzofuran-1,3'-pyrrolidin]-3-one;

1'-({1-[4-(2-Pyridin-3-yl-1,3-thiazol-4-yl)phenyl]cyclopropyl}carbonyl)-3H-spiro[2-benzofuran-1,3'-pyrrolidin]-3-one;

1'-[(1-{4-[5-(Trifluoromethyl)-1,3,4-oxadiazol-2-yl]phenyl}cyclopropyl)carbonyl]-3H-spiro[2-benzofuran-1,3'-pyrrolidin]-3-one;

1'-{[1-(4-tert-Butyl-1,3-thiazol-2-yl)cyclopropyl]carbonyl}-3H-spiro[2-benzofuran-1,3'-pyrrolidin]-3-one;

1'-({1-[4-(4-Chlorophenyl)-1,3-thiazol-2-yl]cyclopropyl}carbonyl)-3H-spiro[2-benzofuran-1,3'-pyrrolidin]-3-one;

1',1'''-[1,4-Phenylenebis(cyclopropane-1,1-diylcarbonyl)]bis(3H-spiro[2-benzofuran-1,3'-pyrrolidin]-3-one);

1'-[(1-Pyridin-3-ylcyclobutyl)carbonyl]-3H-spiro[2-benzofuran-1,3'-pyrrolidin]-3-one;

1'-{[1-(4-Chlorophenyl)cyclobutyl]carbonyl}-3H-spiro[2-benzofuran-1,3'-pyrrolidin]-3-one;

1'-{[1-(4-Chlorophenyl)cyclobutyl]carbonyl}-7H-spiro[furo[3,4-b]pyridine-5,3'-pyrrolidin]-7-one;

1'-{[1-(6-Chloropyridin-3-yl)cyclopropyl]carbonyl}-7H-spiro[furo[3,4-b]pyridine-5,3'-pyrrolidin]-7-one;

1'-{[1-(4-Methylphenyl)cyclopropyl]carbonyl}-7H-spiro[furo[3,4-b]pyridine-5,3'-pyrrolidin]-7-one; and 1'-({1-[4-(Trifluoromethyl)phenyl]cyclopropyl}carbonyl)-7H-spiro[furo[3,4-b]pyridine-5,3'-pyrrolidin]-7-one, or a pharmaceutically acceptable salt thereof.

16. A compound of claim 1 selected from:

{[1-(4-Methoxyphenyl)cyclopropyl]carbonyl}-7H-spiro[furo[3,4-b]pyridine-5,3'-pyrrolidin]-7-one;

1'-({1-[4-(Trifluoromethoxy)phenyl]cyclopropyl}carbonyl)-7H-spiro[furo[3,4-b]pyridine-5,3'-pyrrolidin]-7-one;

1'-{[1-(4-Fluorophenyl)cyclopropyl]carbonyl}-7H-spiro[furo[3,4-b]pyridine-5,3'-pyrrolidin]-7-one;

1'-{[1-(2-Chloro-4-fluorophenyl)cyclopropyl]carbonyl}-7H-spiro[furo[3,4-b]pyridine-5,3'-pyrrolidin]-7-one;

1'-{[1-(2,4-Difluorophenyl)cyclopropyl]carbonyl}-7H-spiro[furo[3,4-b]pyridine-5,3'-pyrrolidin]-7-one;

1'-{[1-(3-Chlorophenyl)cyclopropyl]carbonyl}-7H-spiro[furo[3,4-b]pyridine-5,3'-pyrrolidin]-7-one;

1'-{[1-(3,4-Dichlorophenyl)cyclopropyl]carbonyl}-7H-spiro[furo[3,4-b]pyridine-5,3'-pyrrolidin]-7-one;

1'-{[1-(2,3-Difluorophenyl)cyclopropyl]carbonyl}-7H-spiro[furo[3,4-b]pyridine-5,3'-pyrrolidin]-7-one;

1'-{[1-(2,4-Dichlorophenyl)cyclopropyl]carbonyl}-7H-spiro[furo[3,4-b]pyridine-5,3'-pyrrolidin]-7-one;

Ethyl 4-[5-(1-{[3-oxo-1'H,3H-spiro[2-benzofuran-1,3'-pyrrolidin]-1'-yl]carbonyl}cyclopropyl)pyridin-2-yl]piperazine-1-carboxylate;

1'-[(1-{6-[4-(ethylsulfonyl)piperazin-1-yl]pyridin-3-yl}cyclopropyl)carbonyl]-3H-spiro[2-benzofuran-1,3'-pyrrolidin]-3-one;

1'-({1-[6-(4-Methylpiperazin-1-yl)pyridin-3-yl]cyclopropyl}carbonyl)-3H-spiro[2-benzofuran-1,3'-pyrrolidin]-3-one;

1'-({1-[6-(4-Phenylpiperazin-1-yl)pyridin-3-yl]cyclopropyl}carbonyl)-3H-spiro[2-benzofuran-1,3'-pyrrolidin]-3-one;

1'-[(1-{6-[4-(3-Methylbutanoyl)piperazin-1-yl]pyridin-3-yl}cyclopropylcarbonyl]-3H-spiro[2-benzofuran-1,3'-pyrrolidin]-3-one;

1'-[(1-{6-[4-(Cyclopropylmethyl)piperazin-1-yl]pyridin-3-yl}cyclopropyl)carbonyl]-3H-spiro[2-benzofuran-1,3'-pyrrolidin]-3-one;

1'-({1-[6-(2,5-Dihydro-1H-pyrrol-1-yl)pyridin-3-yl]cyclopropyl}carbonyl)-3H-spiro[2-benzofuran-1,3'-pyrrolidin]-3-one;

{[1-(6-Piperidin-1-ylpyridin-3-yl)cyclopropyl]carbonyl}-3H-spiro[2-benzofuran-1,3'-pyrrolidin]-3-one;

1'-({1-[4-(4-Methyl-2-oxopiperazin-1-yl)phenyl]cyclopropyl}carbonyl)-3H-spiro[2-benzofuran-1,3'-pyrrolidin]-3-one;

1'-({1-[4-(4-Acetyl-2-oxo-piperazin-1-yl)phenyl]cyclopropyl}carbonyl)-3H-spiro[2-benzofuran-1,3'-pyrrolidin]-3-one;

tert-Butyl 4-[4-(1-{[3-oxo-1'H,3H-spiro[2-benzofuran-1,3'-pyrrolidin]-1'-yl]carbonyl}cyclopropyl)phenyl]piperazine-1-carboxylate;

1'-({1-[4-(4-Isobutyrylpiperazin-1-yl)phenyl]cyclopropyl}carbonyl)-3H-spiro[2-benzofuran-1,3'-pyrrolidin]-3-one;

1'-[(1-{4-[4-(Cyclopropylcarbonyl)piperazin-1-yl]phenyl}cyclopropyl)carbonyl]-3H-spiro[2-benzofuran-1,3'-pyrrolidin]-3-one;

1'-[(1-{4-[4-(Methylsulfonyl)piperazin-1-yl]phenyl}cyclopropylcarbonyl]-3H-spiro[2-benzofuran-1,3'-pyrrolidin]-3-one;

1'-({1-[4-(4-Methylpiperazin-1-yl)phenyl]cyclopropyl}carbonyl)-3H-spiro[2-benzofuran-1,3'-pyrrolidin]-3-one;

N-Methyl-N-[4-(1-{[3-oxo-1'H,3H-spiro[2-benzofuran-1,3'-pyrrolidin]-1'-yl]carbonyl}cyclopropyl)phenyl]cyclopropanecarboxamide;

N-[4-(1-{[3-Oxo-1'H,3H-spiro[2-benzofuran-1,3'-pyrrolidin]-1'-yl]carbonyl}cyclopropyl)phenyl]acetamide;

1'-({1-[4-(2-Oxopyrrolidin-1-yl)phenyl]cyclopropyl}carbonyl)-3H-spiro[2-benzofuran-1,3'-pyrrolidin]-3-one;

1'-({1-[4-(2-Oxo-1,3-oxazolidin-3-yl)phenyl]cyclopropyl}carbonyl)-3H-spiro[2-benzofuran-1,3'-pyrrolidin]-3-one;

1'-({1-[4-(1H-Pyrazol-1-yl)phenyl]cyclopropyl}carbonyl)-3H-spiro[2-benzofuran-1,3'-pyrrolidin]-3-one;

1'-({1-[4-(2-Oxopiperidin-1-yl)phenyl]cyclopropyl}carbonyl)-3H-spiro[2-benzofuran-1,3'-pyrrolidin]-3-one;

1-Methyl-3-[4-(1-{[3-oxo-1'H,3H-spiro[2-benzofuran-1,3'-pyrrolidin]-1'-yl]carbonyl}cyclopropyl)phenyl]imidazolidine-2,4-dione;

1'-{[1-(4-Morpholin-4-ylphenyl)cyclopropyl]carbonyl}-3H-spiro[2-benzofuran-1,3'-pyrrolidin]-3-one;

1'-[(1-Pyridin-3-ylcyclopropyl)carbonyl]-3H-spiro[2-benzofuran-1,3'-pyrrolidin]-1'-3-one;

N-Methyl-4-[5-(1-{[3-oxo-1'H,3H-spiro[2-benzofuran-1,3'-pyrrolidiin]-1'-yl]carbonyl}cyclopropyl)pyridin-2-yl]benzamide;

N,N-Dimethyl-4-[5-(1-{[3-oxo-1'H,3H-spiro[2-benzofuran-1,3'-pyrrolidin]-1'-yl]carbonyl}cyclopropyl)pyridin-2-yl]benzamide;

1'-[(1-{6-[4-(Methylsulfonyl)phenyl]pyridin-3-yl cyclopropyl)carbonyl]-3H-spiro[2-benzofuran-1,3'-pyrrolidin]-3-one;

1'-[1-(4-Methoxyphenyl)cyclopropyl]carbonyl]-3H-spiro[2-benzofuran-1,3'-pyrrolidin]-3-one;

1'-({1-[4-(Pyridin-2-yloxy)phenyl]cyclopropyl}carbonyl)-3H-spiro[2-benzofuran-1,3'-pyrrolidin]-3-one;

1'-({1-[4-(Pyridin-3-ylmethoxy)phenyl]cyclopropyl}carbonyl}-3H-spiro[2-benzofuran-1,3'-pyrrolidin]-3-one;

1'-({1-[4-(Isoquinolin-1-ylmethoxy)phenyl]cyclopropyl}carbonyl)-3H-spiro[2-benzofuran-1,3'-pyrrolidin]-3-one;

1'-{[1-(4-Vinylphenyl)cyclopropyl]carbonyl}-3H-spiro[2-benzofuran-1,3'-pyrrolidin]-3-one;

Methyl 4-[4-({[3-oxo-1'H,3H-spiro[2-benzofuran-1,3'-pyrrolidin]-1'-yl]carbonyl}cyclopropyl)phenyl]-3,6-dihydropyridine-1(2H)-carboxylate;

Ethyl 4-[4-(1-{[3-oxo-1'H,3H-spiro[2-benzofuran-1,3'-pyrrolidin]-1'-yl]carbonyl}cyclopropyl)phenyl]-3,6-dihydropyridine-1(2H)-carboxylate;

1'-({1-[4-(1-Acetyl-1,2,3,6-tetrahydropyridin-4-yl)phenyl]cyclopropyl}carbonyl)-3H-spiro[2-benzofuran-1,3'-pyrrolidin]-3-one;

1'-[(1-{4-[1-(3-Methylbutanoyl)-1,2,3,6-tetrahydropyridin-4-yl]phenyl}cyclopropyl)carbonyl]-3H-spiro[2-benzofuran-1,3'-pyrrolidin]-3-one;

1'-({1-[4-(Pyrrolidin-1-ylmethyl)phenyl]cyclopropyl}carbonyl)-3H-spiro[2-benzofuran-1,3'-pyrrolidin]-3-one;

1'-{[1-(6-Pyrrolidin-1-ylpyridin-3-yl)cyclopropyl]carbonyl}-3H-spiro[furo[3,4-c]pyridine-1,3'-pyrrolidin]-3-one;

1'-({[1-[6-(4-Phenylpiperazin-1-yl)pyridin-3-yl]cyclopropyl}carbonyl)-3H-spiro[furo[3,4-c]pyridine-1,3'-pyrrolidin]-3-one;

Methyl 4-[5-(1-{[3-oxo-1'H,3H-spiro[furo[3,4-c]pyridine-1,3'-pyrrolidin]-1'-yl]carbonyl}cyclopropyl)pyridin-2-yl]piperazine-1-carboxylate;

Ethyl 4-(5-{1-[(3-oxo-1'H,3H-spiro[furo[3,4-c]pyridine-1,3'-pyrrolidin]-1'-yl)carbonyl]cyclopropyl}pyridin-2-yl)piperazine-1-carboxylate;

Isopropyl 4-(5-{1-[(3-oxo-1'H,3H-spiro[furo[3,4-c]pyridine-1,3'-pyrrolidin]-1'-yl)carbonyl]cyclopropyl}pyridin-2-yl)piperazine-1-carboxylate;

1'({1-[6-(4-Chlorophenyl)pyridin-3-yl]cyclopropyl}carbonyl)-3H-spiro[furo[3,4-c]pyridine-1,3'-pyrrolidin]-3-one;

1'-({1-[6-(4-Fluorophenyl)pyridin-3-yl]cyclopropyl}carbonyl)-3H-spiro[furo[3,4-c]pyridine-1,3'-pyrrolidin]-3-one;

1'-({1-[6-(4-Fluoro-2-methylphenyl)pyridin-3-yl]cyclopropyl}carbonyl)-3H-spiro[furo[3,4-c]pyridine-1,3'-pyrrolidin]-3-one;

1'-[(1-Quinolin-4-ylcyclopropyl)carbonyl]-3H-spiro[furo[3,4-c]pyridine-1,3'-pyrrolidin]-3-one;

1'-[(1-{4-[(4-Fluorobenzyl)oxy]phenyl}cyclopropyl)carbonyl]-3H-spiro[furo[3,4-c]pyridine-1,3'-pyrrolidin]-3-one;

1'-{[1-(4-{[4-(Trifluoromethyl)benzyl]oxy}phenyl)cyclopropyl]carbonyl}-3H-spiro[furo[3,4-c]pyridine-1,3'-pyrrolidin]-3-one;

1'-[(1-{4-[(2-Chloro-4-fluorobenzyl)oxy]phenyl}cyclopropyl)carbonyl]-3H-spiro[furo[3,4-c]pyridine-1,3'-pyrrolidin]-3-one;

1'-[(1-{4-[(4-Bromo-2-fluorobenzyl)oxy]phenyl}cyclopropyl)carbonyl]-3H-spiro[furo[3,4-c]pyridine-1,3'-pyrrolidin]-3-one;

3-Fluoro-4-[(4-{1-[3-oxo-1'H,3H-spiro[furo[3,4-c]pyridine-1,3'-pyrrolidin]-1'-yl)carbonyl]cyclopropyl}phenoxy)methyl]benzonitrile;

1'-[(1-{4-[1-(2-Fluorophenyl)ethoxy]phenyl}cyclopropyl)carbonyl]-3H-spiro[furo[3,4-c]pyridine-1,3'-pyrrolidin]-3-one;

4-[1-(4-{1-[(3-Oxo-1'H,3H-spiro[furo[3,4-c]pyridine-1,3'-pyrrolidin]-1'-yl)carbonyl]cyclo-propyl}phenoxy)ethyl]benzonitrile;

1'-({1-[4-(Quinolin-2-ylmethoxy)phenyl]cyclopropyl}carbonyl)-3H-spiro[furo[3,4-c]pyridine-1,3'-pyrrolidin]-3-one;

1'-{[1-(4-Methoxyphenyl)cyclopropyl]carbonyl}-3H-spiro[furo[3,4-c]pyridine-1,3'-pyrrolidin]-3-one;

1'-({1-[4-(Cyclopentyloxy)phenyl]cyclopropyl}carbonyl)-3H-spiro[furo[3,4-c]pyridine-1,3'-pyrrolidin]-3-one;

1'-({1-[4-(Allyloxy)phenyl]cyclo-propyl}carbonyl)-3H-spiro[furo[3,4-c]pyridine-1,3'-pyrrolidin]-3-one;

1'-({1-[4-(2-Methoxyethoxy)phenyl]cyclopropyl}carbonyl)-3H-spiro[furo[3,4-c]pyridine-1,3'-pyrrolidin]-3-one;

1'-({1-[4-(Cyclopropylmethoxy)phenyl]cyclopropyl}carbonyl)-3H-spiro[furo[3,4-c]pyridine-1,3'-pyrrolidin]-3-one;

1'-{[1-(4-Methylphenyl)cyclopropyl]carbonyl}-3H-spiro[furo[3,4-c]pyridine-1,3'-pyrrolidin]-3-one;

1'-({1-[4-(Trifluoromethyl)phenyl]
cyclopropyl}carbonyl)-3H-spiro[furo[3,4-c]pyridine-
1,3'-pyrrolidin]-3-one;
1'-{[1-(4-Vinylphenyl)cyclopropyl]carbonyl}-3H-spiro
[furo[3,4-c]pyridine-1,3'-pyrrolidin]-3-one;
1'-[(1-{4-[(E)-2-Pyridin-2-ylvinyl]phenyl}cyclopropyl)
carbonyl]-3H-spiro[furo[3,4-c]pyridine-1,3'-pyrroli-
din]-3-one;
1'-({1-[4-(1-Isobutyryl-1,2,3,6-tetrahydropyridin-4-yl)
phenyl]cyclopropyl}carbonyl)-3H-spiro[furo[3,4-c]py-
ridine-1,3'-pyrrolidin]-3-one;
1'-({1-[4-(1-Acetylpiperidin-4-yl)phenyl]
cyclopropyl}carbonyl)-3H-spiro[furo[3,4-c]pyridine-
1,3'-pyrrolidin]-3-one;
Ethyl 4-(4-{1-[(3-oxo-1'H,3H-spiro[furo[3,4-c]pyridine-
1,3'-pyrrolidin]-1'-yl)carbonyl]cyclopropyl}phenyl)pi-
peridine-1-carboxylate;
1'-({1-[4-(1-Isobutyrylpiperidin-4-yl)phenyl]
cyclopropyl}carbonyl)-3H-spiro[furo[3,4-c]pyridine-
1,3'-pyrrolidin]-3-one;
1'-({1-[4-(1-Propionylpiperidin-4-yl)phenyl]
cyclopropyl}carbonyl)-3H-spiro[furo[3,4-c]pyridine-
1,3'-pyrrolidin]-3-one;
1'-[(1-{4-[1-(3-Methylbutanoyl)piperidin-4-yl]
phenyl}cyclopropyl)carbonyl]-3H-spiro[furo[3,4-c]py-
ridine-1,3'-pyrrolidin]-3-one;
1'-({1-[4-(2-Isopropyl-1,3-thiazol-4-yl)phenyl]
cyclopropyl}carbonyl)-3H-spiro[furo[3,4-c]pyridine-
1,3'-pyrrolidin]-3-one;
1'-[(1-{4-[2-(Dimethylamino)-1,3-thiazol-4-yl]
phenyl}cyclopropyl)carbonyl]-3H-spiro[furo[3,4-c]py-
ridine-1,3'-pyrrolidin]-3-one;
1'-({1-[4-(2-Amino-1,3-thiazol-4-yl)phenyl]
cyclopropyl}carbonyl)-3H-spiro[furo[3,4-c]pyridine-
1,3'-pyrrolidin]-3-one;
3-Fluoro-4-{1-[(3-oxo-1'H,3H-spiro[furo[3,4-c]pyridine-
1,3'-pyrrolidin]-1'-yl)carbonyl]cyclo-
propyl}benzonitrile;
1'-({1-[2-Fluoro-4-(4-methyl-1,3-thiazol-2-yl)phenyl]
cyclopropyl}carbonyl)-3H-spiro[furo[3,4-c]pyridine-
1,3'-pyrrolidin]-3-one; and
1'-[(1-{4-[5-(Trifluoromethyl)-1,3,4-oxadiazol-2-yl]
phenyl}cyclo-propyl)carbonyl]-3H-spiro[furo[3,4-c]
pyridine-1,3'-pyrrolidin]-3-one,
or a pharmaceutically acceptable salt thereof.

17. A compound of claim 1 selected from:
1'-({1-[4-(3-Methylisoxazol-4-yl)phenyl]
cyclopropyl}carbonyl)-3H-spiro[furo[3,4-c]pyridine-
1,3'-pyrrolidin]-3-one;
1'-({1-[4-(2-Pyridin-2-ylethyl)phenyl]
cyclopropyl}carbonyl)-3H-spiro[furo[3,4-c]pyridine-
1,3'-pyrrolidin]-3-one;
1'-({1-[2-Fluoro-4-(1H-pyrazol-1-yl)phenyl]
cyclopropyl}carbonyl)-3H-spiro[furo[3,4-c]pyridine-
1,3'-pyrrolidin]-3-one;
1'-({1-[2-Fluoro-4-(3-methyl-1H-pyrazol-1-yl)phenyl]
cyclopropyl}carbonyl)-3H-spiro[furo[3,4-c]pyridine-
1,3'-pyrrolidin]-3-one;
1'-({1-[4-(3-Amino-1H-pyrazol-1-yl)phenyl]
cyclopropyl}carbonyl)-3H-spiro[furo[3,4-c]pyridine-
1,3'-pyrrolidin]-3-one;
1'-({1-[4-(1H-Benzimidazol-1-yl)-2-fluorophenyl]
cyclopropyl}carbonyl)-3H-spiro[furo[3,4-c]pyridine-
1,3'-pyrrolidin]-3-one;
1'-[(1-{2-Fluoro-4-[2-(trifluoro-methyl)-1H-benzimida-
zol-1-yl]phenyl}cyclopropyl)carbonyl]-3H-spiro[furo
[3,4-c]pyridine-1,3'-pyrrolidin]-3-one;
1'-({1-[4-(2-Methoxy-1H-benzimidazol-1-yl)phenyl]
cyclopropyl}carbonyl)-3H-spiro[furo[3,4-c]pyridine-
1,3'-pyrrolidin]-3-one;
Ethyl 4-(4-{1-[(3-oxo-1'H,3H-spiro[furo[3,4-c]pyridine-
1,3'-pyrrolidin]-1'-yl)carbonyl]cyclo-propyl}phenyl)
piperazine-1-carboxylate;
Isopropyl 4-[4-(1-{[3-oxo-1'H,3H-spiro[furo[3,4-c]pyri-
dine-1,3'-pyrrolidin]-1'-yl]carbonyl}cyclo-propyl)phe-
nyl]piperazine-1-carboxylate;
1'({1-[4-(4-Propionylpiperazin-1-yl)phenyl]
cyclopropyl}carbonyl)-3H-spiro[furo[3,4-c]pyridine-
1,3'-pyrrolidin]-3-one;
1'-({1-[4-(4-Isobutyrylpiperazin-1-yl)phenyl]
cyclopropyl}carbonyl)-3H-spiro[furo[3,4-c]pyridine-
1,3'-pyrrolidin]-3-one;
1'-[(1-{4-[4-(Cyclopropylcarbonyl)piperazin-1-yl]
phenyl}cyclopropyl)carbonyl]-3H-spiro[furo[3,4-c]py-
ridine-1,3'-pyrrolidin]-3-one;
1'-[(1-{4-[4-(Methylsulfonyl)piperazin-1-yl]
phenyl}cyclopropyl)carbonyl]-3H-spiro[furo[3,4-c]py-
ridine-1,3'-pyrrolidin]-3-one;
1'-({1-[4-(2-Oxopyridin-1(2H)-yl)phenyl]
cyclopropyl}carbonyl)-3H-spiro[furo[3,4-c]pyridine-
1,3'-pyrrolidin]-3-one;
Methyl [4-(1-{[3-oxo-1'H,3H-spiro[furo[3,4-c]pyridine-
1,3'-pyrrolidin]-1'-yl]carbonyl}cyclo-propyl)phenyl]
carbamate;
N-[4-(1-{[3-Oxo-1'H,3H-spiro[furo[3,4-c]pyridine-1,3'-
pyrrolidin]-1'-yl]carbonyl}cyclo-propyl)phenyl]meth-
anesulfonamide;
1'-{[1-(2-Fluorophenyl)cyclo-propyl]carbonyl}-3H-spiro
[furo[3,4-c]pyridine-1,3'-pyrrolidin]-3-one;
1'-{[1-(2-Chlorophenyl)cyclopropyl]carbonyl}-3H-spiro
[furo[3,4-c]pyridine-1,3'-pyrrolidin]-3-one;
1'-{[1-(2-Bromophenyl)cyclopropyl]carbonyl}-3H-spiro
[furo[3,4-c]pyridine-1,3'-pyrrolidin]-3-one;
1'-({[1-[2-(Trifluoromethyl)phenyl]
cyclopropyl}carbonyl)-3H-spiro[furo[3,4-c]pyridine-
1,3'-pyrrolidin]-3-one;
1'-{[1-(2-Methoxyphenyl)cyclopropyl]carbonyl}-3H-
spiro[furo[3,4-c]pyridine-1,3'-pyrrolidin]-3-one;
1'-{[1-(2-Methylphenyl)cyclopropyl]carbonyl}-3H-spiro
[furo[3,4-c]pyridine-1,3'-pyrrolidin]-3-one;
1'-{[1-(2,3-Difluorophenyl)cyclo-propyl]carbonyl}-3H-
spiro[furo[3,4-c]pyridine-1,3'-pyrrolidin]-3-one;
1'-{[1-(2-Chloro-6-fluorophenyl)cyclo-propyl]carbonyl}-
3H-spiro[furo[3,4-c]pyridine-1,3'-pyrrolidin]-3-one;
1'-{[1-(1-Naphthyl)cyclopropyl]carbonyl}-3H-spiro[furo
[3,4-c]pyridine-1,3'-pyrrolidin]-3-one;
1'-{[1-(2,4-Dichlorophenyl)cyclo-propyl]carbonyl}-3H-
spiro[furo[3,4-c]pyridine-1,3'-pyrrolidin]-3-one;
1'-{[1-(4-Chloro-2-fluorophenyl)cyclopropyl]carbonyl}-
3H-spiro[furo[3,4-c]pyridine-1,3'-pyrrolidin]-3-one;
1'-{[1-(2-Chloro-4-fluorophenyl)cyclo-propyl]carbonyl}-
3H-spiro[furo[3,4-c]pyridine-1,3'-pyrrolidin]-3-one;
1'-{[1-(2,4-Difluorophenyl)cyclo-propyl]carbonyl}-3H-
spiro[furo[3,4-c]pyridine-1,3'-pyrrolidin]-3-one;
1'-({1-[4-(Methylthio)phenyl]cyclo-propyl}carbonyl)-
3H-spiro[furo[3,4-c]pyridine-1,3'-pyrrolidin]-3-one;
1'-[(1-{4-[(Trifluoromethyl)thio]phenyl}cyclopropyl)car-
bonyl]-3H-spiro[furo[3,4-c]pyridine-1,3'-pyrrolidin]-
3-one;
1'-{[1-(4-Chlorophenyl)cyclo-pentyl]carbonyl}-3H-spiro
[2-benzofuran-1,3'-pyrrolidin]-3-one;
Methyl 4-[5-(1-{[3-oxo-1'H,3H-spiro[2-benzofuran-1,3'-
pyrrolidin]-1'-yl]carbonyl}cyclopropyl)pyridin-2-yl]
piperazine-1-carboxylate;

N,N-Dimethyl-4-[4-(1-{[3-oxo-1'H,3H-spiro[2-benzofuran-1,3'-pyrrolidin]-1'-yl]carbonyl}cyclo-propyl)phenyl]piperazine-1-carboxamide;

Methyl 4-[3-fluoro-4-(1-{[3-oxo-1'H,3H-spiro[2-benzofuran-1,3'-pyrrolidin]-1'-yl]carbonyl}cyclo-propyl)phenyl]piperazine-1-carboxylate;

1'-({1-[2-Fluoro-4-(4-propionylpiperazin-1-yl)phenyl]cyclo-propyl}carbonyl)-3H-spiro[2-benzofuran-1,3'-pyrrolidin]-3-one;

1'-({1-[2-Fluoro-4-(4-isobutyrylpiperazin-1-yl)phenyl]cyclo-propyl}carbonyl)-3H-spiro[2-benzofuran-1,3'-pyrrolidin]-3-one;

1'-[(1-{4-[4-(Cyclopropylcarbonyl)piperazin-1-yl]-2-fluoro-phenyl}cyclopropyl)carbonyl]-3H-spiro[2-benzofuran-1,3'-pyrrolidin]-3-one;

1'-({1-[4-(4-Acetylpiperazin-1-yl)-2-fluorophenyl]cyclopropyl}carbonyl)-3H-spiro[2-benzofuran-1,3'-pyrrolidin]-3-one;

4-[3-Fluoro-4-(1-{[3-oxo-1'H,3H-spiro[2-benzofuran-1,3'-pyrrolidin]-1'-yl]carbonyl}cyclopropyl)phenyl]-N,N-dimethylpiperazine-1-carboxamide;

1'-({1-[4-(4-Hydroxypiperidin-1-yl)phenyl]cyclopropyl}carbonyl)-3H-spiro[2-benzofuran-1,3'-pyrrolidin]-3-one;

N,N-Dimethyl-1-[4-(1-{[3-oxo-1'H,3H-spiro[2-benzofuran-1,3'-pyrrolidin]-1'-yl]carbonyl}cyclo-propyl)phenyl]piperidine-4-carboxamide;

Methyl 4-[4-(1-{[3-oxo-1'H,3H-spiro[2-benzofuran-1,3'-pyrrolidin]-1'-yl]carbonyl}cyclopropyl)phenyl]piperidine-1-carboxylate;

Ethyl 4-[4-(1-{[3-oxo-1'H,3H-spiro[2-benzofuran-1,3'-pyrrolidin]-1'-yl]carbonyl}cyclopropyl)phenyl]piperidine-1-carboxylate;

1'-({1-[4-(1-Acetylpiperidin-4-yl)phenyl]cyclopropyl}carbonyl)-3H-spiro[2-benzofuran-1,3'-pyrrolidin]-3-one;

1'-({1-[4-(1-Isobutyrylpiperidin-4-yl)phenyl]cyclopropyl}carbonyl)-3H-spiro[2-benzofuran-1,3'-pyrrolidin]-3-one;

1'-({1-[4-(1-Propionylpiperidin-4-yl)phenyl]cyclopropyl}carbonyl)-3H-spiro[2-benzofuran-1,3'-pyrrolidin]-3-one;

1'-[(1-{4-[1-(3-Methylbutanoyl)piperidin-4-yl]phenyl}cyclopropyl)carbonyl]-3H-spiro[2-benzofuran-1,3'-pyrrolidin]-3-one;

1'-({1-[4-(1-Acetylpiperidin-4-yl)phenyl]cyclopropyl}carbonyl)-3H-spiro[furo[3,4-c]pyridine-1,3'-pyrrolidin]-3-one;

1'-({1-[4-(1-Isobutyrylpiperidin-4-yl)phenyl]cyclopropyl}carbonyl)-3H-spiro[furo[3,4-c]pyridine-1,3'-pyrrolidin]-3-one;

1'-({1-[4-(1-Propionylpiperidin-4-yl)phenyl]cyclopropyl}carbonyl)-3H-spiro[furo[3,4-c]pyridine-1,3'-pyrrolidin]-3-one;

1'-[(1-{4-[1-(3-Methylbutanoyl)piperidin-4-yl]phenyl}cyclo-propyl)carbonyl]-3H-spiro[furo[3,4-c]pyridine-1,3'-pyrrolidin]-3-one;

Methyl 4-[4-(1-{[3-oxo-1'H,3H-spiro[furo[3,4-c]pyridine-1,3'-pyrrolidin]-1'-yl]carbonyl}cyclopropyl)phenyl]piperidine-1-carboxylate;

Ethyl 4-[4(1-{[3-oxo-1'H,3H-spiro[furo[3,4-c]pyridine-1,3'-pyrrolidin]-1'-yl]carbonyl}cyclopropyl)phenyl]piperidine-1-carboxylate;

Isopropyl 4-[4-(1-{[3-oxo-1'H,3H-spiro[furo[3,4-c]pyridine-1,3'-pyrrolidin]-1'-yl]carbonyl}cyclopropyl)phenyl]piperidine-1-carboxylate;

Methyl 4-hydroxy-4-[4-(1-{[3-oxo-1'H,3H-spiro[2-benzofuran-1,3'-pyrrolidin]-1'-yl]carbonyl}cyclo-propyl)phenyl]piperidine-1-carboxylate;

Ethyl 4-hydroxy-4-[4-(1-{[3-oxo-1'H,3H-spiro[2-benzofuran-1,3'-pyrrolidin]-1'-yl]carbonyl}cyclo-propyl)phenyl]piperidine-1-carboxylate;

Isopropyl 4-[4-(1-{[3-oxo-1'H,3H-spiro[2-benzofuran-1,3'-pyrrolidin]-1'-yl]carbonyl}cyclo-propyl)phenyl]piperazine-1-carboxylate;

1'-[(1-{4-[6-(Pyrrolidin-1-ylcarbonyl)pyridin-3-yl]phenyl}cyclo-propyl)carbonyl]-3H-spiro[2-benzofuran-1,3'-pyrrolidin]-3-one;

N-Ethyl-N-methyl-5-[4-(1-{[3-oxo-1'H,3H-spiro[2-benzofuran-1,3'-pyrrolidin]-1'-yl]carbonyl}cyclo-propyl)phenyl]pyridine-2-carboxamide;

N,N-Diethyl-5-[4-(1-{[3-oxo-1'H,3H-spiro[2-benzofuran-1,3'-pyrrolidin]-1'-yl]carbonyl}cyclo-propyl)phenyl]pyridine-2-carboxamide;

tert-Butyl {4-[5-(1-{[3-oxo-1'H,3H-spiro[2-benzofuran-1,3'-pyrrolidin]-1'-yl]carbonyl}cyclo-propyl)pyridin-2-yl]phenyl}carbamate;

N,N-Dimethyl-1-[5-(1-{[3-oxo-1'H,3H-spiro[2-benzofuran-1,3'-pyrrolidin]-1'-yl]carbonyl}cyclo-propyl)pyridin-2-yl]piperidine-4-carboxamide; and 1'-{[1-(6-Piperidin-1-ylpyridin-3-yl)cyclopropyl]carbonyl}-3H-spiro[furo[3,4-c]pyridine-1,3'-pyrrolidin]-3-one, or a pharmaceutically acceptable salt thereof.

18. A compound of claim 1 selected from:

1'-({1-[2-Fluoro-4-(2-oxopyrrolidin-1-yl)phenyl]cyclopropyl}carbonyl)-3H-spiro[2-benzofuran-1,3'-pyrrolidin]-3-one;

1'-({1-[2-Fluoro-4-(2-oxo-1,3-oxazolidin-3-yl)phenyl]cyclopropyl}carbonyl)-3H-spiro[furo[3,4-c]pyridine-1,3'-pyrrolidin]-3-one;

1'-({1-[4-(2-Oxoazetidin-1-yl)phenyl]cyclopropyl}carbonyl)-3H-spiro[2-benzofuran-1,3'-pyrrolidin]-3-one;

1'-({1-[2-Fluoro-4-(2-oxoazetidin-1-yl)phenyl]cyclopropyl}carbonyl)-3H-spiro[2-benzofuran-1,3'-pyrrolidin]-3-one;

1'-({1-[4-(2-oxoazetidin-1-yl)phenyl]cyclopropyl}carbonyl)-3H-spiro[furo[3,4-c]pyridine-1,3'-pyrrolidin]-3-one;

1'-({1-[2-Fluoro-4-(2-oxoazetidin-1-yl)phenyl]cyclopropyl}carbonyl)-3H-spiro[furo[3,4-c]pyridine-1,3'-pyrrolidin]-3-one;

Propyl 4-[5-(1-{[3-oxo-1'H,3H-spiro[2-benzofuran-1,3'-pyrrolidin]-1'-yl]carbonyl}cyclopropyl)pyridin-2-yl]piperazine-1-carboxylate;

Isobutyl 4-[5-(1-{[3-oxo-1'H,3H-spiro[2-benzofuran-1,3'-pyrrolidin]-1'-yl]carbonyl}cyclopropyl)pyridin-2-yl]piperazine-1-carboxylate;

Isopropyl 4-[5-(1-{[3-oxo-1'H,3H-spiro[2-benzofuran-1,3'-pyrrolidin]-1'-yl]carbonyl}cyclopropyl)pyridin-2-yl]piperazine-1-carboxylate;

Ethyl 4-[4-(1-{[3-oxo-1'H,3H-spiro[2-benzofuran-1,3'-pyrrolidin]-1'-yl]carbonyl}cyclopropyl)phenyl]piperazine-1-carboxylate;

Propyl 4-[4-(1-{[3-oxo-1'H,3H-spiro[2-benzofuran-1,3'-pyrrolidin]-1'-yl]carbonyl}cyclopropyl)phenyl]piperazine-1-carboxylate;

Isobutyl 4-[4-(1-{[3-oxo-1'H,3H-spiro[2-benzofuran-1,3'-pyrrolidin]-1'-yl]carbonyl}cyclopropyl)phenyl]piperazine-1-carboxylate;

1'-[(1-{4-[4-(Cyclopropylacetyl)piperazin-1-yl]phenyl}cyclopropyl)carbonyl]-3H-spiro[2-benzofuran-1,3'-pyrrolidin]-3-one;

1'-[(1-{4-[4-(Cyclopropylacetyl)piperazin-1-yl]-2-fluorophenyl}cyclopropyl)carbonyl]-3H-spiro[2-benzofuran-1,3'-pyrrolidin]-3-one;

1'-[(1-{4-[4-(3-Methylbutanoyl)piperazin-1-yl]phenyl}cyclopropyl)carbonyl]-3H-spiro[2-benzofuran-1,3'-pyrrolidin]-3-one;

1'-[(1-{2-Fluoro-4-[4-(3-methylbutanoyl)piperazin-1-yl]phenyl}cyclopropyl)carbonyl]-3H-spiro[2-benzofuran-1,3'-pyrrolidin]-3-one;

1'-[(1-{4-[4-(Tetrahydro-2H-pyran-4-ylcarbonyl)piperazin-1-yl]phenyl}cyclopropyl)carbonyl]-3H-spiro[2-benzofuran-1,3'-pyrrolidin]-3-one;

Ethyl 4-[3-fluoro-4-(1-{[3-oxo-1'H,3H-spiro[2-benzofuran-1,3'-pyrrolidin]-1'-yl]carbonyl}cyclopropyl)phenyl]piperazine-1-carboxylate;

Propyl 4-[3-fluoro-4-(1-{[3-oxo-1'H,3H-spiro[2-benzofuran-1,3'-pyrrolidin]-1'-yl]carbonyl}cyclopropyl)phenyl]piperazine-1-carboxylate;

4-[3-Fluoro-4-(1-{[3-oxo-PH,3H-spiro[2-benzofuran-1,3'-pyrrolidin]-1'-yl]carbonyl}cyclopropyl)phenyl]-N-methylpiperazine-1-carboxamide;

1'-({1-[2-Fluoro-4-(4-isobutyrylpiperazin-1-yl)phenyl]cyclopropyl}carbonyl)-3H-spiro[2-benzofuran-1,3'-pyrrolidin]-3-one;

1'-[(1-{4-[4-(Cyclopropylacetyl)piperazin-1-yl]-2-fluorophenyl}cyclopropyl)carbonyl]-3H-spiro[2-benzofuran-1,3'-pyrrolidin]-3-one;

Methyl 4-[3-fluoro-4-(1-{[3-oxo-1'H,3H-spiro[furo[3,4-c]pyridine-1,3'-pyrrolidin]-1'-yl]carbonyl}cyclopropyl)phenyl]piperazine-1-carboxylate;

Ethyl 4-[3-fluoro-4-(1-{[3-oxo-1'H,3H-spiro[furo[3,4-c]pyridine-1,3'-pyrrolidin]-1'-yl]carbonyl}cyclopropyl)phenyl]piperazine-1-carboxylate;

Propyl 4-[3-fluoro-4-(1-{[3-oxo-1'H,3H-spiro[furo[3,4-c]pyridine-1,3'-pyrrolidin]-1'-yl]carbonyl}cyclopropyl)phenyl]piperazine-1-carboxylate;

iso-Propyl 4-[3-fluoro-4-(1-{[3-oxo-1'H,3H-spiro[furo[3,4-c]pyridine-1,3'-pyrrolidin]-1'-yl]carbonyl}cyclopropyl)phenyl]piperazine-1-carboxylate;

iso-Butyl 4-[3-fluoro-4-(1-{[3-oxo-1'H,3H-spiro[furo[3,4-c]pyridine-1,3'-pyrrolidin]-1'-yl]carbonyl}cyclopropyl)phenyl]piperazine-1-carboxylate;

1'-[(1-{4-[4-(Cyclopropylcarbonyl)piperazine-1-yl]-2-fluorophenyl}cyclopropyl)carbonyl]-3H-spiro[furo[3,4-c]pyridine-1,3'-pyrrolidin]-3-one;

1'-[(1-{2-Fluoro-4-[4-(3-methylbutanoyl)piperazin-1-yl]phenyl}cyclopropyl)carbonyl]-3H-spiro[furo[3,4-c]pyridine-1,3'-pyrrolidin]-3-one;

N,N-Dimethyl-5-[4-(1-{[3-oxo-1'1-1,3H-spiro[2-benzofuran-1,3'-pyrrolidin]-1'-yl]carbonyl}cyclopropyl)phenyl]pyridine-2-carboxamide;

N-Ethyl-5-[4-(1-{[3-oxo-1'H,3H-spiro[2-benzofuran-1,3'-pyrrolidin]-F-yl]carbonyl}cyclopropyl)phenyl]pyridine-2-carboxamide;

N-Isopropyl-5-[4-(1-{[3-oxo-1'H,3H-spiro[2-benzofuran-1,3'-pyrrolidin]-1'-yl]carbonyl}cyclopropyl)phenyl]pyridine-2-carboxamide;

5-[3-Fluoro-4-(1-{[3-oxo-1'H,3H-spiro[2-benzofuran-1,3'-pyrrolidin]-1'-yl]carbonyl}cyclopropyl)phenyl]-N-methylpyridine-2-carboxamide;

5-[3-Fluoro-4-(1-{[3-oxo-1'H,3H-spiro[2-benzofuran-1,3'-pyrrolidin]-1'-yl]carbonyl}cyclopropyl)phenyl]-N-ethylpyridine-2-carboxamide;

5-[3-Fluoro-4-(1-{[3-oxo-1'H,3H-spiro[2-benzofuran-1,3'-pyrrolidin]-1'-yl]carbonyl}cyclopropyl)phenyl]-N-i-propylpyridine-2-carboxamide;

5-[3-Fluoro-4-(1-{[3-oxo-1'H,3H-spiro[2-benzofuran-1,3'-pyrrolidin]-1'-yl]carbonyl}cyclopropyl)phenyl]-N,N-dimethylpyridine-2-carboxamide;

5-[3-Fluoro-4-(1-{[3-oxo-1'H,3H-spiro[furo[3,4-c]pyridine-1,3'-pyrrolidin]-1'-yl]carbonyl}cyclopropyl)phenyl]-N-methylpyridine-2-carboxamide;

N-Ethyl-5-[3-fluoro-4-(1-{[3-oxo-1'H,3H-spiro[furo[3,4-c]pyridine-1,3'-pyrrolidin]-1'-yl]carbonyl}cyclopropyl)phenyl]pyridine-2-carboxamide;

5-[3-Fluoro-4-(1-{[3-oxo-1'H,3H-spiro[furo[3,4-c]pyridine-1,3'-pyrrolidin]-1'-yl]carbonyl}cyclopropyl)phenyl]-N-isopropylpyridine-2-carboxamide;

5-[3-Fluoro-4-(1-{[3-oxo-1'H,3H-spiro[furo[3,4-c]pyridine-1,3'-pyrrolidin]-1'-yl]carbonyl}cyclopropyl)phenyl]-N,N-dimethylpyridine-2-carboxamide;

6-[3-Fluoro-4-(1-{[3-oxo-1'H,3H-spiro[2-benzofuran-1,3'-pyrrolidin]-1'-yl]carbonyl}cyclopropyl)phenyl]-N-methylnicotinamide;

6-[3-Fluoro-4-(1-{[3-oxo-1'H,3H-spiro[2-benzofuran-1,3'-pyrrolidin]-yl]carbonyl}cyclopropyl)phenyl]-N,N-dimethylnicotinamide;

N-Methyl-6-[4-(1-{[3-oxo-1'H,3H-spiro[2-benzofuran-1,3'-pyrrolidin]-1'-yl]carbonyl}cyclopropyl)phenyl]nicotinamide;

N,N-Dimethyl-6-[4-(1-{[3-oxo-1'H,3H-spiro[2-benzofuran-1,3'-pyrrolidin]-1'-yl]carbonyl}cyclopropyl)phenyl]nicotinamide;

1'-({1-[4-(1-Isobutyryl-1,2,3,6-tetrahydropyridin-4-yl)phenyl]cyclopropyl}carbonyl)-3H-spiro[2-benzofuran-1,3'-pyrrolidin]-3-one;

1'-({1-[4-(1-Propionyl-1,2,3,6-tetrahydropyridin-4-yl)phenyl]cyclopropyl}carbonyl)-3H-spiro[2-benzofuran-1,3'-pyrrolidin]-3-one;

1'-({1-[3-Fluoro-4-(3-methyl-1H-pyrazol-1-yl)phenyl]cyclopropyl}carbonyl)-3H-spiro[furo[3,4-c]pyridine-1,3'-pyrrolidin]-3-one;

1'-{[1-(6-Azetidin-1-ylpyridin-3-yl)cyclopropyl]carbonyl}-3H-spiro[furo[3,4-c]pyridine-1,3'-pyrrolidin]-3-one;

1'-({1-[6-(2-Oxoazetidin-1-yl)pyridin-3-yl]cyclopropyl}carbonyl)-3H-spiro[2-benzofuran-1,3'-pyrrolidin]-3-one;

Methyl [3-fluoro-4-(1-{[3-oxo-1'H,3H-spiro[furo[3,4-c]pyridine-1,3'-pyrrolidin]-1'-yl]carbonyl}cyclopropyl)phenyl]carbamate;

Methyl [3-fluoro-4-(1-{[3-oxo-1'H,3H-spiro[2-benzofuran-1,3'-pyrrolidin]-1'-yl]carbonyl}cyclopropyl)phenyl]carbamate;

1'-({1-[4-(2-Oxopyrrolidin-1-yl)phenyl]cyclopropyl}carbonyl)-3H-spiro[furo[3,4-c]pyridine-1,3'-pyrrolidin]-3-one;

1'-[(1-{4-[4-(Cyclopropylcarbonyl)piperazin-1-yl]phenyl}cyclobutyl)carbonyl]-3H-spiro[2-benzofuran-1,3'-pyrrolidin]-3-one;

Ethyl 4-[4-(1-{[3-oxo-1'H,3H-spiro[furo[3,4-c]pyridine-1,3'-pyrrolidin]-1'-yl]carbonyl}cyclopropyl)phenyl]piperazine-1-carboxylate;

N,N-Diethyl-5-[3-fluoro-4-(1-{[3-oxo-1'H,3H-spiro[2-benzofuran-1,3'-pyrrolidin]-1'-yl]carbonyl}cyclopropyl)phenyl]pyridine-2-carboxamide;

1'-({1-[4-(2-Oxopyrrolidin-1-yl)phenyl]cyclopropyl}carbonyl)-3H-spiro[2-benzofuran-1,3'-pyrrolidin]-3-one;

1'-({1-[2-Fluoro-4-(1H-1,2,3-triazol-1-yl)phenyl]cyclopropyl}carbonyl)-3H-spiro[2-benzofuran-1,3'-pyrrolidin]-3-one;

1'-({1-[2-Fluoro-4-(2H-1,2,3-triazol-2-yl)phenyl]cyclopropyl}carbonyl)-3H-spiro[2-benzofuran-1,3'-pyrrolidin]-3-one;

1'-({1-[2-Fluoro-4-(1H-1,2,4-triazol-1-yl)phenyl]cyclopropyl}carbonyl)-3H-spiro[2-benzofuran-1,3'-pyrrolidin]-3-one;

1'-({1-[2-Fluoro-4-(4H-1,2,4-triazol-4-yl)phenyl]cyclopropyl}carbonyl)-3H-spiro[2-benzofuran-1,3'-pyrrolidin]-3-one;

N-Ethyl-5-[3-fluoro-4-(1-{[3-oxo-1'H,3H-spiro[2-benzofuran-1,3'-pyrrolidin]-1'-yl]carbonyl}cyclopropyl)phenyl]pyridine-2-carboxamide; and 5-[3-Fluoro-4-(1-{[3-oxo-1'H,3H-spiro[2-benzofuran-1,3'-pyrrolidin]-1'-yl]carbonyl}cyclopropyl)phenyl]-N-isopropylpyridine-2-carboxamide;

or a pharmaceutically acceptable salt thereof.

19. A pharmaceutical composition comprising a compound of claim 1, or a pharmaceutically acceptable salt thereof, and a pharmaceutically acceptable carrier.

20. A compound according to claim 1, or a pharmaceutically acceptable salt thereof, wherein one of $Q^1$ is O and $Q^2$ is CO.

21. A compound according to claim 1, or a pharmaceutically acceptable salt thereof, wherein $Q^3$ is CH and $Q^4$ is CH.

22. A compound according to claim 20, or a pharmaceutically acceptable salt thereof, wherein $Q^3$ is CH and $Q^4$ is CH.

23. A compound according to claim 1, or a pharmaceutically acceptable salt thereof, wherein Cy is phenyl optionally substituted by 1, 2, 3, 4 or 5—W—X—Y—Z.

24. A compound according to claim 20, or a pharmaceutically acceptable salt thereof, wherein Cy is phenyl optionally substituted by 1, 2, 3, 4 or 5—W—X—Y—Z.

25. A compound according to claim 22, or a pharmaceutically acceptable salt thereof, wherein Cy is phenyl optionally substituted by 1, 2, 3, 4 or 5—W—X—Y—Z.

26. A compound according to claim 20, or a pharmaceutically acceptable salt thereof, wherein —W—X—Y—Z is halo, cyano, $C_{1-4}$ cyanoalkyl, nitro, $C_{1-8}$ alkyl, $C_{1-8}$ alkenyl, $C_{1-8}$ haloalkyl, $C_{1-10}$ alkoxy, $C_{1-4}$ haloalkoxy, OH, $C_{1-8}$ alkoxyalkyl, amino, $C_{1-4}$ alkylamino, $C_{2-8}$ dialkylamino, OC(O)NR$^c$R$^d$, NR$^c$C(O)R$^d$, NR$^c$C(O)OR$^a$, aryloxy, heteroaryloxy, arylalkyloxy, heteroarylalkyloxy, heteroaryloxyalkyl, aryloxyalkyl, aryl, heteroaryl, cycloalkyl, heterocycloalkyl, arylalkyl, arylalkenyl, arylalkynyl, heteroarylalkyl, heteroarylalkenyl, heteroarylalkynyl, cycloalkylalkyl, or heterocycloalkylalkyl;
wherein each of said $C_{1-8}$ alkyl, $C_{1-8}$ alkenyl, $C_{1-8}$ haloalkyl, $C_{1-8}$ alkoxy, aryloxy, heteroaryloxy, arylalkyloxy, heteroarylalkyloxy, heteroaryloxyalkyl, aryloxyalkyl, aryl, heteroaryl, cycloalkyl, heterocycloalkyl, arylalkyl, arylalkenyl, arylalkynyl, heteroarylalkyl, heteroarylalkenyl, heteroarylalkynyl, cycloalkylalkyl, or heterocycloalkylalkyl is optionally substituted by 1, 2, or 3 substituents independently selected from halo, cyano, nitro, hydroxyl-($C_{1-6}$ alkyl), aminoalkyl, dialkylaminoalkyl, $C_{1-4}$ alkyl, $C_{1-4}$ haloalkyl, $C_{1-4}$ alkoxy, $C_{1-4}$ haloalkoxy, OH, $C_{1-8}$alkoxyalkyl, amino, $C_{1-4}$ alkylamino, $C_{2-8}$ dialkylamino, C(O)NR$^c$R$^d$, C(O)OR$^a$, NR$^c$C(O)R$^d$, NR$^c$S(O)$_2$R$^d$, ($C_{1-4}$ alkyl)sulfonyl, arylsulfonyl, aryl, heteroaryl, cycloalkyl, and heterocycloalkyl.

27. A compound according to claim 22, or a pharmaceutically acceptable salt thereof, wherein —W—X—Y—Z is halo, cyano, $C_{1-4}$ cyanoalkyl, nitro, $C_{1-8}$ alkyl, $C_{1-8}$ alkenyl, $C_{1-8}$ haloalkyl, $C_{1-10}$ alkoxy, $C_{1-4}$ haloalkoxy, OH, $C_{1-8}$ alkoxyalkyl, amino, $C_{1-4}$ alkylamino, $C_{2-8}$ dialkylamino, OC(O)NR$^c$R$^d$, NR$^c$C(O)R$^d$, NR$^c$C(O)OR$^a$, aryloxy, heteroaryloxy, arylalkyloxy, heteroarylalkyloxy, heteroaryloxyalkyl, aryloxyalkyl, aryl, heteroaryl, cycloalkyl, heterocycloalkyl, arylalkyl, arylalkenyl, arylalkynyl, heteroarylalkyl, heteroarylalkenyl, heteroarylalkynyl, cycloalkylalkyl, or heterocycloalkylalkyl;
wherein each of said $C_{1-8}$ alkyl, $C_{1-8}$ alkenyl, $C_{1-8}$ haloalkyl, $C_{1-8}$ alkoxy, aryloxy, heteroaryloxy, arylalkyloxy, heteroarylalkyloxy, heteroaryloxyalkyl, aryloxyalkyl, aryl, heteroaryl, cycloalkyl, heterocycloalkyl, arylalkyl, arylalkenyl, arylalkynyl, heteroarylalkyl, heteroarylalkenyl, heteroarylalkynyl, cycloalkylalkyl, or heterocycloalkylalkyl is optionally substituted by 1, 2, or 3 substituents independently selected from halo, cyano, nitro, hydroxyl-($C_{1-6}$ alkyl), aminoalkyl, dialkylaminoalkyl, $C_{1-4}$ alkyl, $C_{1-4}$ haloalkyl, $C_{1-4}$ alkoxy, $C_{1-4}$ haloalkoxy, OH, $C_{1-8}$ alkoxyalkyl, amino, $C_{1-4}$ alkylamino, $C_{2-8}$ dialkylamino, C(O)NR$^c$R$^d$, C(O)OR$^a$, NR$^c$C(O)R$^d$, NR$^c$S(O)$_2$R$^d$, ($C_{1-4}$ alkyl)sulfonyl, arylsulfonyl, aryl, heteroaryl, cycloalkyl, and heterocycloalkyl.

28. A compound according to claim 25, or a pharmaceutically acceptable salt thereof, wherein —W—X—Y—Z is halo, cyano, $C_{1-4}$ cyanoalkyl, nitro, $C_{1-8}$ alkyl, $C_{1-8}$ alkenyl, $C_{1-8}$ haloalkyl, $C_{1-10}$ alkoxy, $C_{1-4}$ haloalkoxy, OH, $C_{1-8}$ alkoxyalkyl, amino, $C_{1-4}$ alkylamino, $C_{2-8}$ dialkylamino, OC(O)NR$^c$R$^d$, NR$^c$C(O)R$^d$, NR$^c$C(O)OR$^a$, aryloxy, heteroaryloxy, arylalkyloxy, heteroarylalkyloxy, heteroaryloxyalkyl, aryloxyalkyl, aryl, heteroaryl, cycloalkyl, heterocycloalkyl, arylalkyl, arylalkenyl, arylalkynyl, heteroarylalkyl, heteroarylalkenyl, heteroarylalkynyl, cycloalkylalkyl, or heterocycloalkylalkyl;
wherein each of said $C_{1-8}$ alkyl, $C_{1-8}$ alkenyl, $C_{1-8}$ haloalkyl, $C_{1-8}$ alkoxy, aryloxy, heteroaryloxy, arylalkyloxy, heteroarylalkyloxy, heteroaryloxyalkyl, aryloxyalkyl, aryl, heteroaryl, cycloalkyl, heterocycloalkyl, arylalkyl, arylalkenyl, arylalkynyl, heteroarylalkyl, heteroarylalkenyl, heteroarylalkynyl, cycloalkylalkyl, or heterocycloalkylalkyl is optionally substituted by 1, 2, or 3 substituents independently selected from halo, cyano, nitro, hydroxyl-($C_{1-6}$ alkyl), aminoalkyl, dialkylaminoalkyl, $C_{1-4}$ alkyl, $C_{1-4}$ haloalkyl, $C_{1-4}$ alkoxy, $C_{1-4}$ haloalkoxy, OH, $C_{1-8}$ alkoxyalkyl, amino, $C_{1-4}$ alkylamino, $C_{2-8}$ dialkylamino, C(O)NR$^c$R$^d$, C(O)OR$^a$, NR$^c$C(O)R$^d$, NR$^c$S(O)$_2$R$^d$, ($C_{1-4}$ alkyl)sulfonyl, arylsulfonyl, aryl, heteroaryl, cycloalkyl, and heterocycloalkyl.

29. A compound according to claim 1, or a pharmaceutically acceptable salt thereof, wherein —W—X—Y—Z is halo, cyano, $C_{1-4}$ cyanoalkyl, nitro, $C_{1-4}$ nitroalkyl, $C_{1-4}$ alkyl, $C_{1-4}$ haloalkyl, $C_{1-4}$ alkoxy, $C_{1-4}$ haloalkoxy, OH, ($C_{1-4}$ alkoxy)-$C_{1-4}$ alkyl, amino, $C_{1-4}$ alkylamino, $C_{2-8}$ dialkylamino, aryl, heteroaryl, cycloalkyl, heterocycloalkyl, arylalkyl, heteroarylalkyl, cycloalkylalkyl, or heterocycloalkylalkyl;
wherein aryl or heteroaryl, is optionally substituted by 1, 2, or 3 substituents independently selected from halo, cyano, nitro, hydroxyl-($C_{1-6}$ alkyl), aminoalkyl, dialkylaminoalkyl, $C_{1-4}$ alkyl, $C_{1-4}$ haloalkyl, $C_{1-4}$ alkoxy, $C_{1-4}$ haloalkoxy, OH, $C_{1-8}$ alkoxyalkyl, amino, $C_{1-4}$ alkylamino, $C_{2-8}$ dialkylamino, C(O)NR$^c$R$^d$, C(O)OR$^a$, $NR^cC(O)R^d$, $NR^cS(O)_2R^d$, ($C_{1-4}$ alkyl)sulfonyl, arylsulfonyl, aryl, heteroaryl, cycloalkyl, and heterocycloalkyl.

30. A compound according to claim 20, or a pharmaceutically acceptable salt thereof, wherein —W—X—Y—Z is halo, cyano, $C_{1-4}$ cyanoalkyl, nitro, $C_{1-4}$ nitroalkyl, $C_{1-4}$ alkyl, $C_{1-4}$ haloalkyl, $C_{1-4}$ alkoxy, $C_{1-4}$ haloalkoxy, OH, ($C_{1-4}$ alkoxy)-$C_{1-4}$ alkyl, amino, $C_{1-4}$ alkylamino, $C_{2-8}$ dialkylamino, aryl, heteroaryl, cycloalkyl, heterocycloalkyl, arylalkyl, heteroarylalkyl, cycloalkylalkyl, or heterocycloalkylalkyl;

wherein aryl or heteroaryl, is optionally substituted by 1, 2, or 3 substituents independently selected from halo, cyano, nitro, hydroxyl-($C_{1-6}$ alkyl), aminoalkyl, dialkylaminoalkyl, $C_{1-4}$ alkyl, $C_{1-4}$ haloalkyl, $C_{1-4}$ alkoxy, $C_{1-4}$ haloalkoxy, OH, $C_{1-8}$ alkoxyalkyl, amino, $C_{1-4}$ alkylamino, $C_{2-8}$ dialkylamino, $C(O)NR^cR^d$, $C(O)OR^a$, $NR^cC(O)R^d$, $NR^cS(O)_2R^d$, ($C_{1-4}$ alkyl)sulfonyl, arylsulfonyl, aryl, heteroaryl, cycloalkyl, and heterocycloalkyl.

31. A compound according to claim 22, or a pharmaceutically acceptable salt thereof, wherein —W—X—Y—Z is halo, cyano, $C_{1-4}$ cyanoalkyl, nitro, $C_{1-4}$ nitroalkyl, $C_{1-4}$ alkyl, $C_{1-4}$ haloalkyl, $C_{1-4}$ alkoxy, $C_{1-4}$ haloalkoxy, OH, ($C_{1-4}$ alkoxy)-$C_{1-4}$ alkyl, amino, $C_{1-4}$ alkylamino, $C_{2-8}$ dialkylamino, aryl, heteroaryl, cycloalkyl, heterocycloalkyl, arylalkyl, heteroarylalkyl, cycloalkylalkyl, or heterocycloalkylalkyl;

wherein each of said aryl or heteroaryl, is optionally substituted by 1, 2, or 3 substituents independently selected from halo, cyano, nitro, hydroxyl-($C_{1-6}$ alkyl), aminoalkyl, dialkylaminoalkyl, $C_{1-4}$ alkyl, $C_{1-4}$ haloalkyl, $C_{1-4}$ alkoxy, $C_{1-4}$ haloalkoxy, OH, $C_{1-8}$ alkoxyalkyl, amino, $C_{1-4}$ alkylamino, $C_{2-8}$ dialkylamino, $C(O)NR^cR^d$, $C(O)OR^a$, $NR^cC(O)R^d$, $NR^cS(O)_2R^d$, ($C_{1-4}$ alkyl)sulfonyl, arylsulfonyl, aryl, heteroaryl, cycloalkyl, and heterocycloalkyl.

32. A compound according to claim 25, or a pharmaceutically acceptable salt thereof, wherein —W—X—Y—Z is halo, cyano, $C_{1-4}$ cyanoalkyl, nitro, $C_{1-4}$ nitroalkyl, $C_{1-4}$ alkyl, $C_{1-4}$ haloalkyl, $C_{1-4}$ alkoxy, $C_{1-4}$ haloalkoxy, OH, ($C_{1-4}$ alkoxy)-$C_{1-4}$ alkyl, amino, $C_{1-4}$ alkylamino, $C_{2-8}$ dialkylamino, aryl, heteroaryl, cycloalkyl, heterocycloalkyl, arylalkyl, heteroarylalkyl, cycloalkylalkyl, or heterocycloalkylalkyl;

wherein each of said aryl or heteroaryl is optionally substituted by 1, 2, or 3 substituents independently selected from halo, cyano, nitro, hydroxyl-($C_{1-6}$ alkyl), aminoalkyl, dialkylaminoalkyl, $C_{1-4}$ alkyl, $C_{1-4}$ haloalkyl, $C_{1-4}$ alkoxy, $C_{1-4}$ haloalkoxy, OH, $C_{1-8}$ alkoxyalkyl, amino, $C_{1-4}$ alkylamino, $C_{2-8}$ dialkylamino, $C(O)NR^cR^d$, $C(O)OR^a$, $NR^cC(O)R^d$, $NR^cS(O)_2R^d$, ($C_{1-4}$ alkyl)sulfonyl, arylsulfonyl, aryl, heteroaryl, cycloalkyl, and heterocycloalkyl.

33. A compound of Formula VIII:

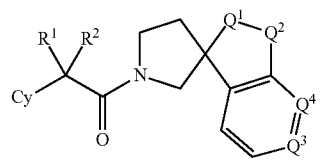

VIII or a pharmaceutically acceptable salt thereof, wherein:

Cy is phenyl optionally substituted by 1, 2, 3, 4 or 5-W—X—Y—Z;

$R^1$ and $R^2$ together with the C atom to which they are attached form a cyclopropyl group;

$Q^1$ is O;

$Q^2$ is CO;

$Q^3$ is CH;

$Q^4$ is CH;

—W—X—Y—Z is halo, cyano, $C_{1-4}$ cyanoalkyl, nitro, $C_{1-8}$ alkyl, $C_{1-8}$ alkenyl, $C_{1-8}$ haloalkyl, $C_{1-10}$ alkoxy, $C_{1-4}$ haloalkoxy, OH, $C_{1-8}$ alkoxyalkyl, amino, $C_{1-4}$ alkylamino, $C_{2-8}$ dialkylamino, $OC(O)NR^cR^d$, $NR^cC(O)R^d$, $NR^cC(O)OR^a$, aryloxy, heteroaryloxy, arylalkyloxy, heteroarylalkyloxy, heteroaryloxyalkyl, aryloxyalkyl, aryl, heteroaryl, cycloalkyl, heterocycloalkyl, arylalkyl, arylalkenyl, arylalkynyl, heteroarylalkyl, heteroarylalkenyl, heteroarylalkynyl, cycloalkylalkyl, or heterocycloalkylalkyl;

wherein each of said $C_{1-8}$ alkyl, $C_{1-8}$ alkenyl, $C_{1-8}$ haloalkyl, $C_{1-8}$ alkoxy, aryloxy, heteroaryloxy, arylalkyloxy, heteroarylalkyloxy, heteroaryloxyalkyl, aryloxyalkyl, aryl, heteroaryl, cycloalkyl, heterocycloalkyl, arylalkyl, arylalkenyl, arylalkynyl, heteroarylalkyl, heteroarylalkenyl, heteroarylalkynyl, cycloalkylalkyl, or heterocycloalkylalkyl is optionally substituted by 1, 2, or 3 substituents independently selected from halo, cyano, nitro, hydroxyl-($C_{1-6}$ alkyl), aminoalkyl, dialkylaminoalkyl, $C_{1-4}$ alkyl, $C_{1-4}$ haloalkyl, $C_{1-4}$ alkoxy, $C_{1-4}$ haloalkoxy, OH, $C_{1-8}$ alkoxyalkyl, amino, $C_{1-4}$ alkylamino, $C_{2-8}$ dialkylamino, $C(O)NR^cR^d$, $C(O)OR^a$, $NR^cC(O)R^d$, $NR^cS(O)_2R^d$, ($C_{1-4}$ alkyl)sulfonyl, arylsulfonyl, aryl, heteroaryl, cycloalkyl, and heterocycloalkyl;

$R^a$ is H, $C_{1-6}$ alkyl, $C_{1-6}$ haloalkyl, $C_{2-6}$ alkenyl, ($C_{1-6}$ alkoxy)-$C_{1-6}$ alkyl, $C_{2-6}$ alkynyl, aryl, cycloalkyl, heteroaryl or heterocycloalkyl; and $R^c$ and $R^d$ are each, independently, H, $C_{1-6}$ alkyl, $C_{1-6}$ haloalkyl, $C_{2-6}$ alkenyl, $C_{2-6}$ alkynyl, aryl, cycloalkyl, arylalkyl, or cycloalkylalkyl;

or $R^a$ and $R^d$ together with the N atom to which they are attached form a 4-, 5-, 6- or 7-membered heterocycloalkyl group.

34. A compound according to claim 33, or a pharmaceutically acceptable salt thereof, wherein —W—X—Y—Z is halo, cyano, $C_{1-4}$ cyanoalkyl, nitro, $C_{1-4}$ nitroalkyl, $C_{1-4}$ alkyl, $C_{1-4}$ haloalkyl, $C_{1-4}$ alkoxy, $C_{1-4}$ haloalkoxy, OH, ($C_{1-4}$ alkoxy)-$C_{1-4}$ alkyl, amino, $C_{1-4}$ alkylamino, $C_{2-8}$ dialkylamino, aryl, heteroaryl, cycloalkyl, heterocycloalkyl, arylalkyl, heteroarylalkyl, cycloalkylalkyl, or heterocycloalkylalkyl;

wherein each of said aryl and heteroaryl, is optionally substituted by 1, 2, or 3 substituents independently selected from halo, cyano, nitro, hydroxyl-($C_{1-6}$ alkyl), aminoalkyl, dialkylaminoalkyl, $C_{1-4}$ alkyl, $C_{1-4}$ haloalkyl, $C_{1-4}$ alkoxy, $C_{1-4}$ haloalkoxy, OH, $C_{1-8}$alkoxyalkyl, amino, $C_{1-4}$ alkylamino, $C_{2-8}$ dialkylamino, $C(O)NR^cR^d$, $C(O)OR^a$, $NR^cC(O)R^d$, $NR^cS(O)_2R^d$, ($C_{1-4}$ alkyl)sulfonyl, arylsulfonyl, aryl, heteroaryl, cycloalkyl, and heterocycloalkyl.

35. The compound of claim 1 selected from:

N-Cyclopropyl-5-[4-(1-{[3-oxo-1'H,3H-spiro[2-benzofuran-1,3'-pyrrolidin]-1'-yl]carbonyl}cyclopropyl)phenyl]pyridine-2-carboxamide;

N-Methyl-5-[4-(1-{[3-oxo-1'H,3H-spiro[2-benzofuran-1,3'-pyrrolidin]-1'-yl]carbonyl}cyclopropyl)phenyl]pyridine-2-carboxamide;

N-Ethyl-N-methyl-5-[4-(1-{[3-oxo-1'H,3H-spiro[2-benzofuran-1,3'-pyrrolidin]-1'-yl]carbonyl}cyclopropyl)phenyl]pyridine-2-carboxamide;

N,N-Diethyl-5-[4-(1-{[3-oxo-1'H,3H-spiro[2-benzofuran-1,3'-pyrrolidin]-1'-yl]carbonyl}cyclopropyl)phenyl]pyridine-2-carboxamide;

N,N-Dimethyl-5-[4-(1-{[3-oxo-1'H,3H-spiro[2-benzofuran-1,3'-pyrrolidin]-1'-yl]carbonyl}cyclopropyl)phenyl]pyridine-2-carboxamide;

N-Ethyl-5-[4-(1-{[3-oxo-1'H,3H-spiro[2-benzofuran-1,3'-pyrrolidin]-1'-yl]carbonyl}cyclopropyl)phenyl]pyridine-2-carboxamide;

N-Isopropyl-5-[4-(1-{[3-oxo-1'H,3H-spiro[2-benzofuran-1,3'-pyrrolidin]-1'-yl]carbonyl}cyclopropyl)phenyl]pyridine-2-carboxamide;

5-[3-Fluoro-4-(1-{[3-oxo-1'H,3H-spiro[2-benzofuran-1,3'-pyrrolidin]-1'-yl]carbonyl}cyclopropyl)phenyl]-N-methylpyridine-2-carboxamide;

5-[3-Fluoro-4-(1-{[3-oxo-1'H,3H-spiro[2-benzofuran-1,3'-pyrrolidin]-1'-yl]carbonyl}cyclopropyl)phenyl]-N-ethylpyridine-2-carboxamide;

5-[3-Fluoro-4-(1-{[3-oxo-1'H,3H-spiro[2-benzofuran-1,3'-pyrrolidin]-1'-yl]carbonyl}cyclopropyl)phenyl]-N-i-propylpyridine-2-carboxamide;

5-[3-Fluoro-4-(1-{[3-oxo-1'H,3H-spiro[2-benzofuran-1,3'-pyrrolidin]-1'-yl]carbonyl}cyclopropyl)phenyl]-N,N-dimethylpyridine-2-carboxamide;

5-[3-Fluoro-4-(1-{[3-oxo-1'H,3H-spiro[furo[3,4-c]pyridine-1,3'-pyrrolidin]-1'-yl]carbonyl}cyclopropyl)phenyl]-N-methylpyridine-2-carboxamide;

N-Ethyl-5-[3-fluoro-4-(1-{[3-oxo-1'H,3H-spiro[furo[3,4-c]pyridine-1,3'-pyrrolidin]-1'-yl]carbonyl}cyclopropyl)phenyl]pyridine-2-carboxamide;

5-[3-Fluoro-4-(1-{[3-oxo-1'H,3H-spiro[furo[3,4-c]pyridine-1,3'-pyrrolidin]-1'-yl]carbonyl}cyclopropyl)phenyl]-N-isopropylpyridine-2-carboxamide;

5-[3-Fluoro-4-(1-{[3-oxo-1'H,3H-spiro[furo[3,4-c]pyridine-1,3'-pyrrolidin]-1'-yl]carbonyl}cyclopropyl)phenyl]-N,N-dimethylpyridine-2-carboxamide;

N,N-Diethyl-5-[3-fluoro-4-(1-{[3-oxo-1'H,3H-spiro[2-benzofuran-1,3'-pyrrolidin]-1'-yl]carbonyl}cyclopropyl)phenyl]pyridine-2-carboxamide;

N-Ethyl-5-[3-fluoro-4-(1-{[3-oxo-1'H,3H-spiro[2-benzofuran-1,3'-pyrrolidin]-1'-yl]carbonyl}cyclopropyl)phenyl]pyridine-2-carboxamide; and 5-[3-Fluoro-4-(1-{[3-oxo-1'H,3H-spiro[2-benzofuran-1,3'-pyrrolidin]-1'-yl]carbonyl}cyclopropyl)phenyl]-N-isopropylpyridine-2-carboxamide;

or a pharmaceutically acceptable salt thereof.

\* \* \* \* \*

UNITED STATES PATENT AND TRADEMARK OFFICE
CERTIFICATE OF CORRECTION

PATENT NO. : 8,058,288 B2
APPLICATION NO. : 12/817887
DATED : November 15, 2011
INVENTOR(S) : Yao et al.

It is certified that error appears in the above-identified patent and that said Letters Patent is hereby corrected as shown below:

On the title page, item [75], delete "Kenneth" and insert -- Kennett --.

On the title page, item [56], Col. 2, Line 2; delete "Dehydrogenease" and insert -- Dehydrogenase --.

In the Claims

Col. 188, Line 46, Claim 1; delete "$C_{2-4}$" and insert -- $C_{2-8}$ --.

Col. 188, Line 57, Claim 1; delete "$C_{2-4}$" and insert -- $C_{2-8}$ --.

Col. 189, Line 23, Claim 3; delete "thereof;" and insert -- thereof, --.

Col. 190, Line 4, Claim 8; delete "(cyclocalkylalkyl)" and insert -- (cycloalkylalkyl) --.

Col. 190, Line 6, Claim 8; delete "$S(O)_2R^d$," and insert -- $S(O)_2R^d$, $SR^d$, --.

Col. 190, Line 34, Claim 10; delete "thereof;" and insert -- thereof, --.

Col. 190, Line 41, Claim 11; delete "thereof;" and insert -- thereof, --.

Col. 191, Lines 10-11, Claim 12; delete "-3,4-" and insert -- -3H- --.

Col. 191, Line 20, Claim 13; delete "oxo" and insert -- Oxo --.

Col. 191, Line 23, Claim 13; delete "oxopyrrolidin" and insert -- Oxopyrrolidin --.

Col. 191, Lines 36-37, Claim 13; delete "phenyl}cyclopropyl)carbonyl]" and insert -- phenyl]cyclopropyl}carbonyl) --.

Col. 191, Line 51, Claim 13; delete "oxo" and insert -- Oxo --.

Col. 192, Line 22, Claim 13; delete "({1-{4-[3-Methyl" and insert -- ({1-[4-(3-Methyl --.

Col. 192, Lines 25-26, Claim 13; delete "phenyl cyclopropyl}" and insert -- phenyl}cyclopropyl) --.

Col. 193, Line 40, Claim 13; delete "oxo" and insert -- Oxo --.

Col. 193, Line 62-63, Claim 13; delete "pyrrolidin]-yl]" and insert -- pyrrolidin]-1'-yl] --.

Signed and Sealed this
Twenty-first Day of July, 2015

Michelle K. Lee
*Director of the United States Patent and Trademark Office*

CERTIFICATE OF CORRECTION (continued)
U.S. Pat. No. 8,058,288 B2

Col. 194, Line 6, Claim 13; delete "1'({1" and insert -- 1'-({1 --.

Col. 194, Line 10, Claim 13; delete "-1'yl]" and insert -- -1'-yl] --.

Col. 194, Line 18, Claim 13; delete "({[1-" and insert -- {[1- --.

Col. 194, Line 62, Claim 13; delete "oxo" and insert -- Oxo --.

Col. 195, Line 7, Claim 13; delete "oxo" and insert -- Oxo --.

Col. 195, Line 20, Claim 13; delete "oxo" and insert -- Oxo --.

Col. 196, Line 35, Claim 14; delete "pyrrolidin]-yl]" and insert -- pyrrolidin]-1'-yl] --.

Col. 196, Line 66, Claim 14; delete "pyrrolidin]-yl]" and insert -- pyrrolidin]-1'-yl] --.

Col. 197, Line 15, Claim 14; delete "3'H" and insert -- 3H --.

Col. 197, Line 42, Claim 14; delete "1'[(" and insert -- 1'-[( --.

Col. 197, Line 44, Claim 14; delete "1-{[" and insert -- 1'-{[ --.

Col. 199, Line 54-55, Claim 15; delete "yl]cyclopropyl}carbonyl)" and insert -- yl)cyclopropyl]carbonyl} --.

Col. 200, Line 10, Claim 16; delete "{[1-" and insert -- 1'-{[1- --.

Col. 200, Line 51, Claim 16; delete "{[1-" and insert -- 1'-{[1- --.

Col. 201, Line 30, Claim 16; delete "pyrrolidin]-1'-3-one;" and insert -- pyrrolidin]-3-one; --.

Col. 201, Line 32, Claim 16; delete "pyrrolidiin" and insert -- pyrrolidin --.

Col. 201, Line 37, Claim 16; delete "pyridin-3-yl" and insert -- pyridin-3-yl} --.

Col. 201, Line 40, Claim 16; delete "1'-[1-(4-" and insert -- 1'-{[1-(4- --.

Col. 201, Line 46, Claim 16; delete "carbonyl}-3H" and insert -- carbonyl)-3H --.

Col. 201, Line 53, Claim 16; delete "Methyl 4-[4-({[3" and insert -- Methyl 4-[4-(1-{[3 --.

Col. 202, Line 4, Claim 16; delete "1'-({[1-[6" and insert -- 1'-({1-[6 --.

Col. 202, Line 41, Claim 16; delete "{1-[3-oxo" and insert -- {1-[(3-oxo --.

Col. 204, Line 37, Claim 17; delete "1'-({[1-(2" and insert -- 1'-({1-[2 --.

Col. 205, Line 62, Claim 17; delete "Ethyl 4-[4(1" and insert -- Ethyl 4-[4-(1 --.

Col. 206, Line 44, Claim 18; delete "oxoazetidin" and insert -- Oxoazetidin --.

Col. 207, Line 23, Claim 18; delete "PH,3H" and insert -- 1'H,3H --.

Col. 207, Line 56, Claim 18; delete "1'1-1,3H" and insert -- 1'H,3H --.

Col. 207, Line 60, Claim 18; delete "pyrrolidin]-F-yl]" and insert -- pyrrolidin]-1'-yl] --.

Col. 208, Line 28, Claim 18; delete "pyrrolidin]-yl]" and insert -- pyrrolidin]-1'-yl] --.

Col. 209, Line 67, Claim 26; delete "$C_{1-8}$alkoxyalkyl" and insert -- $C_{1-8}$ alkoxyalkyl --.

Col. 211, Line 18, Claim 30; delete "$NR^cC(O)R^d$," and insert -- $NR^cC(O)R^d$, --.

Col. 212, Line 41, Claim 33; delete "$R^a$ and $R^d$" and insert -- $R^c$ and $R^d$ --.

Col. 212, Line 57, Claim 34; delete "$C_{1-8}$alkoxyalkyl" and insert -- $C_{1-8}$ alkoxyalkyl --.